US008128963B2

(12) United States Patent
Pinsky et al.

(10) Patent No.: US 8,128,963 B2
(45) Date of Patent: Mar. 6, 2012

(54) METHODS FOR TREATING ISCHEMIC DISORDERS USING CARBON MONOXIDE

(75) Inventors: David J. Pinsky, Ann Arbor, MI (US); David M. Stern, Augusta, GA (US); Charles J. Prestigiacome, East Hanover, NJ (US)

(73) Assignee: The Trustees of Columbia University in the City Of New York, New York, NY (US)

(*) Notice: Subject to any disclaimer, the term of this patent is extended or adjusted under 35 U.S.C. 154(b) by 1749 days.

(21) Appl. No.: 10/679,135

(22) Filed: Oct. 3, 2003

(65) Prior Publication Data

US 2005/0048133 A1 Mar. 3, 2005

Related U.S. Application Data

(63) Continuation-in-part of application No. 09/671,100, filed on Sep. 27, 2000, now abandoned, which is a continuation of application No. PCT/US99/07175, filed on Apr. 1, 1999.

(51) Int. Cl.
*A61K 33/00* (2006.01)
*A61P 9/10* (2006.01)
(52) U.S. Cl. .................................. 424/699; 435/1.1
(58) Field of Classification Search .................. 424/699; 435/1.1
See application file for complete search history.

(56) References Cited

U.S. PATENT DOCUMENTS

| | | | |
|---|---|---|---|
| 4,053,590 A | 10/1977 | Bonsen et al. | |
| 4,264,739 A | 4/1981 | Grabner et al. | |
| 4,711,848 A | 12/1987 | Insley et al. | |
| 4,885,277 A | 12/1989 | Nawroth | 514/15 |
| 4,923,817 A | 5/1990 | Mundt | |
| 5,084,380 A | 1/1992 | Carney | |
| 5,180,366 A | 1/1993 | Woods | |
| 5,240,912 A | 8/1993 | Todaro | |
| 5,293,875 A | 3/1994 | Stone | |
| 5,378,464 A | 1/1995 | McEver | 424/143.1 |
| 5,449,665 A | 9/1995 | Sollevi | |
| 5,476,764 A | 12/1995 | Bitensky | |
| 5,664,563 A | 9/1997 | Schroeder et al. | |
| 5,731,326 A | 3/1998 | Hart et al. | |
| 5,763,431 A | 6/1998 | Jackson | |
| 5,792,325 A | 8/1998 | Richardson, Jr. | |
| 5,807,980 A | 9/1998 | Lasters et al. | |
| 5,839,443 A | 11/1998 | Rose et al. | 128/898 |
| 5,882,674 A | 3/1999 | Hermann | |
| 5,885,621 A | 3/1999 | Head et al. | |
| 5,914,316 A | 6/1999 | Brown et al. | |
| 6,066,333 A | 5/2000 | Willis et al. | |
| 6,069,132 A | 5/2000 | Revanker et al. | |
| 6,203,991 B1 | 3/2001 | Nabel et al. | |
| 6,313,144 B1 | 11/2001 | McCullough et al. | |
| 6,315,995 B1 | 11/2001 | Pinsky et al. | 424/94.63 |
| 6,316,403 B1 | 11/2001 | Pinsky et al. | 514/2 |
| 6,391,300 B1 | 5/2002 | Rose et al. | 424/145.1 |
| 7,045,140 B2 | 5/2006 | Motterlini et al. | |
| 7,238,469 B2 | 7/2007 | Bach et al. | |
| 2002/0155166 A1* | 10/2002 | Choi et al. | 424/600 |
| 2003/0009127 A1 | 1/2003 | Trescony et al. | |
| 2003/0039638 A1 | 2/2003 | Bach et al. | |
| 2003/0064114 A1 | 4/2003 | Motterlini et al. | |
| 2003/0068387 A1 | 4/2003 | Buelow et al. | |
| 2004/0067261 A1 | 4/2004 | Haas et al. | |
| 2004/0131703 A1* | 7/2004 | Bach et al. | 424/718 |
| 2004/0197271 A1 | 10/2004 | Kunka et al. | |
| 2005/0250688 A1 | 11/2005 | Pinsky et al. | |
| 2006/0003922 A1* | 1/2006 | Bach et al. | 514/6 |

FOREIGN PATENT DOCUMENTS

| | | |
|---|---|---|
| AU | 735258 | 11/1997 |
| CA | 2141642 | 8/1995 |
| EP | 0 951 292 B1 | 4/2007 |
| EP | 1 829 550 A2 | 5/2007 |
| EP | 1 829 550 A3 | 4/2008 |
| FR | 2 816 212 | 5/2002 |
| JP | 56079957 | 6/1981 |
| JP | 8-502242 | 3/1996 |
| JP | 8-503617 | 4/1996 |
| WO | 9405314 A | 3/1994 |
| WO | WO 94/22482 | 10/1994 |
| WO | WO 95/20400 | 8/1995 |
| WO | WO 95/21180 | 8/1995 |

(Continued)

OTHER PUBLICATIONS

Thom, S.R. et al., "'Therapeutic' Carbon Monoxide May Be Toxic," American Journal of Respiratory and Critical Care Medicine, vol. 171, p. 1318 (2005).*
Choi, A.M.K. et al., "'Therapeutic' Carbon Monoxide May Be a Reality Soon," American Journal of Respiratory and Critical Care Medicine, vol. 171, pp. 1318-1319 (2005).*
U.S. Appl. No. 09/671,100, Pinsky et al., Methods for Treating an Ischemic Disorder and Improving Stroke Outcome, filed Sep. 27, 2000 (Exhibit 2 ).
Benedict C.R., et al. (1994) Endothelial-Dependent Procoagulant and Anticoagulant Mechanisms, Recent Advances in Understanding. Texas Heart Institute Journal 21:86-90.

(Continued)

*Primary Examiner* — John Pak
(74) *Attorney, Agent, or Firm* — John P. White; Cooper & Dunham LLP

(57) ABSTRACT

The present invention provides for a method for treating an ischemic disorder in a subject which comprises administering to the subject a pharmaceutically acceptable form of a selectin antagonist in a sufficient amount over a sufficient time period to prevent white blood cell accumulation so as to treat the ischemic disorder in the subject. The invention further provides a method for treating an ischemic disorder in a subject which comprises administering to the subject carbon monoxide gas in a sufficient amount over a sufficient period of time thereby treating the ischemic disorder in the subject. The invention further provides a method for treating an ischemic disorder in a subject which comprises administering to the subject a pharmaceutically acceptable form of inactivated Factor IX in a sufficient amount over a sufficient period of time to inhibit coagulation so as to treat the ischemic disorder in the subject.

14 Claims, 60 Drawing Sheets

FOREIGN PATENT DOCUMENTS

| | | |
|---|---|---|
| WO | WO 95/35105 | 12/1995 |
| WO | 9742900 | 11/1997 |
| WO | WO 98/08523 | 3/1998 |
| WO | 9813058 | 4/1998 |
| WO | WO 99/47512 | 9/1999 |
| WO | 9949803 | 10/1999 |
| WO | 9949880 | 10/1999 |
| WO | WO 02/09731 | 2/2002 |
| WO | WO 02/078684 | 10/2002 |
| WO | WO 02/092075 | 11/2002 |
| WO | WO 03/000114 | 1/2003 |

OTHER PUBLICATIONS

Bronner et al. (1995) Primary prevention of stroke. The New England J. Med. 333:1392-1400.
Brown and Piantadosi (1992) Recovery of Energy Metabolism in Rat After Carbon Monoxide Hypoxia. J. Clin. Invest. 89:666-672.
Carlos and Harlan (1994) Leukocyte-Endothelial Adhesion Molecules. Blood. 24:2068-2102.
Connolly et al. (1996) Cerebral Protection in Homozygous Null ICAM-1 Mice After Middle Cerebral Artery Occlusion. J. Clin. Invest. 97:209-216.
Connolly et al. (1996) Procedural and Strain-Related Variables Significantly Affect Outcome in a Murine Model of Focal Cerebral Ischemia. Neurogurgery. 38:523-532.
Dawson and Snyder (1994) Gases as biological messengers; nitric oxide and carbon monoxide in the brain. J. Neuroscience. 5147-5159.
Dietrich et al. (1995) Influence of High-Dose Aprotinin on Anticoagulation, Heparin Requirement, and Celite-and Kaolin-Activated Clotting Tie in Heparin-pretreated Patients Undergoing Open-Heart Surgery. Anesthesiology, 83(4)679-689.
Fassbender et al. (1995) Circulating Selectin-and Immunoglobin-Type Adhesion Molecules in Acute Ischemic Stroke. Stroke. 26:1361-1364.
Fujita, T. et al., (2001) Paradoxical rescue from ischemic lung injury by inhaled carbon monoxide driven by derepression of fibrinolysis. Nature Medicine. 7(5):598-604 (Exhibit 3).
Holdright, D., et al. (1994) Comparison of the Effect of Heparin and Aspirin Versus Aspirin Alone on Transient Myocardial Ischemia and In-hospital Prognosis in Patients With Unstable Angina J. Am. Coll. Cardiol. 24:39-45.
Iberti, T.J. et al., (1994) Abnormal Coagulation Profile in Brain Tumor Patients During Surgery. Neurosurgery 34:389-395.
Ishimaru et al. (1991) Effects of successive carbon monoxide exposures on delayed neuronal death in mice under maintenance of normal body temperature. Biochem. Biophys. Res. Comm. 179:836-840.
Jerome et al. (1994) P-selectin and ICAM-1-Dependent Adherence Reactions: Role in the Genesis of Postischemic No-Reflow. Am. J. Physiol. 226:H1316-H1321.
Kim et al. (1995) Adhesive Glycoproteins CD11a and Cd18 are Upregulated in the Leukocytes from Patients with Ischemic Stroke and Transient Ischemic Attacks. J. Neurol. Sci. 128:45-50.
Kochaneck and Hallenbeck (1992) Polymorphonuclear Leukocytes and Monocytes/Macrophages in the Pathogenesis of Cerebral Ischemia and Stroke. Stroke. 23:1367-1379.
Kuwabara, K. et al., (1995) Calreticulin, an Antithrombotic Agent which Binds to Vitamin K-Dependent Coagulation Factors, Stimulates Endothelial Nitric Oxide Production, and Limits Thrombosis in Canine Coronary Arteries. J. Biol. Chem. 270:8179-8187.
Mayevsky et al. (1995) Multiparametic monitoring of the awake brain exposed to carbon monoxide. J. Appl. Physiol. 78:1188-1196.
Okada et al. (1994) P-selectin and Intercellular Adhesion Molecule-1 Expression After Focal Brain Ischemia and Reperfusion. Stroke. 25:202-211.
Pinsky et al. (1996) Hypoxia-Induced Exocytosis of Endothelial Cell Weibel-Palade Bodies, a Mechanism for Rapid Neutrophil Recruitment After Cardiac Preservation. J. Clin. Invest. 97:493-500.
Schroeter et al. (1994) Local Immune Response in the Rat Cerebral Cortex After Middle Cerebral Artery Occlusion. J. Neuroimmunol. 55:195-203.
Seekamp et al. (1994) Role of Selectins in Local and Remote Tissue Injury Following Ischemia and Reperfusion. Am. J. Pathol. 44:592-598.
Tijburg et al., (1991) Activation of the coagulation mechanism on tumor necrosis factor-stimulated cultured endothelial cells and their extracellular matrix. The role of flow and Factor IX/IXa. J. Biol. Chem. 266:12067-12074.
Verma et al. (1993) Carbon monoxide: a putative neural messenger. Science. 259:381-384.
Weyrich et al. (1993) In Vivo Neutralization of P-selectin Protects Feline Heart Endothelium in Myocardial Ishchemia and Reperfusion Injury. J. Clin. Invest. 91:2620-2629.
BBC News report, Health segment, Apr. 30, 2001, Deadly gas 'could save lives' (Exhibit 4).
International Search Report, Aug. 29, 1997 for PCT/US97/08282 (Exhibit 5).
International Preliminary Examination, Apr. 20, 1998 for PCT/US97/08282 (Exhibit 6).
Search Report Oct. 27, 2000 from Patent Office regarding European Patent Application No. 97926541.0 (Exhibit 7).
International Search Report, Jun. 18, 1999 for PCT/US99/07173 (Exhibit 8).
International Preliminary Examination, Jan. 7, 2000 for PCT/US99/07173 (Exhibit 9).
Search Report, May 28, 2002 from Patent Office regarding European Patent Application No. 99916264.7 (Exhibit 10).
International Search Report, Feb. 5, 1998 for PCT/US97/17229 (Exhibit 11).
Written Opinion Sep. 14, 1998 for PCT/US97/17229 (Exhibit 12).
International Preliminary Examination, Jan. 8, 1999 for PCT/US97/17229 (Exhibit 13).
International Search Report, Aug. 4, 1999 for PCT/US99/07175 (Exhibit 14).
Written Opinion Feb. 3, 2000 for PCT/US99/07175 (Exhibit 15).
International Preliminary Examination, Jul. 11, 2000 for PCT/US99/07175 (Exhibit 16).
U.S. Appl. No. 10/692,439, Pinsky et al., Method for Treating Ischemic Disorder. Improving Stroke Outcome, filed Oct. 22, 2003 (Exhibit 2).
Partial European Search Report, Mar. 1, 2004 from European Patent Office on European Patent Application No. EP 97944453.6 (Exhibit 3).
Raju, V. S. et al. (1996) Renal Ischemia/Reperfusion Up-Regulates Heme Oxygenase-1 (HSP32) Expression and Increases CGMP in Rat Heart. JPET 277:1814-1822 (Exhibit 1).
Eyssen-Hernandez, R. et al. (1996) Differential Regulation of Cardiac Heme Oxygenase-1 and Vascular Endothelial Growth Factor mRNA Expressions by Hemin, Heavy Metals, Heat Shock and Anoxia. FEBS Letters 382:229-233 (Exhibit 2).
Paschen, W. et al. (1994) Hemeoxygenase Expression after Reversible Ischemia of Rat Brain. Neuroscience Letters 180:5-8 (Exhibit 3).
Fujita, T. et al. (2001) Paradoxical Rescue from Ischemic Lung Injury by Inhaled Carbon Monoxide Driven by Depression of Fibrinolysis. Nature Medicine 7:5 (Exhibit 4).
Benedict, C. R. et al. (1991) Active Site-blocked Factor IXa Prevents Intravascular Thrombus Formation in the Coronary Vasculature without Inhibiting Extravascular Coagulation in a Canine Thrombosis Model. J. Clin. Invest. 88-1760-1765 (Exhibit 5).
Benedict, C. R. et al. (1994) Endothelial-Dependant Procoagulant and Anticoagulant Mechanisms. Molecular and Cellular Cardiology 21:1 (Exhibit 6).
Choudhri, T. F. et al. (1999) Targeted Inhibition of Intrinsic Coagulation Limits Cerebral Injury in Stroke without Increasing Intracerebral Hemorrhage. J. Exp. Med. 190:1:91-99 (Exhibit 7).
Partial European Search Report, Jun. 16, 2004 from European Patent Office on European Patent Application No. EP 97944453.6 (Exhibit 8).
Benedict C. R., et al. (1993) Active Site-Blocked Factor Xa Prevents Thrombus Formation in the Coronary Vasculature in Parallel With Inhibition of Extravascular Coagulation in a Canine Thrombosis Model. Blood 81 (8) :2059-2066.
Partial European Search Report, Sep. 30, 2004 from European Patent Office on European Patent Application No. EP 99916266.2-2107.

Ryter, S.W. and Choi, A.M., "Therapeutic applications of carbon monoxide in lung disease" Current Opinion on Pharmacology 6:257-262 (2006).

Mayr, F.B., et al., "Effects of Carbon Monoxide Inhalation during Experimental Endotoxemia in Humans" Am. J. Respir. Crit Care Med. 171:354-360 (2005).

Dolinay, T. et al., "Can Inhalation Carbon Monoxide Be Utilized as a Therapeutic Modality in Human Diseases?" *Breath Analysis for Clinical Diagnosis and Therapeutic Monitoring*, edited by Amann, A. and Smith, D., pp. 203-236 (2005).

McCord, J.M. "Oxygen-Derived Free Radicals in Post-Ischemic Tissue Injury", N. Engl. J. Med. Jan. 17, 1985; 312(3): 159-63.

Unruh, H.W. "Lung Preservation and Lung Injury" Chest Surg. Clin. N. Am. Feb. 1995; 5(1): 91-106.

Novick, R.J., et al. "New Trends in Lung Preservation: A Collective Review", J. Heart Lung Transplant. Mar.-Apr. 1992; 11 (2 Pt 1): 377-92.

Johnson, C.P., et l. "Factors influencing weight gain after renal transplantation", abstract, Transplantation. Oct. 1993; 56(4): 822-7.

Murphy, B.G., et al. "Effect of immunosuppressive drug regime on cardiovascular risk profile following kidney transplantation", abstract, Atherosclerosis. Aug. 1995; 116(2): 241-5.

Weston, M.W., et al. "Normalization of circulating atrial natriuretic peptides in cardiac transplant recipients", abstract, Am. Heart J. Jan. 1994; 127(1): 129-42.

Lambert, S.B., et al. "Bronchoalveolar lavage fluid endotoxin elevation in human single lung transplant recipients during rejection", abstract, Transpl. Immunol. Mar. 1995; 3(1):81-5.

Keeffe, E.B. et al., "Controversies in patient selection for liver transplantation", abstract, West. J. Med. Nov. 1993; 159(5):586-93.

Johnson, C.P., et l. "Factors influencing weight gain after renal transplantation", Transplantation. Oct. 1993; 56(4): 822-7.

Murphy, B.G., et al. "Effect of immunosuppressive drug regime on cardiovascular risk profile following kidney transplantation", Atherosclerosis. Aug. 1995; 116(2): 241-5.

Weston, M.W., et al. "Normalization of circulating atrial natriuretic peptides in cardiac transplant recipients", Am. Heart J. Jan. 1994; 127(1): 129-42.

Lambert, S.B., et al. "Bronchoalveolar lavage fluid endotoxin elevation in human single lung transplant recipients during rejection", Transpl. Immunol. Mar. 1995; 3(1):81-5.

Keeffe, E.B. et al., "Controversies in patient selection for liver transplantation", West. J. Med. Nov. 1993;159(5):586-93.

Printout from U.S. Environmental Protection Agency website <http://epa.gov>; Green Book entry for carbon monoxide, revised as of Jul. 1, 2001.

Printout from U.S. Department of Labor website <http://www.osha.gov>; Occupational Safety and Health Guidelines for Carbon Monoxide, printed Aug. 1, 2007.

Printout from World Health Organization website <http://www.euro.who.int/document/aiq/5_5carbonmonoxide.f>; Air Quality Guidelines, $2^{nd}$ Edition, Chapter 5.5 (2000).

Bathoorn, et al. "Effects of low dose inhaled carbon monoxide in patients with COPD" Recent advances in the treatment of COPD and acute lung injury, abstract P3840, p. 661s (2006).

Investigational New Drug Application submitted Oct. 20, 2006 under section 505(i) of the Federal Food, Drug, and Cosmetic Act for Covox™ (carbon monoxide) single dose inhalation for INO Therapeutics.

Dec. 27, 2007 Communication and Supplementary Partial European Search Report issued in connection with European Patent Application No. 07006886.1.

U.S. Appl. No. 09/617,100, filed Sep. 27, 2000, Pinsky et al.

Product Use Sheet for 1,5-Dansyl-Glu-Gly-Arg Chloromethyl ketone from Calbiochem, revised May 27, 1997, one page.

Skolnick et al. (2000) Trends in Biotechnology, vol. 18, No. 1, pp. 34-39.

Toledo-Pereya (1991) Klin Wochenschr, vol. 69, pp. 1099-1104.

Whisstock et al. (2003) Quarterly Reviews of Biophysics, vol. 36, pp. 307-340.

International Search Report issued Feb. 5, 1998 in connection with International Publication No. PCT/US97/17229.

Communication forwarding Extended European Search Report and Search Opinion issued Mar. 31, 2008 in connection with International Application No. 07006886.1.

Advisory Action issued Dec. 3, 2007 in connection with U.S. Appl. No. 10/692,439.

Final Office Action issued Aug. 7, 2007 in connection with U.S. Appl. No. 10/692,439.

Office Action issued Nov. 17, 2006 in connection with U.S. Appl. No. 10/692,439.

Office Action issued Mar. 3, 2006 in connection with U.S. Appl. No. 10/692,439.

Office Action issued Apr. 22, 2003 in connection with U.S. Appl. No. 09/671,100.

Office Action issued Aug. 29, 2001 in connection with U.S. Appl. No. 09/671,100.

Appel et al., "The pig as a source of cardiac xenografts," Journal of Cardiac Surgery 16 (5) : 345-56 (Sep. 2001) (Abstract).

Mori et al., "Evaluation of hypothermic heart preservation with UW solution in heteoptopically and orthotopically transplanted canine hearts," J. Heart and Lung Transplantation 13 (4) : 688-95 (1994) (Abstract).

Abidin et al., "The combined effect of carbon monoxide and normobaric hyperoxia on animals," Kosmicheskaya Biologiya I Aviakosmicheskaya Meditsina (1978), No. 6, 63-67.

Arita et al., "Prevention of Primary Islet Isograft Nonfunction in Mice with Pravastatin," Transplantation, 65:1429-33, 1998.

Arnush et al., "IL-1 Produced and Released Endogenously within Human Islets Inhibits .beta. Cell Function," J. Clin Invest. 702:516-26, 1998.

Bach et al., "Accommodation of vascularized xenografts: Expression of "protective genes" by donor endothelial cells in a host Th2 cytokine environment," Nature Med. 3:196-202, 1997.

Berney et al., "Islet cell transplantation: the future?" Langenbechs Arch. Surg. 385: 378-8, 2000.

Bentley et al., "Successful cardiac transplantation with methanol or carbon monoxide-poisoned donors," Thorac Surg Apr. 2001; 71(4):1194-7.

Brouard et al., "Carbon monoxide generated by heme oxygenase-1 suppresses endothelial cell apoptosis," J Exp Med Oct. 2. 2000; 192(7):1015-26.

Cantrell et al., "Low-Dose Carbon Monoxide Does Not Reduce Vasoconstriction in Isolated Rat Lungs," Experimental Lung Research 22:21-32, 1996.

Cardell et al., "Bronchodilation in vivo by carbon monoxide, a cyclic GMP related messenger," British Journal of Pharmacology 124:1065-1068, 1998.

Carlsson et al., "Measurement of Oxygen Tension in Native and Transplanted Rat Pancreatic Islets," Diabetes 47:1027-32, 1998.

Cecil Textbook of Medicine (21st Ed. 2000), vol. 1, pp. 273-279, 357-372, 387-419, 425-427, 436-448, 466-475, 507-512, 1060-1074.

Cecil Textbook of Medicine (21st Ed. 2000), vol. 2, pp. 1492-1499, 2042-2047, 2079-2081.

Choi et al., "Heme oxygenase-1: Function, regulation, and implication of a novel stress-inducible protein in oxidant-induced lung injury," American Journal of Respiratory Cell and Molecular Biology (1996), vol. 15, No. 1, 9-19.

Christodoulides et al., "Vascular Smooth Muscle Cell Heme Oxygenases Generate Guanylyl Cyclase-Stimulatory Carbon Monoxide," Circulation 97:2306-9, 1995.

Corbett et al., "Nitric oxide mediates cytokine-induced inhibition of insulin secretion by human islets of Langerhans," Proc. Natl. Acad. Sci USA 90:1731-5, 1993.

Friebe et al., "YC-1 Potentiates Nitric Oxide- and Carbon Monoxide-Induced Cyclic GMP Effects in Human Platelets," Molecular Pharmacology 54(6)962-967, 1998.

Gaine et al., "Induction of heme oxygenase-1 with hemoglobin depresses vasoreactivity in rat aorta," Vasc Res Mar.-Apr. 1999; 36(2):114-9.

Grau et al., "Effect of carbon monoxide breathing on hypoxia and radiation response in the SCCVII tumor in vivo," Int J Radiat Oncol Biol Phys Jun. 15, 1999; 29(3):449-54.

Grau et al., "Influence of Carboxyhemoglobin Level on Tumor Growth, Blood Flow, and Radiation Response in an Experimental Model," Int. J. Radiation Oncology Biol. Phys. 22:421-424, 1992.

Hantson et al., "Organ transplantation from victims of carbon monoxide poisoning," Ann Emerg Med May 1996; 27(5):673-4.

Hebert et al., "Transplantation of kidneys from a donor with carbon monoxide poisoning," New Engl J Med Jun. 4, 1992; 326(23):1571.

Iberer et al., "Cardiac allograft harvesting after carbon monoxide poisoning. Report of a successful orthotopic heart transplantation," J Heart Lung Transplant May-Jun. 1993; 12(3):499-500.

Kaufman et al., "Differential Roles of Mac-1.sup.+ Cells, and CD4.sup.+ and CD8.sup.+ T Lymphocytes in Primary Nonfunction and Classic Rejection of Islet Allografts," J Exp Med. 772:291-302, 1990.

Koerner et al., "Extended donor criteria: use of cardiac allografts after carbon monoxide poisoning," Transplantation May 15, 1997; 63(9):1358-60.

Lacy et al., "Transplantation of Pancreatic Islets," Annu. Rev. Immunol., 2:183-98, 1984.

Lefer et al., "A comparison of vascular biological actions of carbon-monoxide and nitric-oxide," Methods and Findings in Experimental and Clinical Pharmacology (1993), vol. 15, No. 9, 617-622.

Leikin et al., "The toxic patient as a potential organ donor," Am J Emerg Med Mar. 1994; 12(2):151-4.

Mandrup-Poulsen et al., "Human Tumor Necrosis Factor Potentiates Human Interleukin 1-Mediated Rat Pancreatic beta-Cell Cytotoxicity," J. Immunol. 739:4077-82, 1987.

Mansouri et al., "Alteration of Platelet Aggregation by Cigarette Smoke and Carbon Monoxide," Thromb Haemost. 48:286-8, 1982.

The Merck Manual (16th ed. 1992), pp. 646-657.

Nagata et al., "Destruction of Islet Isografts by Severe Nonspecific Inflammation," Transplant Proc. 22:855-6, 1990.

The New Encyclopedia Britannica (15th ed. 1994), vol. 26, Macropaedia, p. 756.

Otterbein et al., "Carbon Monoxide has Anti-Inflammatory Effects Involving the Mitogen-Activated Protein Kinase Pathway," Nature Medicine 6(4):422-428, 2000.

Otterbein et al., "Carbon Monoxide Provides Protection Against Hyperoxic Lung Injury," The American Physiological Society, L688-L694, 1999.

Petrache et al., "Heme oxygenase-1 inhibits TNF-.alpha.- induced apoptosis in cultured fibroblasts," Am. J. Physiol. Lung Cell Mol. Physiol. 287: L312-L319, 2000.

Pozzoli et al., "Carbon Monoxide as a Novel Neuroendocrine Modulator: Inhibition of Stimulated Corticotropin-Releasing Hormone Release from Acute Rat Hypothalamic Explants," Endocrinology 735:2314-2317, 1994.

Rabinovitch et al., "Transfection of Human Pancreatic Islets With an Anti-Apoptotic Gene (bcl-2) Protects beta-Cells From Cytokine-Induced Destruction," Diabetes 48:1223-9, 199.

Ringel et al., "Carbon Monoxide-induced Parkinsonism," J. Neurol. Sci., 1972, 16:245-251.

Roberts et al., "Successful heart transplantation from a victim of carbon monoxide poisoning," Ann Emerg Med Nov. 1995; 26(5):652-5.

Sato et al., "Carbon monoxide generated by heme oxygenase-1 suppresses the rejection of mouse to rat cardiac transplants," J. Immunol. 166: 4185-4194 (2001).

Schipper et al., "Expression of heme oxygenase-1 in the senescent and Alzheimer-diseased brain," Annals of Neurology (1995), vol. 37, No. 6, 758-768.

Shapiro et al., "Islet Transplantation in Seven Patients with Type 1 Diabetes Mellitus Using a Glucocorticoid-Free Immunosuppressive Regimen," N Engl. J. Med., 343:230-8, 2000.

Shennib et al., "Successful transplantation of a lung allograft from a carbon monoxide-poisoning victim," Heart Lung Transplant Jan.-Feb. 1992; 11(1 Pt 1): 68-71.

Siow et al., "Heme oxygenase-carbon monoxide signaling pathway in atherosclerosis: anti-atherogenic actions of bilirubin and carbon monoxide?" Cardiovascular Research 41:385-394, 1999.

Smith et al., "Successful heart transplantation with cardiac allografts exposed to carbon monoxide poisoning," Heart Lung Transplant Jul.-Aug. 1992; 11(4 Pt. 1):698-700.

Soares et al., "Expression of heme oxygenase-1 can determine cardiac xenograft survival," Nat Med. 4:1073-1077, 1998.

Stephens, "Further Observations regarding Carbon Monoxide Gas as an Important Factor in the Causation of Industrial Cancer," The Medical Press and Circular, vol. CXXXVI, No. 4924, 283-288 (1933).

Tenderich et al., "Hemodynamic follow-up of cardiac allografts from poisoned donors," Transplantation Nov. 15, 1998; 66(9): 1163-7.

Tenhunen et al., "The Enzymatic Conversion of Heme to Bilirubin by Microsomal Heme Oxygenase," Proc Natl Acad Sci USA 61:748-755, 1968.

Utz et al., "Carbon Monoxide Relaxes Ileal Smooth Muscle Through Activation of Guanylate Cyclase," Biochem Pharmacol. 47:1195-201, 1991.

Vassalli et al., "Inhibition of hypoxic pulmonary vasoconstriction by carbon monoxide in dogs," Eur. Resp. J. (1998), 12, Suppl. 28, 237s.

Verran et al., "Use of liver allografts from carbon monoxide poisoned cadaveric donors," Transplantation Nov. 27, 1996; 62(10):1514-5.

Weir et al., "Scientific and Political Impediments to Successful Islet Transplantation," Diabetes 46:1247-56, 1997.

Weir et al., "Islet Transplantation as a treatment for diabetes," J. Am. Optom. Assoc. 69:727-32, 2000.

Yuan et al., "Evidence of increased endogenous carbon monoxide production in newborn rat endotoxicosis," Chinese Medical Sciences Journal (1997), vol. 12, No. 4, 212-215.

Brown et al., "In vivo binding of carbon monoxide to cytochrome c oxidase in rat brain," American Physiological Society, pp. 604-610 (1990).

Campbell, "Living At Very High Altitudes," The Lancet 1:370-373 (1930).

Campbell, "The Effect of Carbon Monoxide and Other Agents the Rate of Tumour Growth," J Pathology & Bacteriology 35:379-394 (1932).

Campbell, "Cancer of Skin and Increase in Incidence of Primary Tumours of Lung in Mice Exposed to Dust Obtained from Tarred Roads," Brit. J Exper. Pathol. XV(5):24, 289-294 (1934).

Chapman et al., "Exogenous Carbon Monoxide Attenuates Aeroallergen-induced Eosinophilic Inflammation in Mice," J Respiratory Critical Care Med 159(3):A218 (1999).

Chapman et al., "Carbon Monoxide Attenuates Aeroallergen-induced Inflammation in Mice," Am. J. Physiol. Lung Cell Mol Physiol. 281:L209-L216 (2001).

Davidson et al., "Inflammatory Modulation and Wound Repair" J Investigative Dermatology xi-xii (2003).

Dioum et al., "NPAS2: A Gas-Responsive Transaction Factor," Sciencexpress/www.sciencexpress.org/Nov. 21, 2002/pp. 1-6/10.1126/science.1078456.

Donnelly et al., "Expression of Heme-Oxygenase in Human Airway Primary Epithelial Cells," J Respiratory Critical Care Med 159(3):A218 (1999).

Katori et al., "Heme Oxygenase-1 System in Organ Transplantation," Transplantation 74(7):905-912 (2002).

Maxwell et al., "Studies in Cancer Chemotherapy: XI. The Effect of CO, HCN, and Pituitrin Upon Tumor Growth," Dept. of Cancer Research, Santa Barbara Cottage Hospital, pp. 270-282 (Jan. 30, 1933).

Meilin et al., Effects of carbon monoxide on the brain may be mediated by nitric oxide, J Appl Physiol. 81(3):1078-83 (1996).

Minamino et al., "Targeted expression of heme oxygenase-1 prevents the pulmonary inflammatory and vascular responses to hypoxia," PNAS 98(15):8798-8803 (2001).

Myers, "Cirrhotic cardiomyopathy and liver transplantation," Liver Transpl 6(4 Suppl 1):S44-52 (2000).

Otterbein et al., "Mechanism of hemoglobin-induced protection against endotoxemia in rats: a ferritin-independent pathway," Am J Physiol Lung Cell Mol Physiol 272:L268-275 (1997).

Otterbein et al., "Carbon monoxide provides protection against hyperoxic lung injury in rats," J Respiratory Critical Care Med 159(3):A218 (1999).

Paredi et al., "Increased Carbon Monoxide in Exhaled Air of Cystic Fibrosis Patients," J Respiratory Critical Care Med 159(3):A218 (1999).

Piantadosi et al., "Production of Hydroxyl Radical in the Hippocampus After CO Hypoxia Hypoxia in the Rat," Free Radical Biol. & Med. 22(4):725-732 (1997).
Singhal et al., "Effects of Normobaric Hyperoxia in a Rat Model of Focal Cerebral Ischemia-Reperfusion," J Cerebral Blood Flow & Medicine 22:861-868 (2002).
Tamayo et al., "Carbon monoxide inhibits hypoxic pulmonary vasoconstriction in rats by a cGMP-independent mechanism," Pflugers Arch. 434(6):698-704 (1997).
Taylor, "Anti-TNF Therapy for Rheumatoid Arthritis and Other Inflammatory Diseases," Molecular Biotechnology 19:153-168 (2001).
Tulis et al., "Adenovirus-Mediated Heme Oxygenase-1 Gene Delivery Inhibits Injury-Induced Vascular Neointima Formation," Circulation 104:2710-2715 (2001).
Wang et al., "Resurgence of carbon monoxide: an endogenous gaseous vasorelaxing factor," Can. J. Physiol. Pharmacol. 76:1-15 (1998).
Welty et al., "Hyperoxic Lung Injury is Potentiated by SPC-Promotor Driven Expression of an HO-1 Transgene in Mice," J Respiratory Critical Care Med 159(3):A218 (1999).
Weng et al., "Transpulmonary HO-1 Gene Delivery in Neonatal Mice," J Respiratory Critical Care Med 159(3):A218 (1999).
Carraway et al., "Induction of ferritin and heme oxygenase-1 by endotoxin in the lung," Am. J. Physiol. Lung Cell. Mol. Physiol. 275:L583-92 (1998).
Choi, "Heme Oxygenase-1 Protects the Heart," Circulation Research 89:105-7 (2001).
Clayton et al., "Inhaled carbon monoxide and hyperoxic lung injury in rats," Am. J. Physiol. Lung Cell Mol. Physiol. 281:L949-57 (2001).
Hayes et al., "A Review of Modern Concepts of Healing of Cutaneous Wounds," J. Dermatol. Surg. Oncol. 3(2):188-93 (1977).
Kyokane et al., "Carbon Monoxide From Heme Catabolism Protects Against Hepatobiliary Dysfunction in Endotoxin-Treated Rat Liver," Gastroenterology 120:1227-40 (2001).
Lee et al., "Intestinal Motility and Absorption in Acute Carbon Monoxide Poisoning," Seoul J. Med. 15:95-105 (1974) (and an English translation thereof).
Lee et al., "Regulation of Heme Oxygenase-1 Expression in Vivo and in Vitro in Hyperoxic Lung Injury," Am. J. Respir. Cell Biol. 14:556-568 (1996).
Liu et al., "Carbon monoxide and nitric oxide suppress the hypoxic induction of vascular endothelial growth factor gene via the 5' enhancer," J. Biol. Chem. 273(24):15257-62 (1998).
Nachar at al., "Low-Dose Inhaled Carbon Monoxide Reduces Pulmonary Vascular Resistance During Acute Hypoxemia in Adult Sheep," High Altitude Medicine & Biology 2:377-385 (2001).
Nakao et al., "Immunomodulatory effects of inhaled carbon monoxide on rat syngeneic small bowel graft motility," Gut 52: 1278-85 (2003).
Pannen et al., "Protective Role of Endogenous Carbon Monoxide in Hepatic Microcirculatory Dysfunction after Hemorrhagic Shock in Rats," J. Clin. Invest. 102:1220-1228 (1998).
Peek et al., "Extracorporeal Membrane Oxygenation for Adult Respiratory Failure," Chest 112(3)759-64 (1997).
Ringel et al., "Carbon Monoxide-induced Parkinsonism," J. neurol. Sci. 16:245-251 (1972).
Zuckerbraun et al., "Carbon monoxide attenuated the development of necrotizing enterocolitis in an animal model," Surgical Infection Society 3:83 (2002).
Sato et al., "Carbon monoxide can fully substitute Heme Oxygenase-1 in suppressing the rejection of mouse to rat cardiac transplants," Acta Haematologica, 103 (Suppl. 1):87, Abstract 348 (2000).
Sato et al., "Heme oxygenase-1 or carbon monoxide prevents the inflammatory response associated with xenograft rejection," Acta Haematologica, 103 (Suppl. 1):87, Abstract 345 (2000).
Toda et al., "Exogenous carbon monoxide protects endothelial cells against oxidant stress and improves graft function after lung transplantation," Circulation, 98(17):I265 (1998).
Bach, "Heme oxygenase-1 as a protective gene," Wien. Klin. Wochenschr. 114(Suppl):4:1-3 (2002).
Billiar, "The diverging roles of carbon monoxide and nitric oxide in resuscitated hemorrhagic shock," Crit. Care Med. 27:2842-3 (1999).
Bracho et al., "Carbon Monoxide Protects against Organ Injury in Hemorrhagic Shock/Resuscitation," Journal of Surgical Research, 107:270, (2002), Abstract.
Brouard et al., "Carbon monoxide generated by Heme Oxygenase-1 (HO-1) suppresses endothelial cell apoptosis via activation of the p38 mitogen activated protein kinase (MAPK) pathway," Acta Haematologica 103(Suppl 1):64, (2000), Abstract.
Brouard et al., "Heme oxygenase-1-derived carbon monoxide requires the activation of transcription factor NF-kappa B to protect endothelial cells from tumor necrosis factor-alpha-mediated apoptosis," J. Biol. Chem., 277(20):17950-17961, (2002).
Brouard et al., "Molecular mechanism underlying the anti-apoptotic effect of Heme oxygenase-1 derived carbon monoxide," Xenotransplantation, 8(Suppl 1): p. 22 (2001).
Calabrese et al., "Carbon Monoxide (CO) Prevents Apoptotic Events Related to Ischemia/Reperfusion (IR) Injury in an hDAF Pig-to-Primate Xenotransplantion Model," Xenotransplantation 10.488, (2003), Abstract.
Carbon Monoxide Poisoning—Symptoms; http://my.webmd.com/hw/home.sub.-health/aa7304.asp;retrieved Jul. 11, 2005.
Carbon Monoxide Poisoning—What Happens; http://my.webmd.com/hw/home.sub.-health/aa7326.aps;retrieved Jul. 11, 2005.
Chapman and Choi, "Exhaled monoxides as a pulmonary function test: use of exhaled nitric oxide. and carbon monoxide," Clin. Chest Med. 22:817-836 (2001).
Chin et al., "Transcriptional regulation of the HO-1 gene in cultured macrophages exposed to model airborne particulate matter," Am. J. Physiol. Lung Cell. Mol. Physiol., 284(3):L473-L480, (2003).
Choi and Otterbein, "Emerging role of carbon monoxide in physiologic and pathophysiologic states," Antioxid. Redox Signal. 4:227-228 (2002).
Cozzi et al., "Donor Preconditioning with Carbon Monoxide (CO) in Pig-to-Primate Xenotransplantation," Xenotransplantation 10:528, (2003), Abstract.
Crapo et al., "Single-breath carbon monoxide diffusing capacity," Clin. Chest Med., 22:637-649, (2001).
Deng et al., "Carbon Monoxide Potentiates Cerulein-Induced Pancreatitis in Chronic Alcohol-Fed Rats," Gastroenterology, 124(4):A618-19, (2003), Abstract.
Dyck et al., "Carbon Monoxide (CO) Attenuates Lipopolysaccharide (LPS)-Induced Cytokine Expression of IL-6," Acta Haematologica 103(Suppl 1):64, (2000), Abstract.
Farrugia and Szurszewski, "Heme oxygenase, carbon monoxide, and interstitial cells of Cajal," Microsc. Res. Tech. 47:321-4, (1999).
Gunther et al., "Carbon monoxide protects pancreatic beta-cells from apoptosis and improves islet function/survival after transplantation," Diabetes, 51(4):994-999, (2002).
Hartsfield and Choi, "Mitogen activated protein kinase (MAPK) is modulated by both endogenous and exogenous carbon monoxide," FASEB Journal 12:A187, 1088, (1998), Abstract.
Hartsfield et al., "Differential signaling pathways of HO-1 gene expression in pulmonary and systemic vascular cells," Am. J. Physiol., 277(6 Pt 1):L1133-L1141, (1999).
Hartsfield et al., "Regulation of heme oxygenase-1 gene expression in vascular smooth muscle cells by nitric oxide," Am. J. Physiol., 273(5Pt 1):L980-988, (1997).
Hartsfield, "Targeted Overexpression of Heme Oxygenase-1 (HO-1) Attenuates Hypoxia-Induced Right Ventricular Hypertrophy," FASEB Journal 13:A827, (1999), Abstract.
Horvath et al., "Haemoxygenase-1 induction and exhaled markers of oxidative stress in lung diseases', summary of the ERS Research Seminar in Budapest, Hungary, Sep. 1999," Eur. Respir. J., 18(2):420-430, (2001).
Huizinga Jan D., "Physiology and Pathophysiology of the Interstitial Cell of Cajal: From Bench to Bedside: II. Gastric motility: lessons from mutant mice on slow waves and innervation," Am. J. Physiol. 281:1129-1134, (2001).
Kozma et al., "Role of carbon monoxide in heme-induced vasodilation," Eur. J. Pharmacol., 323:R1-2 (1997).

Moore et al., "Carbon Monoxide Protects against Intestinal Dysmotility Associated with Small Bowel Transplantation," Gastroenterology 122:A38, (2002), Abstract.
Moore et al., "Carbon Monoxide Suppresses the Development of Ileus Associated with Surgical Manipulation of the Small Intestine," Gastroenterology 122:A61-A62, (2002), Abstract.
Moore et al., "Pre-treatment with Low Concentration of Carbon Monoxide (250 to 75 ppm) for 3 hr prior to Laparotomy Protects Against Postoperative Ileus," Digestive Disease Week Abstracts and Intinerary Planner 2003: Abstract No. M1337 (2003).
Morse et al., "Carbon monoxide-dependent signaling," Crit. Care Med., 30:S12-S17, (2001).
Morse et al., "Suppression of inflammatory cytokine production by carbon monoxide involves the JNK pathway and AP-1," J. Biol. Chem., 278(39):36993-36998, (2003).
Nakao et al., "Protective effect of carbon monoxide inhalation for cold-preserved small intestinal grafts," Surgery, 134:285-92, (2003).
Ning et al., "TGF-beta1 stimulates HO-1 via the p38 mitogen-activated protein kinase in A549 pulmonary epithelial cells," Am. J. Physiol. Lung Cell. Mol. Physiol., 283(5):L1094-L1102, (2002).
Otterbein et al., "Carbon Monoxide suppresses arteriosclerotic lesions associated with chronic graft rejection and with balloon injury," Nature Medicine 9:183-90 (2003).
Otterbein et al., "Carbon monoxide at low concentrations induces growth arrest and modulates tumor growth in mice," Exp. Biol. Med., 228(5):633, (2003), Abstract.
Otterbein et al., "Carbon Monoxide Inhibits TNF.alpha.-Induced Apoptosis and Cell Growth in Mouse Fibroblasts," American Journal of Respiratory and Critical Care Medicine 159(3 Suppl.):A285 (1999).
Otterbein et al., "Carbon Monoxide Modulates Lipolysaccaride (LPS)-Induced Inflammatory Responses in vivo and in vitro," American Journal of Respiratory and Critical Care Medicine 159(3 Suppl.):A481 (1999).
Otterbein et al., "Carbon Monoxide, A Gaseous Molecule with Anti-Inflammatory Properties," pp. 133-156 in Disease Markers in Exhaled Breath, Marczin et al., eds., Marcel Dekker, Inc., New York, (2003).
Otterbein et al., "Carbon Monoxide Mediates Anti-Inflammatory Effects Via the P38 Mitogen Activated Protein Kinase Pathway," Acta Haematologica 103:64, (2000), Abstract.
Otterbein et al., "Carbon Monoxide Protects Against Oxidant-Induced Lung Injury in Mice Via the p38 Mitogen Activated Protein Kinase Pathway," Acta Haematologica 103:83, (2000), Abstract.
Otterbein et al., "Exogenous administration of heme oxygenase-1 by gene transfer provides protection against hyperoxia-induced lung injury," J. Clin. Invest., 103(7):1047-1054, (1999).
Otterbein et al., "Heme oxygenase: colors of defense against cellular stress," Am. J. Physiol. Lung Cell Mol. Physiol., 279(6):L1029-L1037, (2000).
Otterbein et al., "Protective effects of heme oxygenase-1 in acute lung injury," Chest. 116:61S-63S, (1999).
Otterbein, "Anti-Inflammatory Effects of Carbon Monoxide in the Lung," CRISP Data Base National Institute of Health; (2003).
Otterbein, "Carbon monoxide: innovative anti-inflammatory properties of an age-old gas molecule," Antioxid. Redox Signal., 4:309-319, (2002).
Pileggi et al., "Heme oxygenase-1 induction in islet cells results in protection from apoptosis and improved in vivo function after transplantation," Diabetes, 50(9):1983-1991, (2001).
Ryter and Choi, "Heme Oxygenase-1: Molecular Mechanisms of Gene Expression in Oxygen-Related Stress," Antioxid. Redox Signal. 4:625-632, (2002).
Ryter et al., "Heme oxygenase/carbon monoxide signaling pathways: Regulation and functional significance," Mol. Cell. Biochem., 234-235(1-2):249-263, (2002.
Ryter et al., "Mitogen Activated Protein Kinase (MAPK) Pathway Regulates Heme Oxygenase-1 Gene Expression by Hypoxia in Vascular Cells," Exp. Biol. Med., 225(5):607, (2003), Abstract.
Sarady et al., "Carbon monoxide modulates endotoxin-induced production of granulocyte macrophage colony-stimulating factor in macrophages," Am. J. Respir. Cell. Mol. Biol., 27(6):739-745, (2002).

Sarady et al., "Cytoprotection by heme oxygenase/CO in the lung," in Disease Markers in Exhaled Breath, Marczin and Yacoub, eds., IOS Press, 346:73-78, (2002).
Sasidhar et al., "Exogenous Carbon Monoxide Attenuates Mitogen Activated Protein Kinase (MAPK) Activation in Rat Pulmonary Artery Endothelial Cells Exposed to Hypoxia," American Journal of Respiratory and Critical Care Medicine. 1999;159(3 Suppl.):A352.
Sass et al., "Heme Oxygenase-1 Induction Prevents Apoptotic Liver Damage in Mice," Naunyn-Schmiedelberg's Archives of Pharmacology 367:R78, (2003).
Sethi et al, "Differential modulation by exogenous carbon monoxide of TNF-alpha stimulated mitogen-activated protein kinases in rat pulmonary artery endothelial cells," Antioxid. Redox Signal., 4:241-8, (2002).
Sethi et al., "Differential Effects of Exogenous Carbon Monoxide on TNF-alpha-Induced Mitogen Activated Protein (MAP) Kinase Signaling Pathway in Rat Pulmonary Artery Endothelial Cells," American Journal of Respiratory and Critical Care Medicine 159(3 Suppl.):A350 (1999).
Seyfried et al., "HO-1 induction protects mice from Immune-mediated liver injury," Naunyn-Schmiedeberg's Archives of Pharmacology 367:R80 (2003).
Slebos et al., "Heme oxygenase-1 and carbon monoxide in pulmonary medicine," Respir Res. 4(7):1-13, (2003).
Soares et al., "Heme oxygenase-1, a protective gene that prevents the rejection of transplanted organs," Immunol. Rev. 184:275-285, (2001).
Soares et al., "Modulation of endothelial cell apoptosis by heme oxygenase-1-derived carbon monoxide," Antioxid. Redox Signal., 4:321-329, (2002).
Soares et al., "Heme Oxygenase-1 and/or Carbon Monoxide can Promote Organ Graft Survival," in Disease Markers in Exhaled Breath, Marczin and Yacoub, eds., IOS Press, 346:267-273, (2002).
Song et al., "Carbon monoxide induces cytoprotection in rat orthotopic lung transplantation via anti-inflammatory and anti-apoptotic effects," Am. J. Pathol., 163(1):231-242, (2003).
Song et al., "Carbon monoxide inhibits human airway smooth muscle cell proliferation via mitogen-activated protein kinase pathway," Am. J. Respir. Cell. Mol. Biol. 27(5):603-610, (2002).
Song et al., "Regulation of IL-1beta-induced GM-CSF production in human airway smooth muscle cells by carbon monoxide," Am. J. Physiol. Lung Cell. Mol. Physiol., 284(1):L50-L56, (2003).
Stupfel and Bouley, "Physiological and Biochemical Effects on Rats and Mice Exposed to Small Concentrations of Carbon Monoxide for Long Periods," Ann. N.Y. Acad. Sci. 174:343-368 (1970).
Tobiasch et al., "Heme oxygenase-1 protects pancreatic beta cells from apoptosis caused by various stimuli," J. Investig. Med., 49:566-71, (2001).
Yamashita et al., "Effects of HO-1 induction and carbon monoxide on cardiac transplantation in mice," Exp. Biol. Med., 228(5):616, (2003), Abstract.
Zhang et al., "Carbon monoxide inhibition of apoptosis during ischemia-reperfusion lung injury is dependent on the p38 mitogen-activated protein kinase pathway and involves caspase 3," J. Biol. Chem., 278:(2):1248-1258, (2003).
Zhang et al., "Mitogen-activated protein kinases regulate HO-1 gene transcription after ischemia-reperfusion lung injury," Am. J. Physiol. Lung Cell. Mol. Physiol., 283(4):L815-L829, (2002).
Zhou et al., "Endogenous carbon monoxide and acute lung injury," Section of Respiratory System Foreign Medical Sciences 19:185-187 (1999) (and a translation thereof).
Zuckerbraun and Billiar, "Heme oxygenase-1: a cellular Hercules" Hepatology, 37(4):742-744, (2003).
Zuckerbraun et al., "Carbon monoxide inhibits intestinal inducible nitric oxide synthase production and ameliorates intestinal inflammation in experimental NEC," J. Amer. College of Surgeons 197:S50 (2003).
Zuckerbraun et al., "Carbon Monoxide Protects Hepatocytes TNF-alpha/Actinomycin D Induced Cell Death," Critical Care Medicine 29:A59 (2001).
Choi et al., "Therapeutic carbon monoxide may be a reality soon," Am. J. Respir. Crit. Care Med., 171(11):1318-1319, (2005).

Dolinay et al., "Inhaled carbon monoxide confers antiinflammatory effects against ventilator-induced lung injury," Am. J. Respir. Crit. Care Med. 170:613-620 (2004).

Ryter et al., "Heme oxygenase-1/carbon monoxide: from basic to therapeutic applications," Physiol. Rev. 86(2):583-650 (2006).

Favory et al., "Myocardial Dysfunction and Potential Cardiac Hypoxia in Rats Induced by Carbon Monoxide Inhalation," Am. J. Respir. Crit. Care Med. 174:320-325 (2006).

Mazzola et al., "Carbon monoxide pretreatment prevents respiratory derangement and ameliorates hyperacute endotoxic shock in pigs," FASEB J. 19:2045-2047 (2005).

American Thoracic Society, "Single breath carbon monoxide diffusing capacity (transfer factor): recommendations for a standard technique," Am. Rev. Respir. Dis. 136: 1299-1307 (1987).

American Thoracic Society, "Single breath carbon monoxide diffusing capacity (transfer factor): recommendations for a standard technique—1995 update," Am. J. Respir. Crit. Care. Med. 152: 2185-2198 (1995).

Arcasoy et al., "Erythropoietin (EPO) Stimulates Angiogenesis in Vivo and Promotes Wound Healing," Blood 98: 822A-823A, Abstract (2001).

Caplan et al., "Role of asphyxia and feeding in a neonatal rat model of necrotizing enterocolitis," Pediatr. Pathol., 14: 1017-1028 (1994).

Czlonkowska et al., "Immune processes in the pathogenesis of Parkinson's disease—a potential role for microglia and nitric oxide," Med. Sci. Monit. 8:RA165-RA177 (2002).

Goldberg and Schneider, "Similarities between the oxygen-sensing mechanisms regulating the expression of vascular endothelial growth factor and erythropoietin," J. Biol. Chem. 269: 4355-359 (1994).

Guo, "The Research Status of the Gas Messanger Molecules of Nitric Oxide and Carbon Monoxide in the Biomedicine Field," Practical Journal of Cardiac, Cerebral and Pulmonary Vascular Diseases vol. 8(2) (2000) (and an English translation thereof).

Harmey and Bouchier-Hayes, "Vascular endothelial growth factor factor (VEGF), a survival factor for tumour cells: implications for anti-angiogenic therapy," Bioessays 24: 280-83 (2003).

Josko, "Vascular endothelial growth factor (VEGF) and its effect on angiogenesis," Medical Science Monitor 6: 1047-52 (2000).

Krause et al., "Recombinant human erythropoietin and VEGF have equal angiogenic potency: Investigation in a novel in vitro assay of human vascular tissues," European Heart J. 22: 154 Abstract (2001).

Omaye, "Metabolic modulation of carbon monoxide toxicity," Toxicol. 180:139-150 (2002).

Potter et al., "The inflammation-induced pathological chaperones ACT and apo-E are necessary catalysts of Alzheimer amyloid formation," Neurobiology of Aging 22:923-30 (2001).

Shahin et al., "Carboxyhemoglobin in pediatric sepsis and the systematic inflammatory response syndrone," Clinical Intensive Care 11(6): 311-17 (2000).

Stewart, "The effect of carbon monoxide on humans," J. Occup. Med. 18: 304-309 (1976).

Stewart, "The effects of low concentrations of carbon monoxide in man," Scand. J. redpir. Dis. Suppl. 91: 56-62 (1974).

Thiemermann "Inhaled Co: deadline gas or novel therapeutic?" Nature Medicine 7(5): 534-35 (2001).

Vreman et al., "Carbon monoxide and carboxyhemoglobin," Adv. Pediatr. 42: 303-34 (1995).

Wright and Shephard, "Physiological effects of carbon monoxide," Int. Rev. Physiol. 20: 311-68 (1979).

Zegdi et al., "Increased endogenous CO production in severe sepsis," Intensive Care Medicine 23: 793-96 (2002).

Zuckerbraun et al., "Carbon Monoxide protects against Liver Failure through Nitric Oxide-induced Heme Oxygenase 1," J. Exp. Med. 198: 1707-716 (2003).

Jul. 24, 2009 Official Action issued in connection with Canadian Patent Application No. 2,266,640.

Aug. 6, 2009 Official Action issued in connection with European Patent Application No. 07006886.1.

Nov. 10, 2009 Official Action issued in connection with Japanese Patent Application No. 1998-515905 in Japanese language and English language translation thereof.

* cited by examiner

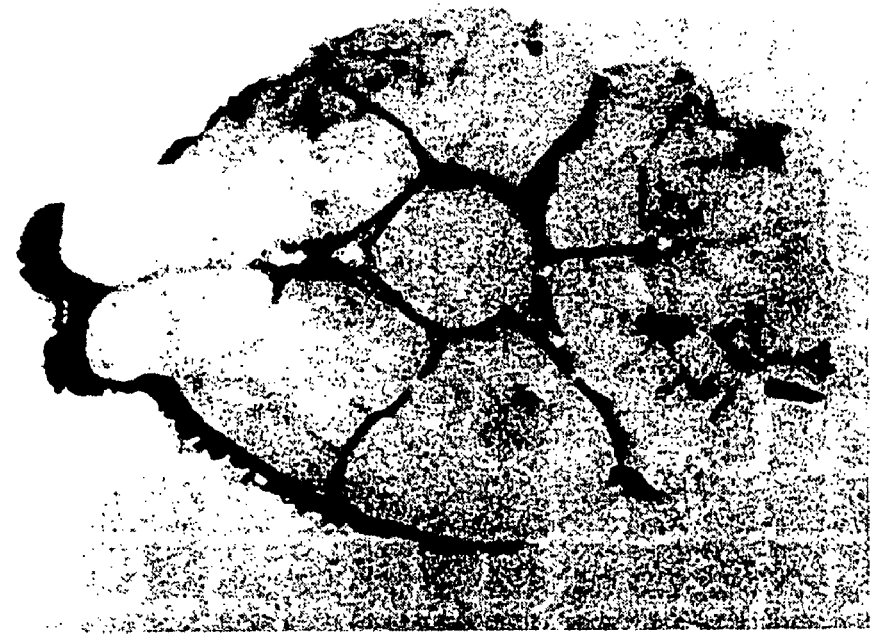
FIGURE 5B  ICAM-1 (−/−)
FIGURE 5A  Wild Type

Wild Type

ICAM-1 (−/−)

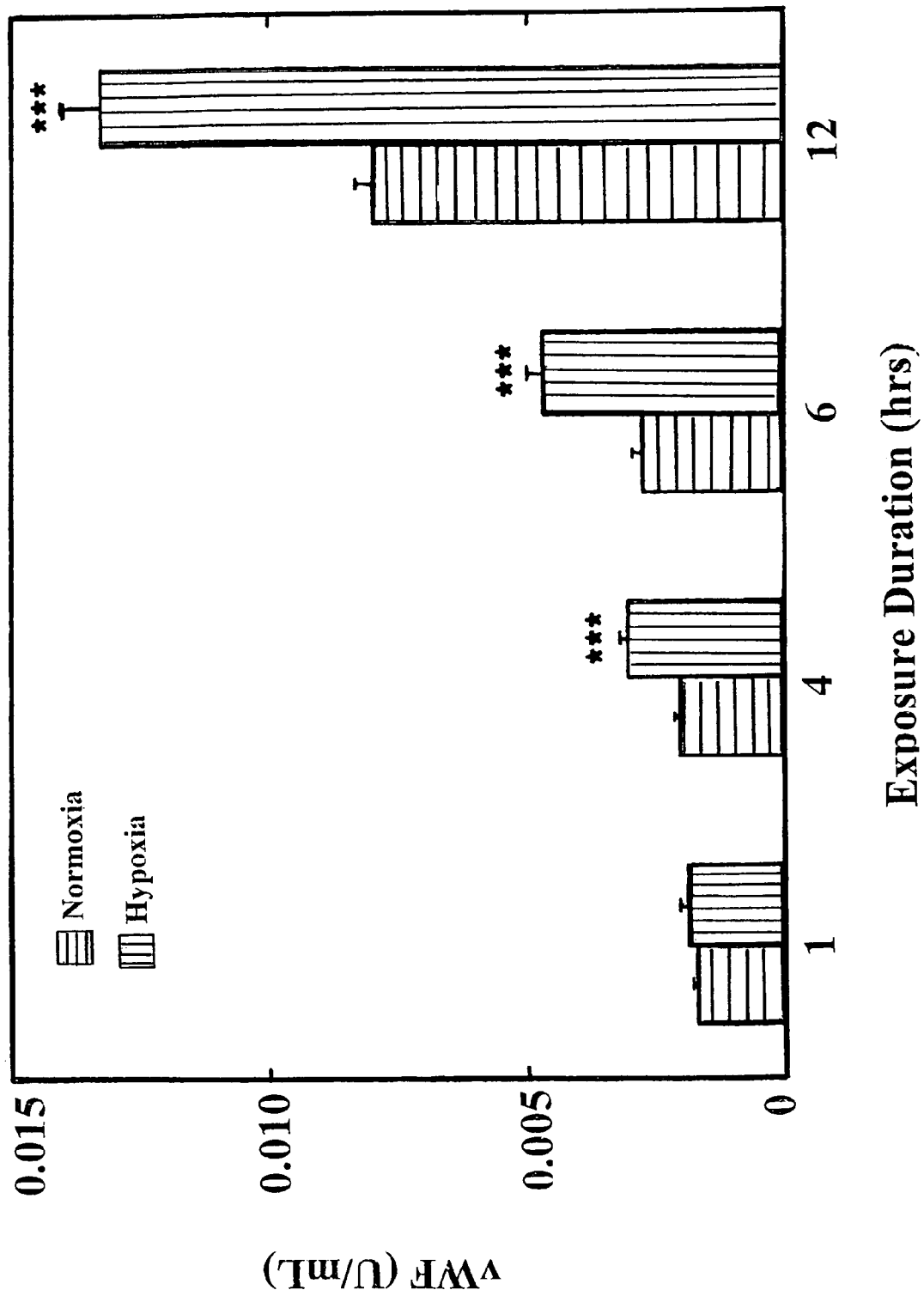

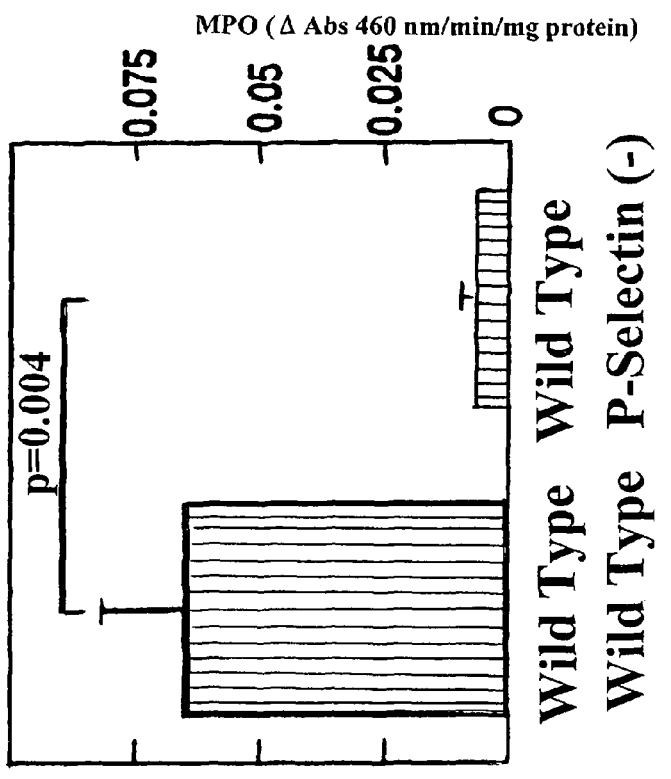
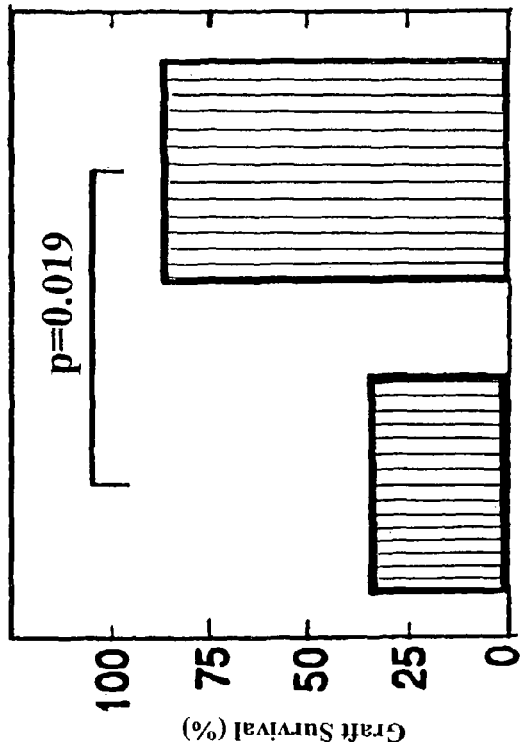
FIGURE 10B  FIGURE 10C

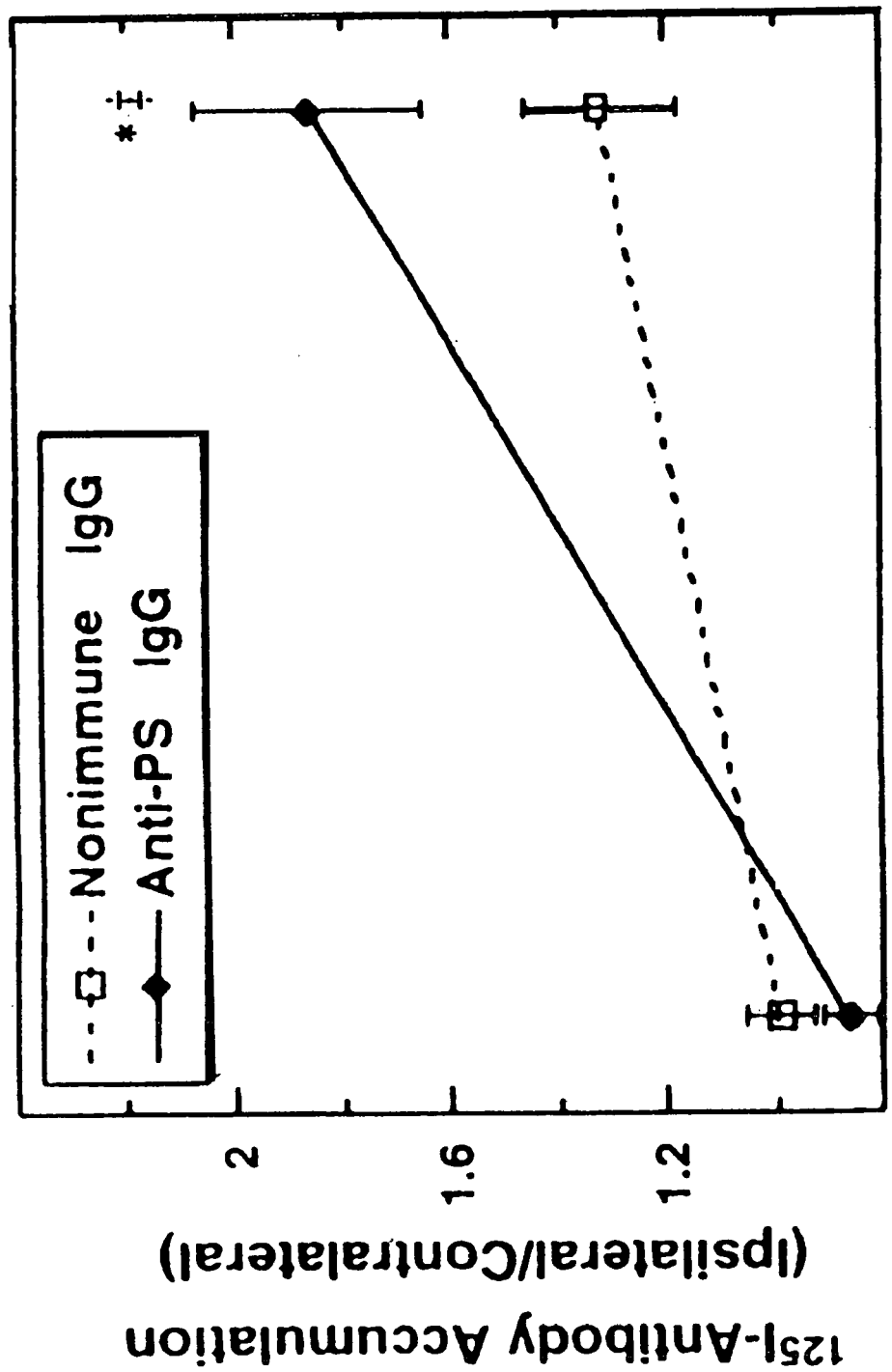

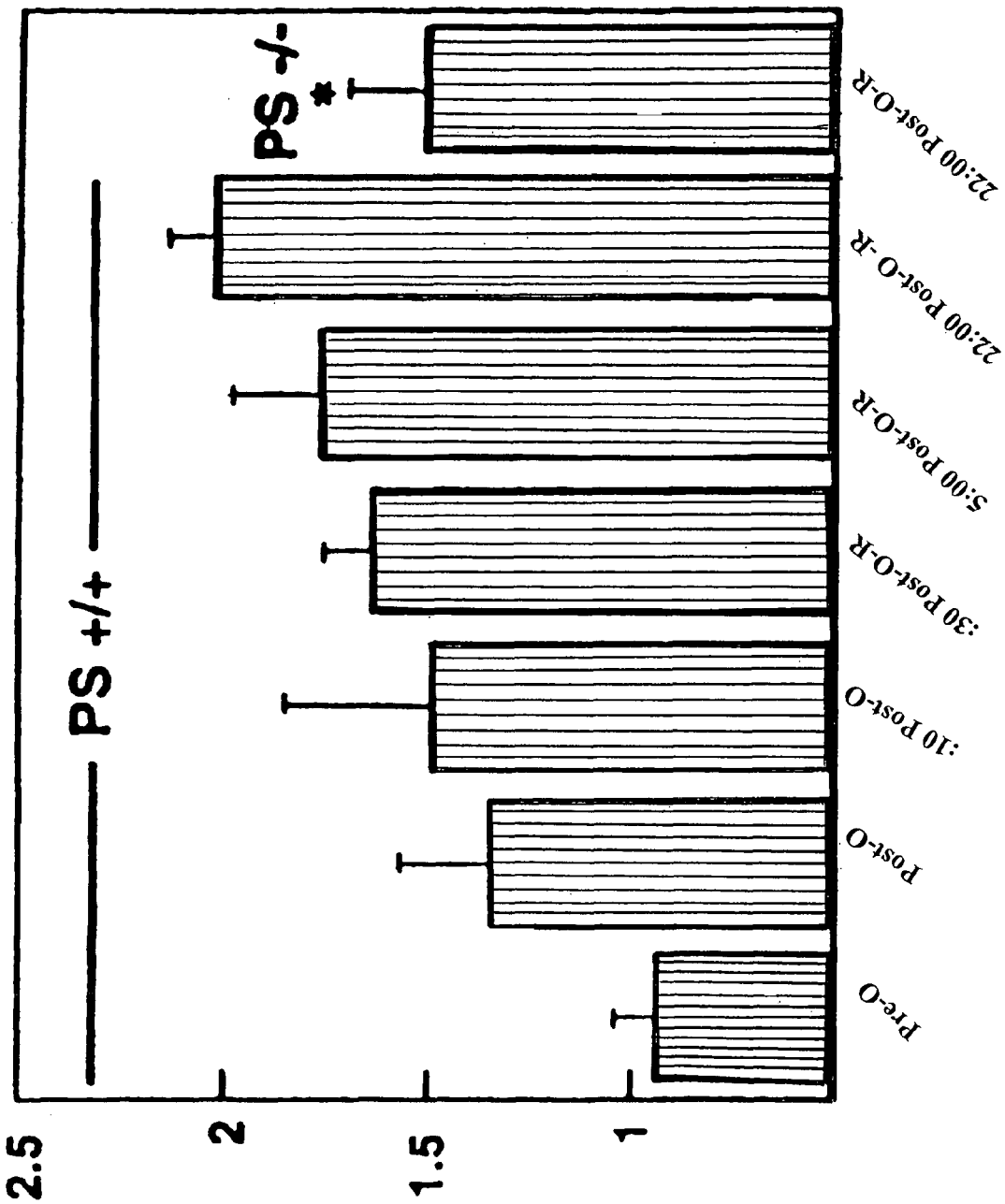

**p = 0.02

**p = 0.02

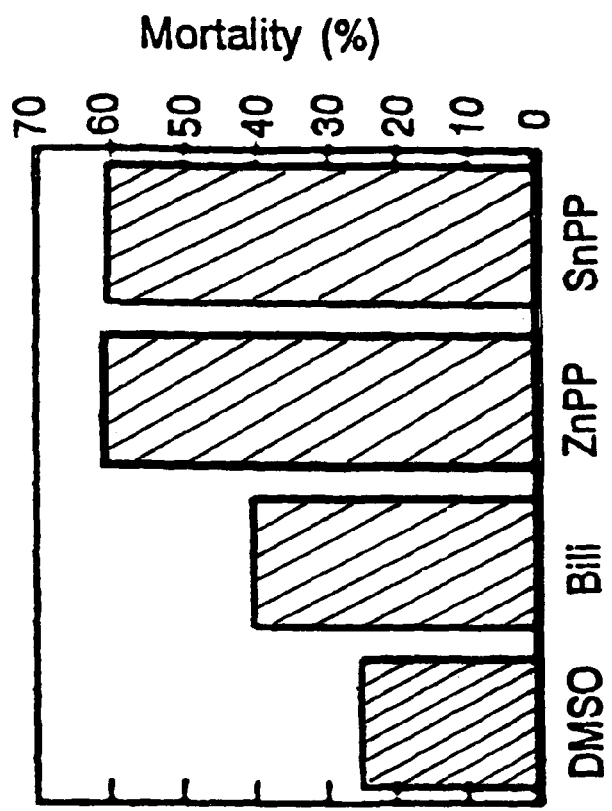
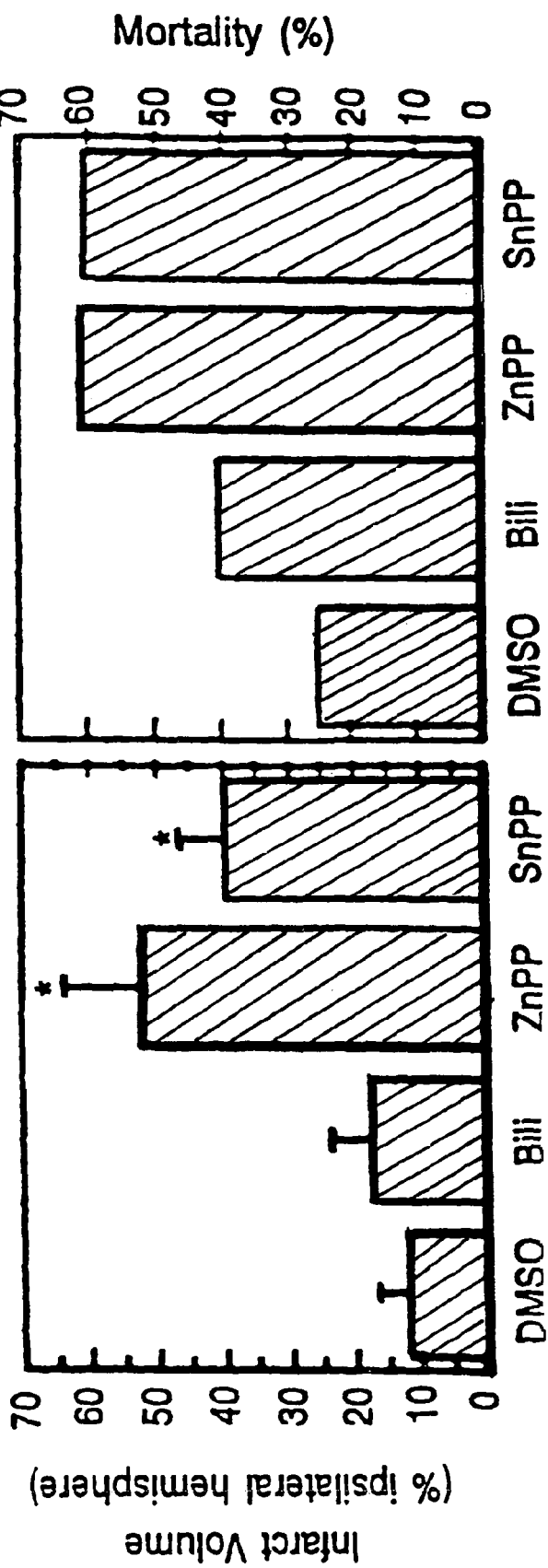
FIGURE 24C
FIGURE 24B

Effect of Inhaled CO Pretreatment on Cerebral Infarction Volume

Control     CO

FIGURE 26A  FIGURE 26B  FIGURE 26C
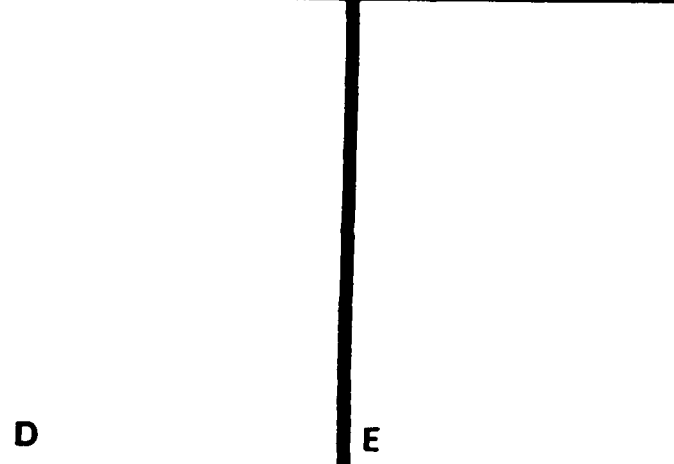
FIGURE 26D  FIGURE 26E  FIGURE 26F Effect of Cerebral Ischemia on Induction of HO-I Effect of Hypoxia on Cerebral HO Induction In Vivo Hypoxia-Induced Expression of HO-I Antigen in Murine Brain Endothelial Cells Effect of Hypoxia on HO-I mRNA Induction in Murine Brain Endothelial Cells

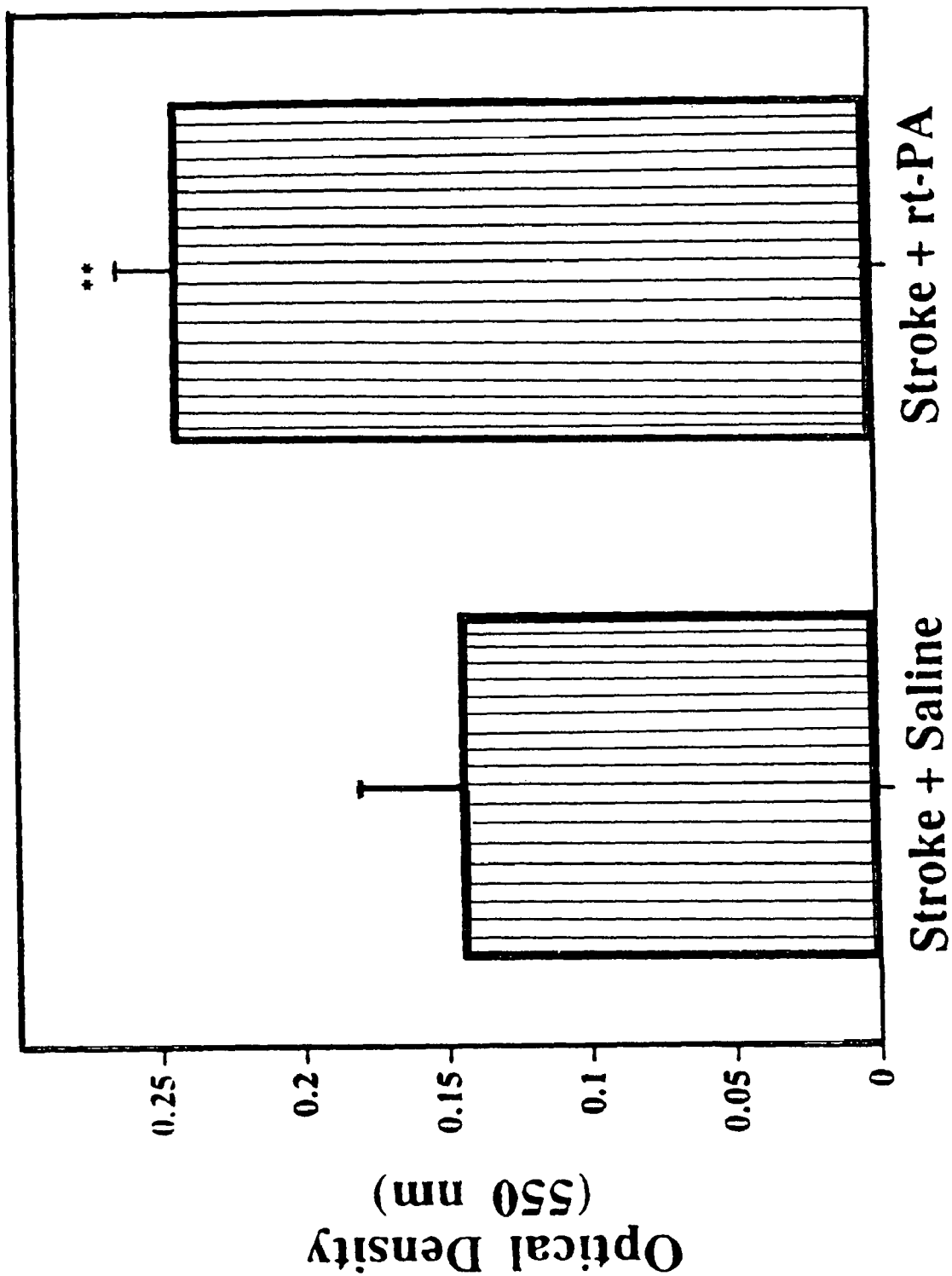

FIGURE 37
0
1
2
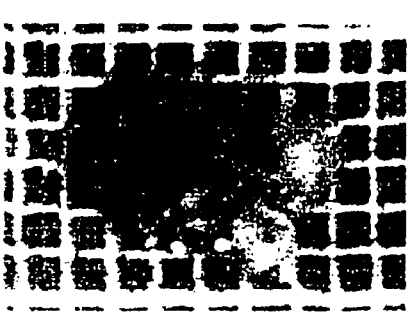
3
4

METHODS FOR TREATING ISCHEMIC DISORDERS USING CARBON MONOXIDE

This application is a continuation-in-part of U.S. Ser. No. 09/671,100, filed Sep. 27, 2000, now abandoned, which is a continuation of PCT International Application No. PCT/US99/07175, filed Apr. 1, 1999.

Throughout this application, various publications are referenced. The disclosures of these publications in their entireties are hereby incorporated by reference into this application in order to more fully describe the state of the art as known to those skilled therein as of the date of the invention described and claimed herein.

The invention disclosed herein was made with Government support under National Institutes of Health, National Heart, Lung and Blood Institute award HL55397 of the Department of Health and Human Services. Accordingly, the U.S. Government has certain rights in this invention.

BACKGROUND OF THE INVENTION

Treatment of ischemic disorders has been the focus of research for many years. The recent availability of transgenic mice has led to a burgeoning number of reports describing the effects of specific gene products on the pathophysiology of stroke. Although focal cerebral ischemia models in rats have been well-described, descriptions of a murine model of middle cerebral artery occlusion are scant, and sources of potential experimental variability remain undefined.

Acute neutrophil recruitment to postischemic cardiac or pulmonary tissue has deleterious effects in the early reperfusion period, but the mechanisms and effects of neutrophil influx in the pathogenesis of evolving stroke remains controversial.

SUMMARY OF THE INVENTION

The present invention provides for a method for treating an ischemic disorder in a subject which comprises administering to the subject a pharmaceutically acceptable form of a selectin antagonist in a sufficient amount over a sufficient time period to prevent white blood cell accumulation so as to treat the ischemic disorder in the subject. The invention further provides a method for treating an ischemic disorder in a subject which comprises administering to the subject carbon monoxide gas in a sufficient amount over a sufficient period of time thereby treating the ischemic disorder in the subject. The invention further provides a method for treating an ischemic disorder in a subject which comprises administering to the subject a pharmaceutically acceptable form of inactivated Factor IX in a sufficient amount over a sufficient period of time to inhibit coagulation so as to treat the ischemic disorder in the subject.

BRIEF DESCRIPTION OF THE DRAWINGS

FIG. 2A. Infarct volumes, calculated based on TTC stained serial cerebral sections, and expressed as the % ipsilateral hemispheric volume. FIG. 2B. Neurologic deficit score graded prior to anesthesia 24 hours following transient middle cerebral artery occlusion; 4 represents the most severe neurologic deficit. FIG. 2C. Cerebral blood flow, measured by laser doppler flow measurements 2 mm posterior to the bregma, expressed as % contralateral hemispheric blood flow. FIG. 2D. Mortality at 24 hours following transient middle cerebral artery occlusion. (*=p<0.05, =p<0.01, *=p<0.001).

FIG. 4A. Cerebral microvessel in the contralateral (noninfarcted) section of a brain obtained 24 hours after middle cerebral artery occlusion. FIG. 4B. Cerebral microvessel from the ipsilateral (infarcted) hemisphere from the same section of brain as shown in FIG. 4A. Endothelial cells from ipsilateral cerebral microvessels demonstrate increased expression of ICAM-1 (bright red staining). Magnification 250×.

FIGS. 5A and 5B. Cerebrovascular anatomy in homozygous null ICAM-1 mice (FIG. 5B) and wild type controls (FIG. 5A). India ink staining of cerebrovascular anatomy with an inferior view of the Circle of Willis demonstrates that there were no gross anatomic differences in the vascular pattern of the cerebral circulation, with intact posterior communicating arteries in both.

FIG. 7A. Effect of ICAM-1 on infarct volume, FIG. 7B. neurologic deficit score, FIG. 7C. cerebral blood flow, and FIG. 7D. mortality. (*=p<0.05, **=p<0.01).

FIGS. 8A and 8B. Effect of hypoxia on Weibel-Palade body exocytosis. FIG. 8A. Human umbilical veins were exposed to hypoxia (pO$_2$ 15-20 Torr) or normoxia for the indicated durations, and vonWillebrand factor (vWF) secretion quantified by ELISA. ***=p<0.001 for hypoxia vs normoxia. FIG. 8B. Similar experiments were performed for 8 hrs in the presence of 2 mM $Ca^{++}$ ($Ca^{++}$ 2 mM), 0 mM $Ca^{++}$ ($Ca^{++}$-free), or 0 mM $Ca^{++}$ with 2 mM EGTA added to chelate residual extracellular $Ca^{++}$ ($Ca^{++}$-free+EGTA)'.

FIG. 9A. P-selectin expression on HUVECs exposed to normoxia or hypoxia, determined by specific binding of radiolabelled monoclonal anti-P-selectin IgG (WAPS12.2 clone). Data are expressed as relative binding compared with the 4 hr normoxic time point. FIG. 9B. Effect of inhibiting protein synthesis on hypoxia-induced. P-selectin expression. In a separate experiment, the effect of cyloheximide (10 μg/mL, +CHX) added at the start of the 4 hour normoxic or hypoxic period on P-selectin expression is shown. Comparison is made to simultaneous experiments performed in the absence of cyloheximide (−CHX), with data expressed as relative binding compared with normoxic (−CHX) binding. Means±SEM are shown; *=p<0.05 vs normoxia (−CHX); †=p<0.05 vs normoxia (+CHX). Inset: Effect of cyloheximide (10 μg/mL) on protein synthesis at 4 hrs, measured as trichloroacetic acid-precipitable $^{35}$S-labeled proteins following $^{35}$S-methionine and $^{35}$S-cysteine administration. FIG. 9C. $^{111}$Indium-labeled neutrophil binding to normoxic (N) or hypoxic (H) human umbilical vein endothelial monolayers at 4 hrs, in the presence of a blocking anti-P-selectin antibody (WAPS 12.2 clone) or a nonblocking anti-P-selectin antibody (AC1.2 clone). Means±SEM are shown; **=p<0.01.

FIGS. 10A, 10B and 10C. Role of neutrophils and endothelial P-selectin in rodent cardiac preservation followed by heterotopic transplantation. FIG. 10A. Rat cardiac preservation. Hearts were transplanted immediately after harvest (Fresh, n=8) or preserved for 16 hrs in lactated Ringer's solution at 4° C. followed by transplantation (Prsvd, n=4). The effect of administering non-blocking anti-P-selectin antibody (AC1.2, n=3), immunodepleting recipients of neutrophils prior to donor heart implantation (−PMN, n=4), or administering 250 μg of blocking anti-P-selectin IgG (n=4) 10 minutes prior to reperfusion on cardiac graft survival (shaded bars) and leukostasis (myeloperoxidase activity, dark bars). Means±SEM are shown; For graft survival, c vs a, p<0.0001; g vs c, p<0.05; i vs e or c, p<0.05. For graft neutrophil infiltration, d vs b, p<0.01; h vs d, p<0.05; j vs d or f, p<0.05. FIG. 10B. Role of coronary endothelial P-selectin in cardiac preservation, using donor hearts from P-selectin null (or wild type control) mice that were flushed free of blood prior to preservation. Graft survival was assessed by the presence/absence of cardiac electrical/mechanical activity exactly ten minutes following reestablishment of blood flow. FIG. 10C: Quantification of neutrophil infiltration by measurement of myeloperoxidase activity (dABs 460 nm/min) as described[15,18]. (For bars shown from left to right, n=14, 8, 13, and 7, respectively, with P values indicated).

FIG. 11A. Coronary sinus blood was sampled at the start ($CS_1$) and conclusion ($CS_2$) of the ischemic period (aortic cross-clamping). ELISAs were performed for thrombomodulin (TM) and vWF. FIG. 11B. vWF immunoelectrophoresis of a representative sample of $CS_1$ and $CS_2$ blood from the same patient (dilution factors are indicated) There is an increase in high molecular weight multimers detected in the $CS_2$ samples.

FIG. 12A. Suture based retraction system is shown in the diagram.

FIG. 14A. Effects of strain on infarct volume, determined as a percentage of ipsilateral hemispheric volume, as described in the Methods section. FIG. 14B. Effects of strain on neurological deficit score, graded from no neurologic deficit (0) to severe neurologic deficit (4), with scores determined as described in the Methods section. FIG. 14C. Effects of strain on cerebral blood flow, measured by laser doppler flowmetry as relative flow over the infarcted territory compared with blood flow over the contralateral (noninfarcted) cortex. Strains included 129J (n=9), CD1 (n=11), and C57/Bl6 mice (n=11); *=p<0.05 vs 129J mice.

FIG. 15A. Effects of animal/suture size on infarct volume, FIG. 15B. neurological deficit score, and FIG. 15C. cerebral blood flow, measured as described in FIG. 14. P values are as shown.

FIG. 16A. infarct volume, FIG. 16B. neurological deficit score, and FIG. 16C. cerebral blood flow, measured as described in FIG. 3. *=p<0.05 values are as shown.

FIG. 17A. infarct volume, FIG. 17B. neurological deficit score, and FIG. 17C. cerebral blood flow, measured as described in FIG. 14.

FIGS. 18A and 18B. P-selectin expression and neutrophil (PMN) accumulation following middle cerebral artery occlusion (MCAO) in mice. FIG. 18A. P-selectin expression following MCAO and reperfusion. Relative expression of P-selectin antigen in the ipsilateral cerebral hemisphere following middle cerebral artery occlusion was demonstrated using either a $^{125}$I-labeled rat monoclonal anti-P-selectin IgG or a $^{125}$I-labeled nonimmune rat IgG to control for nonspecific extravasation. Experiments were performed as described in the legend to FIG. 18. Values are expressed as ipsilateral cpm/contralateral cpm. n=6 for each group, except for control 30 min (n=4); $^I$=p<0.001, 30 min reperfusion vs immediate pre-occlusion; *=p<0.025, change in P-selectin accumulation vs change in control IgG accumulation. FIG. 18B. Time course of PMN accumulation following focal cerebral ischemia and reperfusion in the mouse. For these experiments, ≈3.3×10$^5$ $^{111}$In-labeled PANS were injected intravenously into PS wild type (PS +/+) mice 15 minutes prior to middle cerebral artery occlusion (MCAO). $^{111}$In-PMN accumulation was measured immediately following sacrifice as the ratio of ipsilateral/contralateral cpm under the following experimental conditions: prior to MCAO (Pre-O, n=4), immediately following MCAO (Post-O, n=6), and 10 minutes following MCAO but still prior to reperfusion (:10 Post-O, n=6). To establish the effect of reperfusion on PMN accumulation, reperfusion was initiated following 45 minutes of ischemia. PMN accumulation was measured following 30 minutes (n=6), 300 minutes (n=3), and 22 hours (n=8) of reperfusion. Under identical conditions, PMN accumulation was measured in P-selectin null (PS –/–) mice after 45 minutes of ischemia and 22 hours of reperfusion (n=7, *=p<0.05 vs 45 min MCAO/22 hrs reperfusion in PS +/+animals).

FIG. 19C represents an overlay of the top two panels, with error bars omitted for clarity.

FIGS. 21A, 21B and 21C. Effect of the P-selectin gene on stroke outcomes. Middle cerebral artery occlusion was performed for 45 minutes, followed by 22 hours of reperfusion in P-selectin +/+ (n=10) or P-selectin –/– (n=7) mice. Effect of P-selectin on: FIG. 21A. infarct volume, as evidenced by 2% 2,3,5, triphenyl, 2H-tetrazolium chloride (TTC) staining, and calculated as percent of ipsilateral hemisphere; FIG. 21B. neurologic deficit score, (1=normal spontaneous movements; 2=clockwise circling; 3=clockwise spinning; 4=unresponsiveness to noxious stimuli); FIG. 21C. percent survival at time of sacrifice. (*=p<0.05).

FIG. 22A. Cerebral blood flows at thirty minutes following reperfusion; After 22 hours of reperfusion, infarct volumes FIG. 22B., neurological deficit scores FIG. 22C., and mortality FIG. 22D. are shown. (n=7 for each group, *=p<0.05).

FIG. 23A. The effect of carbon monoxide inhalation on cerebral infarct volumes. Mice were placed in bell jars, in which they were exposed to 0.1% CO for 12 hours. After this treatment, they were removed from the bell jars and subjected to intraluminal occlusion of the middle cerebral artery. At 24 hours, animals were sacrificed and infarct volumes measured by triphenyltetrazolium chloride (TTC) staining as shown in FIG. 25. Quantification of infarction volumes (mean±SEM) is expressed as the percent of infarction of the ipsilateral hemisphere. These data show that inhaled CO reduces infarct volumes following stroke.

FIG. 23B. The effect of carbon monoxide inhalation on mortality following stroke. Experiments were performed as described above. Mortality at 24 hours is shown. These data show that inhaled CO reduces mortality following stroke.

FIGS. 24A, 24B and 24C. FIG. 24A. Dose-response of inhaled carbon monoxide on stroke outcome. Experiments are described above. CO was inhaled at the indicated doses. These data show that inhaled CO reduces infarct volume in a dose-dependent fashion, with 0.1% providing optimal protection. FIG. 24B and 24C. Role of heme oxygenase, the enzyme which makes CO, in stroke. Animals were given either vehicle (DMSO) alone as a control or zinc protoporphyrin IX (ZnPP) or tin protoporphyrin IX (SnPP). In a final group, mice were given biliverdin (Bili), a compound which is formed along with CO during the process of heme degradation by heme oxygenase. Left panel shows infarction volumes. Right panel shows mortality. These experiments demonstrate that when heme oxygenase activity is blocked, stroke outcomes are worse (larger infarcts and higher mortalities) Because biliverdin administration is not protective, these data suggest that the other coproduct of heme oxygenase activity (CO) is protective.

FIGS. 26A-26F. Effect of focal cerebral ischemia on heme oxygenase I (HO-I) induction. FIGS. 26A-26C show in situ hybridization of HO-I mRNA in stroke (FIG. 26B) and in controls (FIGS. 26A and 26C). FIGS. 26D-26F show immunohistochemistry of HO-I protein. FIG. 26E shows that the protein is expressed in blood vessels and astrocytes following stroke. FIGS. 26D and 26F show that the protein is not expressed in blood vessels and astrocytes in controls.

FIG. 31A. P-selectin expression following MCAO and reperfusion. Relative expression of P-selectin antigen in the ipsilateral cerebral hemisphere following middle cerebral artery occlusion was demonstrated using either a $^{125}$I-labelled rat monoclonal anti-P-selectin IgG or a $^{125}$I-labelled nonimmune rat IgG to control for nonspecific extravasation. Values are expressed as ipsilateral cpm/contralateral cpm. n=6 for each group, except for control 30 min (n=4); $^{I}$=p<0.001, 30 min reperfusion vs immediate pre-occlusion; *=p<0.025, change in P-selectin accumulation vs change in control IgG accumulation. FIG. 31B and 31C. Immunohistochemical localization of P-selectin expression in a section of brain from a mouse subjected to 45 minutes of MCAO followed by 1 hour of reperfusion. Ipsilateral and contralateral cerebral cortical sections are shown from the same mouse. Arrows point to a cerebral microvessel, with dark brown color representing P-selectin expression at the endothelial cell surface. FIG. 31D. Time course of PMN accumulation following focal cerebral ischemia and reperfusion in the mouse. For these experiments, ≈3.3×10$^5$ $^{111}$In-labelled PMNs were injected intravenously into PS wild type (PS +/+) mice 15 minutes prior to middle cerebral artery occlusion (MCAO). $^{111}$In-PMN accumulation was measured immediately following sacrifice as the ratio of ipsilateral/contralateral cpm under the following experimental conditions: prior to MCAO (Pre-O, n=4), immediately following MCAO (Post-O, n=6), and 10 minutes following MCAO but still prior to reperfusion (:10 Post-O, n=6). To establish the effect of reperfusion on PMN accumulation, reperfusion was initiated following 45 minutes of ischemia. PMN accumulation was measured following 30 minutes (n=6), 300 minutes (n=3), and 22 hours (n=8) of reperfusion. Under identical conditions, PMN accumulation was measured in P-selectin null (PS −/−) mice after 45 minutes of ischemia and 22 hours of reperfusion (n=7, *=p<0.05 vs 45 min MCAO/22 hrs reperfusion in PS +/+ animals).

FIGS. 33A-33B. Effect of the P-selectin gene on stroke outcomes. Middle cerebral artery occlusion was performed for 45 minutes, followed by 22 hours of reperfusion in P-selectin +/+ (n=10) or P-selectin −/− (n=7) mice. Effect of P-selectin on: FIG. 33A. infarct volume, as evidenced by 2% 2,3,5, triphenyl, 2H-tetrazolium chloride (TTC) staining, and calculated as percent of ipsilateral hemisphere; FIG. 33B. percent survival at time of sacrifice. Means±SEM are indicated, with the numbers of animals from which the percentage survial was calculated indicated above the survival bars (*=p<0.05).

FIG. 35A. Standard curve in which known concentrations of hemoglobin were reduced to cyanomethemoglobin, after which the OD at 550 nm was measured. N=5 determinations at each point, with means±SEM shown. The equation for the best-fit line and r value are shown. FIG. 35B. Known concentrations of hemoglobin (using autologous blood diluted in saline) were added to fixed volumes of fresh brain tissue homogenate and the spectrophotometric hemoglobin assay was performed. Brains were divided into hemispheres; for each animal, one hemisphere was immersed in physiological saline for 20 minutes (NS, solid line), and the other hemisphere was placed in triphenyltetrazolium chloride (TTC, dashed line) for 20 minutes (similar to the procedure that would be done to measure cerebral infarction volume). For each concentration of added hemoglobin, spectrophotometric hemoglobin assay was performed on 6 hemispheres. Means±SEM are shown.

FIGS. 36A-36B. Quantitative spectrophotometric hemoglobin assay. FIG. 36A. Effects of collagenase-infusion and rt-PA on murine quantitative ICH. Mice were stereotactically infused with ICH-inducing agents into the right deep cortex/basal ganglia. Brains were harvested 24 h later and the spectrophotometric hemoglobin assay was performed to quantify ICH. Mice were subjected to 1) no treatment (Control), 2) stereotactic infusion of 1 µl normal saline solution (Sham), 3) stereotactic infusion of 0.024 µg collagenase B in 1 µl normal saline solution (Collagenase), or 4) stereotactic infusion of collagenase B (as above) followed by intravenous tissue plasminogen activator (1 mg/kg in 0.2 µl normal saline solution) by dorsal penile vein injection (Collagenase+rt-PA). p<0.001 vs. Sham or Control. FIG. 36B. Effect of rt-PA following focal ischemic stroke on murine quantitative ICH. Mice were subjected to 45 minutes of MCA occlusion followed by reperfusion and then 1) intravenous 0.2 µl of normal saline solution (Stroke+Saline) or 2) intravenous tissue plasminogen activator (15 mg/kg in 0.2 µl normal saline solution) (Stroke+rt-PA). Brains were harvested 24 h later and the spectrophotometric hemoglobin assay was performed to quantify ICH. p<0.05.

FIG. 37. Demonstration of the scoring system used for the visual determination of ICH following stroke. Each slice, taken from different animals subjected to stroke, represents the coronal slice of brain which exhibits the maximal hemorrhagic diameter. The numbers correspond to the visually determined hemorrhage score, as defined in the Methods section.

FIG. 38A. Effects of collagenase-infusion and rt-PA on murine visual ICH score. Mice were stereotactically infused with ICH-inducing agents into the right deep cortex/basal ganglia. Mice were subjected to 1) no treatment (Control), 2) stereotactic infusion of 1 µl normal saline solution (Sham), 3) stereotactic infusion of 0.024 µg collagenase B in 1 µl normal saline solution (Collagenase), or 4) stereotactic infusion of collagenase B (as above) followed by intravenous tissue plasminogen activator (1 mg/kg in 0.2 µl normal saline solution) by dorsal penile vein injection (Collagenase+rt-PA). Brains were harvested 24 h later, sectioned into 1 mm coronal slices, and scored by a blinded observer as described, in the Methods section. *$p<0.05$ vs. Collagenase, $p<0.005$ vs. Sham or Control. FIG. 38B. Effect of rt-PA following focal ischemic stroke on murine visual ICH score. Mice were subjected to 45 minutes of MCA occlusion followed by reperfusion and then 1) intravenous 0.2 µl of normal saline solution (Stroke+Saline) or 2) intravenous tissue plasminogen activator (15 mg/kg in 0.2 µl normal saline solution) (Stroke+rt-PA). Brains were harvested 24 h later, sectioned into 1 mm coronal slices, and scored by a blinded observer as described in the Methods section *$p<0.01$. Individual values for visual ICH scores are shown, with the median value for each group indicated by a horizontal line.

FIG. 40A. Effect of stroke and Factor IXai administration in stroke on the accumulation of radiolabeled platelets. [111]Indium-platelets were administered either in control animals without stroke (n=4), or in animals immediately prior to stroke with (n=7) or without preoperative administration of Factor IXai (300 µg/kg, n=7). Platelet accumulation is expressed as the ipsilateral cpm/ contralateral cpm. Means±SEM are shown. *$p<0.05$ vs No Stroke; **$p<0.05$ vs Stroke+Vehicle. FIG. 40B. Accumulation of fibrin in infarcted cerebral tissue. Twenty-two hours following focal cerebral ischemia and reperfusion, a brain was harvested from a representative mouse which had been pretreated prior to surgery with either vehicle (leftmost two lanes) or Factor IXai (300 µg/kg, rightmost two lanes). The brains were divided into ipsilateral (R) and contralateral (L) hemispheres, and plasmin digestion performed to solubilize accumulated fibrin. Immunoblotting was performed using a primary antibody directed against a neoepitope expressed on the gamma-gamma chain dimer of crosslinked fibrin. FIG. 40C-40F. Immunohistochemical identification of sites of fibrin formation in stroke. Using the same antibody as described in FIG. 2b to detect fibrin, brains were harvested from two mice following stroke (upper and lower panels each represent a mouse). Arrows identify cerebral microvessels. Note that in both ipsilateral hemispheres (right panels), intravascular fibrin can be clearly identified by the red stain, which is not seen in the contralateral (left panels), nonischemic hemispheres.

FIG. 41A. Effect of Factor IXai on relative CBF in a murine stroke model, measured by laser doppler. CBF in Factor IXai-treated animals (300 µg/kg, n=48, dashed line) is significantly higher at 24 hours than vehicle-treated controls (n=62). Means±SEM are shown. *$p<0.05$. FIG. 41B. Effect of Factor IXai on infarct volumes in a murine stroke model, measured by TTC-staining of serial coronal sections. Animals were given vehicle (n=62) or Factor IXai (300 µg/kg, n=48). Means±SEM are shown. *$p<0.05$. FIG. 41C. Dose-response of Factor IXai in stroke. Factor IXai was administered immediately prior to the onset of stroke, and cerebral infarct volumes determined as described in FIG. 41B above. N=62, 48, 6, and 6, for Vehicle, 300 µg/kg, 600 µg/kg, and 1200 µg/kg doses respectively. Means±SEM are shown. *$p<0.05$ vs vehicle-treated animals.

FIG. 42A. Spectrophotometric hemoglobin assay was performed as described in the Methods section. O.D. at 550 nm is linearly related to brain hemoglobin content[11,12]. FIG. 42B. Visually-determined ICH score by a blinded observer, as described in the methods section. ICH score correlates with spectrophotometrically-determined brain hemoglobin content[11,12]. Means±SEM are shown. *$p<0.05$ vs vehicle-treated animals.

DETAILED DESCRIPTION OF THE INVENTION

Figure 1:
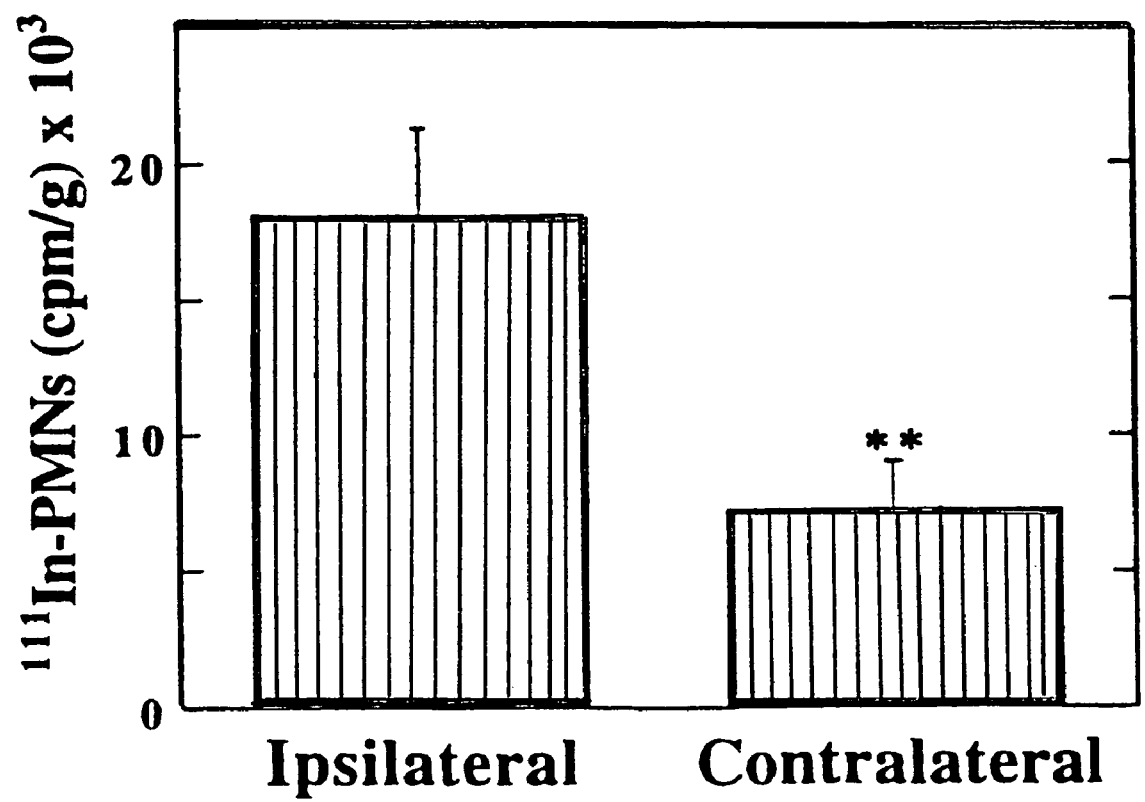
FIG. 1. Neutrophil accumulation following focal cerebral ischemia and reperfusion in the mouse. Right middle cerebral artery occlusion was performed for 45 minutes, followed by 23 hours of reperfusion in male C57Bl/J6 mice. One hour prior to middle cerebral artery occlusion, $\approx 3.3 \times 10^5$ $^{111}$In-labeled neutrophils were injected into the tail vein. Ipsilateral (right hemispheric) and contralateral (left hemispheric) counts were obtained and normalized per gm of tissue. (n=7, **=p<0.01).

The present invention provides for a method for treating an ischemic disorder in a subject which includes administering to the subject a pharmaceutically acceptable form of a selectin antagonist in a sufficient amount over a sufficient time period to prevent white blood cell accumulation so as to treat the ischemic disorder in the subject. The selectin antagonist may be a peptide mimetic, a nucleic acid molecule, a ribozyme, a polypeptide, a small molecule, a carbohydrate molecule, a monosaccharide, an oligosaccharide or an antibody. The selectin may be a P-selectin, an E-selectin, or an L-selectin. The antibody may be a P-selectin antibody. The antibody may further include a polyclonal antibody or a monoclonal antibody. The P-selectin antagonist may include a nitric oxide (NO) precursor such as L-arginine, an NO donor such as nitroglycerin or nitroprusside, a cyclic nucleotide analog such as a cyclic GMP or cyclic AMP analog, or a phosphodiesterase inhibitor.

The pharmaceutically acceptable form of P-selectin antagonist may include a P-selectin antagonist and a pharmaceutically acceptable carrier. The carrier may include an aerosol, intravenous, oral or topical carrier.

The white blood cell may be a neutrophil or a monocyte. The subject may be a mammal. The mammal may be a human, a cow, a pig, a sheep, a dog, a cat, a monkey, a fowl or any animal model of a human disease or disorder.

The ischemic disorder may include, but is not limited to a peripheral vascular disorder, a venous thrombosis, a pulmonary embolus, a myocardial infarction, a transient ischemic attack, unstable angina, a reversible ischemic neurological deficit, sickle cell anemia or a stroke disorder.

The subject may be undergoing heart surgery, lung surgery, spinal surgery, brain surgery, vascular surgery, abdominal surgery, or organ transplantation surgery. The organ transplantation surgery may include heart, lung, pancreas or liver transplantation surgery.

The present invention further provides for a method for treating an ischemic disorder in a subject which comprises administering to the subject carbon monoxide gas in a sufficient amount over a sufficient period of time thereby treating the ischemic disorder in the subject.

The administration of carbon monoxide may be via inhalation by the subject or via extracorporeal exposure to blood or body fluids of the subject.

The amount of carbon monoxide which may be sufficient to treat the subject includes but is not limited to from about 0.00011 carbon monoxide in an inert gas to about 2% carbon monoxide in an inert gas. The inert gas may be oxygen, nitrogen, argon or air. In one embodiment of the present invention, the amount of carbon monoxide administered may be 0.1% carbon monoxide in air.

The period of time sufficient to administer carbon monoxide to a subject to treat an ischemic disorder includes but is not limited to from about 1 day before surgery to about 1 day after surgery. The period of time may be from about 12 hours before surgery to about 12 hours after surgery. The period of time may further include from about 12 hours before surgery to about 1 hour after surgery. The period of time may further include from about 1 hour before surgery to about 1 hour after surgery. The period of time may further include from about 20 minutes before surgery to about 1 hour after surgery. The period of time sufficient to treat an ischemic disorder in a subject who is not undergoing surgery may include before and during any physical manifestation of such disorder. Administration of carbon monoxide is preferable before the manifestation in order to lessen such manifestation of an ischemic disorder. Carbon monoxide administration has been shown as described hereinbelow to be protective of ischemia in a subject if administered prior to surgery.

As used herein, the "ischemic disorder" encompasses and is not limited to a peripheral vascular disorder, a venous thrombosis, a pulmonary embolus, a myocardial infarction, a transient ischemic attack, lung ischemia, unstable angina, a reversible ischemic neurological deficit, adjunct thromolytic activity, excessive clotting conditions, sickle cell anemia or a stroke disorder.

The subject may be undergoing heart surgery, lung surgery, spinal surgery, brain surgery, vascular surgery, abdominal surgery, or organ transplantation surgery. The organ transplantation surgery may include heart, lung, pancreas or liver transplantation surgery.

The carbon monoxide may be administered in an indirect manner. Rather than the subject directly inhaling or receiving carbon monoxide gas or a gas mixture, the subject may be given compunds to stimulate the in vivo production of carbon monoxide. Such compounds may include but are not limited to heme, ferritin, hematin, endogenous precursors to heme oxygenase or heme oxygenase stimulators. In addition, the subject may be exposed to an environment of low oxygen level compared to the normal atmosphere.

Heme oxygenase is an endogenous enzyme which synthesizes carbon monoxide from precursor heme (it is part of the normal way in which heme is degraded and metabolized in the body). When mice were exposed to either hypoxia or tissue ischemia, levels of both the messenger RNA which codes for heme oxygenase protein and the protein itself were increased. In addition, the activity of the enzyme was increased, as indicated by measurements of carbon monoxide in the tissue.

Another embodiment of the present invention is a method for treating an ischemic disorder in a subject which comprises administering to the subject a pharmaceutically acceptable form of inactivated Factor IX in a sufficient amount over a sufficient period of time to inhibit coagulation so as to treat the ischemic disorder in the subject. The sufficient amount may include but is not limited to from about 75 µg/kg to about 550 µg/kg. The amount may be 300 µg/kg. The pharmaceutically acceptable form of inactivated Factor IX includes inactivated Factor IX and a pharmaceutically acceptable carrier.

The Factor IX may be inactivated by the standard methods known to one of skill in the art, such as heat inactivation. Factor IX may be inactivated or Factor IX activity may be inhibited by an antagonist. Such antagonist may be a peptide mimetic, a nucleic acid molecule, a ribozyme, a polypeptide, a small molecule, a carbohydrate molecule, a monosaccharide, an oligosaccharide or an antibody.

The present invention provides for a method for identifying a compound that is capable of improving an ischemic disorder in a subject which includes: a) administering the compound to an animal, which animal is a stroke animal model; b) measuring stroke outcome in the animal, and c) comparing the stroke outcome in step (b) with that of the stroke animal model in the absence of the compound so as to identify a compound capable of improving an ischemic disorder in a subject. The stroke animal model includes a murine model of focal cerebral ischemia and reperfusion. The stroke outcome may be measured by physical examination, magnetic resonance imaging, laser doppler flowmetry, triphenyl tetrazolium chloride staining, chemical assessment of neurological deficit, computed tomography scan, or cerebral cortical blood flow. The stroke outcome in a human may be measured also by clinical measurements, quality of life scores and neuropsychometric testing. The compound may include a P-selectin antagonist, an E-selectin antagonist or an L-selectin antagonist.

The present invention further provides a method for identifying a compound that is capable of preventing the accumulation of white blood cells in a subject which includes: a) administering the compound to an animal, which animal is a stroke animal model; b) measuring stroke outcome in the animal, and c) comparing the stroke outcome in step (b) with that of the stroke animal model in the absence of the compound so as to identify a compound capable of preventing the accumulation of white blood cells in the subject.

The white blood cell may be, but is not limited to, a neutrophil, a platlet or a monocyte. The compound may be but is not limited to a selectin inhibitor, a monocyte inhibitor, a platelet inhibitor or a neutrophil inhibitor. The selectin inhibitor may be but is not limited to a P-selectin, E-selectin or L-selectin inhibitor. Selectins are expressed on the surface of platlets and such selectin inhibitors or antagonists as described herein may prevent the expression of such selectins on the surface of the cell. The prevention of expression may be at the transcriptional, translational, post-translational levels or preventing the movement of such selectins through the cytosol and preventing delivery at the cell surface.

The present invention provides for treatment of ischemic disorders by inhibiting the ability of the neutrophil, monocyte or other white blood cell to adhere properly. This may be accomplished removing the counter ligand, such as CD18. It has been demonstrated as discussed hereinbelow, that "knock-out" CD18 mice (mice that do not have expression of the normal CD18 gene) are protected from adverse ischemic conditions. The endothelial cells on the surface of the vessels in the subject may also be a target for treatment. In a mouse model of stroke, administration of TPA as a thrombolytic agent caused some visible hemorrhaging along with improvement of the stroke disorder. However, administration of a P-selectin antagonist also improved stroke disorder in the animal model, but without the coincident hemorrhaging. The present invention may be used in conjunction with a thrombolytic therapy to increase efficacy of such therapy or to enable lower doses of such therapy to be administered to the subject so as to reduce side effects of the thrombolytic therapy.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions including therapeutically effective amounts of protein compositions and compounds capable of treating stroke disorder or improving stroke outcome in the subject of the invention together with suitable diluents, preservatives, solubilizers, emulsifiers, adjuvants, and/or carriers useful in treatment of neuronal degradation due to aging, a learning disability, or a neurological disorder. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound capable of alleviating the symptoms of the stroke disorder or improving the stroke outcome in the subject.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Portions of the compound of the invention may be "labeled" by association with a detectable marker substance (e.g., radiolabeled with $^{125}$I or biotinylated) to provide reagents useful in detection and quantification of compound or its receptor bearing cells or its derivatives in solid tissue and fluid samples such as blood, cerebral spinal fluid or urine.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of alleviating symptoms of a cognitive disorder of memory or learning may be delivered in a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or halcacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

By means of well-known techniques such as titration and by taking into account the observed pharmacokinetic characteristics of the agent in the individual subject, one of skill in the art can determine an appropriate dosing regimen. See, for example, Benet, et al., "Clinical Pharmacokinetics" in ch. 1 (pp. 20-32) of Goodman and Gilman's The Pharmacological Basis of Therapeutics, 8th edition, A. G. Gilman, et al. eds. (Pergamon, New York 1990).

The present invention provides for a pharmaceutical composition which comprises an agent capable of treating a stroke disorder or improving stroke outcome and a pharmaceutically acceptable carrier. The carrier may include but is not limited to a diluent, an aerosol, a topical carrier, an aquous solution, a nonaqueous solution or a solid carrier.

This invention is illustrated in the Experimental Detail section which follows. These sections are set forth to aid in an understanding of the invention but are not intended to, and should not be construed to, limit in any way the invention as set forth in the claims which follow thereafter.

EXPERIMENTAL DETAILS

Abbreviations: EC, endothelial cell; PMN, polymorphonuclear leukocyte; WP, Weibel-Palade body; vWF, von Willebrand factor; EGTA, ethyleneglycol bis (aminoethylether) tetraacetic acid; HBSS, Hank's balanced salt solution; CS; coronary sinus; IL, interleukin; PAF, platelet activating factor; ICAM-1, intercellular adhesion molecule-1; HUVEC, human umbilical vein EC; LR, lactated Ringer's solution; MCAO, middle cerebral artery occlusion; rt-PA, recombinant tissue plasminogen activator; HO-I or HOI or HO I, heme oxygenase I; ICH, intracerebral hemorrhage; OD, optical density; MCA, middle cerebral artery; rt-PA, recombinant tissue-type plasminogen activator; TIA, transient ischemic attack; TTC, triphenyltetrazolium chloride.

Example 1

Cerebral Protection in Homozygous Null ICAM-1 Mice Following Middle Cerebral Artery Occlusion: Role of Neutrophil Adhesion in the Pathogenesis of Stroke To investigate whether polymorphonuclear leukocytes (PMNs) contribute to adverse neurologic sequelae and mortality following stroke, and to study the potential role of the leukocyte adhesion molecule Intercellular Adhesion Molecule-1 (ICAM-1) in the pathogenesis of stroke, a murine model of transient focal cerebral ischemia was employed consisting of intraluminal middle cerebral artery (MCA) occlusion for 45 minutes followed by 22 hours of reperfusion. PMN accumulation, monitored by deposition of $^{111}$Indium-labelled PMNs in postischemic cerebral tissue, was increased 2.5-fold in the ipsilateral (infarcted) hemisphere compared with the contralateral (noninfarcted) hemisphere ($p<0.01$). Mice immunodepleted of neutrophils prior to surgery demonstrated a 3.0-fold reduction in infarct volumes ($p<0.001$), based on triphenyltetrazolium chloride staining of serial cerebral sections, improved ipsilateral cortical cerebral blood flow (measured by laser doppler) and reduced neurological deficit compared with controls. In wild type mice subjected to 45 minutes of ischemia followed by 22 hours of reperfusion, ICAM-1 mRNA was increased in the ipsilateral hemisphere, with immunohistochemistry localizing increased ICAM-1 expression on cerebral microvascular endothelium. The role of ICAM-1 expression in stroke was investigated in homozygous null ICAM-1 mice (ICAM-1 −/−) in comparison with wild type controls (ICAM-1+/+). ICAM-1 −/− mice demonstrated a 3.7-fold reduction in infarct volume ($p<0.005$), a 35% increase in survival ($p<0.05$), and reduced neurologic deficit compared with ICAM-1 +/+ controls. Cerebral blood flow to the infarcted hemisphere was 3.1-fold greater in ICAM-1 −/− mice compared with ICAM-1 +/+ controls ($p<0.01$), suggesting an important role for ICAM-1 in the genesis of post-ischemic cerebral no-reflow. Because PMN-depleted and ICAM-1 deficient mice are relatively resistant to cerebral ischemia-reperfusion injury, these studies suggest an important role for ICAM-1-mediated PMN adhesion in the pathophysiology of evolving stroke.

Introduction:

Neutrophils (PMNs) are critically involved in the earliest stages of inflammation following tissue ischemia, initiating scavenger functions which are later subsumed by macrophages. There is a darker side to neutrophil influx, however, especially in postischemic tissues[1-7], where activated PMNs may augment damage to vascular and parenchymal cellular elements. Experimental evidence points to a pivotal role for endothelial cells in establishing postischemic PMN recruitment, in that hypoxic/ischemic endothelial cells synthesize the proinflammatory cytokine IL-1[8] as well as the potent neutrophil chemoattractant and activator IL-8[9]. Firm adhesion of PMNs to activated endothelium in a postischemic vascular milieu is promoted by translocation of P-selectin to the cell surface[10] as well as enhanced production of platelet activating factor and ICAM-1[11].

While strategies to block each of these mechanisms of neutrophil recruitment are protective in various models of ischemia and reperfusion injury, their effectiveness in cerebral ischemia/reperfusion injury remains controversial. There is considerable evidence that in the brain, as in other tissues, an early PMN influx follows an ischemic episode[12-17]. Immunohistochemical studies have described increased expression of the PMN adhesion molecules P-selectin and intercellular adhesion molecule-1 (ICAM-1) in the postischemic cerebral vasculature[12,18-20]. The pathogenic relevance of adhesion molecule expression in the brain remains controversial, however; data from a trial of a monoclonal anti-ICAM-1 antibody in stroke in humans is not yet available. In animal models, there is conflicting experimental evidence regarding the effectiveness of anti-adhesion molecule strategies in the treatment of experimental stroke[21-23]. To determine whether ICAM-1 participates in the pathogenesis of postischemic cerebral injury, the experiments reported here were undertaken in a murine model of focal cerebral ischemia and reperfusion so that the role of a single, critical mediator of PMN adhesion (ICAM-1) could be determined. These studies demonstrate that enhanced ICAM-1 expression and neutrophil influx follow an episode of focal cerebral ischemia. Furthermore, these studies show that both neutrophil-deficient and transgenic ICAM-1 null mice are relatively resistant to cerebral infarction following ischemia and reperfusion, providing strong evidence for an exacerbating role of ICAM-1 in the pathophysiology of stroke.

Materials and Methods

Mice: Experiments were performed with transgenic ICAM-1 deficient mice created as previously reported[24] by gene targeting in J1 embryonic stem cells, injected into C57BL/6 blastocysts to obtain germline transmission, and backcrossed to obtain homozygous null ICAM-1 mice. All experiments were performed with ICAM-1 −/− or wild-type (ICAM-1 +/+) cousin mice from the fifth generation of back-crossings with C57BL/6 mice. Animals were seven to nine weeks of age and weighed between 25-36 grams at the time of experiments. For certain experiments, neutrophil depletion of C57BL/6 mice was accomplished by administering polyclonal rabbit anti-mouse neutrophil antibody[25] (Accurate Scientific, Westbury N.Y.) preadsorbed to red blood cells as a daily intraperitoneal injection (0.3 mL of 1:12 solution) for 3 days. Experiments in these mice were performed on the fourth day after confirming agranulocytosis by Wright-Giemsa stained peripheral blood smears.

Transient Middle Cerebral Artery Occlusion[26]: Mice were anesthetized with an intraperitoneal injection of 0.3 ml of ketamine (10 mg/cc) and xylazine (0.5 mg/cc). Animals were positioned supine on a rectal-temperature controlled operating surface (Yellow Springs Instruments, Inc., Yellow Springs, Ohio). Animal core temperature was maintained at 36-38° C. intraoperatively and for 90 minutes post-operatively. Middle cerebral artery occlusion was performed as follows; A midline neck incision was created to expose the right carotid sheath under the operating microscope (16-25× zoom, Zeiss, Thornwood, N.Y.). The common carotid artery was freed from its sheath, and isolated with a 4-0-silk, and the occipital and pterygopalatine arteries were each isolated and divided. Distal control of the internal carotid artery was obtained and the external carotid was cauterized and divided just proximal to its bifurcation into the lingual and maxillary divisions. Transient carotid occlusion was accomplished by advancing a 13 mm heat-blunted 5-0 nylon suture via the external carotid stump to the origin of the middle cerebral artery. After placement of the occluding suture, the external carotid artery stump was cauterized to prevent bleeding through the arteriotomy, and arterial flow was reestablished. In all cases, the duration of carotid occlusion was less than two minutes. After 45 minutes, the occluding suture was withdrawn to establish reperfusion. These procedures have been previously described in detail[26].

Measurement of cerebral cortical blood flow: Transcranial measurements of cerebral blood flow were made using laser doppler flow measurements (Perimed, Inc., Piscataway, N.J.) after reflection of the skin overlying the calvarium, as previously described[27] (transcranial readings were consistently the same as those made after craniectomy in pilot studies). Using a 0.7 mm straight laser doppler probe (model #PF303, Perimed, Piscataway, N.J.) and previously published landmarks (2 mm posterior to the bregma, 6 mm to each side of midline), relative cerebral blood flow measurements were made as indicated; immediately after anesthesia, after occlusion of the middle cerebral artery, immediately after reperfusion, and at 24 hours just prior to euthanasia. Data are expressed as the ratio of the doppler signal intensity of the ischemic compared with the nonischemic hemisphere. Although this method does not quantify cerebral blood flow per gram of tissue, use of laser doppler flow measurements at precisely defined anatomic landmarks serves as a means of comparing cerebral blood, flows in the same animal serially over time. The surgical procedure/intraluminal middle cerebral artery occlusion and reperfusion were considered to be technically adequate if ≧50% reduction in relative cerebral blood flow was observed immediately following placement of the intraluminal occluding suture and a ≧33% increase in flow over baseline occlusion was observed immediately following removal of the occluding suture. These methods have been used in previous studies[26].

Preparation and administration of $^{111}$In-labelled of murine neutrophils: Citrated blood from wild type mice was diluted 1:1 with NaCl (0.9%) followed by gradient ultracentrifugation on Ficoll-Hypaque (Pharmacia, Piscataway, N.J.). Following hypotonic lysis of residual erythrocytes (20 sec exposure to distilled $H_2O$ followed by reconstitution with 1.8% NaCl), the neutrophils were suspended in phosphate buffered saline (PBS). 5-7.5×10$^6$ neutrophils were suspended in PBS with 100 μCi of [111]Indium oxine (Amersham Mediphysics, Port Washington, N.Y.) for 15 minutes at 37° C. After washing with PBS, the neutrophils were gently pelleted (450 g), and resuspended in PBS to a final concentration of 1.0×10$^6$ cells/ml. Immediately prior to surgery, 100 μL of radiolabelled PMNs admixed with physiologic saline to a total volume of 0.3 mL (≈3×10$^6$ cpm) was administered by penile vein injection. Following humane euthanasia, brains were obtained as described, and neutrophil deposition quantified as cpm/gm of each hemisphere.

Neurological Exam: Twenty-four hours after middle cerebral artery occlusion and reperfusion, prior to giving anesthesia, mice were examined for neurological deficit using a four-tiered grading system[26]: A score of (1) was given if the animal demonstrated normal spontaneous movements; a score of (2) was given if the animal was noted to be turning to the right (clockwise circles) when viewed from above (i.e., towards the contralateral side); a score of (3) was given if the animal was observed to spin longitudinally (clockwise when viewed from the tail); a score of (4) was given if the animal was crouched on all fours, unresponsive to noxious stimuli. This scoring system has been previously described in mice[26], and is based upon similar scoring systems used in rats[28,29] which are based upon the contralateral movement of animals with stroke; following cerebral infarction, the contralateral side is "weak" and so the animal tends to turn towards the weakened side. Previous work in rats[28] and mice[26] demonstrates that larger cerebral infarcts are associated with a greater degree of contralateral movement, up to the point where the infarcts are so large that the animal remains unresponsive.

Calculation of Infarct Volume: After neurologic examination, mice were given 0.3 mL of ketamine (10 mg/ml) and xylazine (0.5 mg/ml), and final cerebral blood flow measurements were obtained. Humane euthanasia was performed by decapitation under anesthesia, and brains were removed and placed in a mouse brain matrix (Activational Systems Inc., Warren, Mich.) for 1 mm sectioning. Sections were immersed in 2% 2,3,5, triphenyl, 2H-tetrazolium chloride (TTC, Sigma Chemical Co., St. Louis, Mo.) in 0.9% phosphate-buffered saline, incubated for 30 minutes at 37° C., and placed in 10% formalin[26,30,32]. Infarcted brain was visualized as an area of unstained tissue, in contrast to viable tissue, which stains brick red. Infarct volumes were calculated from planimetered serial sections and expressed as the percentage of infarct in the ipsilateral hemisphere.

RNA extraction and Northern blot analysis: 24 hours following focal ischemia and reperfusion, brains were obtained and divided into ipsilateral (infarct) and contralateral (noninfarct) hemispheres. To detect ICAM-1 transcripts, total RNA was extracted from each hemisphere using an RNA isolation kit (Stratagene, La Jolla, Calif.). Equal amounts of RNA (20 μg/lane) were loaded onto a 1.4% agarose gel containing 2.2 M formaldehyde for size fractionation, and then transferred overnight to nylon (Nytran) membranes with 10× SSC buffer by capillary pressure. A murine ICAM-1 cDNA probe[33] (1.90 kb, ATCC, Rockville, Md.) was labelled with $^{32}P$-α-dCTP by random primer labelling (Prime-A-Gene kit, Promega), hybridized to blots at 42° C., followed by 3 washes of 1× SSC/0.05% SDS. Blots were developed with X-Omat AR film exposed with light screens at −70° for 7 days. A β-actin probe (ATCC) was used to confirm equal RNA loading.

Immunohistochemistry: Brains were removed at the indicated times following middle cerebral artery occlusion, fixed in 10% formalin, paraffin embedded and sectioned for immunohistochemistry. Sections were stained with a rat anti-murine ICAM-1 antibody (1:50 dilution, Genzym, Cambridge Mass.), and sites of primary antibody binding were visualized by an alkaline phosphatase conjugated secondary antibody detected with FastRed (TR/naphthol AS-MX, Sigma Chemical Co., St. Louis Mo.).

Data Analysis: Cerebral blood flow, infarct volumes and neurologic outcome scores were compared using Student's t-test for unpaired variables. $^{111}$Indium-neutrophil deposition was evaluated as paired data [comparing contralateral (noninfarct) to ipsilateral (infarct) hemisphere], to control for variations in injected counts or volume of distribution. Survival differences between groups was tested using contingency analysis with the Chi-square statistic. Values are expressed as means±SEM, with a p<0.05 considered statistically significant.

Results:

Neutrophil Accumulation in Stroke: Previous pathologic studies have shown neutrophil accumulation following cerebral infarction[15-17,34-36]. To determine whether neutrophils accumulate in the murine model of focal cerebral ischemia and reperfusion, neutrophil accumulation following transient (45 min) ischemia and reperfusion (22 hrs) was quantified by measuring the deposition of $^{111}$In-labeled neutrophils given to wild-type mice prior to the ischemic event. These experiments demonstrated significantly greater neutrophil accumulation (2.5-fold increase) in the ipsilateral (infarcted) compared with the contralateral (noninfarcted) hemispheres (n=7, p<0.01; FIG. 1). Similar results were obtained when neutrophil influx was monitored by myeloperoxidase assays, though low levels of activity were recorded in the latter assay (data not shown).

Figure 2A:
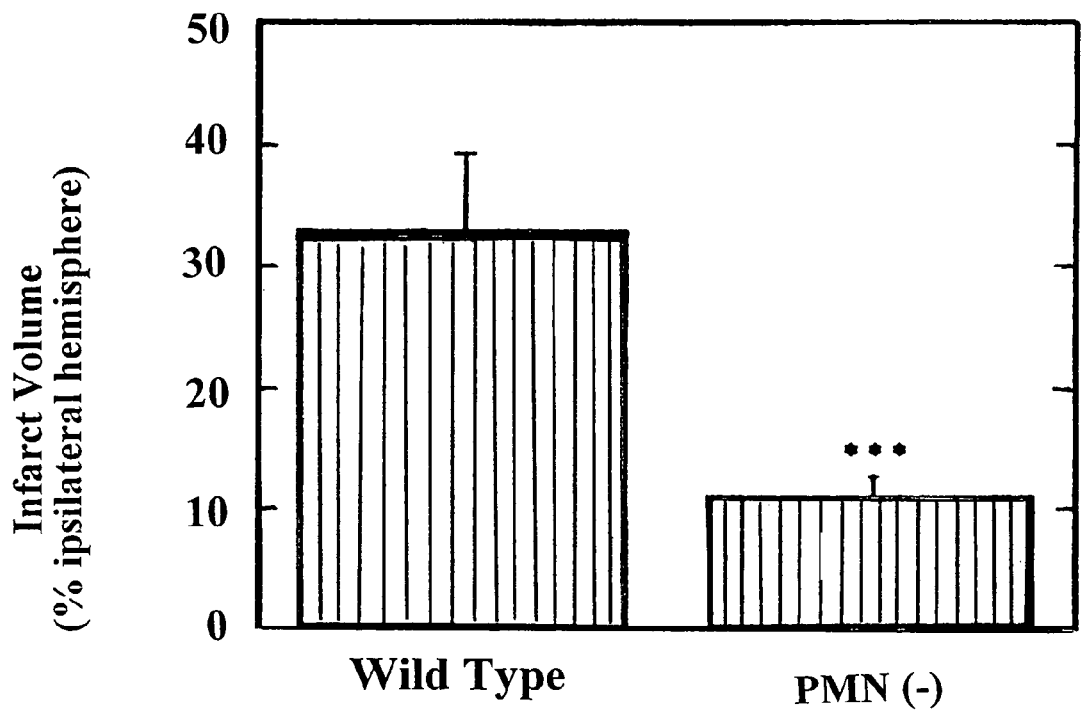
FIGS. 2A, 2B, 2C and 2D. Effect of preoperative neutrophil depletion on indices of stroke outcome. C57Bl/J6 male mice were subjected to transient middle cerebral artery occlusion as described above (Wild Type, n=16), and compared with a similar procedure performed in mice immunodepleted of neutrophils during the three days prior to the day of surgery (PMN −, n=18).
Figure 2B:
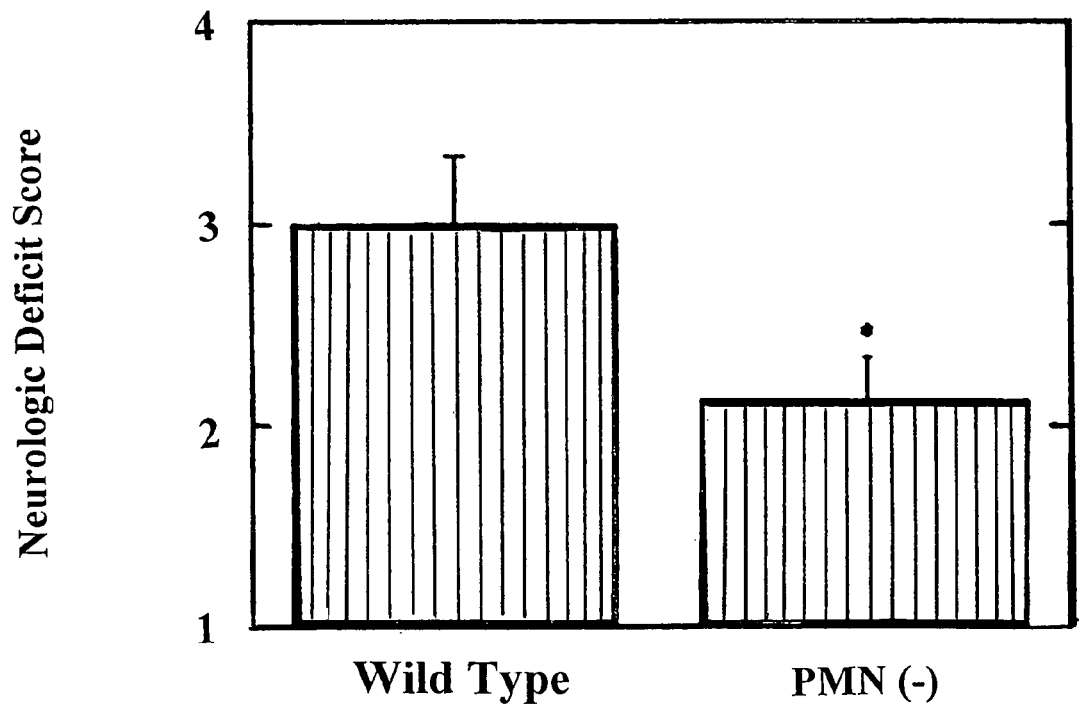
Figure 2C:
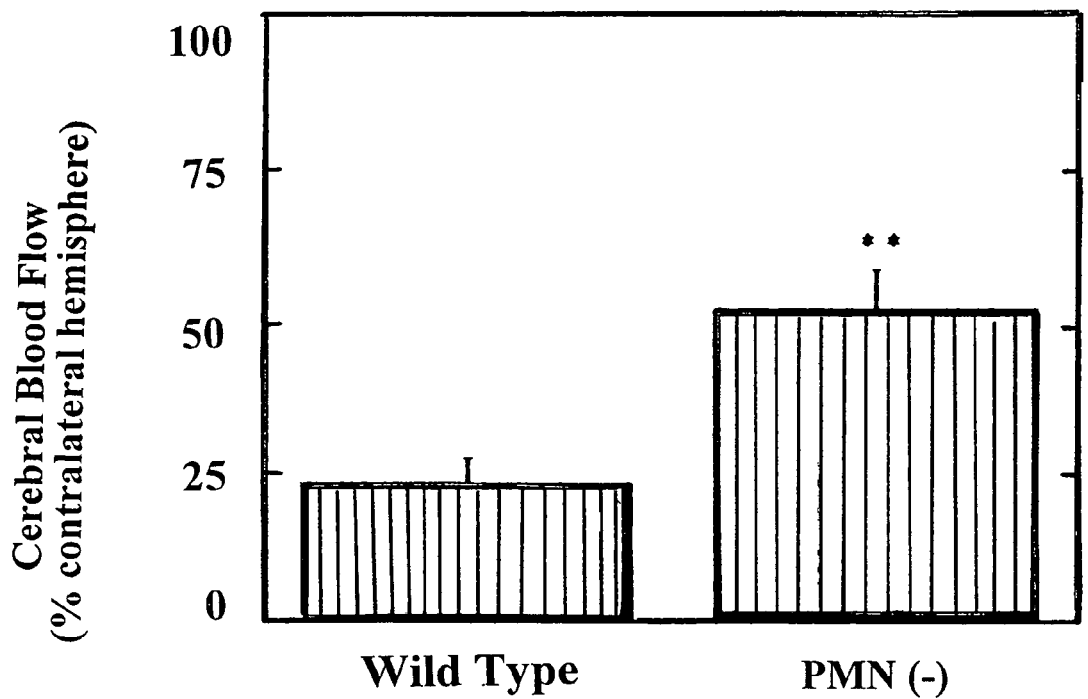
Figure 2D:
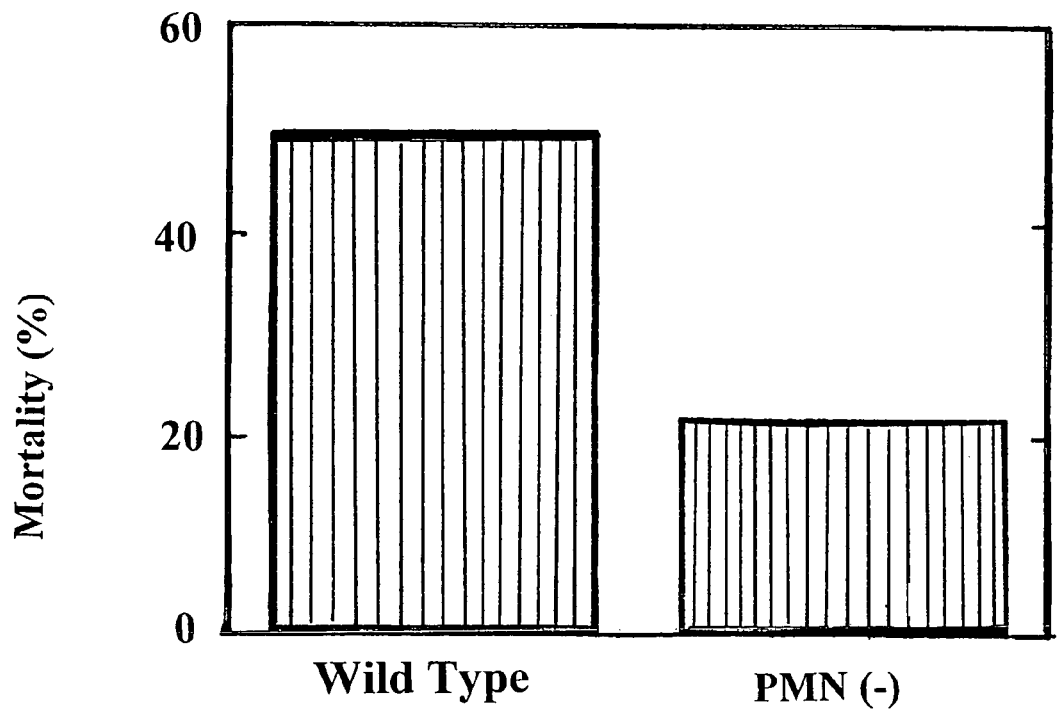

Effect of Neutrophil Depletion on Stroke Outcome: To determine the effect of neutrophil influx on indices of stroke outcome, mice were immunodepleted of neutrophils beginning three days prior to surgery. When surgery was performed on the fourth day, nearly complete agranulocytosis was evident on smears of peripheral blood. Neutropenic mice (n=18) were subjected to 45 min cerebral ischemia and 22 hours of reperfusion, and indices of stroke outcome determined. Infarct volumes were 3-fold smaller in neutropenic animals compared with wild type controls (11.1±1.6% vs 33.1±6.4%, p<0.001; FIG. 2A). The decrease in infarct volumes in neutropenic mice was paralleled by reduced neurologic deficit scores (FIG. 2B), increased post-reperfusion cerebral cortical blood flows (FIG. 2C), and a trend towards reduced overnight mortality (22% mortality in neutropenic mice vs 50% mortality in controls, FIG. 2D).

Figure 3:
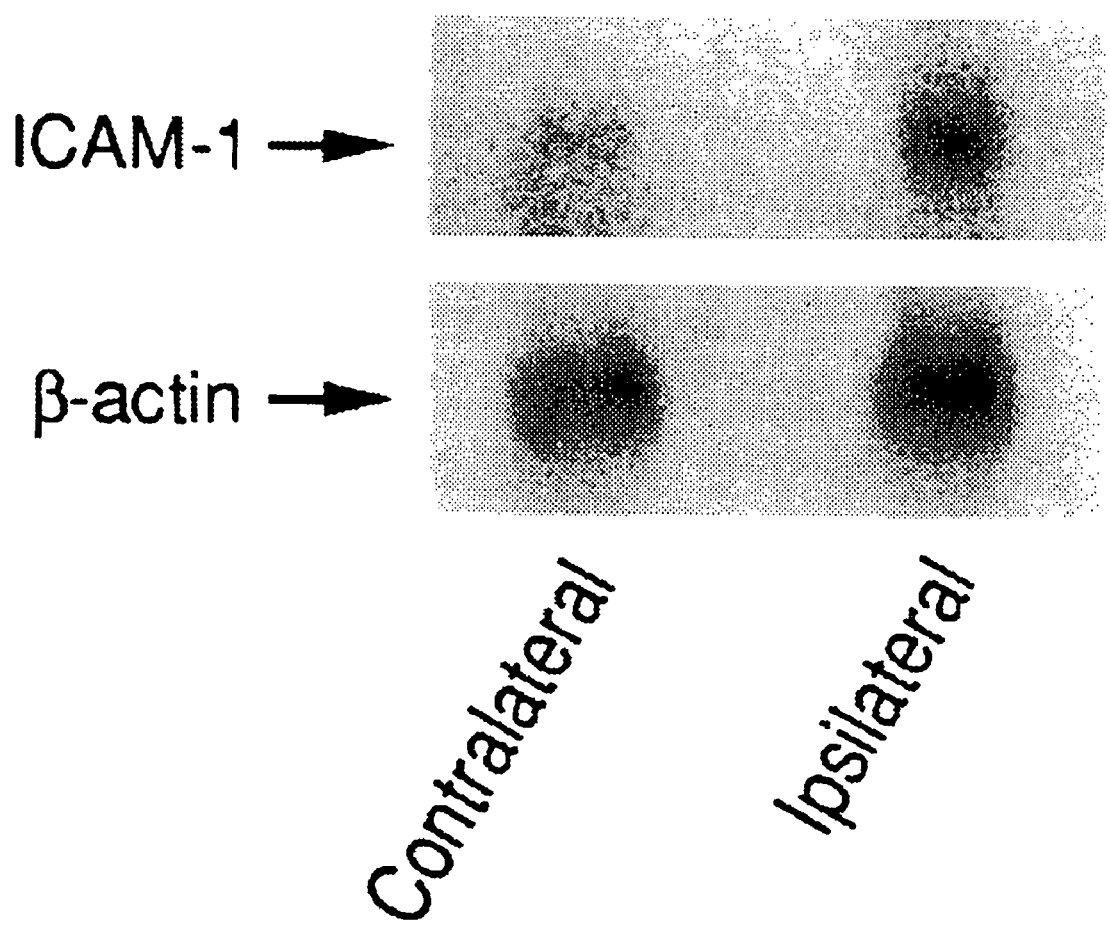
FIG. 3. Expression of Intercellular Adhesion Molecule-1 (ICAM-1) transcripts 24 hours following middle cerebral artery occlusion. RNA was prepared from the ipsilateral (infarct) and the contralateral (noninfarct) hemispheres from the same mouse, and an agarose gel was loaded with 20 µg of total RNA per lane. After overnight transfer to a nylon membrane, the Northern blot was probed with a $^{32}$P-labeled 1.90 kb murine ICAM-1 cDNA[33]. A β-actin probe was used for a control.
Figures 4A, 4B:
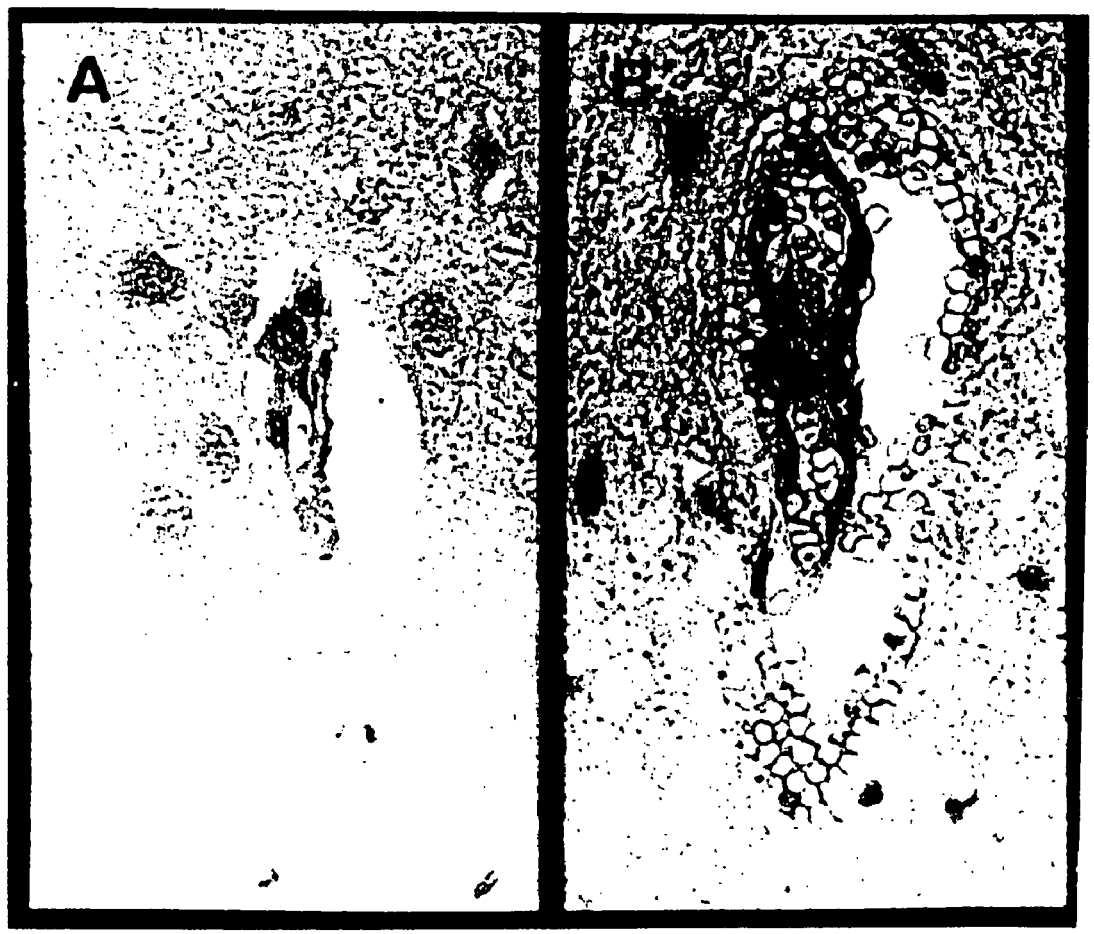
FIGS. 4A and 4B. Expression of Intercellular Adhesion Molecule-1 (ICAM-1) antigen in the cerebral microvasculature 24 hours following middle cerebral artery occlusion. A coronal section of brain was obtained for ICAM-1 immunostaining, so that the noninfarcted and infarcted hemispheres from the same brain could be compared under identical staining conditions. Staining was performed using a rat anti-murine ICAM-1 antibody, with sites of primary antibody binding visualized by alkaline phosphatase.

ICAM-1 Expression in Murine Stroke: To establish the effect of cerebral ischemia/reperfusion in the murine model, ICAM-1 mRNA levels were evaluated following cerebral ischemia and reperfusion in wild type mice. Ipsilateral (infarcted) cerebral hemisphere demonstrated increased ICAM-1 mRNA by Northern blot analysis compared with RNA obtained from the contralateral (noninfarcted) hemisphere from the same animal (FIG. 3). To evaluate ICAM-1 antigen expression in this murine model, wild type mice were subjected to 45 minutes of ischemia followed by 23 hours of reperfusion, and the cerebral microvasculature examined by immunohistochemistry. ICAM-1 antigen expression was not detectable in the cerebral microvasculature contralateral to the infarct (FIG. 4A), but was markedly increased on the ipsilateral side, with prominent ICAM-1 staining of cerebral endothelial cells (FIG. 4B).

Role of ICAM-1 in Stroke: To explore the role of ICAM-1 in stroke, transgenic mice which were homozygous ICAM-1 deficient[24] were studied in the murine model of focal cerebral ischemia and reperfusion. Because variations in cerebrovascular anatomy have been reported to result in differences in susceptibility to experimental stroke in mice[37], India ink staining was performed on the Circle of Willis in homozygous null (ICAM-1 −/−) and ICAM-1 +/+ mice. These experiments (FIG. 5) demonstrated that there were no gross anatomic differences in the vascular pattern of the cerebral circulation. To determine the role of the intercellular adhesion molecule-1 in neutrophil influx following focal cerebral ischemia and reperfusion, neutrophil accumulation was measured in homozygous null ICAM-1 mice (ICAM-1 −/−) mice (n=14) and wild-type controls (n=7) infused with $^{111}$In-labeled neutrophils. Relative neutrophil accumulation (ipsilateral cpm/contralateral cpm) was diminished (39% reduction) in the ICAM-1 −/− mice compared with ICAM-1 +/+ controls (1.70±0.26 vs. 2.9±0.52, p<0.5).

Figure 6A:
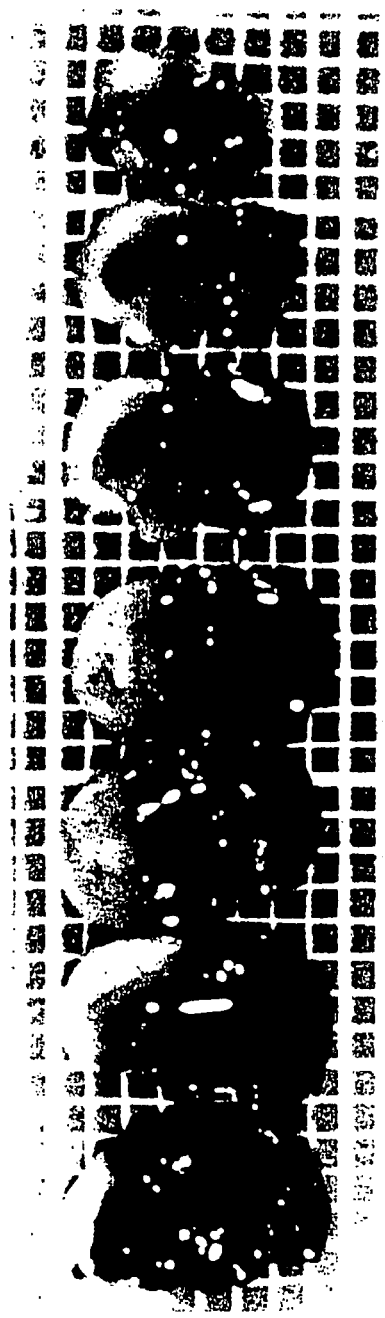
FIGS. 6A and 6B. TTC-stained serial sections at 24 hours from representative wild type (FIG. 6A) or homozygous null ICAM-1 mice (FIG. 6B) subjected to transient middle cerebral artery occlusion. The pale white area in the middle cerebral artery territory represents infarcted brain tissue, whereas viable tissue stains brick red. Quantification of infarct volumes by planimetry of serial cerebral sections in multiple experiments is shown in FIG. 7A.
Figure 6B:
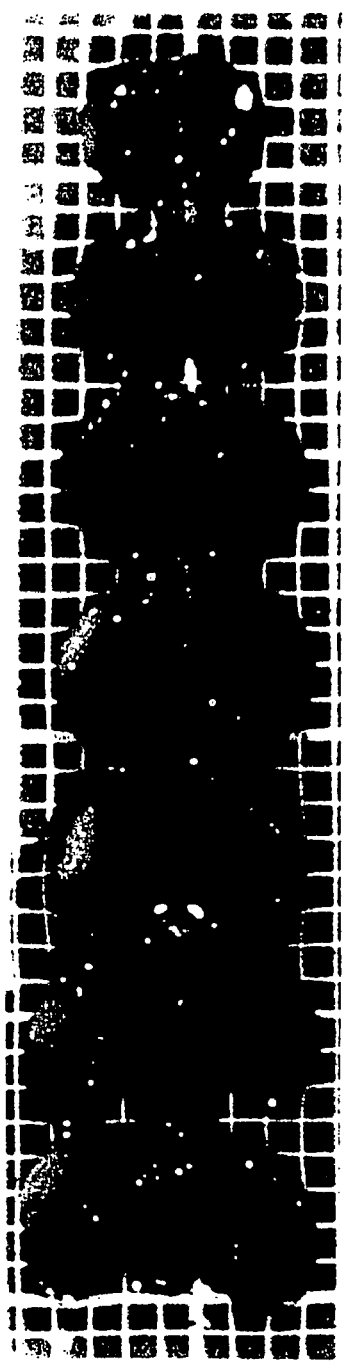
Figure 7A:
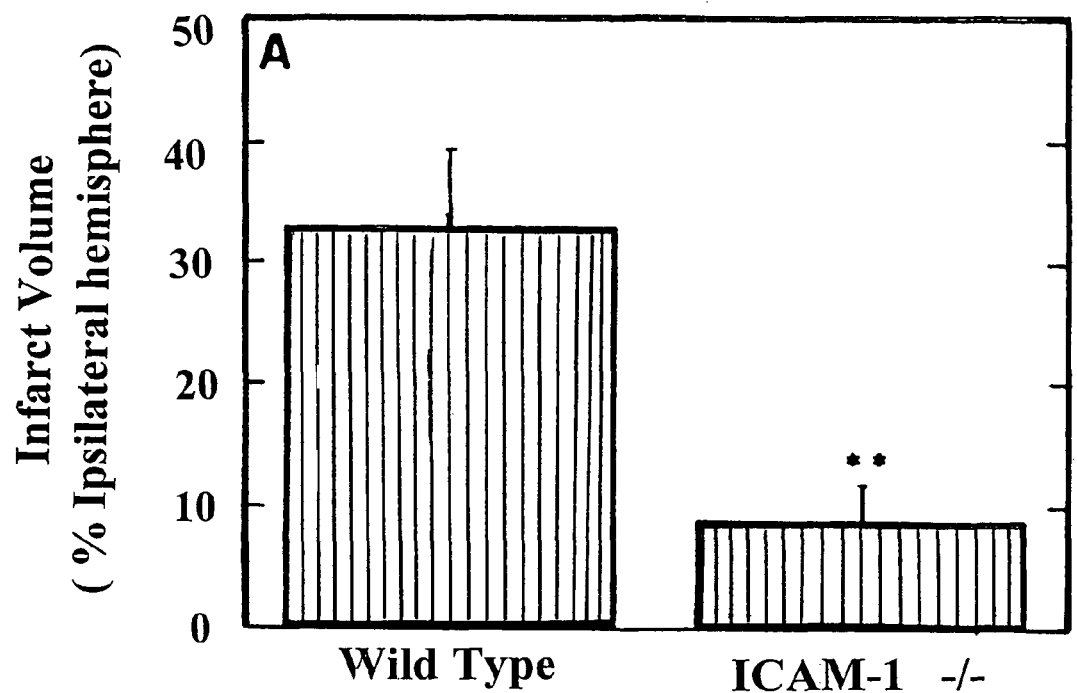
FIGS. 7A, 7B, 7C and 7D. Role of ICAM-1 in stroke outcome. Transient middle cerebral artery occlusion was performed as described in ICAM-1 +/+ (Wild Type, n=16) or ICAM-1 −/− (n=13) mice, and indices of stroke outcome measured as described in FIG. 2.
Figure 7B:
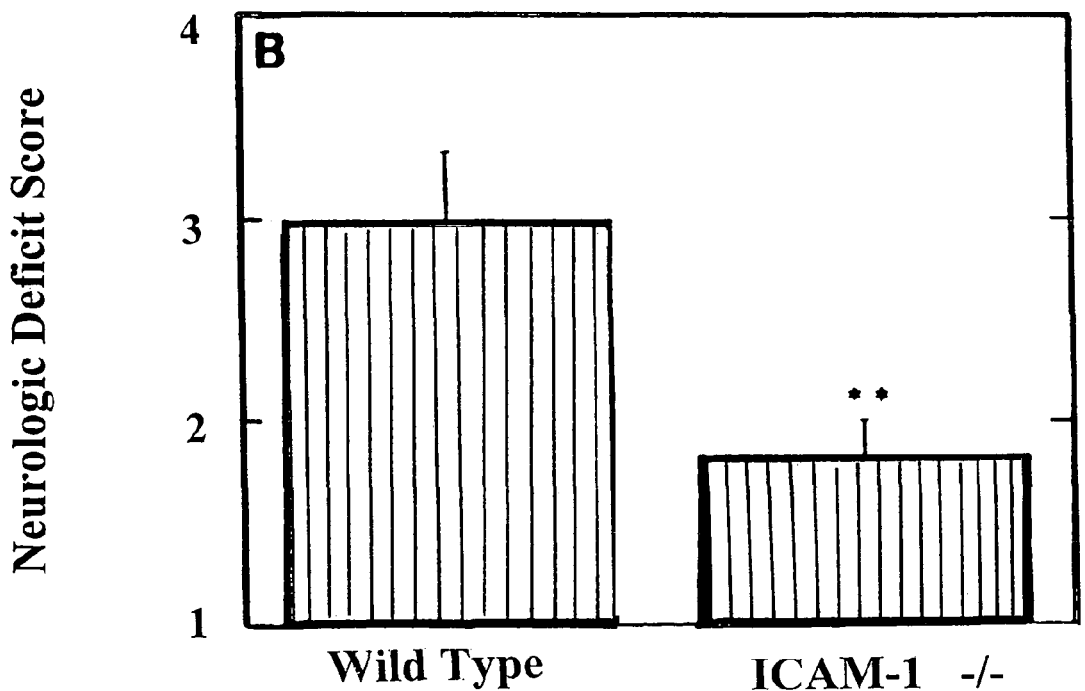
Figure 7C:
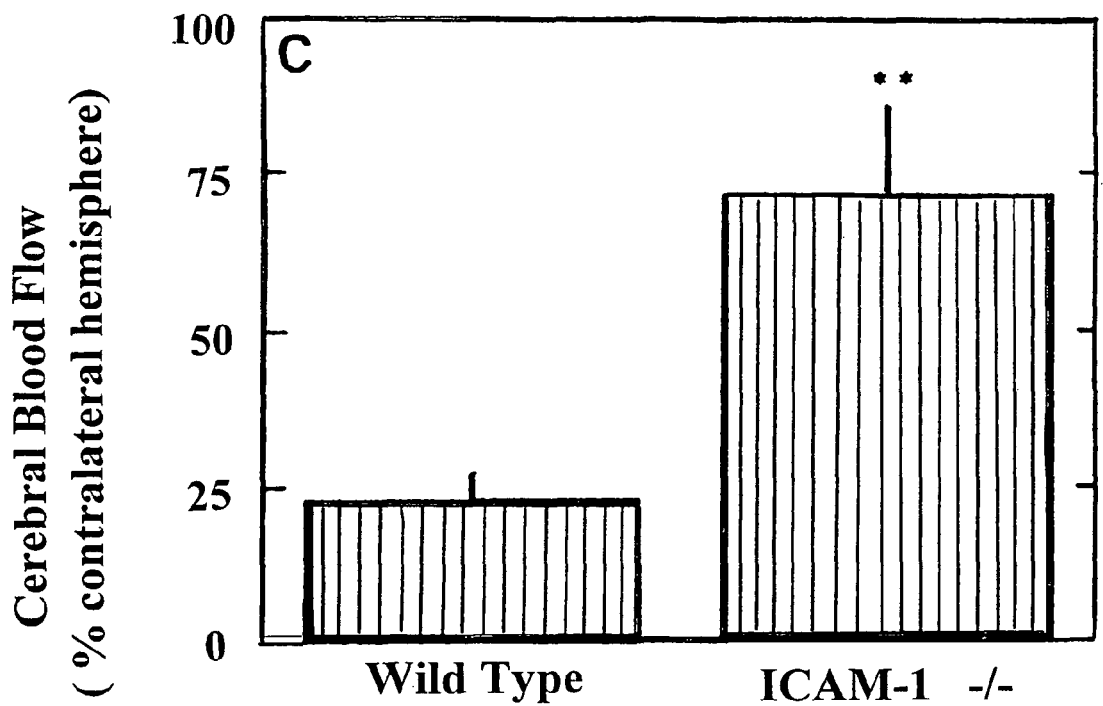
Figure 7D:
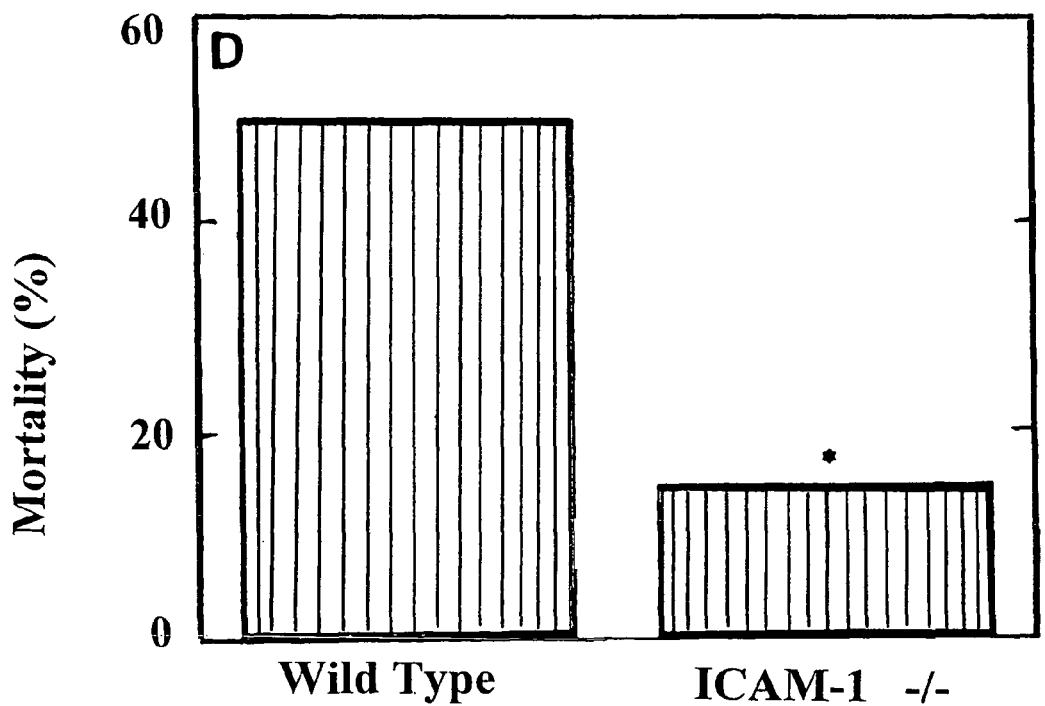

Experiments were then performed to investigate whether expression of ICAM-1 has a pathophysiologic role in outcome following stroke. ICAM-1 −/− mice (n=13) were significantly protected from the effects of focal cerebral ischemia and reperfusion, based on a 3.7-fold reduction in infarct volume (p<0.01) compared with ICAM-1 +/+ controls (FIGS. 6 and 7A). This reduction in infarct volume was accompanied by reduced neurologic deficit (FIG. 7B) and increased post-reperfusion cerebral cortical blood flow (FIG. 7C). Given these results, it was not surprising that mortality was also significantly decreased in the the ICAM-1 −/− mice compared with ICAM-1 +/+ controls (15% vs. 50%, p<0.05; FIG. 7D).

Discussion:

Epidemiologic evidence in humans suggests that neutrophils contribute to both the initiation of stroke[38] as well as to cerebral tissue injury and poor clinical outcome[39], with a potential role for neutrophils in postischemic hypoperfusion, nearonal dysfunction, and scar formation[40-44]. Although there is considerable experimental evidence which suggests that neutrophils can exacerbate tissue damage following stroke[13,45-48], certain pieces of experimental data have stoked controversy by failing to find an association between agents which block neutrophil accumulation and indices of stroke outcome. In a rat model of stroke, antibody-mediated depletion of neutrophils prior to stroke significantly decreased brain water content and infarct size[13]. However, cyclophosphamide-induced leukocytopenia in a gerbil model[49] or anti-neutrophil antibody administration to dogs[50] showed no beneficial effects in global models of cerebral ischemia. Experimental therapy targeted at interfering with neutrophil-endothelial interactions has also produced mixed results. In a feline model of transient focal cerebral ischemia, treatment with antibody to CD18 (the common subunit of $\beta_2$ integrins, which bind to intercellular adhesion molecule-1[51]) did not alter recovery of cerebral blood flow, return of evoked potentials, or infarct volume[23]. Other experiments, however, have found that microvascular patency after transient focal ischemia in primates is improved by antibodies to CD18[14]. In a similar rat model, anti-CD11b/CD18 antibody has also been shown to reduce both neutrophil accumulation and ischemia-related neuronal damage[52].

The experiments reported here show that in a murine model of focal cerebral ischemia and reperfusion, neutrophils accumulate in postischemic cerebral tissue, a finding corroborated in other models which similarly demonstrate increased granulocyte accumulation in areas of low cerebral blood flow early during the post-ischemic period[15,16,36,45]. Not only do neutrophils accumulate during the post-ischemic period in mice, but their presence exacerbates indices of stroke outcome. When animals were made neutropenic prior to the ischemic event, cerebral infarcts were smaller, with improved cerebral perfusion following the ischemic event. These data are quite similar to that reported in a rabbit model of thromboembolic stroke, in which immunodepletion of neutrophils resulted both in reduced infarction volume and improved blood flow[35]. Because neutrophils contribute to murine post-ischemic cerebral injury, a strategy was pursued to elucidate the role of ICAM-1 in the pathophysiology of stroke using deletionally mutant ICAM-1 mice[24]. Experiments indicate that homozygous null ICAM-1 mice are relatively resistant to the deleterious effects of cerebral ischemia and reperfusion.

To demonstrate the role of both neutrophils and ICAM-1 in the pathogenesis of tissue injury in stroke, the studies reported here used several methods for assessing stroke outcome. Although numerous investigators have used TTC staining to quantify cerebral infarct volumes[26,30-32,37,53], there has been some controversy as to the accuracy of this method, especially when evaluated early following the ischemic event. In the TTC method, 2,3,5 triphenyl 2H-tetrazolium chloride (TTC) reacts with intact oxidative enzymes on mitochondrial cristae and is thereby reduced to a colored formazan[54]. TTC staining is unreliable before 2 hours of ischemia have elapsed, beyond 36 hours, cells infiltrating into the infarcted tissue can stain positively with TTC, thereby obscuring the clear demarcation between infarcted and noninfarcted tissues seen with earlier staining[31]. Although the size of the infarct delineated by TTC staining correlates well with infarct size delineated by hematoxylin and eosin staining[30,32], direct morphometric measurements tend to overestimate infarct volumes due to cerebral edema, especially during the first 3 days following the ischemic event[32]. Even given these limitations, however, the studies reported here incorporate three additional methods to define the role of neutrophils and ICAM-1 in stroke outcome, including neurologic deficit score, relative cerebral blood flow to the affected area, and mortality. These additional measures, which do not depend upon the accuracy of TTC staining, contribute strongly to the identification of a pathogenic role for both neutrophils and ICAM-1 in stroke.

There has been a recent profusion of scientific studies exploring the mechanistic basis for neutrophil recruitment to post-ischemic tissues. Endothelial cells appear to be the chief regulators of neutrophil traffic, regulating the processes of neutrophil chemoattraction, adhesion, and emigration from the vasculature[55]. When exposed to a hypoxic environment as a paradigm for tissue ischemia, endothelial cells synthesize the potent neutrophil chemoattractant and activator Interleukin-8 (IL-8)[9], the blockade of which appears to be beneficial in a lung model of ischemia and reperfusion[6]. In addition, hypoxic endothelial cells synthesize the proinflammatory cytokine Interleukin-1[8], which can upregulate endothelial expression of the neutrophil adhesion molecules. E-selectin and ICAM-1 in an autocrine fashion[8,9,56]. Other neutrophil adhesion mechanisms may also be activated in the brain following ischemia, such as release of P-selectin from pre-formed storage pools within Weibel-Palade body membranes[10]. In a primate model, P-selectin expression was rapidly and persistently enhanced following focal middle cerebral artery ischemia and reperfusion[18]. Although P-selectin-dependent neutrophil recruitment appears to be deleterious following cardiac ischemia and reperfusion[57], its pathophysiologic relevance in the setting of stroke has not yet been determined. While hypoxia induces de nova synthesis of the bioactive lipid platelet activating factor (PAF)[11], in a spinal cord ischemia, reperfusion model, PAF antagonism offered no incremental benefit when given simultaneously with antibody to CD11/CD18[48].

Understanding the role of ICAM-1 in the pathophysiology of stroke appears to be of particular relevance in humans for several reasons. Increased cerebrovascular ICAM-1 expression has been demonstrated in primates by 4 hours of ischemia and reperfusion, particularly in the lenticulostriate microvasculature[18]. An autopsy study of recent cerebral infarcts in humans also demonstrated increased ICAM-1 expression[20]. As rats also express cerebral vascular ICAM-1 within 24 hours in both a photochemically-induced model of rat cerebral ischemia[19] as well as a middle cerebral artery occlusion model[12], these data suggested the potential usefulness of transgenic ICAM-1 deficient mice in elucidating the pathophysiologic significance of increased post-cerebral ischemic ICAM-1 expression. In particular, the time frame of ICAM-1 expression (increased by 4 to 24 hours) in these models suggests that ICAM-1 mediated neutrophil-endothelial interactions may be targeted in future pharmacologic strategies to improve human stroke outcome, as this time frame represents a realistic clinical window for therapeutic intervention.

Although neutropenic animals demonstrated increased regional cerebral blood flow compared with controls, compared with neutropenic animals, ICAM-1 deficient mice tended to have even higher ipsilateral cerebral blood flows at 24 hours. This observation may relate to the no-reflow phenomenon, wherein blood flow fails to return to pre-obstruction levels even following release of a temporary vascular occlusion. A significant body of previous work has implicated neutrophil plugging of capillary microvascular beds in this process[58], although in a model of global cerebral ischemia, an 85% reduction in the circulating leukocyte count did not decrease the incidence or severity of reflow failure[49]. The data suggest that non-neutrophil-dependent mechanisms, which nevertheless involve ICAM-1, may contribute to cerebrovascular post-ischemic no-reflow. As macrophages and lymphocytes both express LFA-1, which mediates an adhesive interaction with endothelial cell ICAM-1[51], it is possible that ICAM-1 deficient mice have diminished recruitment of these mononuclear cells, a possibility which is currently the subject of further investigation. This hypothesis is supported by multiple pathologic observations demonstrating macrophage and lymphocyte accumulation by 1-3 days following cerebral infarction[12,17,19,34,59].

Taken together, the studies indicate that in a murine model of focal cerebral ischemia and reperfusion, neutrophils accumulate in the infarcted hemisphere, and that neutropenic animals demonstrate cerebral protection. Increased expression of ICAM-1 on cerebral endothelial cells appears to be an important mechanism driving this neutrophil recruitment, and mice which are unable to express ICAM-1 demonstrate improved post-ischemic blood flows, reduced infarction volumes, and reduced mortality. These data suggest that pharmacologic strategies targeted at interfering with neutrophil-endothelial interactions may improve the outcome following stroke in humans.

References

2. Pinsky D., M. Oz. H. Liao, S. Morris, J. Brett, A. Morales, M. Karakurum, M. Van Lookeren Campagne, R. Nowygrod, and D. Stern. 1993. Restoration of the cyclic AMP second messenger pathway enhances cardiac preservation for transplantation in a heterotopic rat model, J. Clin. Invest 92:2994-3002.

3. Pinsky D. J., M. C. Oz, S. Koga, Z. Taha, M. J. Broekman, A. J. Marcus, H. Liao, Y. Naka, J. Brett, P. J. Cannon, R. Nowygrod, T. Malinski, and D. M. Stern. 1994. Cardiac preservation is enhanced in a heterotopic rat transplant model by supplementing the nitric oxide pathway, J. Clin. Invest. 93: 2291-2297.

4. Lucchesi B. R., S. W. Werns, and J. C. Fantone. 1989. The role of the neutrophil and free radicals in ischemic myocardial injury. J Mol Cell Cardiol 21:1241-1251.

5. Pinsky D. J., Y. Naka, N. C. Chowdhury, H. Liao, M. C. Oz, R. E. Michler, E. Kubaszewski, T. Malinski, and D. M. Stern. 1994. The nitric oxide/cyclic GMP pathway in organ transplantation: critical role in successful lung preservation, Proc. Natl. Acad. Sci. (USA) 91:12086-12090.

6. Sekido N., N. Mukaida, A. Harada, I. Nakanishi, Y. Watanabe, and K. Matsushima. Prevention of lung reperfusion injury in rabbits by a monoclonal antibody against interleukin-8. Nature 1993;365:654-657.

7. Granger D. Role of xanthine oxidase and granulocytes in ischemia-reperfusion injury. Am. J. Physiol. 255:H1269-1275, 1988.

8. Shreeniwas R., S. Koga, M. Karakurum, D. Pinsky, E. Kaiser, J. Brett, B. A. Wolitzky, C. Norton, J. Plocinski, W. Benjamin, D. K. Burns, A. Goldstein, and D. Stern. 1992. Hypoxia-mediated induction of endothelial cell interleukin 1-alpha: an autocrine mechanism promoting expression of leukocyte adhesion molecules on the vessel surface, J. Clin. Invest. 90: 2333-2339.

9. Karakurum M., R. Shreeniwas, J. Chen, D. Pinsky, S. D. Yan, M. Anderson, K. Sunouchi, J. Major, T. Hamilton, K. Kuwabara, A. Rot, R. Nowygrod, and D. Stern. 1994. Hypoxic induction of interleukin-8 gene expression in human endothelial cells, J. Clin. Invest. 93:1564-1570.

10. Geng J-G., M. P. Bevilacqua, K. L. Moore, T. M. McIntyre, S. M. Prescott, J. M. Kim, G. A. Bliss, G. A. Zimmerman; and R. P. McEver. 1990. Rapid neutrophil adhesion to activated endothelium mediated by GMP-140. Nature 343: 757-760.

11. Arnould T., C. Michiels, and J. Remacle. 1993. Increased PMN adherence on ECs after hypoxia: involvement of PAF, CD11/CD18, and ICAM-1. Am. J. Physiol. 264: C1102-1110.

12. Schroeter M., S. Jander, O. W. Witte, and G. Stoll. 1994. Local immune responses in the rat cerebral cortex after middle cerebral artery occlusion. J. Neuroimmunol. 55:195-203.

13. Matsuo Y., H. Onodera, Y. Shiga, M. Nakamura, M. Ninomiya, T. Kihora, and K. Kogure. 1994. Correlation between myeloperoxidase-quantified neutrophil accumulation and ischemic brain injury in the rat: effects of neutrophil depletion. Stroke 25: 1469-75.

14. Mori E., G. J. del Zoppo, J. D. Chambers, B. R. Copeland, and K. E. Arfors. 1992. Inhibition of polymorphonuclear leukocyte adherence suppresses no-reflow after focal cerebral ischemia in baboons. Stroke 23: 712-8.

15. Obrenovitch T. P., K. K. Kumaroo, and J. M. Hallenbeck J M. 1984. Autoradiographical detection of indium-111-labelled platelets in brain tissue section. Stroke 15: 1049-56.

16. Hallenbeck J. M., A. J. Dutka, P. Tanishima, P. M. Kochanek, K. K. Kumaroo, C. B. Thompson, T. P. Obrenovitch, and T. J. Contreras. 1986. Polymorphonuclear leukocyte accumulation in brain regions with low blood flow during the early postischemic period. Stroke 17: 246-53.

17: Garcia J. H. and Y. Kamijyo. 1974. Cerebral infarction: evolution of histopathological changes after occlusion of a middle cerebral artery in primates. J Neuropathol Exp Neurol 33: 408-21.

18. Okada Y., B. R. Copeland, E. Mori, M. M. Tung, W. S. Thomas, and G. J. del Zoppo. 1994. P-selectin and intercellular adhesion molecule-1 expression after focal brain ischemia and reperfusion. Stroke 25: 202-11.

19. Jander S., M. Kraemer, M. Schroeter, O. W. Witte, and G. Stoll. 1995. Lymphocytic infiltration and expression of intercellular adhesion molecule-1 in photochemically induced ischemia in the rat cortex. J. Cerebr. Blood Flow and Metabol. 15:42-51.

20. Sobel R. A., M. E. Mitchell, and G. Fondren. 1990. Intercellular adhesion molecule-1 in cellular immune reactions in the human central nervous system. Am. J. Pathol. 136: 337-354.

21. Clark W. M., K. P. Madden, R. Rothlein, and J. A. Zivin. 1991. Reduction of central nervous system ischemic injury by monoclonal antibody to intercellular adhesion molecule. J Neurosurg 75: 623-27.

22. Clark W. M., K. P. Madden, R. Rothlein, and J. A. Zivin. 1991. Reduction of central nervous system ischemic injury in rabbits using leukocyte adhesion antibody treatment. Stroke 22:877-883.

23. Takeshima R., J. R. Kirsch, R. C. Koehler, A. W. Gomoll, and R. J. Traystman. 1992. Monoclonal leukocyte antibody does not decrease the injury of transient focal cerebral ischemia in cats. Stroke 23: 247-52.

24. Xu H., J. A. Gonzalo, Y. St. Pierre, I. R. Williams, T. S. Kupper, R. S. Cotran, T. A. Springer, and J-C. Gutierrez-Ramos. 1994. Leukocytosis and resistance to septic shock in intercellular adhesion molecule 1-deficient mice. J. Exp. Med. 180:95-109.

25. Hodes R. J., B. S. Handwerger, and W. D. Terry. 1974. Synergy between subpopulations of mouse spleen cells in the in vitro generation of cell-mediated cytotoxicity: involvement of a non-T cell. J. Exp. Med. 140(6):1646-1659.

27. Dirnagl U., B. Kaplan, M. Jacewicz, and W. Bulsinelli. 1989. Continuous measurement of cerebral blood flow by laser-doppler flowmetry in a rat stroke model. J Cereb Blood Flow Metab 9: 589-96.

28. Menzies, S. A., J. T. Hoff, and A. L. Betz. 1992. Middle cerebral artery occlusion in rats: a neurological and pathological evaluation of a reproducible model. Neurosurgery 31:100-107.

29. Bederson; J. B., L. H. Pitts, and M. Tsuji. 1986. Rat middle cerebral artery occlusion: evaluation of the model and development of a neurologic examination. Stroke 17:472-476.

30. Bederson J. B., L. H. Pitts, M. C. Nishimura, R. L. Davis, and H. M. Bartkowski. 1986. Evaluation of 2,3,5-triphenyltetrazolium chloride as a stain for detection and quantification of experimental cerebral infarction in rats. Stroke 17: 1304-8.

31. Liszczak, T. C., E. T. Hedley-Whyte, J. F. Adams, D. H. Han, V. S. Kolluri, F. X. Vacanti, R. C. Heros, and N. T. Zervas. 1984. Limitations of tetrazolium salts in delineating infarcted brain. Acta Neuropathol. 65:150-157.

32. Lin, T.-N., Y. Y. He, G. Wu, M. Khan, and C. Y. Hsu. 1993. Effect of brain edema on infarct volume in a focal cerebral ischemia model in rats. Stroke 24:117-121.

33. Ballantyne C. M., C. A. Kozak, W. E. O'Brien, and A. L. Beaudet. 1991. Assignment of the gene for intercellular adhesion molecule-1 (Icam-1) to proximal mouse chromosome 9. Genomics 9:547-550.

34. Kochanek P. M., and J. M. Hallenbeck. 1992. Polymorphonuclear leukocytes and monocytes/macrophages in the pathogenesis of cerebral ischemia and stroke. Stroke 23(9): 1367-79.

35. Bednar M. M., S. Raymond, T. McAuliffe, P. A. Lodge, and C. E. Gross. 1991. The role of neutrophils and platelets in a rabbit model of thromboembolic stroke. Stroke. 22(1): 44-50.

36. Pozzilli C., G. L. Lenzi, C. Argentino, A. Caroli, M. Rasura, A. Signore, L. Pozzao, and P. Pozzilli. 1985. Imaging of leukocytic infiltration in human cerebral infarcts. Stroke 16: 251-55.
37. Barone F. C., D. J. Knudsen, A. H. Nelson, G. Z. Feuerstein, and R. N. Willette. 1993. Mouse strain differences in susceptibility to cerebral ischemia are related to cerebral vascular anatomy. J. Cereb. Blood Flow Metab. 13:683-692.
38. Prentice R. L., T. P. Szatrowski, H. Kato, and M. W. Mason. 1982. Leukocyte counts and cerebrovascular disease. J. Chronic Dis. 35:703-714.
39. Pozilli C., G. L. Lenzi, C. Argentino, L. Bozzao, M. Rasura, F. Giuabilei, C. Fieschi. 1985. Peripheral white blood cell count in cerebral ischemic infarction. Acta Neurol. Scand. 71:396-400.
40. Ernst E., A. Matrai, F. Paulsen. 1987. Leukocyte rheology in recent stroke. Stroke 18: 59-62.
41. Grogaard B., L. Schurer, B. Gerdin, and K. E. Arfors. 1989. Delayed hypoperfusion after incomplete forebrain ischemia in the rat: the role of polymorphonuclear leukocytes. J Cereb Blood Flow Metab 9: 500-5.
42. Hallenbeck J. M., A. J. Dutka A J, P. M. Kochanek, A. Siren, G. H. Pezeshkpour, and G. Feurstein. 1988. Stroke risk factors prepare rat brainstem tissues for modified local Shwartzman reaction. Stroke 19: 863-9.
43. Kintner D. B., P. W. Kranner, and D. D.. Gilboe. 1986. Cerebral vascular resistance following platelet and leukocyte removal from perfusate. J Cereb Blood Flow Metab 6: 52-58.
44. Mercuri M., G. Ciuffetti, M. Robinson, and J. Toole. 1989. Blood cell rheology in acute cerebral infarction. Stroke 20: 959-62.
45. Clark R. K., E. V. Lee, R. F. White, Z. L. Jonak, G. Z. Feuerstein, and F. C. Barone. 1994. Reperfusion following focal stroke hastens inflammation and resolution of ischemic injured tissue. Brain Research Bulletin. 35(4): 387-92.
46. Dutka A. J., P. M. Kochanek, and J. M. Hallenbeck. 1989. Influence of granulocytopenia on canine cerebral ischemia induced by air embolism. Stroke 20: 390-5.
47: Clark R. K., E. V. Lee, C. J. Fish, R. F. White, W. J. Price, Z. L. Jonak, G. Z. Feuerstein, and F. C. Barone. 1993. Development of tissue damage, inflammation and resolution following stroke: an immunchistochemical and quantitative planimetric study. Brain Res. Bulletin. 31(5):565-72.
48. Lindsberg P. J., A. L. Siren, G. Z. Feuerstein, and J. M. Hallenbeck. 1995. Antagonism of neutrophil adherence in the deteriorating stroke model in rabbits. J. Neurosurgery. 82(2):269-77.
49. Aspey B. S., C. Jessimer, S. Pereira, M. J. G. Harrison. 1989. Do leukocytes have a role in the cerebrovascular no-reflow phenomenon? J. Neurol. Neurosurg. Psychiatry 52:526-528.
50. Schott R. J.; J. E. Natale, S. W. Ressler, R. E. Burney, L. G. Alecy. 1989. Neutrophil depletion fails to improve outcome after cardiac arrest in dogs. Ann. Emerg. Med. 18:517-522.
51. Springer T. A. 1990. Adhesion receptors of the immune system. Nature 346:425-434.
52. Chopp M., R. L. Zhang, H. Chen, Y. Li, N. Jiang, and J. R. Rusche. 1994. Postischemic administration of an anti-Mac-1 antibody reduces ischemic cell damage after transient middle cerebral artery occlusion in rats. Stroke 25: 869-76.
53. Huang Z., P. L. Huang, N. Panahian, T. Dalkara, M. C. Fishman, and M. A. Moskowitz. 1994. Effects of cerebral ischemia in mice deficient in neuronal nitric oxide synthase. Science 265:1883-85.
54. Nachlas, M. M., K. C. Tson, E. D. Souza, C. S. Chang, and A. M. Seligman. 1963. Cytochemical demonstration of succinic dehydrogenase by the use of a new p-nitrophenyl substituted ditetrazole. J. Histochem. Cytochem. 5:420-436.
55. Pinsky D. J., and D. M. Stern. 1994. Hypoxia-Induced modulation of endothelial cell function, (in Reperfusion injury and clinical capillary leak syndrome, B. Zikria and M. C. Oz, and R. W. Carlson, eds.), Futura Publishing, Connecticut, pp. 31-55.
56. Pober J. 1988. Warner-Lambert Parke Davis Award Lecture: cytokine-mediated activation of vascular endothelium. Am. J. Pathol: 133:426-422.
57. Weyrich, A. S., X-L. Ma, D. J. Lefer, K. H. Albertine, and A. M. Lefer. 1993. In vivo neutralization of P-selectin protects feline heart and endothelium in myocardial ischemia and reperfusion injury. J. Clin. Invest. 91: 2629-2629.
58. Jerome S. N., M. Dore, J. C. Paulson, C. W. Smith, and R. J. Korthuis. 1994. P-selectin and ICAM-1-dependent adherence reactions: role in the genesis of postischemic no-reflow. Am. J. Physiol. 266(4 Pt 2):H1316-21.
59. Sornas R., H. Ostlund, and R. Muller. 1972. Cerebrospinal fluid cytology after stroke. Arch-Neurol 26: 489-501.

Example 2

Hypoxia-Induced Exocytosis of Endothelial Cell Weibel-Palade Bodies: A Mechanism for Rapid Neutrophil Recruitment Following Cardiac Preservation The period of hypoxia (H) is an important priming event for the vascular dysfunction which accompanies reperfusion, with endothelial cells (ECs) and neutrophils (PMNs) playing a central role. It was hypothesized that EC Weibel-Palade (WP) body exocytosis during the hypoxic/ischemic period during organ preservation permits brisk PMN recruitment into post-ischemic tissue, a process further amplified in an oxidant-rich mileu. Exposure of human umbilical vein ECs to an hypoxic environment ($pO_2$=20 torr) stimulated release of von Willebrand factor (vWF), stored in EC WP bodies, as well as increased expression of the WP body-derived PMN-adhesion molecule P-selectin at the EC surface. Increased binding of $^{111}$In-labelled PMNs to hypoxic EC monolayers (compared with normoxic controls) was blocked with a blocking antibody to P-selectin, but was not effected by a nonblocking control antibody. Although increased P-selectin expression and vWF release were also noted during reoxygenation, H alone (even in the presence of antioxidants) was sufficient to increase WP body exocytosis. To determine the relevance of these observations to hypothermic cardiac preservation, during which the $pO_2$ within the cardiac vasculature declines to similarly low levels, experiments were performed in a rodent (rat and mouse) cardiac preservation/transplantation model. Immunodepletion of recipient PMNs or administration of a blocking anti-P-selectin antibody prior to transplantation resulted in reduced graft neutrophil infiltration and improved graft survival, compared with identically preserved hearts transplanted into control recipients. To establish the important role of endothelial P-selectin expression on the donor vasculature, murine cardiac transplants were performed using homozygous P-selectin deficient and wild type control donor hearts flushed free of blood/platelets prior to preservation/transplantation. P-selectin null hearts transplanted into wild-type recipients demonstrated a marked (13-fold) reduction in graft neutrophil infiltration and increased graft survival compared with wild type hearts transplanted into wild type recipients. To determine whether coronary endothelial Weibel-Palade body exocytosis may occur during cardiac preservation in humans, the release of vWF into the coronary sinus was measured in 32 patients during open heart surgery. Coronary sinus samples obtained at the start and conclusion of the ischemic period demonstrated an increase in coronary sinus vWF antigen (by ELISA) consisting of predominantly high molecular weight multimers (by immunoelectrophoresis). These data suggest that EC Weibel-Palade body exocytosis occurs during hypothermic cardiac preservation, priming the vasculature to rapidly recruit PMNs during reperfusion.

Introduction:

Endothelial cells (EC) adapt to hypoxia with a characteristic repertoire of responses (1), ranging from increased expression of endothelin (2) to increased synthesis of basic fibroblast growth factor (3). Recent studies have indicated that many features of the EC response to hypoxia parallel features of the inflammatory response; hypoxia selectively upregulates EC expression of Interleukins-1 (4), 6 (5), and 8 (6), platelet activating factor (PAF) (7,8), and ICAM-1 (4), which serve to fuel neutrophil (PMN) recruitment, adhesion, and activation at ischemic loci. Although these mechanisms may explain the later phases of reperfusion injury, the rapidity with which PMNs are recruited to reperfused myocardium following a period of hypothermic preservation suggests that mechanisms are involved which do not require de novo protein synthesis. In this regard, P-selectin may figure prominently in the earliest phases of PMN adhesion to the reperfused vasculature, as ECs may rapidly express pre-formed P-selectin from subplasmalemmal storage sites in Weibel-Palade body (9) membranes in response to the abundant oxygen free-radicals generated in the reperfusion milieu (10-12). Furthermore, recent data have pointed to a role for P-selectin-mediated leukocyte arrest in leukostasis and tissue damage associated with lung injury (13) and cardiac ischemia (14). Taken together, these findings led to the hypothesis that the hypoxic/ischemic period associated with hypothermic myocardial preservation primes the vasculature for its characteristic reponse during reperfusion by displaying P-selectin prominently at the EC surface prior to reperfusion, serving as a spark which ignites and amplifies the subsequent inflammatory response.

The experiments were designed to establish whether hypoxia per se (or hypothermic cardiac preservation, as occurs during cardiac surgery, in which the $pO_2$ within the coronary bed declines to $pO_2 > 20$ Torr) (15) would result in WP body exocytosis. Furthermore, experiments were undertaken to determine the role of P-selectin-dependent PMN adhesion in the cardiac graft failure which characteristically follows a period of prolonged hypothermic preservation. The results show that hypoxia is sufficient to induce EC WP body exocytosis, even in the absence of reoxygenation (and presence of antioxidants), and that the resulting P-selectin expression causes ECs to bind PMNs in vitro.

In rodents, the adverse consequences of P-selectin expression following hypothermic cardiac preservation can be completely abrogated by either neutrophil depletion, P-selectin blockade, or by transplanting hearts whose endothelial cells fail to express P-selectin. Because WP body exocytosis also occurs in patients undergoing open heart surgery during the period of hypothermic cardiac preservation, these data suggest that P-selectin blockade may represent a target for pharmacological intervention to improve cardiac preservation in humans.

Methods:

Endothelial cell culture and exposure of cells to H or H/R. Human umbilical vein ECs were prepared from umbilical cords and grown in culture by the method of Jaffe (16) as modified by Thornton (17). Experiments utilized confluent ECs (passages 1-4) grown in Medium 199 supplemented with fetal bovine serum (15%; Gemini, Calabasas, Calif.), human serum (5%; Gemini), endothelial growth supplement (Sigma, St. Louis, Mo.), heparin (90 µg/ml; Sigma) and antibiotics, as described (17). When ECs achieved confluence, experiments were performed by placing cultures in an environmental chamber (Coy Laboratory Products, Ann Arbor, Mich.) which provided a controlled temperature (37° C.) and atmosphere with the indicated amount of oxygen, carbon dioxide (5%) and the balance made up of nitrogen. Use of this chamber for cell culture experiments has been described previously (15,18). During exposure of ECs to hypoxia (for a maximum of 16 hours), the oxygen tension in the culture medium was 14-18 torr and there was no change in the medium pH. Reoxygenation was performed by placing ECs in an ambient atmosphere containing carbon dioxide (5%) at 37° C.

Measurement of Weibel-Palade body exocytosis: ECs were plated into 24 well plates, rinsed 3 times with Hank's balanced salt solution, and then exposed to hypoxia or to normoxia for the indicated durations. For experiments in which vWF was measured, cells were maintained in serum-free medium. All other EC experiments were performed in the EC growth medium described above. For measurement of vWF, 200 µL aliquots of culture supernatant was removed at the indicated times, and a commercially available ELISA (American Diagnostica, Greenwich, Conn.), based on a polyclonal goat anti-human vWF antibody, was performed on duplicate specimens, with a standard curve generated using purified human vWF antigen supplied by the same vendor. EC P-selectin expression was determined by measuring the specific binding of a murine monoclonal anti-human P-selectin antibody (WAPS 12.2 clone, Endogen, Cambridge, Mass.; this is an IgG1 which recognizes a calcium sensitive epitope and blocks P-selectin dependent neutrophil adhesion. Antibody was radiolabelled with $^{125}$I by the lactoperoxidase method (19) using Enzymobeads (Bio-Rad, Hercules, Calif.), stored at 4° C. and used within one week of labelling. Binding assays were performed on HUVECs plated on 96 well plates, in which fresh M199 with 0.1% bovine serum albumin (Sigma, St. Louis, Mo.) was added immediately prior to each experiment. Cells were placed in a humidified environment at 37° C., and exposed to normoxia or H (in the presence or absence of 50 µM probucol, as indicated, Sigma) for the indicated durations. Cell monolayers were fixed for 15 min. with 1% paraformaldehyde[10] (cells exposed to H were fixed while still within the hypoxic environment), visually inspected to ensure that the monolayers remained intact, and washed twice with HBSS containing 0.5% bovine serum albumin (HBSS/A). Monolayers were then exposed to $10^5$ cpm of $^{125}$I-labelled anti-P-selectin antibody (WAPS 12.2) in the presence of 200 µg/mL of either unlabelled blocking antibody (WAPS 12.2) or nonblocking anti-P-selectin IgG of the same isotype (anti-GMP-140, AC1.2 clone, Becton-Dickinson, San Jose, Calif.) (20,21). After binding for 1 hour at 37° C., monolayers were washed 4 times with HBSS/A, and bound antibody was eluted with 1% triton X-100 in PBS (200 µL/well) and counted. For certain experiments, cycloheximide (10 µg/mL, Sigma) was added at the start of the 4 hour normoxic or hypoxic period, as indicated. In separate experiments, designed to determine the degree of inhibition of protein synthesis by cycloheximide treatment, ECs were incubated with methionine- and cysteine-poor minimal essential medium (Gibco, Grand Island, N.Y.) in the presence of $^{35}$S-methionine and $^{35}$S-cysteine (either in the presence or absence of cyloheximide, 10 µg/mL) (3). Following 4 hours of normoxic exposure, trichloroacetic acid-precipitable material was collected and counted.

Preparation of human PMNs and Measurement of Binding: In brief, citrated blood from healthy donors was diluted 1:1 with NaCl (0.9%) followed by gradient ultracentrifugation on Ficoll-Hypaque (Pharmacia, Piscataway, N.J.). Following hypotonic lysis of residual erythrocytes (20 sec exposure to distilled $H_2O$ followed by reconstitution with 1.8% NaCl), PMNs were suspended in HBSS with 5 mg/mL of human serum albumin (HBSS/HSA). 50-200×$10^6$ PMNs were suspended in HBSS/HSA in the presence of 0.2-0.5 µCi of $^{111}$Indium oxine (Amersham Mediphysics, Port Washington, N.Y.) for 15 minutes at 37° C. After washing with HBSS/HSA, PMNs were gently pelleted (450 g), and resuspended in HBSS/HSA to a final concentration of 5.5×$10^6$ PMNs/mL. Following gentle agitation, 100 µL of the radiolabelled PMN suspension was added to each well at the indicated time, incubated for 30 minutes at 37° C., and then washed 4 times with HBSS/HSA. Monolayers were then treated with 1 N NaOH and the contents of each well withdrawn and counted.

Heterotopic Rat and Mouse Cardiac Transplant Model. Cardiac transplants were performed in the Ono-Lindsey heterotopic isograft model of cardiac transplantation (15,18,22). Briefly, male Lewis rats (250-300 grams, Harlan Sprague Dawley, Indianapolis, Ind.) were anesthetized, heparinized, and the donor heart rapidly harvested following hypothermic high potassium cardioplegic arrest. Hearts were preserved by flushing the coronary arteries with 4° C. lactated Ringer's (LR) solution (Baxter, Edison, N.J.); sixteen hours of immersion in the same solution at 4° C., followed by heterotopic transplantation into gender/strain matched recipients, with sequential donor and recipient aortic and donor pulmonary arterial/recipient inferior vena caval anastomoses performed. Graft survival was assessed by the presence/absence of cardiac electrical/mechanical activity exactly ten minutes following reestablishment of blood flow, after which the graft was excised and neutrophil infiltration was quantified by myeloperoxidase activity, measured as previously described (15,18). For certain experiments, neutrophil depletion of recipient rats was accomplished by administering a polyclonal rabbit anti-rat neutrophil antibody (23-25) (Accurate Scientific, Westbury N.Y.) as a single intravenous injection 24 hours prior to the transplantation procedure. Neutrophil depletion in these animals was confirmed and quantified by counting remaining neutrophils, identified on Wright-Giemsa stained smears of peripheral blood. In other experiments, a blocking anti-P-selectin IgG (250 µg/rat, Cytel, San Diego, Calif.) (13,14,26) was administered intravenously 10 minutes prior to the onset of reperfusion. Murine heart transplants were performed in an identical fashion using homozygous P-selectin null or wild-type control male mice with a C57BL/6J background (27), with the harvested hearts immediately flushed free of native blood with 1.0 mL of 4° C. LR administered down a cross-clamped aortic root followed by period of hypothermic preservation consisting of three hours of immersion in lactated Ringer's solution at 4° C.

Measurement of vWF in Coronary Effluent from Hypothermically Preserved Rat and Human Hearts:

Human coronary sinus samples. After obtaining informed consent, coronary sinus blood was obtained at the start and conclusion of routine cardiac surgery in an unselected series of 32 patients, with simultaneous sampling of peripheral (arterial) blood in six. Coronary sinus samples were obtained from a retrogade perfusion catheter which was routinely placed in patients undergoing cardiopulmonary bypass. Plasma samples were centrifuged for 5 min at 1500× g to sediment cellular elements, and the plasma aliquoted and frozen at −70° C. until the time of assay. ELISAs were performed for vWF (as described above) and thrombomodulin (Asserchron Thrombomodulin, Diagnostica Stago).

vWF immunoelectrophoresis: Multimeric composition of the vWF in coronary sinus plasma samples and endothelial cell supernatants was evaluated by performing agarose gel immunoelectrophoresis. Samples were diluted 1:10, 1:20, and 1:30 (as indicated) and incubated for 30 minutes at 37° C. in Native Sample Buffer (Bio-Rad). Samples (20 µL) were then electrophoresed in a 1.5% agarose gel (0.675 g Low $M^r$ agarose, Bio-Rad; 0.045 g SDS; 45 mL Tris-Tricine SDS Buffer [Bio-Rad]). Molecular weight markers run simultaneously on agarose gels were visualized by marking and dividing the gel, with molecular weight marker locations assigned by Coomasie blue staining. The remaining half of the gel was washed in sodium borate (0.01 M) for 30 minutes followed by overnight electrophoretic transfer to a nitrocellulose membrane. The membrane was washed with washing buffer consisting of tris-buffered saline (pH 7.5) with 0.05% Tween-20, and then blocked for 1 hour with 50 mL of washing buffer containing 2.5 g of Carnation instant milk. After rinsing with physiologic saline, the membrane was immersed overnight in washing buffer containing 1 g/dL gelatin and a 1:500 dilution of rabbit anti-human vWF serum (American Bioproducts, Parsippany, N.J.). After washing 5 times with washing buffer, the membrane was immersed for 3 hours with gentle shaking in washing buffer containing 1 g/dL gelatin and 16.6 µL of goat anti-rabbit horseradish peroxidase conjugated IgG (Bio-Rad), and developed with 60 mL of HRP Developer (30 mg HRP Developer powder, Bio-Rad; 10 mL methanol; 50 mL tris-buffered saline; 50 µL of 30% hydrogen peroxide added just prior to use).

Statistics. Analysis of variance was used to compare 3 or more conditions, with post-hoc comparisons tested using Tukey's procedure. Graft survival data was analyzed using contingency analysis with the Chi-square statistic. Paired comparison of serial measurements (human CS and peripheral blood samples at the start and conclusion of cardiac surgery) were compared using Student's t-test for paired variables. Values are expressed as means±SEM, with a p<0.05 considered statistically significant.

Results:

Exposure of cultured ECs to hypoxia results in the release of vWF and translocation of P-selectin to the cell surface. Previous studies have shown that exposure of endothelial cells to hypoxia results in an elevation in intracellular calcium (28). In view of the association of increased cytosolic calcium with EC Weibel-Palade body exocytosis in response to thrombin or histamine (29,30), it was considered whether exposure of ECs to hypoxia could initiate this process. ECs placed in an hypoxic environment (p$O_2$ 20 torr) released more vWF into the culture supernatants than their normoxic counterparts (FIG. 8A, ELISA; confirmed by immunoelectrophoresis, data not shown). Although a trend towards enhanced levels of vWF was first noted by 1 hour of hypoxia, the differences between normoxic and hypoxic vWF levels did not become statistically significant until 4 hours of exposure, thereafter increasing steadily for up to 12 hours of observation. To determine whether the increased vWF release seen by 4 hours of hypoxia was due to release of pre-formed. vWF, similar experiments were performed in the presence of 10 µg/ml cycloheximide to inhibit protein synthesis. These experiments showed that addition of cycloheximide at the start of the hypoxic period decreased hypoxia-induced vWF release by 12.5%, suggesting that the majority of vWF released by hypoxic exposure was preformed.

Figure 8B:
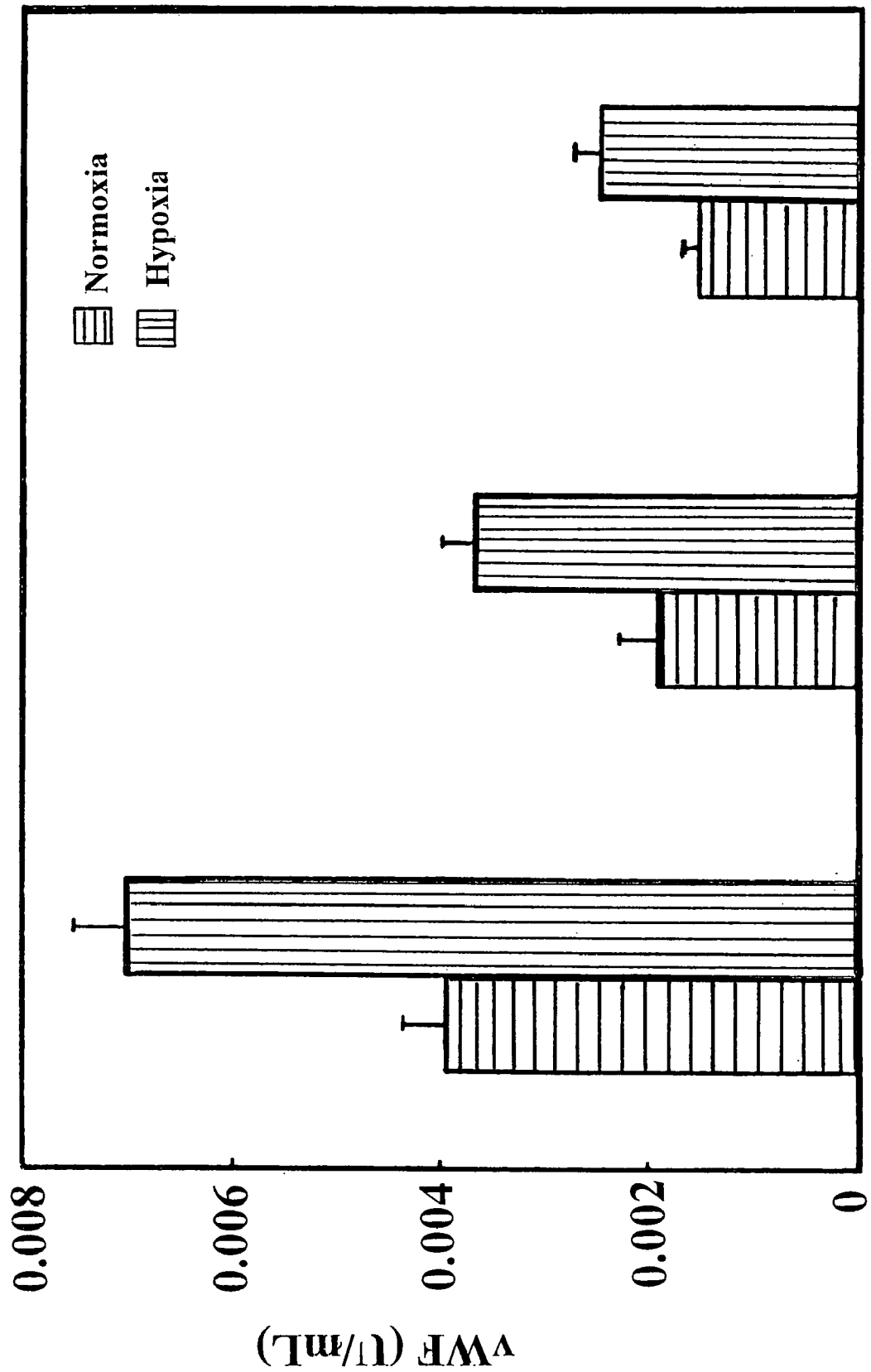

Although these experiments were done in their entirety within the hypoxia environment (i.e., there was no reoxygenation), to further demonstrate that this H-mediated exocytosis of Weibel-Palade bodies was independent of the formation of reactive oxygen intermediates, the antioxidant probucol (50 μM) was added to the ECs at the onset of H and was found to have no effect (vWF $4.7\pm0.31\times10^{-3}$ U/ml at 6 hours of H). The presence of probucol did blunt the further increase in vWF levels seen following reoxygenation of the hypoxic ECs. The calcium-dependence of hypoxia-induced Weibel-Palade body exocytosis was demonstrated by experiments in which ECs were placed in a calcium-free medium at the start of hypoxic exposure. Absence of extracellular calcium attenuated H-induced EC release of vWF, and addition of EGTA had an even more suppressive effect (basal endothelial release of vWF was also diminished by the reduction of extracellular calcium) (FIG. 8B).

Figure 9A:
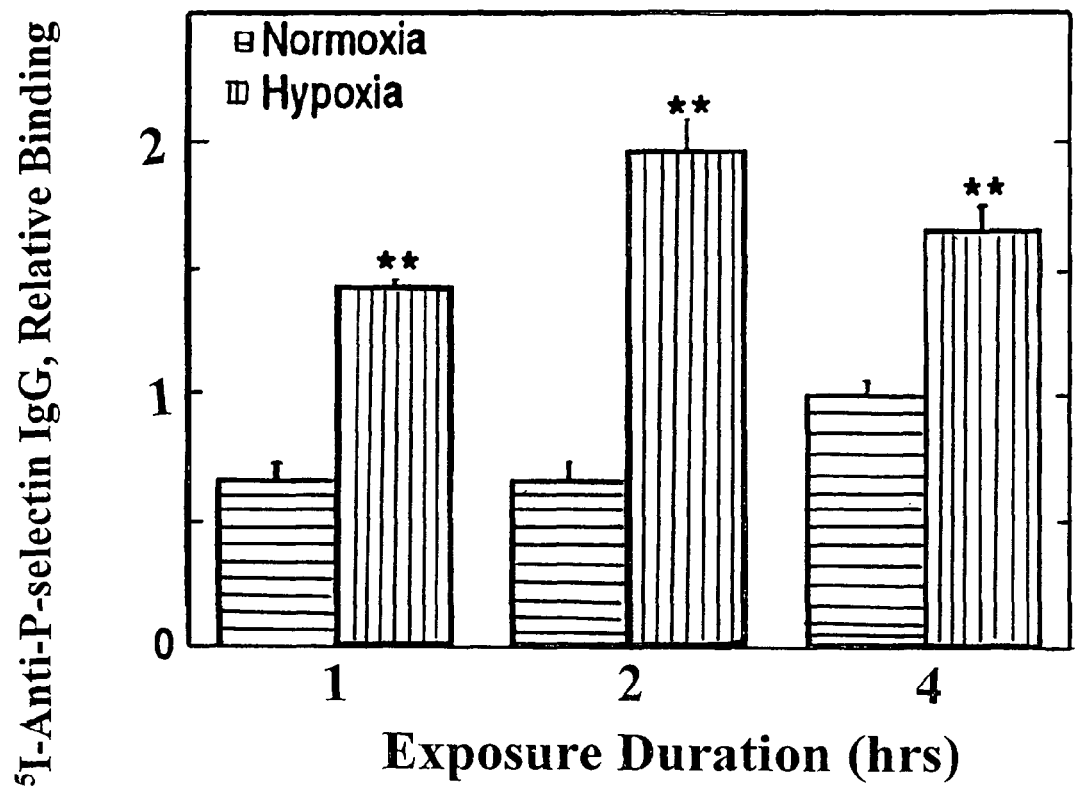
FIGS. 9A, 9B 9C and 9D. Effect of endothelial hypoxia on P-selectin expression and neutrophil adhesion.

To determine whether hypoxia also induced translocation of P-selectin to the EC plasmalemmal surface, specific binding of $^{125}$I-labelled anti-P selectin IgG to normoxic or hypoxic EC monolayers was examined. Binding studies were performed on EC monolayers fixed with paraformaldehyde while still within the hypoxic environment, to obviate oxygen-free radical-induced P-selectin expression during reoxygenation. These studies demonstrated enhanced binding of $^{125}$I-anti-P-selectin IgG by hypoxic compared with normoxic ECs (FIG. 9A). This binding was blocked by unlabelled blocking anti-P-selectin IgG, but not by a nonblocking control anti-P-selectin IgG of the same isotype. Surface expression of P-selectin was noted at the earliest time points observed (60 minutes of H), and was observed at similar levels throughout the period of hypoxic exposure (up to 4 hours of observation). It is possible that hypoxia-induced endothelial P-selectin expression was detected at time points preceding a statistically significant increase of vWF release in similarly treated cells, because a portion of the initially secreted vWF binds tightly to subendothelial matrix (31).

Figure 9B:
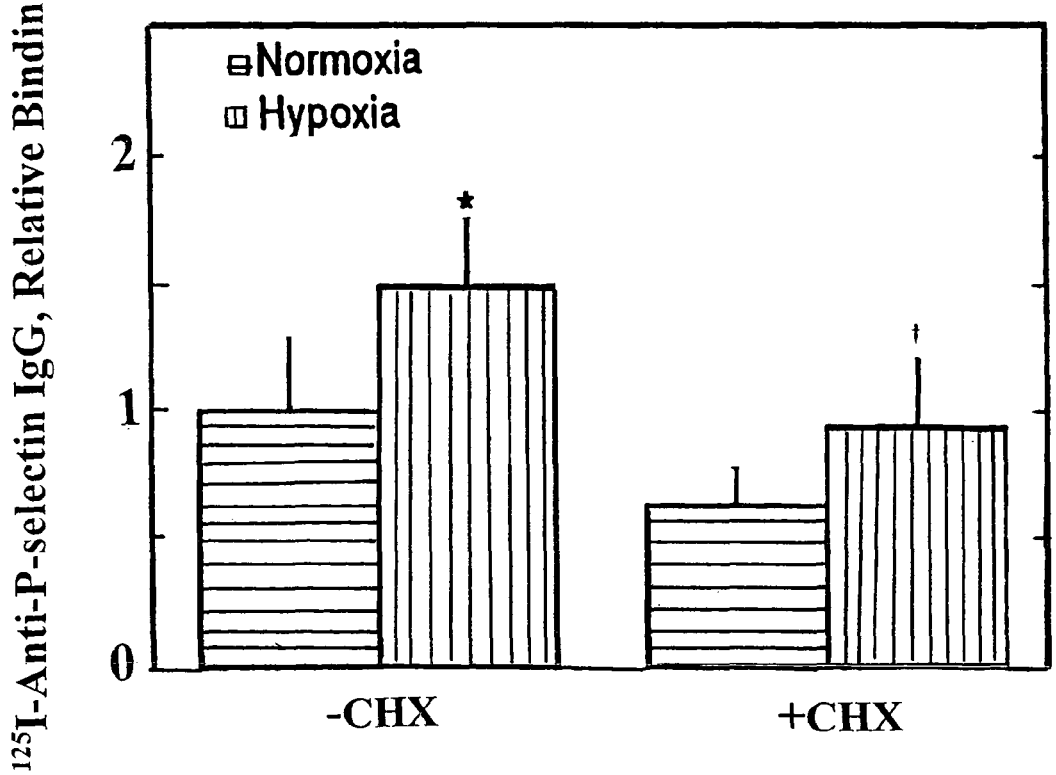
Figure 9C:
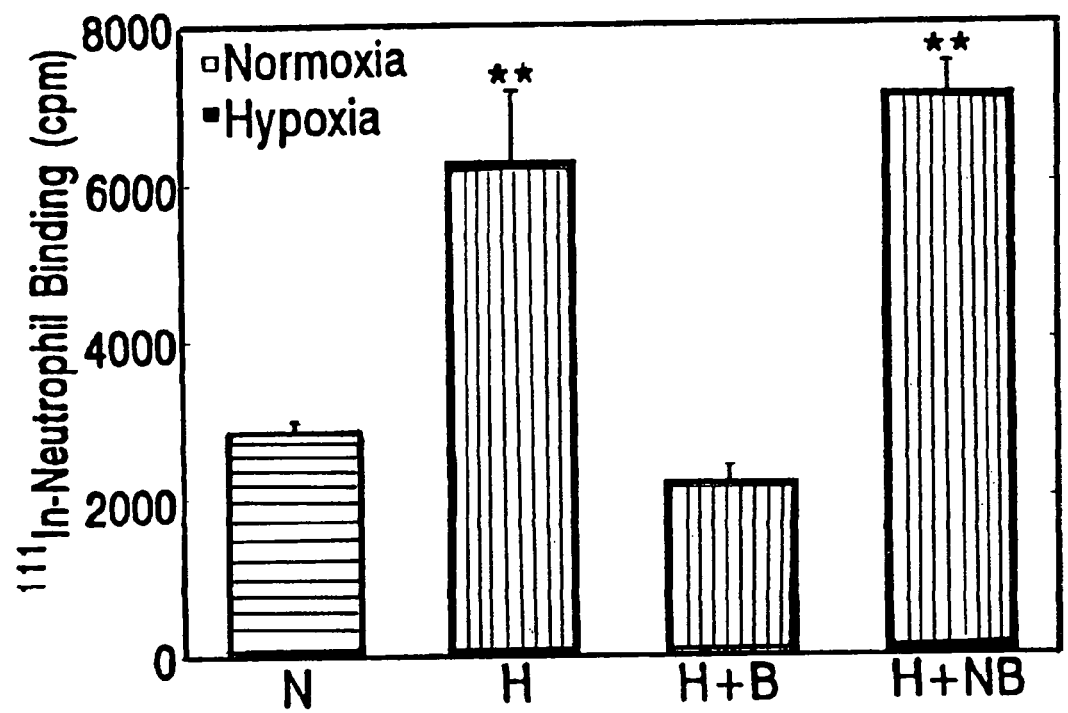
Figure 9D:
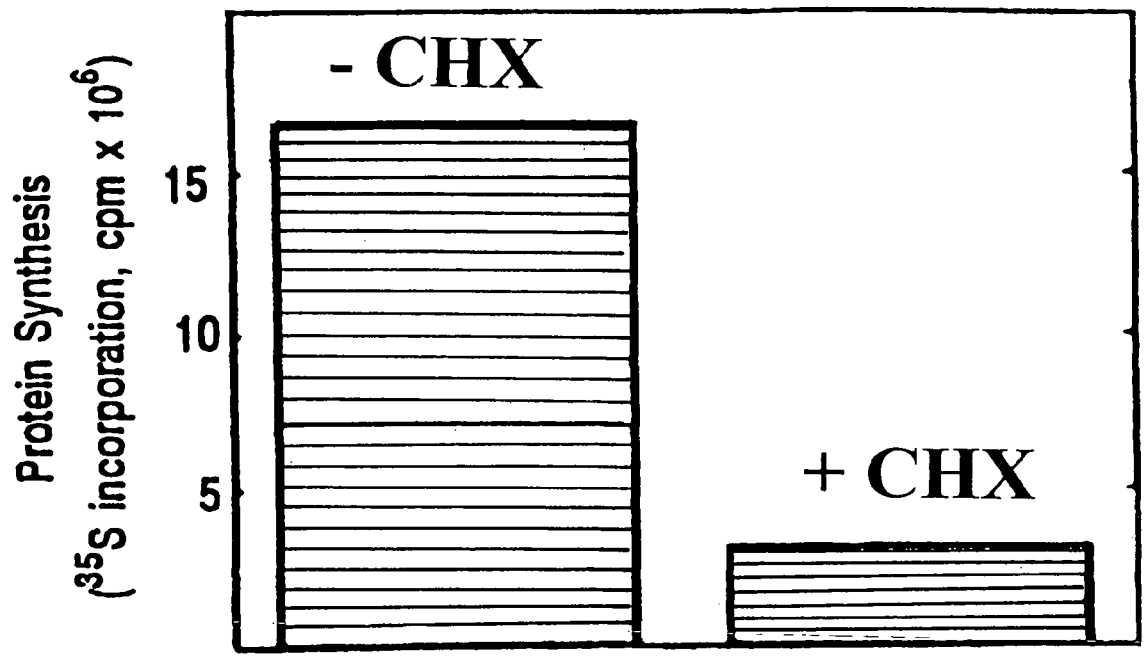

To determine whether protein synthesis was required for hypoxia-induced P-selectin expression, a separate experiment was performed in which cyloheximide was given at the onset of normoxia or H, and binding of radiolabelled anti-P-selectin IgG determined at the 4 hour time point. This experiment demonstrated that even with >85% inhibition of protein synthesis (FIG. 9B, Inset), hypoxia still increased endothelial P-selectin expression, albeit at reduced levels (FIG. 9B). To establish that hypoxia-induced cell-surface P-selectin may participate in neutrophil binding, human neutrophils radiolabelled with $^{111}$indium oxine were incubated with hypoxic ECs; enhanced binding to hypoxic monolayers was observed. Hypoxia-induced $^{111}$In-PMN binding was blocked by the addition of a blocking anti-P-selectin IgG, but not by a nonblocking anti-P-selectin IgG (FIG. 9C).

Figure 10A:
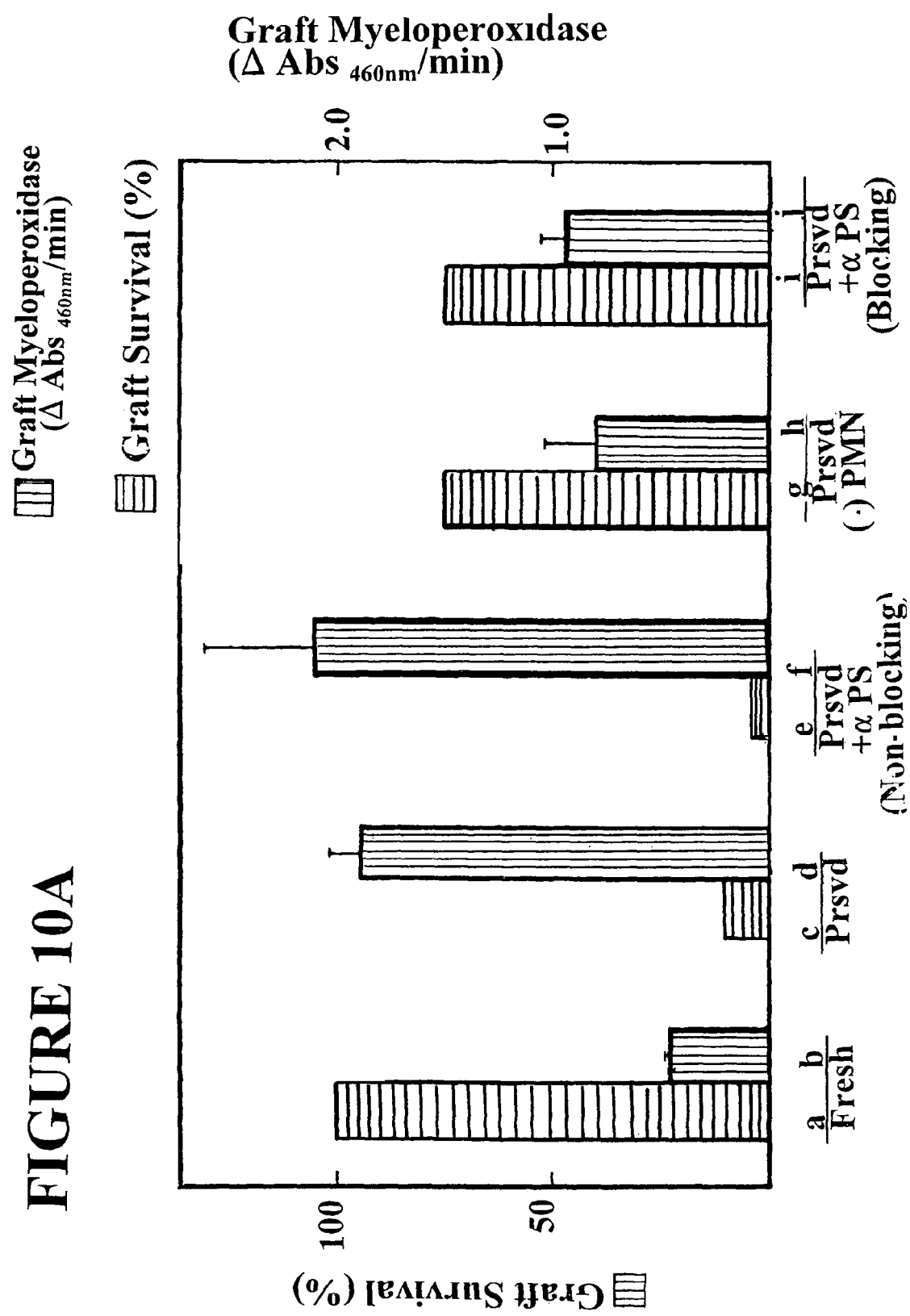

Role of P-selectin dependent neutrophil adhesion in hypothermic/ischemic myocardial preservation. To establish the relevance of these observations to hypothermic myocardial preservation (in which the $pO_2$ of the preservation solution within the coronary vasculature drops below 20 Torr (15)), hearts were harvested from male Lewis rats and subjected to hypothermic preservation as described in the methods section. Because neutrophil-mediated damage following cardiac ischemia is well established (32-38), the potential pathophysiologic role of endothelial P-selectin expression was investigated in an orthotopic rat heart transplant model in which reperfusion occurred following a period of hypothermic preservation. These experiments showed excellent graft survival and little neutrophil infiltration if heart transplantation was performed immediately following harvest (FIG. 10A, Fresh). However, when similar experiments were performed with an intervening (16 hour) period of hypothermic preservation between the harvest and transplantation procedures, there was a high incidence (90%) of graft failure and marked leukostasis, confirmed histologically and by determining myeloperoxidase activity (FIG. 10A, Prsvd). To demonstrate that neutrophil adhesion was responsible, at least in part, for graft failure following prolonged preservation, transplants were performed following neutrophil depletion of recipient rats. The polyclonal rabbit anti-rat PMN antibody used (23-25) eliminated virtually all circulating PMNs in the recipients (PMN count $1471\pm56$ vs $67\pm11$ PMNs/mm$^3$ for control and immunodepleted animals, respectively, $p<0.001$), with little effect on other cell types. When 16 hour preserved hearts were transplanted into neutrophil-depleted recipients to provide a neutrophil-free reperfusion milieu, there was a significant reduction in graft myeloperoxidase activity and an increase in graft survival (FIG. 10A, Prsvd (−) PMN). Normal recipient rats infused with blocking anti-P-selectin IgG 10 minutes prior to reestablishment of blood flow demonstrated a reduction of both myeloperoxidase activity as well as improvement in graft survival (FIG. 10A, α-PS, Blocking) of a similar magnitude as neutrophil-depleted recipients. This reduced PMN infiltration and improved graft survival was observed despite 16 hours of hypothermic preservation of the donor heart. In sharp contrast, administration of a nonblocking control antibody (AC1.2) had no beneficial effect on graft leukostasis or graft survival (FIG. 10A, α-PS, Non-blocking).

Because in addition to the interactions between ECs and PMNs, platelets may also interact with PMNs via a P-selectin-dependent mechanism (39), an experiment was designed to isolate the contribution of endothelial P-selectin to the leukostasis and graft failure which occur following prolonged hypothermic cardiac preservation. For these experiments, donor hearts from homozygous P-selectin deficient mice could be flushed free of blood, so that P-selectin null coronary endothelial cells could be transplanted into wild type recipients with P-selectin containing platelets. Using a murine heterotopic heart transplant model performed identically to the rat operation, donor hearts were obtained from either homozygous P-selectin null mice (27) or wild-type controls; all hearts were transplanted into wild-type recipients. These experiments, demonstrated a significantly higher graft survival rate in the P-selectin null—wild type transplants compared with wild type—wild type transplants (FIG. 10B). This improved graft survival in the former group was paralleled by a marked (13-fold) reduction in graft leukostasis (FIG. 10C). Because these hearts had been flushed free of blood at the start of preservation, these studies implicate coronary endothelial (rather than platelet-derived) P-selectin in the poor preservation and leukocyte arrest noted after hypothermic myocardial preservation.

Figure 11A:
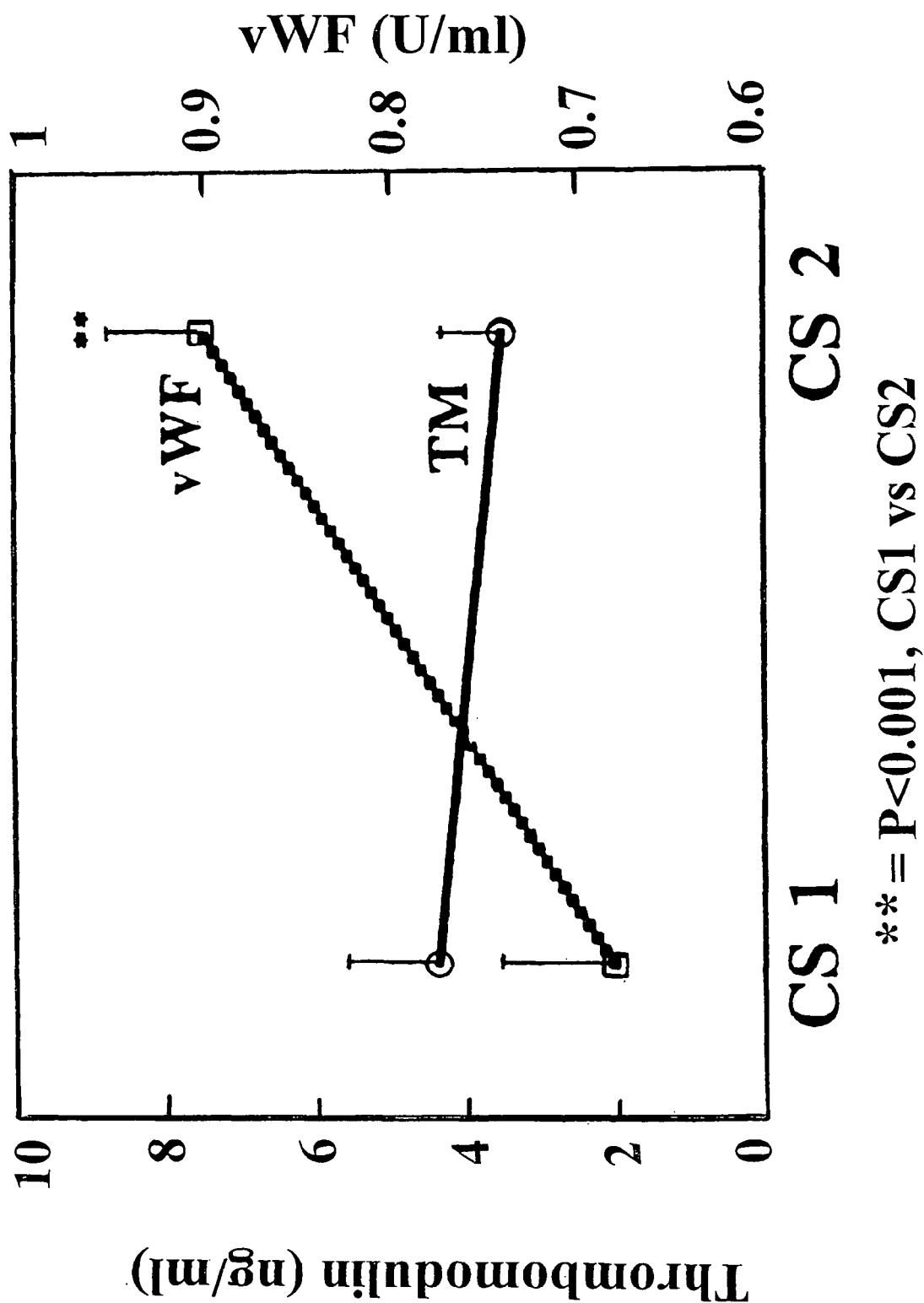
FIGS. 11A and 11B. Weibel-Palade body release during human cardiac surgery in 32 patients.

Weibel-Palade body exocytosis during human cardiac surgery. To establish the relevance of these findings to humans, the next set of experiments were designed to demonstrate that coronary ECs release the contents of Weibel-Palade bodies during hypothermic cardiac preservation as occurs during routine cardiac surgery. Measurements were made of vWF release from the coronary vasculature during a well-defined period of cardiac ischemia, that which occurs during the period of aortic cross-clamping. Coronary sinus (draining the heart) blood was sampled at the start ($CS_1$) and conclusion ($CS_2$) of aortic cross clamping in 32 patients (this interval represents the ischemic period). These patients (23 male, 9 female) had a clinical history of valvular heart disease (n=11) or ischemic heart disease (n=21), and underwent either valve repair/replacement or coronary artery bypass grafting, respectively. Capture ELISAs performed for the integral membrane protein thrombomodulin (40) demonstrated no change in levels between the $CS_1$ and the $CS_2$ samples (4.35±1.2 ng/mL vs 3.48±0.8 ng/mL, p=NS), suggesting that ECs were not sloughed and cell membrane integrity was maintained during cardiac preservation. Similar measurements performed for vWF showed that there was a consistent and significant increase in vWF that is secreted during the course of cardiac preservation (0.68±0.06 U/ml vs 0.90±0.05 U/ml, $CS_1$ vs $CS_2$, p<0.01) (FIG. 11A).

Figure 11B:
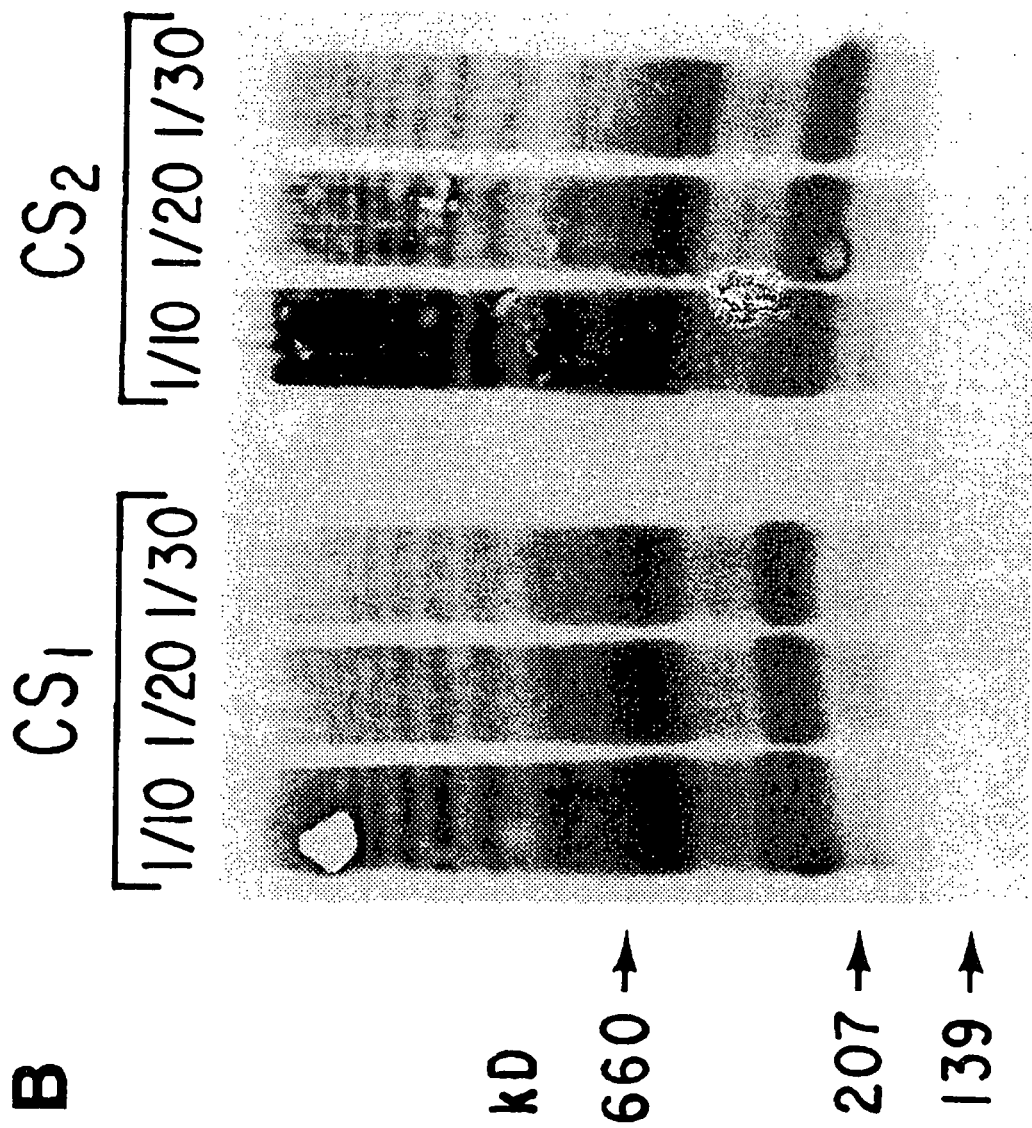

To demonstrate that this vWF was likely to be of coronary-endothelial rather than of platelet origin, and hence not simply a consequence of cardiopulmonary bypass, peripheral blood samples were obtained simultaneously with the $CS_1$ and $CS_2$ samples, and showed that levels of vWF were unchanged (0.813±0.52 U/mL vs 0.900±0.41 U/mL, p=NS), suggesting that mechanical perturbation of platelets during cardiopulmonary bypass was not causative. Because vWF is present in plasma as multimers with a range of $M_r$'s. (41-44), with those vWF multimers from the stimulatable pool (as opposed to those constitutively secreted) being of the highest molecular weight (45), immunoelectrophoresis was performed on the CS samples. These gels demonstrated that in addition to an overall increase in vWF in the $CS_2$ samples, there appeared to be an increase in high molecular weight multimers, suggesting release from a stimulatable pool, as is found in endothelial cells (FIG. 11B).

Discussion:

The vasculature plays a critical role in maintaining the extracellular milieu of organs subjected to ischemia and reperfusion, a role which is chiefly orchestrated by the ECs lining the endovascular lumen. The EC responds to a period of oxygen deprivation by striking phenotypic modulation, becoming prothrombotic (46) and proinflammatory (1,4,6). ECs exposed to hypoxia secrete the proinflammatory cytokines IL-1 (4) and IL-8 (6) which may serve to direct leukocyte traffic to areas of ischemia. Because these processes require de novo protein synthesis, they do not explain the immediate events which occur following a period of hypothermic preservation. While enhanced expression of ICAM-1 and induction of E-selectin may contribute at later times to leukocyte arrest in cardiac grafts, this does not explain the rapid leukostasis observed following cold preservation, in which protein synthesis is likely to be considerably slowed. In this context, cycloheximide pre-treatment does not alter the early (90-120 minute) PMN adhesion seen following hypoxic exposure of ECs (7), suggesting that de novo protein synthesis need not be involved in hypoxia-mediated increases in PMN binding. Although platelet activating factor (PAF) may participate in hypoxia-mediated PMN adhesion (7,47) and activation (48, 49), PAF is not stored and must be synthesized, which may lessen its importance during the hypothermic period during myocardial preservation. It is for this reason that rapid EC expression of pre-formed P-selectin from subplasmalemmal storage sites in Weibel-Palade bodies (9,50,51) may represent the most important mechanism for early PMN recruitment following hypothermic preservation. Weibel-Palade bodies are found in abundance within the coronary microvasculature (52), suggesting their particular importance in cardiac preservation.

The data show Weibel-Palade exocytosis occurs both in response to hypoxia per se, as well as in human hearts during hypothermic preservation. While it is difficult to precisely identify an endothelial origin for the vWF observed in the human coronary sinus samples, studies of platelets following cardiopulmonary bypass demonstrate no increase in surface P-selectin expression or α-granule secretion (53,54). This suggests that the observed increase in coronary sinus vWF following aortic cross-clamping is not of platelet origin. Two aspects of the data also suggest that the vWF released following ischemia is of endothelial origin; (1) Peripheral vWF levels remained unchanged while coronary sinus levels are increased following myocardial ischemia, suggesting that the elevated vWF was emanating from the heart, not the cardiopulmonary bypass apparatus; (2) The transgenic, P-selectin null donor hearts were flushed free of donor blood at the onset of preservation, so that when transplanted into wild-type recipients, presumably coronary endothelial (not platelet) P-selectin is absent. These experiments demonstrate the important contribution of endothelial P-selectin to the neutrophil recruitment which accompanies reperfusion.

It is not surprising that P-selectin should be important following hypothermic myocardial preservation; recent studies have demonstrated that P-selectin is an important mediator of neutrophil-induced reperfusion damage following normothermic ischemia, as has been shown in rabbit ear (26) and feline cardiac ischemia (14); models. Because oxidants cause expression of P-selectin at the EC surface (10) it was important in these studies to evaluate the role of the hypoxic period alone as it may prime ECs to recruit the first wave of PMNs, with further PMN recruitment amplified with the onslaught of reactive oxygen intermediates produced in the reperfusion microenvironment. Although one report has suggested that hypoxia might induce EC P-selectin expression, these experiments (7) were actually performed following reoxygenation, a condition which is known to induce both superoxide (18,55) and neutrophil adherence to cultured ECs (56). By contrast, the experiments described herein were performed entirely within a hypoxic environment to completely prevent the possibility of reoxygenation, and antioxidants failed to block hypoxia-induced P-selectin expression, suggesting that the observations described herein reflect hypoxia hypoxia per se rather than reoxygenation. Furthermore, the cardiac protection demonstrated herein using a strategy whereby blood-free preserved hearts from transgenic P-selectin null mice are transplanted into recipients with wild-type platelets demonstrates that endothelial P-selectin expression can be deleterious following hypothermic cardiac preservation. Because Weibel-Palade body exocytosis occurs during hypothermic cardiac preservation in humans, these studies suggest that myocardial preservation may be enhanced by therapeutic strategies designed to block the activity of P-selectin expressed at the endothelial surface.

References:

1. Shreeniwas, R., S. Ogawa, F. Cozzolino, G. Torcia, N. Braunstein, C. Butara, J. Brett, H. Lieberman, M. B. Furie, J. Joseph-Silverstein, and D. M. Stern. 1991. Macrovascular and microvascular emdothelium during long-term exposure to hypoxia: alterations in cell growth, monolayer permeability, and cell surface anticoagulant properties. J. Cell. Physiol. 146:8-17.
2. Kourembanas, S., P. A. Marsden, L. P. McQuillan, and D. V. Faller. 1991. Hypoxia induces endothelin gene expression and secretion in cultured human endothelium. J. Clin. Invest. 88:1054-1057.
3. Kuwabara, K., S. Ogawa, M. Matsumoto, S. Koga, M. Clauss, D. J. Pinsky, L. Witte, J. Joseph-Silverstein, J. Leavy, M. Furie, G. Torcia, F. Cozzolino, T. Kamada and D. M. Stern. 1995. Hypoxia-mediated induction of acidic/ basic FGF and PDGF in mononuclear phagocytes stimulates growth of hypoxic endothelial cells. Proc. Natl. Acad. Sci. (USA), 92(10):4606-10.
4. Shreeniwas, R., S. Koga, M. Karakurum, D.. Pinsky, E. Kaiser, J. Brett, B. A. Wolitzky, C. Norton, J. Plocinski, W. Benjamin, D. K. Burns, A. Goldstein, and D. Stern. 1992. Hypoxia mediated induction of endothelial cell interleukin 1α: an autocrine mechanism promoting expression of leukocyte adhesion molecules on the vessel surface. J. Clin. Invest. 90:2333-2339.
5. Yan, S. F., I. Tritto, D. J. Pinsky, H. Liao, J. Huang, G. Fuller, J. Brett, L. May, and D. M. Stern. 1995. Induction of Interleukin 6 (IL-6) by hypoxia in vascular cells: central role of the binding site for nuclear factor IL-6. J. Biol. Chem. 270 (19):11463-11471.
6. Karakurum, M., R. Shreeniwas, J. Chen, D. Pinsky, S D. Yan, M. Anderson, K. Sunouchi, J. Major, T. Hamilton, K. Kuwabara, A. Rot, R. Nowygrod, and D. Stern. 1994. Hypoxic induction of interleukin-8 gene expression in human endothelial cells, J. Clin. Invest. 93:1564-1570.
7. Arnould, T., C. Michiels, and J. Remacle. 1993. Increased PMN adherence on endothelial cells after hypoxia: involvement PAF, CD18/CD11b, and ICAM-1. Am. J. Physiol. 264:C1102-1110.
8. Milhoan, K. A., T. A. Lane, and C. M. Bloor. 1992. Hypoxia induces endothelial cells to increase their adherence for neutrophils: role of PAF. Am. J. Physiol. 263:H956-H962.
9. Weibel, E. R. and G. E. Pallade. 1964. New cytoplasmic components in arterial endothelia. J. Cell. Bio. 23:101-112.
10. Patel, K. D., G. A. Zimmerman, S. M. Prescott, R. P. McEver, and T. M. McIntyre. Oxygen radicals induce human endothelial cells to express GMP-140 and bind neutrophils. 1991. J. Cell. Biol. 112:749-759.
11. Hattori, R., K. K. Hamilton, R. D. Fugate, R. P. McEver, and P. J. Sims. Stimulated secretion of endothelial von Willebrand factor is accompanied by rapid redistribution to the cell surface of the intracellular granule membrane protein GMP-140. 1989. J. Biol. Chem; 264:7768-7771.
12. Geng J- G., M. P. Bevilacqua, K. L. Moore, T. M. McIntyre, S. M., Prescott, J. M. Kim, G. A. Bliss, G. A. Zimmerman, and R. P. McEver. 1990. Rapid neutrophil adhesion to activated endothelium mediated by GMP-140. Nature 343:757-760.
13. Mulligan, M. S., M. J. Polley,. R. J. Bayer, M. F. Nunn, J. C. Paulson, and P. J. Ward. 1992. Neutrophil-dependent acute lung injury. Requirement for P-selectin (GMP-140). J. Clin. Invest. 90:1600-1607.
14. Weyrich, A. S., X-L. Ma, D. J. Lefer, K. H. Albertine, and A. M. Lefer. 1993. In vivo neutralization of P-selectin protects feline heart and endothelium in myocardial ischemia and reperfusion injury. J. Clin. Invest. 91: 2629-2629.
15. Pinsky, D. J., M. C. Oz, H. Liao, S. Morris, J. Brett, A. Morales, M. Karakurum, M. M. Van Lookeren Campagne, R. Nowygrod, and D. M. Stern. 1993. Restoration of the cAMP second messenger pathway enhances cardiac preservation for transplantation in a heterotopic rat model. J. Clin. Invest. 92:2994-3002.
16. Jaffe, E. A., R. L. Nachman, C. G. Becker, and R. C. Minick. 1973. Culture of human endothelial cells derived from umbilical veins. Identification by morphologic and immunologic criteria. J. Clin. Invest. 52: 2745-2756.
17. Thornton, S. C., S. N. Mueller, and E. M. Levine. 1983. Human endothelial cells: use of heparin in long-term cloning and serial cultivation. Science 222: 623-625.
18. Pinsky, D. J., M. C. Oz, S. Koga, Z. Taha, M. J. Broekman, A. J. Marcus, H. Liao, Y. Naka, J. Brett, P. J. Cannon, R. Nowygrod, T. Malinski, and D. M. Stern. 1994. Cardiac preservation is enhanced in a heterotopic rat transplant model by supplementing the nitric oxide pathway. J. Clin. Invest., 93: 2291-2297.
19. David; G. S., and R. A. Reisfeld. 1974. Protein iodination with solid state lactoperoxidase. Biochem. 13:1014-1021.
20. Larsen, E., A. Celi, G. E. Gilbert, B. C. Furie, J. K. Erban, R. Bonfanti, D. D. Wagner, and B. Furie. 1989. PADGEM protein: a receptor that mediates the interaction of activated platelets with neutrophils and monocytes. Cell 59:305-312.
21. Stone, J. P. and D. D. Wagner. 1993. P-selectin mediates adhesion of platelets to neuroblastoma and small cell lung cancer. J. Clin. Invest. 92:804-813.
22. Ono, K., and E. S. Lindsey. 1969. Improved technique of heart transplantation in rats. J. Thoracic and Cardiovasc. Surg. 57 (2): 225-229.
23. Harkema, J. R. and J. A. Hotchkiss. 1991. In vivo effects of endotoxin on nasal epithelial mucosubstances: quantitative histochemistry. Exp. Lung Res. 17: 743-761.
24. Harkema, J. R. and J. A. Hotchkiss. 1993. In vivo effects of endotoxin on DNA synthesis in rat nasal epithelium. Microscopy Res. and Technique 26: 457-465.
25. Henderson, R. F., J. R. Harkema, J. A., Hotchkiss, and D. S. Boehme. 1991. Effect of blood leukocyte depletion on the inflammatory response of the lung to quartz. Toxicol. and Appl. Pharmacol. 109: 127-136.
26. Winn, R. K., D. Liggitt, N. B. Vedder, J. C. Paulson, and J. M. Harlan. 1993. Anti-P-selectin monoclonal antibody attenuates reperfusion injury to the rabbit ear. J. Clin. Invest. 92: 2042-2047.
27. Mayadas, T. N., R. C. Johnson, H. Rayburn, R. O. Hynes, and D. D. Wagner. 1993. Leukocyte rolling and extravasation are severely compromised in P selectin deficient mice. Cell 74: 541-554.
28. Arnould, T., C. Michiels, I. Alexandre, and J. Remacle. 1992. Effect of hypoxia upon intracellular calcium concentration of human endothelial cells. J. Cellular Physiol: 152: 215-221.
29. Levin, E. G. and L. Santell. 1991. Thrombin- and histamine-induced signal transduction in human endothelial cells. Stimulation and agonist-dependent desensitization of protein phosphorylation. J. Biol. Chem. 266:174-181.
30. Birch, K. A., J. S. Pober, G. B. Zavoico, A. R. Means, and B. M. Ewenstein. 1992. Calcium/calmodulin transduces thrombin-stimulated secretion: studies in intact and minimally permeabilized human umbilical vein endothelial cells. J. Cell Biol. 118:1501-1510.
31. Sporn, L. A., V. J. Marder, and D. D. Wagner. 1987. von Willebrand factor released from Weibel-Palade bodies binds more avidly to extracellular matrix than that secreted constitutively. Blood 69:1531-1534.
32. Crawford, M. H., F. L. Grover, W. P. Kolb, C. A. McMahan, R. A. O'Rourke, L. M. McManus, and R. N. Pinckard. 1988. Complement and neutrophil activation in the pathogenesis of ischemic myocardial injury. Circulation 78:1449-1458.
33. Dreyer, W. J., L. H. Michael, M. S. West, C. W. Smith, R. Rothlein, R. D. Rossen, D. C. Anderson, and M. L. Entman. 1988. Neutrophil accumulation in ischemic canine myocardium. Insights into time course, distribution, and mechanism of localization during early reperfusion. Circulation 84: 400-411.

34. Granger, D. N. 1988. Role of xanthine oxidase and granulocytes in ischemia-reperfusion injury. Am. J. Physiol. 255:H1269-1275.
35. Ma, X-L, D. J. Lefer, A. M. Lefer, and R. Rothlein. 1992. Coronary endothelial and cardiac protective effects of a monoclonal antibody to intercellular adhesion molecule-1 in myocardial ischemia and reperfusion. Circulation 86:937-946.
36. Ma, X., P. S. Tsao, and A. M. Lefer. 1991. Antibody to CD18 exerts endothelial and cardiac protective effects in myocardial ischemia and reperfusion. J. Clin. Invest. 88:1237-1243.
37. Lucchesi, B. R., and K. M. Mullane. 1986. Leukocytes and ischemia induced myocardial injury. Annu. Rev. Pharmacol. Toxicol. 26:201-224.
38. Mullane, K., M. N. Read, J. A. Salmon, and S. Moncada. 1984. Role of leukocytes in acute myocardial infarction in anesthetized dogs: relationship to myocardial salvage by anti-inflammatory drugs. J. Pharmacol. Exp. Ther. 228: 510-522.
39. Nagata, K., T. Tsuji, N. Todoroki, Y. Katagiri, K. Tanoue, H. Yamazaki, N. Hanai, and T. Irimura. 1993. Activated platelets induce superoxide anion release by monocytes and neutrophils through P-selectin (CD62). J. Immunol. 151(6):3267-73.
40. Takano, S., S. Kimura, S. Ohdama, and N. Aoki. 1990. Plasma thrombomodulin in health and disease. Blood 10 (15): 2024-2029.
41. Sadler, J. E. 1991. von Willebrand Factor. J. Biol. Chem. 266(34): 22777-22780.
42. Wen, L. T., J. M. Smolec, J. Coughlin, and R. A. McPherson. 1993. Chemiluminographic detection of von Willebrand factor multimeric composition. J. Clin. Lab. Analysis 7:317-323.
43. Perret, B. A., M. Furlan, and E. A. Beck. 1979. Studies on Factor VIII-related protein: estimation of molecular size differences between Factor VIII oligomers. Biochim. Biophys. Acta 578:169-174.
44. Ruggeri, Z. M. and T. S. Zimmerman. 1981. The complex multimeric composition of Factor VIII/von Willebrand factor. Blood 57(6):1140-1143.
45. Sporn, L. A., V. J. Marder, and D. D. Wagner. 1986. Inducible secretion of large, biologically potent von Willebrand factor multimers. Cell 46:185.
46. Ogawa, S., H. Gerlach, C. Esposito, A. Pasagian-Macaulay, J. Brett, and D. M. Stern. 1990. Hypoxia modulates barrier and coagulant function of cultured bovine endothelium: increased monolayer permeability and cell surface coagulant properties. J. Clin. Invest. 85: 1090-1098.
47. Kubes, P., G. Ibbotson, J. Russel, J. L. Wallace, and D. N. Granger. 1990. Role of platelet-activating factor in ischemia-reperfusion induced leukocyte adherence. Am. J. Physiol. 259: G300-305.
48. Lorant, D. E., K. D. Patel, T. M. McIntyre, R. P. McEver, S. M. Prescott, and G. A. Zimmerman. 1991. Coexpression of GMP-140 and PAF by endothelium stimulated by histamine or thrombin: a juxtacrine system for adhesion and activation of neutrophils. J. Cell Biol. 115:223-234.
49. Lorant, D. E., M. K. Topham, R. E. Whatley, R. P. McEver, T. M. McIntyre, S. M. Prescott, and G. A. Zimmerman. 1993. Inflammatory role of P-selectin. J. Clin. Invest. 92:559-570.
50. McEver, R. P., J. H. Beckstead, K. L. Moore, L. Marshall-Carlson, and D. F. Bainton. 1989. GMP-140, a platelet α-granule membrane protein, is also synthesized by vascular endothelial cells and is localized in Weibel-Palade bodies. J. Clin. Invest. 84:92-99
51. Bonfanti, R., B. C. Furie, B. Furie, and D. D. Wagner. 1989. PADGEM (GMP140) is a component of Weibel-Palade bodies of human endothelial cells. Blood 73(5): 1109-1112.
52. Gebrane-Younes, J., L. Drouet, J. P. Caen, and L. Orcel. 1991. Heterogenous distribution of Weibel-Palade bodies and von Willebrand factor along the porcine vascular tree. Am. J. Pathol. 139(6): 1471-1484.
53. George, J. N., E. B. Pickett, S. Saucerman, R. P. McEver, T. J. Kunicki, N. Kieffer, and P. J. Newman. 1986. Platelet surface glycoproteins. Studies on resting and activated platelets and platelet membrane microparticles in normal subjects and observations in patients during adult respiratory distress syndrome and cardiac surgery. J. Clin. Invest. 78:340-348.
54. Kestin, A. S., C. R. Valeri, S. F. Khuri, J. Loscalzo, P. A. Ellis, H. MacGregor, V. Birjiniuk, H. Quiemet, B. Pasche, M. J. Nelson, S. E. Benoit, L. J. Rodino, M. R. Barnard, and A. D. Michelson. 1993. The platelet function defect of cardiopulmonary bypass. Blood 82 (1): 107-117.
55. Zweier, J. L., P. Kuppusamy, and G. A. Lutty. 1988. Measurements of endothelial cell free radical generation: evidence for a central mechanism of free radical injury in postischemic tissues. Proc Natl Acad Sci (USA) 85:4046-4050.
56. Yoshida, N., D. N. Granger, D. C. Anderson, R. Rothlein, C. Lane, and P. R. Kvietys. 1992. Anoxia/reoxygenation-induced neutrophil adherence to cultured endothelial cells. Am. J. Physiol. 262:H1891-1898.

Example 3

Procedural and Strain-Related Variables Significantly Effect Outcome in a Murine Model of Focal Cerebral Ischemia The recent availability of transgenic mice has led to a burgeoning number of reports describing the effects of specific gene products on the pathophysiology of stroke. Although focal cerebral ischemia models in rats have been well-described, descriptions of a murine model of middle cerebral artery occlusion are scant, and sources of potential experimental variability remain undefined. It was hypothesized that slight technical modifications would result in widely discrepant results in a murine model of stroke, and that controlling surgical and procedural conditions could lead to reproducible physiologic and anatomic stroke outcomes. To test this hypothesis, a murine model was established which would permit either permanent or transient focal cerebral ischemia by intraluminal occlusion of the middle cerebral artery (MCA). This study provides a detailed description of the surgical technique, and reveals important differences between strains commonly used in the production of transgenic mice. In addition to strain-related differences, infarct volume, neurologic outcome, and cerebral blood flow appear to be importantly affected by temperature during the ischemic and post-ischemic periods, mouse size, and size of the suture which obstructs the vascular lumen. When these variables were kept constant, there was remarkable uniformity of stroke outcome. These data emphasize the protective effects of hypothermia in stroke, and should help to standardize techniques among different laboratories to provide a cohesive framework for evaluating the results of future studies in transgenic animals.

Introduction:

The recent advent of genetically altered mice provides a unique opportunity to evaluate the role of single gene products in the pathophysiology of stroke. Although there is an increasing number of reports about the effect of cerebral ischemia in transgenic mice, to date, there exists no detailed description of the murine models involved, nor is there a detailed analysis of potentially important procedural variables which may effect stroke outcome. Most description's of a murine model (1,4,8,9,14,17-19,23,24) are devolved descriptions of the widely used rat models of focal cerebral ischemia (22,26). Although there has been some attention paid to strain related differences in the susceptibility of mice to cerebral ischemia (4), few technical considerations have been addressed in published studies. Because pilot data demonstrated that minor differences in operative procedure or postoperative care translated into major differences in stroke outcome, the current study was undertaken to systematically identify important surgical, technical, and anatomic considerations required to obtain consistent results in a murine model of focal cerebral ischemia. When strokes are created in a rigidly controlled manner, differences, due to the absence (or overexpression) of a single gene product, should be readily discernable.

This study presents a detailed rendering of a reproducible murine model of focal cerebral infarction based on modifications of the original rat model (26). This study identifies procedural variables that have a large impact on stroke outcome which have not been previously reported in technical descriptions of murine stroke models. These variables include suture length and gauge, methods of vascular control, temperature regulation in mice, and differences between strains commonly used in the breeding of transgenic animals. As the model described lends itself to the study of either permanent or transient focal cerebral ischemia, evidence is presented that with carefully chosen ischemia times, infarct volume and mortality in reperfused animals can be made to approximate those seen with permanent occlusion. Understanding potential model-dependent sources of variability in stroke outcome can help to clarify divergent results between different laboratories. Adoption of a standardized model which yields consistent results is an important first step towards the use of transgenic mice in the study of the pathophysiology of stroke.

Materials and Methods:

Animal Purchase and Anesthesia: Male mice of three different strains (C57 BlackJ6, CD-1 and 129J) were purchased from Jackson Laboratories (Bar Harbor, Me.). Animals were eight to ten weeks of age and weighed between 18-37 grams (as indicated) at the time of experiments. Mice were anesthetized with an intraperitoneal injection of 0.3 ml of ketamine (10 mg/cc) and xylazine (0.5 mg/cc). An additional dose of 0.1 cc was given prior to withdrawal of the catheter in animals undergoing transient ischemia. On the day following surgery, anesthesia was repeated immediately prior to laser doppler flow measurement and humane euthansia. These procedures have been approved by the Institutional Animal Care and Use Committee at Columbia University, and are in accordance with AALAC guidelines for the humane care and use of laboratory animals.

Figure 12A:
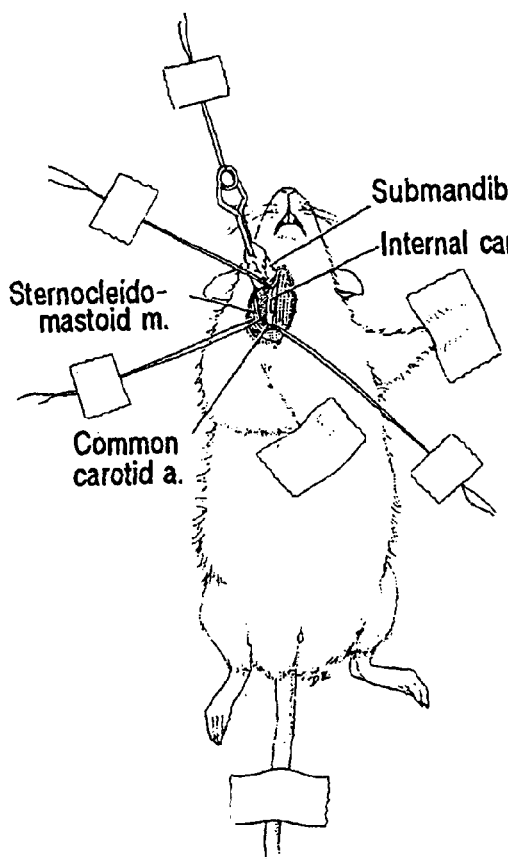
FIGS. 12A. 12B, 12C and 12D. Overview of operative setup for murine focal cerebral ischemia model.
Figure 12B:
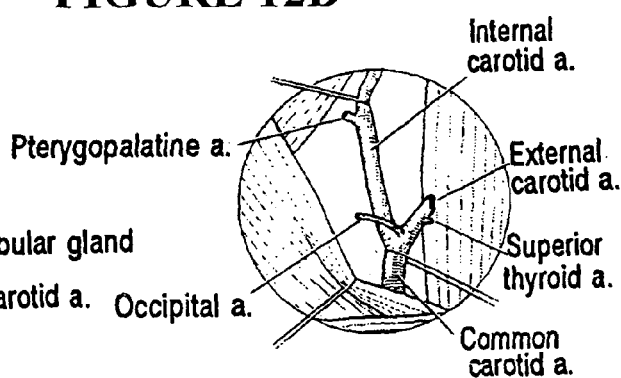
FIG. 12B. View through the operating microscope. The large vascular stump represents the external carotid artery, which is situated inferomedially in the operating field.

Surgical Set-up: The animal was positioned supine on a gauze pad which rests on a temperature controlled operating surface (Yellow Springs Instruments, Inc.[YSI], Yellow Springs, Ohio). A rectal temperature probe (YSI) was inserted, in order to regulate the temperature of the operating surface to maintain a constant animal core temperature of 36-38° C. To facilitate exposure, the right hindpaw and left forepaw were taped to the operating surface, the right forepaw was taped to the animal's chest, and the tail was taped to the rectal probe (FIG. 12A). A midline neck incision was made by gently lifting the loose skin between the manubrium and the jaw and excising a 1 cm² circle of skin. The paired midline submandibular glands directly underlying this area were bluntly divided, with the left gland left in situ. The right gland was retracted cranially with an small straight Sugita aneurysm clip (Mizutto America, Inc., Beverly, Mass.) secured to the table by a 4.0 silk and tape. The sternocleidomastoid muscle was then identified, and a 4.0 silk ligature placed around its belly. This ligature was drawn inferolaterally, and taped to the table, to expose the omohyoid muscle covering the carotid sheath. The exposure is shown in FIG. 12B.

Operative Approach: Once the carotid sheath was exposed, the mouse and the temperature control surface were placed under an operating microscope (16-25× zoom, Zeiss, Thornwood, N.Y.), with a coaxial light source used to illuminate the field. Under magnification, the omohyoid muscle was carefully divided with pickups. The common carotid artery (CCA) was carefully freed from its sheath, taking care not to apply tension to the vagus nerve (which runs lateral to the CCA). Once freed, the CCA was isolated with a 4.0 silk, taped loosely to the operating table. Once proximal control of the CCA was obtained, the carotid bifurcation was placed in view. The occipital artery, which arises from the proximal external carotid artery and courses postero-laterally across the proximal internal carotid artery (ICA) to enter the digastric muscle, was isolated at its origin, and divided using a Malis bipolar microcoagulator (Codman-Schurtleff, Randolph, Mass.). This enabled better visualization of the ICA as it courses posteriorly and cephalad underneath the stylohyoid muscle towards the skull base. Just before the ICA enters the skull it gives off a pterygopalatine branch, which courses laterally and cranially. This branch was identified, isolated, and divided at its origin, during which time the CCA-ICA axis straightens. A 4.0 silk suture was then placed around the internal carotid artery for distal control, the end of which was loosely taped to the operating surface.

Next, the external carotid artery was placed in view. Its cranio-medial course was skeletonized and its first branch, the superior thyroid artery, was cauterized and divided. Skeletonization was subsequently carried out distally by elevation of the hyoid bone to expose the artery's bifurcation into the lingual and maxillary arteries. Just proximal to this bifurcation the external carotid was cauterized and divided. Sufficient tension was then applied to the silk sutures surrounding the proximal common, and distal internal, carotid arteries to occlude blood flow, with care taken not to traumatize the arterial wall. Tape on the occluding sutures was readjusted to maintain occlusion.

Figure 12C:
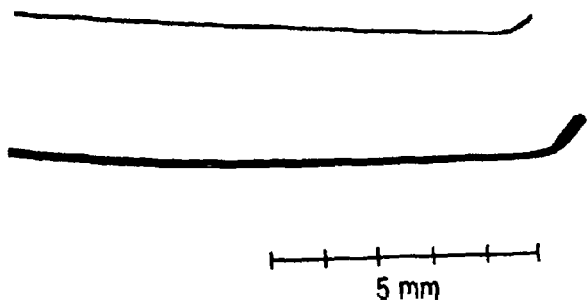
FIG. 12C. Photograph of heat-blunted occluding suture of the indicated gauge (5-0 [bottom] or 6-0 nylon [top]).
Figure 12D:
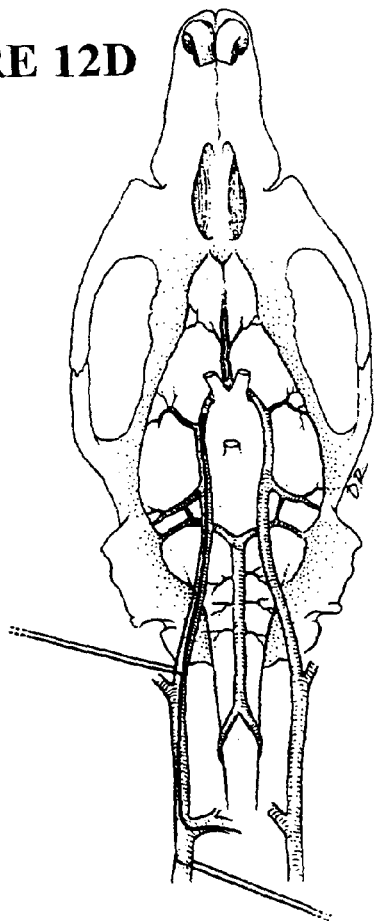
FIG. 12D. Schematic diagram of murine cerebrovascular anatomy, with thread in the anterior cerebral artery, occluding the middle cerebral artery at its point of origin.

Introduction and Threading of the Occluding Intraluminal Suture: Immediately following carotid occlusion, an arteriotomy was fashioned in the distal external carotid wall just proximal to the cauterized area. Through this arteriotomy, a heat-blunted 5.0 or 6.0 nylon suture (as indicated in the Results section) was introduced (FIGS. 12C and 12D). As the suture was advanced to the level of the carotid bifurcation, the external stump was gently retracted caudally directing the tip of the suture into the proximal ICA. Once the occluding suture entered the ICA, tension on the proximal and distal control sutures was relaxed, and the occluding suture was slowly advanced up the ICA towards the skull base under direct visualization (beyond the level of the skull base, sight of the occluding suture is lost). Localization of the distal tip of the occluding suture across the origin of the middle cerebral artery (MCA) (proximal to the origin of the anterior cerebral artery) was determined by the length of suture chosen (12 mm or 13 mm as indicated in the Results section, shown in FIG. 12C), by laser doppler flowmetry (see Ancillary physiological procedures section), and by post-sacrifice staining of the cerbral vasculature (see below). After placement of the occluding suture was complete, the external carotid artery stump was cauterized to prevent bleeding through the arteriotomy once arterial flow was reestablished.

Completion of Surgical Procedure: For all of the experiments shown, the duration of carotid occlusion was less than two minutes. To close the incision, the sutures surrounding the proximal and distal CCA, as well as the sternocleidomastoid muscle, were cut and withdrawn. The aneurysm clip was removed from the submandibular gland and the gland was laid over the operative field. The skin edges were then approximated with one surgical staple and the animal removed from the table.

Removal of the Occluding Suture to Establish Transient Cerebral Ischemia: Transient, cerebral ischemia experiments required reexploration of the wound to remove the occluding suture. For these experiments, initial wound closure was performed with a temporary aneurysm clip rather than a surgical staple to provide quick access to the carotid. Proximal control with a 4-0 silk suture was reestablished prior to removal of the occluding suture to minimize bleeding from the external carotid stump. During removal of the occluding suture, cautery of the external carotid artery stump was begun early, before the distal suture has completely cleared the stump. Once the suture was completely removed, the stump is more extensively cauterized. Reestablishment of flow in the extracranial internal carotid artery was confirmed visually and the wound was closed as for permanent focal ischemia described above. Confirmation of intracranial reperfusion was accomplished with laser doppler flowmetry (see Ancillary physiological procedures section).

Calculation of Stroke Volume: Twenty-four hours after middle cerebral artery occlusion, surviving mice were reanesthetized with 0.3 cc of ketamine (10 mg/ml) and xylazine (0.5 mg/ml) After final weights, temperatures and cerebral blood flow readings were taken (as described below), animals were perfused with 5 ml of a 0.15% solution of methylene blue and saline to enhance visualization of the cerebral arteries. Animals were then decapitated, and the brains were removed. Brains were then inspected for evidence of correct catheter placement, as evidenced by negative staining of the vascular territory subtended by the MCA, and placed in a mouse brain matrix (Activational Systems Inc., Warren, Mich.) for 1 mm sectioning. Sections were immersed in 2% 2,3,5-triphenyltetrazolium chloride (TTC) in 0.9% phosphate-buffered saline, incubated for 30 minutes at 37° C., and placed in 10% formalin (5). After TTC staining, infarcted brain was visualized as an area of unstained (white) tissue in a surrounding background of viable (brick red) tissue. Serial sections were photographed and projected on tracing paper at a uniform magnification; all serial sections were traced, cut out, and the paper weighed by a technician blinded to the experimental conditions. Under these conditions, infarct volumes are proportional to the summed weights of the papers circumscribing the infarcted region, and were expressed as a percentage of the right hemispheric volume. These methods have been validated in previous studies (3,12,15,16).

Ancillary Physiological Studies:

Ancillary physiological studies were performed on each of the three different strains used in the current experiments, immediately prior to and after the operative procedure. Systemic blood pressures were obtained by catheterization of the infrarenal abdominal aorta, and measured using a Grass Model 7 polygraph (Grass Instrument Co., Quincy, Mass.). An arterial blood sample was obtained from this infrarenal aortic catheter; arterial pH, $pCO_2$ (mm Hg), $pO_2$ (mm Hg) and hemoglobin oxygen saturation (%) were measured using a Blood Gas Analyser and Hemoglobinometer (Grass Instrument Co., Quincy, Mass.). Because of the need for arterial puncture and abdominal manipulation to measure these physiologic parameters, animals were designated solely for these measurements (stroke volumes, neurologic outcome, and cerebral blood flows were not measured in these same animals).

Transcranial measurements of cerebral blood flow were made using laser doppler flowmetry (Perimed, Inc., Piscataway, N.J.) after reflection of the skin overlying the calvarium, as previously described (10) (transcranial readings were consistently the same as those made after craniectomy in pilot studies). To accomplish these measurements, animals were placed in a stereotactic head frame, after which they underwent midline skin incision from the nasion to the superior nuchal line. The skin was swept laterally, and a 0.7 mm straight laser doppler probe (model #PF2B) was lowered onto the cortical surface, wetted with a small amount of physiologic saline. Readings were obtained 2 mm posterior to the bregma, both 3 mm and 6 mm to each side of midline using a sterotactic micromanipulator, keeping the angle of the probe perpendicular to the cortical surface. Relative cerebral blood flow measurements were made immediately after anesthesia, after occlusion of the MCA, and immediately prior to euthanasia, and are expressed as the ratio of the doppler signal intensity of the ischemic compared with the nonischemic hemisphere. For animals subjected to transient cerebral ischemia, additional measurements were made just before and just after withdrawal of the suture, initiating reperfusion.

The surgical procedure/intraluminal MCA occlusion was considered to be technically adequate if $\geq 50\%$ reduction in relative cerebral blood flow was observed immediately following placement of the intraluminal occluding catheter (15 of the 142 animals used in this study [10.6%] were exluded due to inadequate drop in blood flow at the time of occlusion). These exclusion criteria were shown in preliminary studies to yield levels of ischemia sufficient to render consistent infarct volumes by TTC staining. Reperfusion was considered to be technically adequate if cerebral blood flow at catheter withdrawal was at least twice occlusion cerebral blood flow (13/17 animals in this study [76%]).

Temperature: Core temperature during the peri-infarct period was carefully controlled throughout the experimental period. Prior to surgery, a baseline rectal temperature was recorded (YSI Model 74 Thermistemp rectal probe, Yellow Springs Instruments, Inc., Yellow Springs, Ohio). Intraoperatively, temperature was controlled using a thermocouple-controlled operating surface. Following MCA occlusion, animals were placed for 90 minutes in an incubator, with animal temperature maintained at 37° C. using the rectal probe connected via thermocouple to a heating source in the incubator. Temperature was similarly controlled in those animals subjected to transient ischemia, including a 45 minute (ischemic) period as well as a 90 minute post-ischemic period in the incubator. Following placement in the core-temperature incubator, animals were returned to their cages for the remaining duration of pre-sacrifice observation.

Neurological Exam: Prior to giving anesthesia at the time of euthanasia, mice were examined for obvious neurological deficit using a four-tiered grading system: (1) normal spontaneous movements, (2) animal circling towards the right, (3) animal spinning to the right, (4) animal crouched on all fours, unresponsive to noxious stimuli. This system was shown in preliminary studies to accurately predict infarct size, and is based on systems developed for use in rats (6).

Data Analysis: Stroke volumes, neurologic outcome scores, cerebral blood flows and arterial blood gas data were compared using an unpaired Student's t-test. Values are expressed as means±SEM, with a p<0.05 considered statistically significant. Mortality data, where presented was evaluated using chi-squared analysis.

Figure 13:
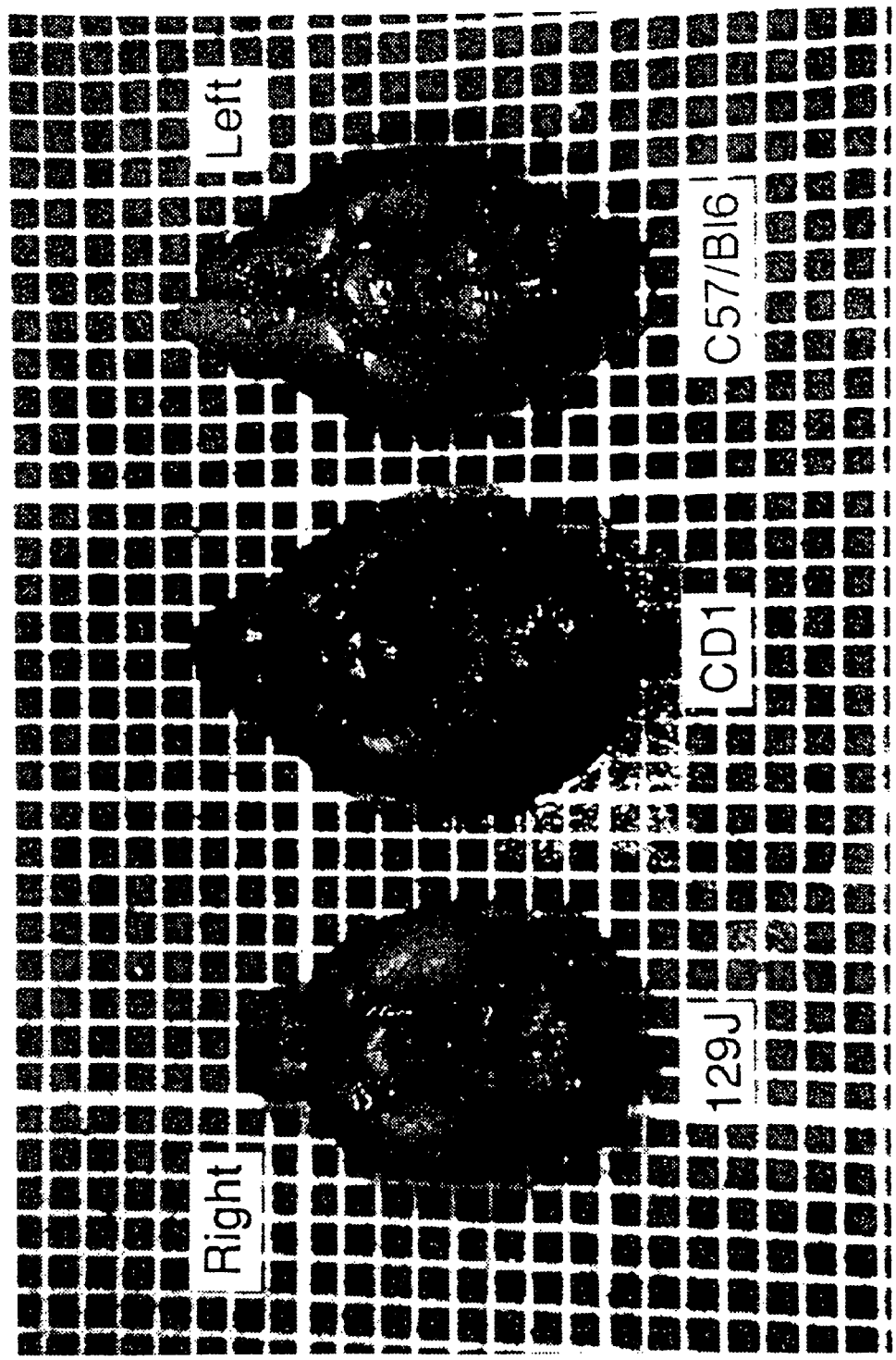
FIG. 13. Comparison of cerebrovascular anatomy between strains of mice. Following anesthesia, mice were given an intracardiac injection of India ink followed by humane euthanasia. An intact Circle of Willis can be observed in all strains, including bilateral posterior communicating arteries, indicating that there are no gross strain-related differences in cerebrovascular anatomy.
Figure 14A:
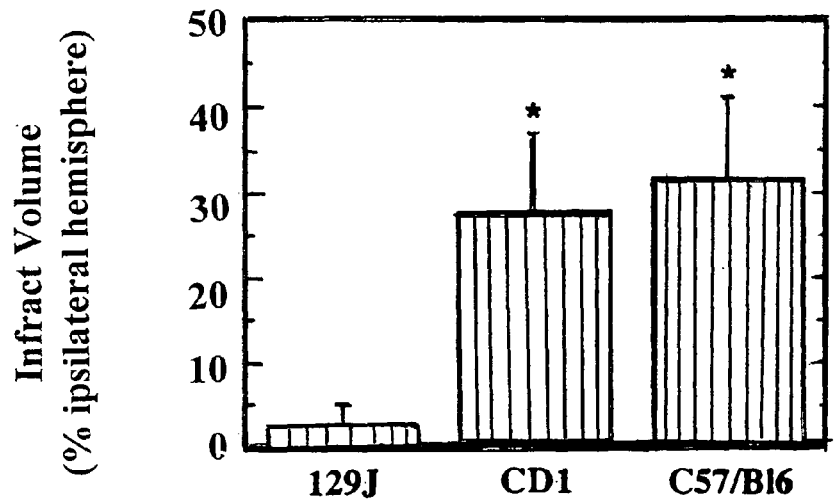
FIGS. 14A, 14B and 14C. Effects of mouse strain on stroke outcome. Mice (20-23 gm males) were subjected to 45 minutes of MCA occlusion (using 12 mm 6.0 occluding suture) followed by 24 hours of reperfusion, and indices of stroke outcome determined.
Figure 14B:
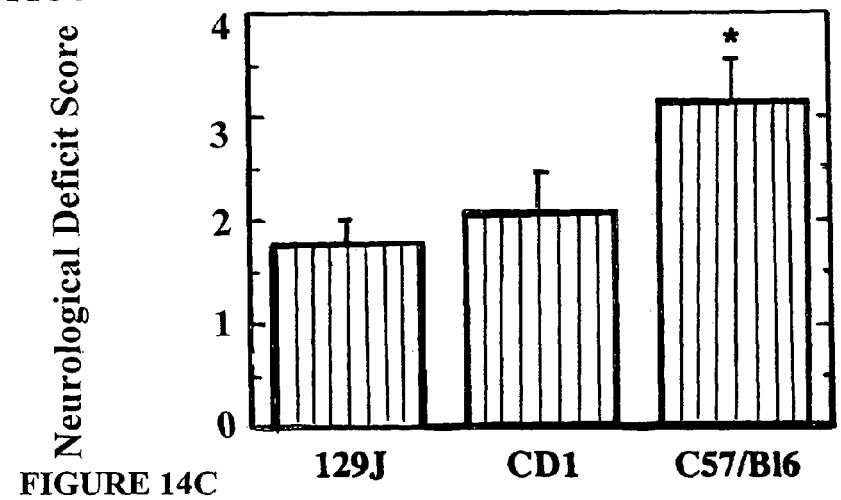

Results:

Effects of Strain: Three different commonly used mouse strains (CD1, C57/Bl6, and 129J) were used to compare the variability in stroke outcome following permanent focal cerebral ischemia. To establish that there were no gross anatomic differences in collateralization of the cerebral circulation, the Circle of Willis was visualized using India ink in all three strains (FIG. 13). These studies failed to reveal any gross anatomic differences. Mice of similar sizes (20±0.8 g, 23±0.4 g, and 23±0.5 g for 129J, CD1, and C57Blmice, respectively) were then subjected to permanent focal ischemia under normothermic conditions using a 12 mm length of 6-0 nylon occluding suture. Significant strain-related differences in infarct volume were noted, with infarcts in 129J mice being significantly smaller than those observed in CD1 and C57/Bl6 mice despite identical experimental conditions (FIG. 14A). Differences in infarct size were paralleled by neurological exam, with the highest scores (i.e., most severe neurologic damage) being seen in the C57/Bl6 and CD1 mice (FIG. 14B).

Figure 14C:
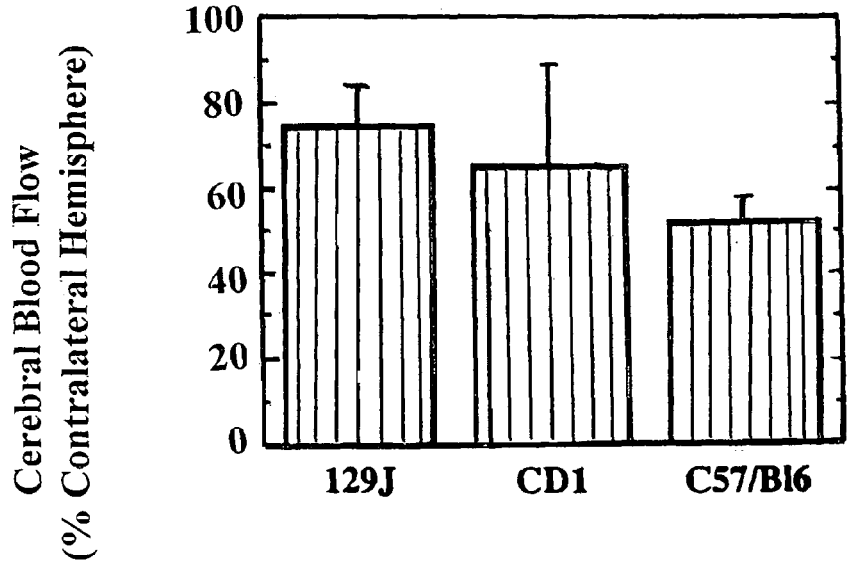

To determine the relationship between infarct volume and cerebral blood flow to the core region, laser doppler flowmetry was performed through the thin murine calvarium. No preoperative strain-related differences in cerebral blood flow were observed, corresponding to the lack of gross anatomic differences in vascular anatomy (FIG. 13). Measurement of cerebral blood flow immediately following insertion of the occluding catheter revealed that similar degees of flow reduction were created by the procedure (the percentage of ipsilateral/contralateral flow immediately following insertion of the obstructing catheter was 23±2%, 19±2%, 17±3% for 129J, CD1, and C57/Bl6 mice, respectively). Not surprisingly, blood flow to the core region measured at 24 hours just prior to euthanasia demonstrated the lowest blood flows in those animals with the most severe neurologic injury (FIG. 14C).

Anatomic and Physiologic Characteristics of Mice: Baseline arterial blood pressures, as well as arterial blood pressures following middle cerebral artery occlusion, were nearly identical for all animals studied, and were not effected by mouse strain or size (Table I). Analysis of arterial blood for pH, $pCO_2$, and hemoglobin oxygen saturation (%) similarly revealed no significant differences (Table I).

Figure 15A:
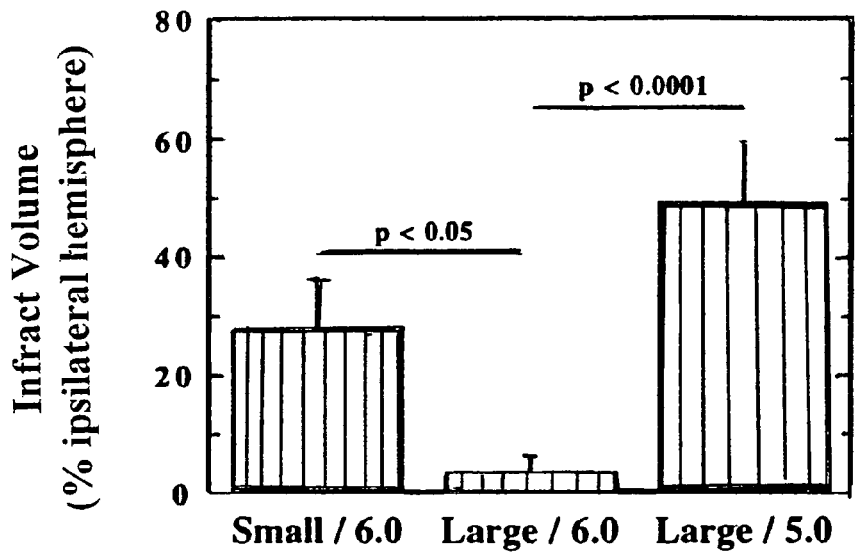
FIGS. 15A, 15B and 15C. Effects of animal size and diameter of the occluding suture on stroke outcome. Male CD-1 mice of the indicated sizes were subjected to middle cerebral artery occlusion (45 minutes) followed by reperfusion (24 hours) as described in the Methods section. Suture size (gauge) is indicated in each panel. Small animals (n=11) were those between 20-25 gm (mean 23 gm), and large animals were between 28-35 gm (mean 32 gm; n=14 for 6.0 suture, n=9 for 5.0 suture).
Figure 15B:
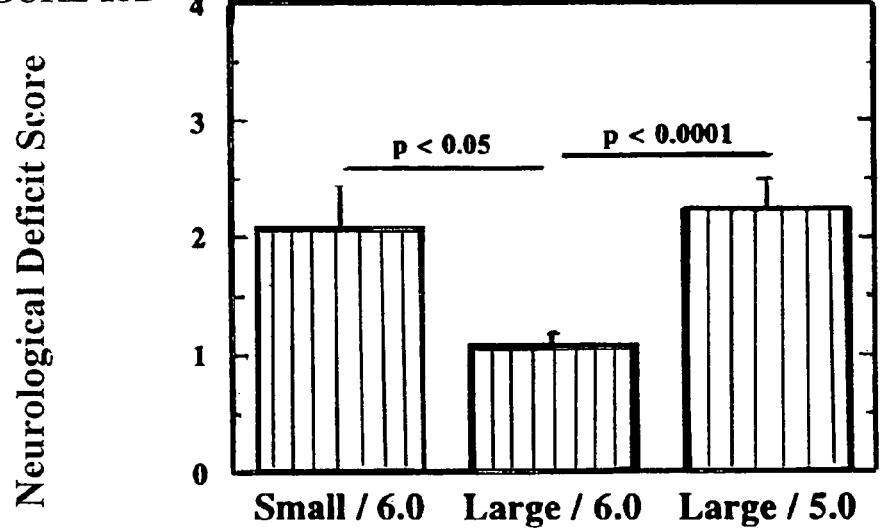
Figure 15C:
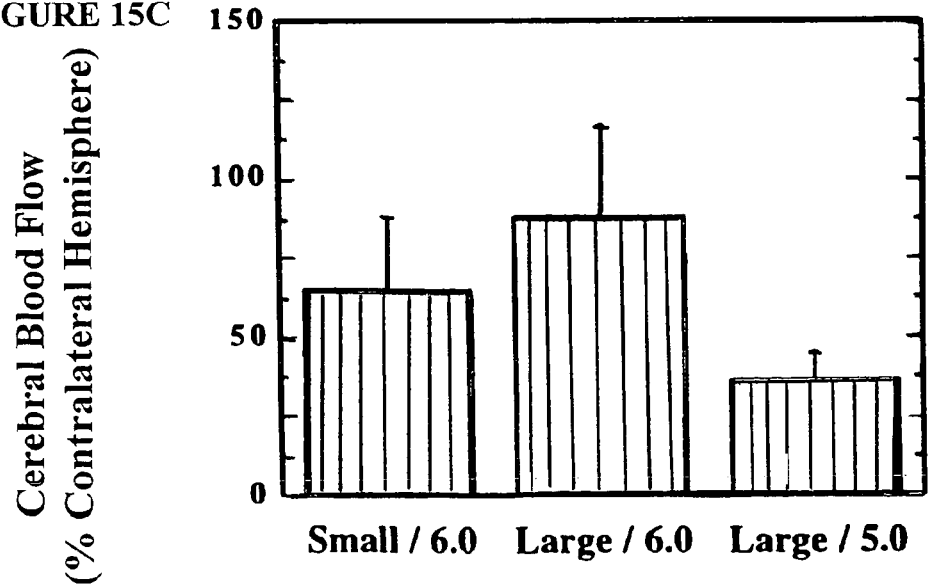

Effect of Animal Size and Bore of the Occluding Suture: To investigate the effects of mouse size on stroke outcome, mice of two different sizes (23±0.4 g and 31±0.7 g) were subjected to permanent focal cerebral ischemia. To eliminate other potential sources of variability in these experiments, experiments were performed under normothermic conditions in mice of the same strain (CD1), using occluding sutures of identical length and bore (12 mm 6-0 nylon). Under these conditions, small mice (23±0.4 g) sustained consistently large infarct volumes (28±9% of ipsilateral hemisphere). Under identical experimental conditions, large mice (31±0.7 g) demonstrated much smaller infarcts (3.2±3%, p=0.02, FIG. 15A), less morbidity on neurological exam (FIG. 15B), and a tendency to maintain higher ipsilateral cerebral blood flow following infarction than smaller animals (FIG. 15C).

Because it was hypothesized that the reduction in infarct size infarcts in these large animals was related to a mismatch in diameter/length between occluding suture and the cerebral blood vessels, longer/thicker occluding sutures were fashioned (13 mm, 5-0 nylon) for use in these larger mice. Large CD1 mice (34±0.8 g) which underwent permanent occlusion with these larger occluding sutures sustained a marked increase in infarct volumes (50±10% of ipsilateral hemisphere, p<0.0001 compared with large mice infarcted with the smaller occluding suture, FIG. 15A). These larger mice infarcted with larger occluding sutures demonstrated higher neurologic deficit scores (FIG. 15B) and lower ipsilateral cerebral blood flows (FIG. 15C) compared with similarly large mice infarcted with smaller occluding sutures.

Figure 16A:
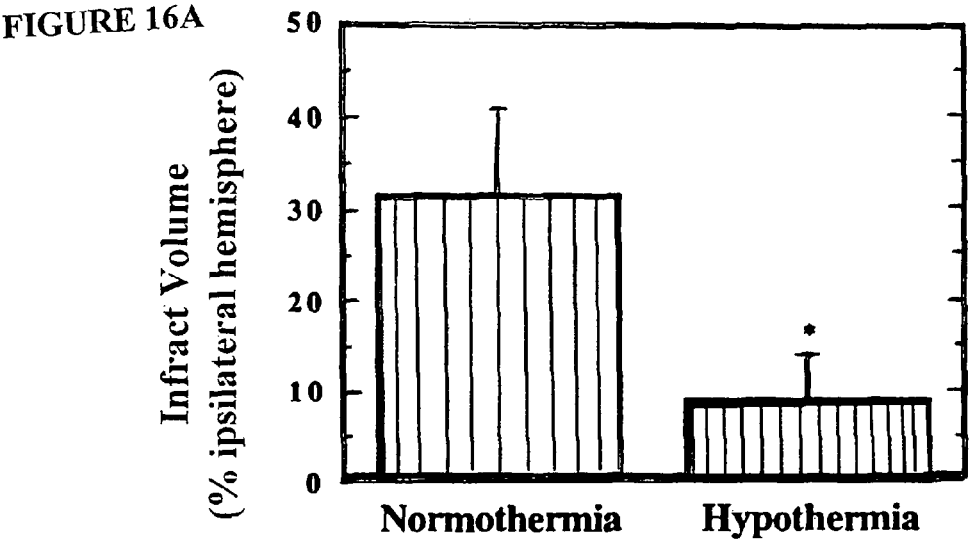
FIGS. 16A, 16B and 16C. Effects of temperature on stroke outcome. Male C57/Bl6 mice were subjected to 45 minutes of MCA occlusion (6.0 suture) followed by reperfusion. Core temperatures were maintained for 90 minutes at 37° C. (normothermia, n=11) using an intrarectal probe with a thermocouple-controlled heating device. In the second group (hypothermia, n=12), animals were placed in cages left at room temperature after an initial 10 minutes of normothermia (mean core temperature 31° C. at 90 minutes). In both groups, after this 90 minute observation period, animals were returned to their cages with ambient temperature maintained at 37° C. for the duration of observation. Twenty-four hours following MCA occlusion, indices of stroke outcome were recorded.
Figure 16B:
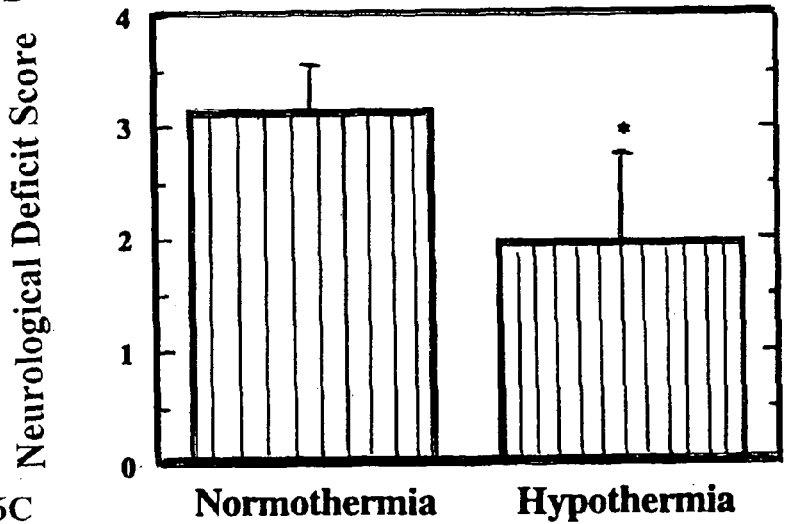
Figure 16C:
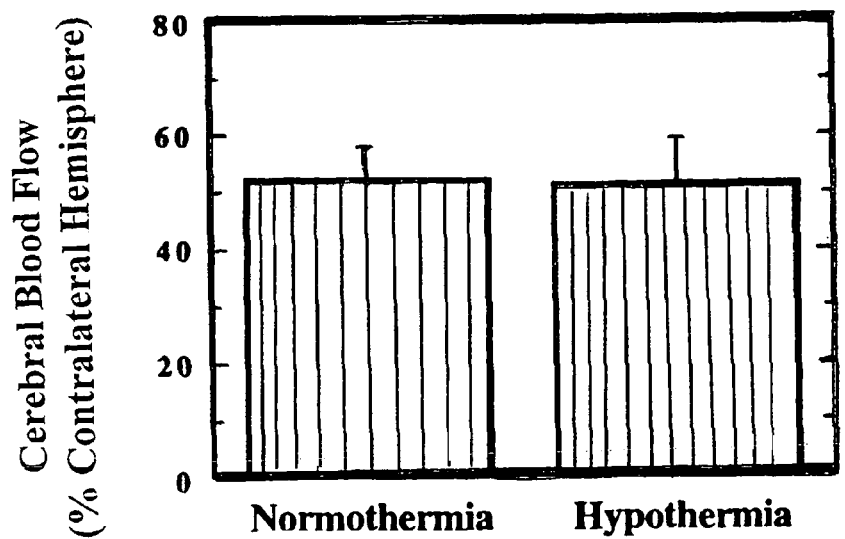

Effects of Temperature: To establish the role of perioperative hypothermia on the stroke volumes and neurologic outcomes following MCA occlusion, small C57/Bl6 mice (22±0.4 g) were subjected to permanent MCA occlusion with 12 mm 6-0 gauge suture, with normothermia maintained for two different durations; Group 1 ("Normothermia") was operated as described above, maintaining temperature at 37° C. from the preoperative period until 90 minutes post-occlusion. Group 2 animals ("Hypothermia") were maintained at 37° C. from preop to only 10 minutes post-occlusion, as has been described previously (14). Within 45 minutes following removal from the thermocouple-controlled warming incubator, core temperature in this second group of animals dropped to 33.1±0.4° C. (and dropped further to 31.3±0.2° C. at 90 minutes). Animals operated under conditions of prolonged normothermia (Group 1) exhibited larger infarct volumes (32±9%) than hypothermic (Group 2) animals (9.2±5%, p=0.03, FIG. 16A). Differences in infarct volume were mirrored by differences in neurological deficit (3.2±0.4 vs. 2.0±0.8, p=0.02, FIG. 16B), but were largely independent of cerebral blood flow (52±5 vs. 52±7, p=NS; FIG. 16C).

Figure 17A:
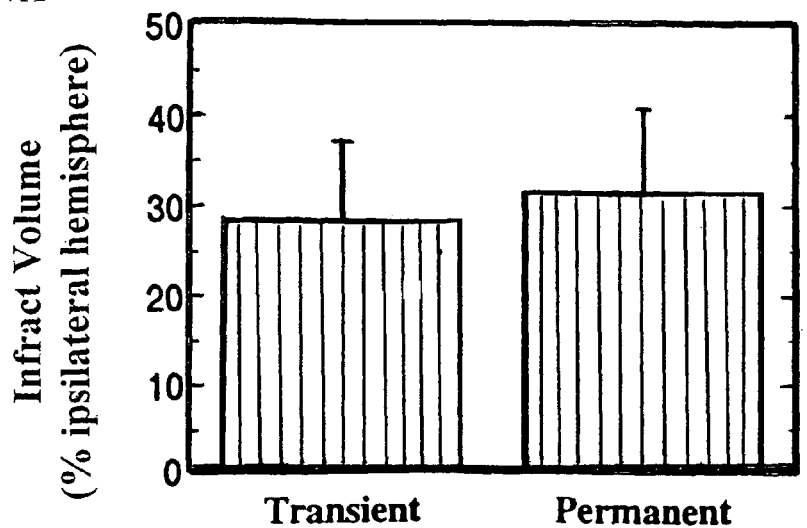
FIGS. 17A, 17B and 17C. Outcome comparisons between permanent focal cerebral ischemia and transient focal cerebral ischemia followed by reperfusion. The MCA was either occluded permanently (n=11) or transiently (45 minutes, n=17) with 6.0 gauge suture in 22 gram Male C57/Bl6 mice, as described in the Methods section. Twenty-four hours following MCA occlusion, indices of stroke outcome were recorded.
Figure 17B:
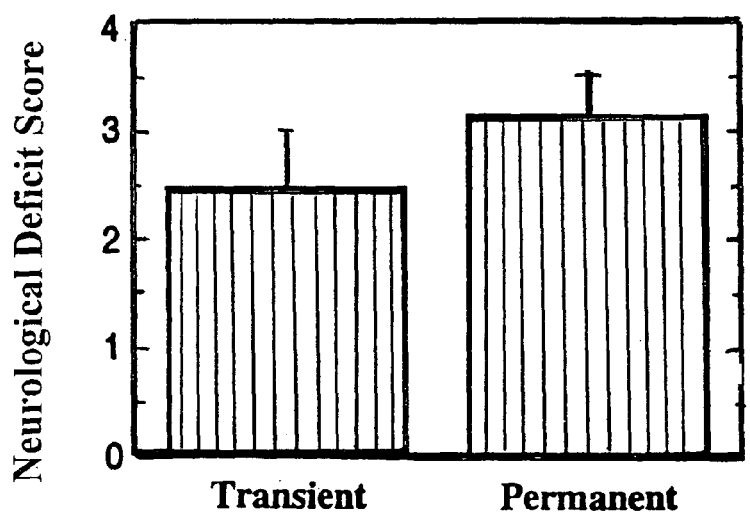
Figure 17C:
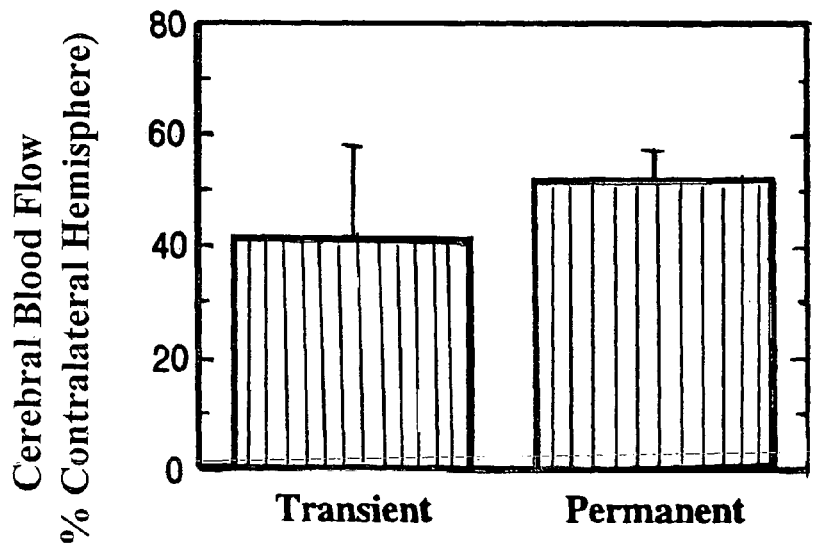

Effects of Transient MCA Occlusion: Because reperfusion injury has been implicated as an important cause of neuronal damage following cerebrovascular occlusion (25), a subset of animals was subjected to a transient (45 minute) period of ischemia followed by reperfusion as described above, and comparisons made with those animals which underwent permanent MCA occlusion. The time of occlusion was chosen on the basis of preliminary studies (not shown) which demonstrated unacceptibly high mortality rates (>85%) with 180 minutes of ischemnia and rare infarction (<15%) with 15 minutes of ischemia. To minimize the confounding influence of other variables, other experimental conditions were kept constant (small (22.5±0.3 g) C57/Bl6 mice were used, the occluding suture consisted of 12 mm 6-0 nyon, and experiments were performed under normothermic conditions). The initial decline in CBF immediately post-occlusion were similar in both groups (16±2% vs 17±3%, for transient vs permanent occlusion groups, respectively, p=NS). Reperfusion was confirmed both by laser doppler (2.3-fold increase in blood flow following removal of the occluding suture to 66±13%), and visually by intracardiac methylene blue dye injection in representative animals. Infarct sizes (29±10% vs. 32±9%), neurologic deficit scores (2.5±0.5 vs. 3.2±0.4), and sacrifice cerebral blood flow (46±18% vs. 53±5%) were quite similar between between animals subjected to transient cerebral ischemia and reperfusion and those subjected to permanent focal cerebral ischemia (p=NS, for all groups) (FIGS. 17A-17C).

Discussion:

The growing availability of genetically altered mice has led to an increasing use of murine models of focal cerebral ischemia to impute specific gene products in the pathogenesis of stroke. Although recent publications describe the use of an intraluminal suture to occlude the middle cerebral artery to create permanent and/or transient cerebral ischemia in mice, there has been only scant description of the necessary modifications of the original technical report in rats (8,14,17-19, 24,26). The experiments described herein not only provide a detailed technical explanation of a murine model suitable for either permanent or transient focal middle cerebral artery ischemia, but also address potential sources of variability in the model.

Importance of Strain:

One of the most important potential sources of variability in the murine cerebral ischemia model described herein is related to the strain of animal used. The data suggest that, of the three strains tested, 129J mice are particularly resistant to neurologic injury following MCA occlusion. Although Barone similarly found differences in stroke volumes between 3 strains of mice (BDF, CFW and BALB/C), these differences were ascribed to variations in the posterior communicating arteries in these strains (4). As anatomical differences in cerebrovascular anatomy were not grossly apparent in the study (FIG. 13), the data suggests that non-anatomic strain-related differences are also important in outcome following MCA occlusion.

As stroke outcome differs significantly between 2 strains of mice (129J and C57/Bl6) commonly used to produce transgenic mice via homologous recombination in embryonic stem cells (11), the data suggest an important caveat to experiments performed with transgenic mice. Because early founder progeny from the creation of transgenic animals with these strains have a mixed 129J/C57/Bl6 background, ideally experiments should be performed either with sibling controls or after a sufficient number of backcrossings to ensure strain purity.

Importance of Size:

Larger animals require a longer and thicker intralumenal suture to sustain infarction volumes which are consistent with those obtained in smaller animals with smaller occluding sutures. Size matching of animal and suture appear to be important not only to produce consistent cerebral infarction, but whereas too small a suture leads to insufficient ischemia, too large a suture leads to frequent intracerebral hemorrhage and vascular trauma (unpublished observation).

The use of animals of similar size is important not only to minimize potential age-related variability in neuronal susceptability to ischemic insult, but also to ensure that small differences in animal size do not obfuscate meaningful data comparison. In this example, it is demonstrated that size differences of as little as 9 grams can have a major impact on infarct volume and neurologic outcome following cerebral ischemia. Further experiments using larger bore occluding suture in larger animals suggest that the increased propensity of smaller animals to have larger strokes was not due to a relative resistance of larger animals to ischemic neuronal damage, but was rather due to small size of the suture used to occlude the MCA in large animals. Although these data were obtained using CD1 mice, similar studies have been performed and found these results to be true with other mouse strains as well, such as C57/Bl6 (unpublished data). Previously published reports use mice of many different sizes (from 21 g to 35 g), as well as different suture diameters and lengths which are often unreported (14,17). The studies indicate that animal and suture size are important methodological issues which must be addressed in scientific reports.

Importance of Temperature:

It has long been recognized that hypothermia protects a number of organs from ischemic injury, including the brain. Studies performed in rats have demonstrated that intraischemic hypothermia up to 1 hour post-MCA occlusion is protective (2,15), reducing both mortality and infarct volumes with temperatures of 34.5 degrees. Although these results have been extrapolated to murine models of cerebral ischemia in that studies often describe maintenance of normothermia in animals, the post-MCA occlusion temperature monitoring periods have been extremely brief ("immediately after surgery" or "10 minutes after surgery") (4,14). The results indicate that animals fail to autoregulate their temperature beyond these brief durations, becoming severely hypothermic during the postoperative period, and that temperature differences up to 90 minutes following MCA occlusion can have a profound effect on indices of stroke outcome following MCA occlusion (longer durations of normothermia were not studied). While others have ensured normothermia using a feedback system based on rectal temperature similar to the one described herein, the duration of normothermia is often not specified (17). The results argue for clear identification of methods for monitoring and maintaining temperature, as well as the durations involved, so that experimental results can be compared both within and between Centers studying the pathophysiology of stroke.

Transient vs Permanent Occlusion:

The pathophysiology of certain aspects of permanent cerebral ischemia may well be different from that of cerebral ischemia followed by reperfusion, so it was important that a model be described which permitted analysis of either condition. Although differences between these two models were not extensively tested in the current series of experiments, under the conditions tested (45 minutes of ischemia followed by 23 hours of reperfusion), no significant differences were found in any index of stroke outcome. Variable durations of ischemia and reperfusion have been reported in other murine models of transient cerebral ischemia, with ischemic times ranging from 10 minutes to 3 hours and reperfusion times ranging from 3 to 24 hours (17,24). Studies in rats have shown that short periods of ischemia followed by reperfusion are associated with smaller infarcts than permanent occlusion (21,25). However as the duration of ischemia increases beyond a critical threshold (between 120 and 180 minutes), reperfusion is associated with larger infarcts (7,21,26). For the current series of experiments, the durations of ischemia and reperfusion were chosen so as to obtain infarcts comparable to those observed following permanent MCA occlusion, which is likely to explain why the data failed to show differences between permanent and transient ischemia. These durations in the transient model were chosen after pilot experiments revealed that shorter ischemic durations (15 minutes) rarely led to infarction, whereas 180 minutes of occlusion followed by reperfusion led to massive infarction and nearly 100% mortality within 4-6 hours in normothermic animals (unpublished observation). Although indices of stroke outcome may be measured earlier than 24 hours, the 24 hour observation time was elected because observation at this time permits the study of delayed penumbral death, which is likely to be clinically relevant to the pathophysiology of stroke in humans. Furthermore, 24 hours has been shown in a rat model to be sufficient for full infarct maturation (3,12,15,16).

Technical Aspects of the Murine Model:

Technical aspects of the surgery needed to create focal cerebral ischemia in mice differ in certain important respects from that in rats. Self-retaining retractors, which have been advocated in previous reports in rats (26), are unweildy in mice. Suture-based retraction secured with tape provides a superior alternative. In rats, clip occlusion of the proximal and distal carotid artery after mobilization of the external carotid artery has been reported (26), but creates more carotid trauma and hemmorhage in mice. Without distal internal carotid control, which has not been previously described in mice, backbleeding from the external carotid artery is consistently uncontrollable. Using the techniques described in this paper, surgery can be completed with virtually no blood loss, which is especially important given the small blood volume in mice.

Unlike the rat model, the occlusion and transection of the external carotid artery branches and the pterygopalatine artery in the murine model is achieved with electrocautery alone. Previous reports of murine surgery have been unclear as to whether or not the pterygopalatine artery was taken (17,24). Others have described a method with permanent occlusion of the common carotid artery and trans-carotid insertion of the suture without attention to either the external carotid system or the pterygopalatine artery. While effective for permanent occlusion, this latter method makes reperfusion studies impossible.

The method of reperfusion originally described in the rat requires blind catheter withdrawal without anesthesia (26). When attempted in pilot studies in mice, several animals hemorrhaged. Therefore, a method of suture removal under direct visualization in the anesthetized animal was developed, which not only allows visual confirmation of extracranial carotid artery reperfusion, but also affords meticulous hemostasis. Further, the method permits immediate pre- and post-reperfusion laser doppler flowmetry readings in the anesthetized animal.

These laser doppler flowmetry readings are similar to those described by Kamii et al. and Yang et al. In that the readings are made intermittently and with the use of a stereotactic micromanipulator (17,24). The readings differ, however, in that the coordinates used (2 mm posterior and 3 and 6 mm lateral to the bregma) are slightly more lateral and posterior than the previously published core and penumbral coordinates (1 mm posterior and 2 mm and 4.5 mm lateral to the bregma). These coordinates, which were adopted based on pilot studies, are the same as those used by Huang et al (14).

Conclusion:

These studies demonstrate specific technical aspects of a murine model of focal cerebral ischemia and reperfusion which permits reproducibility of measurements between different laboratories. In addition, these studies provide a framework for understanding important procedural variables which can greatly impact on stroke outcome, which should lead to a clear understanding of non-procedure related differences under investigation. Most importantly, this study points to the need for careful control of mouse strain, animal and suture size, and temperature in experimental as well as control animals. Conditions can be established so that stroke outcome is similar between models of permanent focal cerebral ischemia and transient focal cerebral ischemia, which should facilitate direct comparison and permit the study of reperfusion injury. The model described in this study should provide a cohesive framework for evaluating the results of future studies in transgenic animals, to facilitate an understanding of the contribution of specific gene products in the pathophysiology of stroke.

TABLE I

| PARAMETER | PREOPERATIVE | SHAM | STROKE |
|---|---|---|---|
| MAP | 102 ± 5.5 | 94 ± 1.9 | 88 ± 4.9 |
| pH | 7.27 ± 0.02 | 7.23 ± 0.04 | 7.28 ± 0.01 |
| pCO$_2$ | 46 ± 1.3 | 44 ± 1.3 | 47 ± 3.5 |

TABLE I-continued

| PARAMETER | PREOPERATIVE | SHAM | STROKE |
|---|---|---|---|
| O$_2$ Sat | 89 ± 1.6 | 91 ± 1.8 | 85 ± 2.2 |
| Hb | 14.6 ± 0.42 | 14.3 ± .12 | 14.2 ± 0.12 |

Pre- and post-operative physiologic parameters.
MAP, mean arterial pressure;
pCO$_2$, partial pressure of arterial CO$_2$ (mm Hg);
O$_2$ Sat, O$_2$ saturation (%);
Hb, hemoglobin concentration (g/dl);
Preoperative, anesthetized animals prior to carotid dissection;
Sham, anesthetized animals undergoing the surgical described in the text, immediately prior to introduction of the occluding suture;
Stroke, anesthetized animals undergoing the surgical described in the text, immediately after introduction of the occluding suture.
p = NS for all between-group comparisons.
(data shown is for small 22 gram C57/Bl6 mice).

References:
1. Backhaub C, Karkoutly C, Welsch M, Krieglstein J: A mouse model of focal cerebral ischemia for screening neuroprotective drug effects: J Pharmacol Methods 27:27-32, 1992.
2. Baker C J, Onesti S T, Solomon R A: Reduction by delayed hypothermia of cerebral infarction following middle cerebral artery occlusion in the rat: a time-course study. J Neurosurg 77:438-444, 1992;
3. Baker C J, Fiore A J, Frazzini V I, Choudhri T F, Zubay G P, Solomon R A: Intraischemic hypothermia decreases the release of glutamate in the cores of permanent focal cerebral infarcts. Neurosurgery 36:1-9, 1995.
4. Barone F C, Knudsen D J, Nelson A H, Feuerstein G Z, Willette R N: Mouse strain differences in susceptibility to cerebral ischemia are related to cerebral vascular anatomy. J Cereb Blood Flow Metab 13:683-692, 1993.
5. Bederson J B, Pitts L H, Germano S M, Nishimura M C, Davis R L, Bartkowski H M: Evaluation of 2,3,5-triphenyltetrazolium chloride as a stain for detection and quantification of experimental cerebral infarction in rats. Stroke 17:1304-1308, 1986.
6. Bederson J B, Pitts L H, Tsuji M: Rat middle cerebral artery occlusion: evaluation of the model and development of a neurologic examination. Stroke 17:472-476, 1986.
7. Buchan A M, Xue D, Slivka A: A new model of temporary focal neocortical ischemia in the rat. Stroke 23:273-279, 1992.
8. Chan P H, Kamii H, Yang G, Gafni J, Epstein C J, Carlson E, Reola L: Brain infarction is not reduced in SOD-1 transgenic mice after permanent focal cerebral ischemia. NeuroReport 5:293-296, 1993.
9. Chiamulera C, Terron A, Reggiani A, Cristofori P: Qualitative and quantitative analysis of the progressive cerebral damage after middle cerebral artery occlusion in mice. Brain Res 606:251-258, 1993.
10. Dirnagl U, Kaplan B, Jacewicz M, Pulsinelli W: Continuous measurement of cerebral cortical blood flow by laser doppler flowmetry in a rat stroke model. J Cereb Blood Flow Metab 9:589-596, 1989.
11. Donehower L A, Harvey M, Slagle B L, McArthur M J, Montgomery C A, Butel J S, Bradley A: Mice deficient for p53 are developmentally normal but susceptible to spontaneous tumours. Nature 356:215-221, 1992.
12. Frazzini V I, Winfree C J, Choudhri H F, Prestigiacomo C J, Solomon R A: Mild hypothermia and MK-801 have similar but not additive degrees of cereboprotection in the rat permanent focal ischemia model. Neurosurgery 34:1040-1046, 1994.
13. Ginsberg M D, Busto R: Rodent: models of cerebral ischemia. Stroke 20:1627-1642, 1989.

14. Huang Z, Huang P L, Panahian N. Dalkara T, Fishman M C, Moskowitz M A: Effects of cerebral ischemia in mice deficient in neuronal nitric oxide synthase. Science 265: 1883-1885, 1994.
15. Kader A, Brisman M H, Maraire N, Huh J-T, Solomon R A: The effect of mild hypothermia on permanent focal ischemia in the rat. Neurosurgery 31:1056-1061, 1992.
16. Kader A, Frazzini V I, Solomon R A, Trifiletti R R: Nitric oxide production during focal cerebral ischemia in rats. Stroke 24:1709-1716, 1993.
17. Kamii H, Kinouchi H, Sharp F R, Koistinaho J, Epstein C J, Chan P H: Prolonged expression of hsp 70 mRNA following transient focal cerebral ischemia in transgenic mice overexpressing CuZn-superoxide dismutase. J Cereb Blood Flow Metab 14:478-486, 1994.
18. Kinouchi H, Epstein C J, Mizui T, Carlson R, Chen S F, Chan P H: Attenuation of focal cerebral ischemic injury in transgenic mice overexpressing CuZn superoxide dismutase. Proc Natl Acad Sci 88: 11158-11162, 1991.
19. Martinou J-C, Dubois-Dauphin M, Staple J K, Rodriguez I, Frankowski H, Missotten M, Albertini P, Talabot D, Catsicas S, Pietra C, Huarte J: Overexpression of BCL-2 in transgenic mice protects neurons from naturally occuring cell death and experimental ischemia. Neuron 13:1017-1030, 1994.
20. Memezawa H; Smith M L, Siesjo B K: Penumbral tissues salvaged by reperfusion following middle cerebral artery occlusion in rats. Stroke 23:552-559, 1992.
21. Menzies S A, Hoff J T., Betz A L: Middle Cerebral Artery Occlusion in Rats: A neurological and pathological evaluation of a reproducible model. Neurosurgery 31:100-107, 1992.
22. Tamura A, Graham D I, McCullough J, Teasdale G M: Focal cerebral ischemia in the rat. 1: description of technique and early neuropathological consequences following middle cerebral artery occlusion. J Cereb Blood Flow Metabol 1: 53-60, 1981.
23. Welsh F A, Sakamoto T, McKee A E, Sims R E: Effect of lactacidosis on pyridine nucleotide stability during ischemia in mouse brain. J Neurochem 49-846-851; 1987.
24. Yang G, Chan P H, Chen J, Carlson E, Chen S F, Weinstein P, Epstein C J, Kamii H: Human copper-zinc superoxide dismutase transgenic mice are highly resistant to reperfusion injury after focal cerebral ischemia. Stroke 25.:165-170, 1994.
25. Yang G-Y, Betz A L: Reperfusion-induced injury to the blood-brain barrier after middle cerebral artery occlusion in rats. Stroke 25: 1658-65, 1994.
26. Zea-Longa E, Weinstein P R, Carlson S, Cummin R W: Reversible middle cerebral artery occlusion without craniectomy in rat. Stroke 20:84-91, 1989.

Example 4

Exacerbation of Cerebral Injury In Mice Which Express the P-Selectin Gene: Identication of P-selectin Blockade as a New Target for the Treatment of Stroke There is currently a stark therapeutic void for the treatment of evolving stroke. Although P-selectin is rapidly expressed by hypoxic endothelial cells in vitro, the functional significance of P-selectin expression in stroke remains unexplored. In order to identify the pathophysiological consequences of P-selectin expression and to identify P-selectin blockade as a potential new approach for the treatment of stroke, experiments were performed using a murine model of focal cerebral ischemia and reperfusion. Early P-selectin expression in the post-ischemic cerebral cortex was demonstrated by the specific accumulation of radiolabelled anti-murine P-selectin IgG. In parallel experiments, neutrophil accumulation in the ischemic cortex of mice expressing the P-selectin gene (PS +/+) was significantly greater than that demonstrated in homozygous P-selectin null mice (PS −/−). Reduced neutrophil influx was accompanied by greater postischemic cerebral reflow (measured by laser doppler) in the PS −/− mice. In addition, PS −/− mice demonstrated smaller infarct volumes (five-fold reduction, $p<0.05$) and improved survival compared with PS +/+ mice (88% vs. 44%, $p<0.05$). Functional blockade of P-selectin in PS +/+ mice using a monoclonal antibody directed against murine P-selectin also improved early reflow and stroke outcome compared with controls. These data are the first to demonstrate a pathophysiological role for P-selectin in stroke, and suggest that P-selectin blockade may represent a new therapeutic target for the treatment of stroke.

Introduction

Ischemic stroke consitutes the third leading cause of death in the United States today [1]. Until very recently, there has been no direct treatment to reduce cerebral tissue damage in evolving stroke. Although the NINDS [2] and ECASS[3] rt-PA acute stroke studies have suggested that there are potential therapeutic benefits of early reperfusion [4], the increased mortality observed following streptokinase treatment of acute ischemic stroke [5] highlights the sobering fact that there is at the present time no clearly effective treatment for evolving stroke. This void in the current medical armamentarium for the treatment of stroke has led to a number of innovative approaches [6], yet other than rt-PA, none have reached the clinical realm. To identify a potential safe and efficacious treatment for evolving stroke, attention has been focussed on the deleterious role of recruited neutrophils. Recent work in a murine model of reperfused stroke has demonstrated that depletion of neutrophils (PMNs) prior to stroke minimizes, cerebral tissue injury and improves functional outcome [7]; mice which lack the specific cell adhesion molecule, ICAM-1, are similarly protected [7]. P-selectin, a molecule which can be rapidly translocated to the hypoxic endothelial surface from pre-formed storage sites [8], is an important early mediator of the neutrophil rolling [9], which facilitates ICAM-1-mediated neutrophil arrest. Although P-selectin is expressed in primate stroke [10], there are no published data which addresses the functional significance of P-selectin expression in any model of either reperfused or nonreperfused stroke.

To explore the pathophysiological role of P-selectin in stroke, a murine model of focal cerebral ischemia and reperfusion [11] was employed using both wild type mice and mice which were homozygous null for the P-selectin gene [9] and a strategy of administering a functionally blocking P-selectin antibody. This study confirms not only that P-selectin expression following middle cerebral artery occlusion is associated with reduced cerebral reflow following reperfusion and a worse outcome following stroke, but that P-selectin blockade confers a significant degree of postischemic cerebral protection. These studies represent the first demonstration of the pathophysiological role of P-selectin expression in stroke, and suggest the exciting possibility that anti-P-selectin strategies may prove useful for the treatment of reperfused stroke.

Methods

Mice: Experiments were performed with transgenic P-selectin deficient mice, created as previously reported [9] by gene targeting in J1 embryonic stem cells, injected into C57BL/6 blastocysts to obtain germline transmission, and backcrossed to obtain homozygous null P-selectin mice (PS −/−). Experiments were performed with PS −/− or wild-type (PS +/+) cousin mice from the third generation of backcrossings with C57BL/6J mice. Animals were seven to twelve weeks of age and weighed between 25-36 grams at the time of experiments.

Transient Middle Cerebral Artery Occlusion: Mice were anesthetized (0:3 cc of 10 mg/cc ketamine and 0.5 mg/cc xylazine, i.p.), and positioned supine on a rectal temperature-controlled, operating surface (Yellow Springs Instruments, Inc., Yellow Springs, Ohio). Animal core temperature was maintained at 37±1° C. intraoperatively and for 90 minutes post-operatively. A midline neck incision was created to expose the right carotid sheath under the operating microscope (16-25× zoom, Zeiss, Thornwood, N.Y.). The common carotid artery was isolated with a 4-0 silk, and the occipital, pterygopalatine, and external carotid arteries were each isolated and divided. Middle cerebral artery occlusion (MCAO) was accomplished by advancing a. 13 mm heat-blunted 5-0 nylon suture via the external carotid stump. After placement of the occluding suture, the external carotid artery stump was cauterized, and the wound was closed. After 45 minutes, the occluding suture was withdrawn to establish reperfusion. These procedures have been previously described in detail [9].

Measurement of cerebral cortical blood flow: Transcranial measurements of cerebral blood flow were made using laser doppler (Perimed, Inc., Piscataway, N.J.), as previously described [12]. Using a 0.7 mm straight laser doppler probe (model #PF303, Perimed, Piscataway, N.J.) and previously published landmarks (2 mm posterior to the bregma, 6 mm to each side of midline) [11,13], relative cerebral blood flow measurements were made as indicated; immediately after anesthesia, 1 and 10 minutes after occlusion of the middle cerebral artery, as well as after 30 minutes, 300 minutes and 22 hours of reperfusion. Data are expressed as the ratio of the doppler signal intensity of the ischemic compared with the nonischemic hemisphere. Although this method does not quantify cerebral blood flow per gram of tissue, use of laser doppler flow measurements at precisely defined anatomic landmarks serves as a means of comparing cerebral blood flows in the same animal serially over time. The surgical procedure was considered to be technically adequate if ≧50% reduction in relative cerebral blood flow was observed immediately following placement of the intraluminal occluding suture. These methods have been used in previous studies [7,11].

Cerebrovascular anatomy was determined in representative animals in the following manner. Mice were anesthetized, and an antemortem injection (0.1 mL) of India ink: carbon black:methanol:physiological saline (1:1:1:1, v:v:v:v) was given by left ventricular puncture. Brains were prepared by rapid decapitation followed by immersion in 10% formalin at 4° C. for 2 days, after which the inferior surfaces were photographed to demonstrate the vascular pattern of the Circle of Willis.

Preparation and administration of $^{125}$I-labelled proteins and $^{111}$In-labelled murine neutrophils: Radioiodinated antibodies were prepared as follows. Monoclonal rat anti-murine P-selectin IgG (Clone RB 40.34, Pharmingen Co., San Diego, Calif.) [14] and non-immune rat IgG (Sigma Chemical Co., St. Louis, Mo.) were radiolabeled with $^{125}$I by the lactoperoxidase method [15] using Enzymobeads (Bio-Rad, Hercules, Calif.). Radiolabelled PMNs were prepared in the following manner. Citrated blood from wild type mice was diluted 1:1 with NaCl (0.9%) followed by gradient ultracentrifugation on Ficoll-Hypaque (Pharmacia, Piscataway, N.J.). Following hypotonic lysis of residual erythrocytes (20 sec exposure to distilled $H_2O$ followed by reconstitution with 1.8% NaCl), the PMNs were suspended in phosphate buffered saline (PBS). Neutrophils (5-7.5×10$^6$) were suspended in PBS with 100 µCi of Indium oxine (Amersham Mediphysics, Port Washington, N.Y.), and subjected to gentle agitation for 15 minutes at 37° C. After washing with PBS, the PMNs were gently pelleted (450× g), and resuspended in PBS to a final concentration of 1.0×10$^6$ cells/mL.

Neurological Exam: Prior to giving anesthesia mice were examined for neurological deficit 22 h after reperfusion using a four-tiered grading system[11]: a score of [1] was given if the animal demonstrated normal spontaneous movements; a score of [2] was given if the animal was noted to be turning towards the ipsilateral side; a score of [3] was given if the animal was observed to spin longitudinally (clockwise when viewed from the tail); a score of [4] was given if the animal was unresponsive to noxious stimuli. This scoring system has been previously described in mice [7,11], and is based upon similar scoring systems used in rats [16,17].

Calculation of Infarct Volumes: After neurologic examination, mice were anesthesized and final cerebral blood flow measurements obtained. Humane euthanasia was performed by decapitation, and brains were removed and placed in a mouse brain matrix (Activational Systems Inc., Warren, Mich.) for 1 mm sectioning. Sections were immersed in 2% 2,3,5-triphenyl-2H-tetrazolium chloride (TTC, Sigma Chemical Co., St. Louis, Mo.) In 0.9% phosphate-buffered saline, incubated for 30 minutes at 37° C., and placed in 10% formalin [18]. Infarcted brain was visualized as an area of unstained tissue. Infarct volumes were calculated from planimetered serial sections and expressed as the percentage of infarct in the ipsilateral hemisphere. This method of calculating infarct volumes has been used previously [7,11,13,18], and has been correlated with the other functional indices of stroke outcome which are described above.

Administration of Unlabeled Antibodies, Radiolabelled PMNs, and Radiolabeled Antibodies: For experiments in which unlabeled antibodies were administered, one of two different antibody types was used; either a blocking monoclonal rat anti-murine P-selectin IgG (Clone RB 40.34, Pharmingen Co., San Diego, Calif.) [14,19,20] or non-immune rat IgG (Sigma Chemical Co., St. Louis, Mo.). Antibodies were prepared as 30 µg in 0.2 mL phosphate buffered saline containing 0.1% bovine serum albumin, which was then administered into the penile vein 10 minutes prior to middle cerebral artery occlusion. In separate experiments, radiolabeled antibodies (0.15 mL, ≈2.6×10$^5$ cpm/µL) were injected intravenously 10 minutes prior to middle cerebral artery occlusion. In a third set of experiments, radiolabelled PMNs were administered intravenously 10 minutes prior to middle cerebral artery occlusion as a 100 µL injection (radiolabelled PMNs were admixed with physiologic saline to a total volume of 0.15 mL; ≈3×10$^6$ cpm/µL). For experiments in which unlabeled antibodies were administered, the time at which measurements were made are indicated in the text, using the methods described above to determine cerebral blood flow, infarction volumes, and mortality. For those experiments in which either radiolabelled antibodies or radiolabelled nPMNs were administered, mice were sacrificed at the indicated time points and brains were immediately removed and divided into ipsilateral (postischemic) and contralateral hemispheres. Deposition of radiolabeled antibodies or neutrophils was measured and expressed as ipsilateral/contralateral cpm.

Data Analysis: Cerebral blood flow, infarct volume, and $^{111}$InPMN deposition were compared using Student's t-test for unpaired variables. Neurological deficit scores were compared using the Mann-Whitney U-test. Two way ANOVA was performed to test for significant differences between baseline and final (30 min) antibody deposition between the two groups (experimental vs sham). Student's t-test for unpaired variables was performed to evaluate within-group differences (baseline vs the 30 min. time point). Survival differences between groups was tested using contingency analysis with the Chi-square 'statistic. Values are expressed as mean±SEM, with a p, value<0.05 considered statistically significant.

Results

P-selectin Expression in Murine Stroke: Because P-selectin mediates the initial phase of leukocyte adhesion to activated endothelial cells [21], early cerebral P-selectin expression was examined in a murine model of reperfused stroke. Mice given a $^{125}$I-labelled rat monoclonal anti-murine P-selectin IgG prior to surgery demonstrated a 216% increase in accumulation of the antibody at 30 minutes of reperfusion compared with sham operated animals (p<0.001, FIG. 18A). To demonstrate that this degree of antibody deposition in the reperfused hemisphere was due to P-selectin expression rather than nonspecific accumulation, comparison was made with identically-treated animals given a $^{125}$I, labelled rat non-immune IgG. These experiments demonstrated that there was significantly greater accumulation of the anti-P-selectin IgG than the nonimmune IgG (p<0.025, FIG. 18A), suggesting that P-selectin is expressed in the brain within 30 minutes of reperfusion.

Neutrophil Accumulation in Murine Stroke: To delineate the time course over which PMN influx occurs following stroke, $^{111}$In-labeled PMN accumulation was measured in wild type (PS +/+) mice prior to MCAO, immediately following and 10 minutes after MCAO, and at 30 min, 300 min, and 22 hrs of reperfusion. In PS +/+ mice, accumulation of PMNs begins early following the initiation of focal ischemia, and continues throughout the period of reperfusion (FIG. 18B). To establish the role for P-selectin in this postischemic neutrophil accumulation, experiments were performed using mice which were homozygous null for the P-selectin gene (PS −/−). PS −/− mice showed significantly reduced PMN accumulation following middle cerebral artery occlusion and reperfusion (FIG. 18B).

Figure 19A:
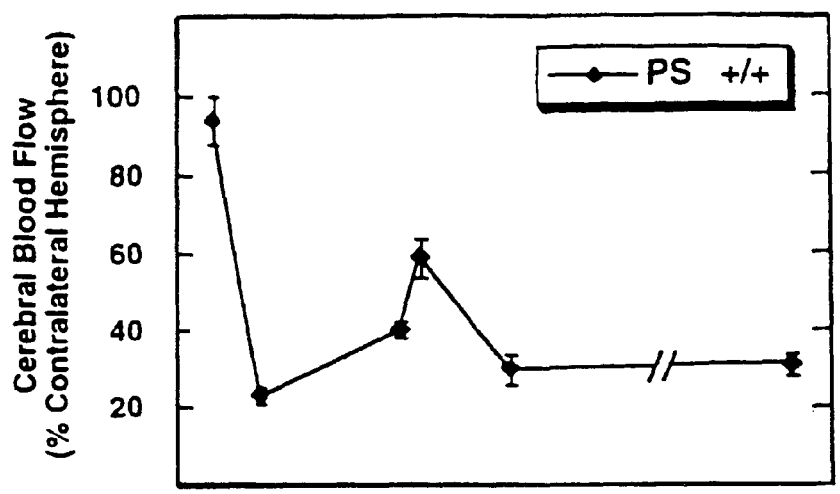
FIG. 19A, 19B and 19C: Role of P-selectin in the cerebrovascular no-reflow. Cerebral blood flow was measured in PS +/+ (FIG. 19A) and PS –/– (FIG. 19B) mice using a laser doppler flow probe, and expressed as the percentage of contralateral (nonischemic) hemispheric blood flow (±SEM). Blood flow was measured at the following time points: a, prior to MCAO (PS +/+, n=16; PS –/–, n=23); b, immediately following MCAO (PS +/+, n=42; PS –/–, n=40); c, 10 minutes following MCAO but still prior to reperfusion (PS +/+, n=36; PS –/–, n=34); d, immediately following reperfusion (PS +/+, n=36; PS –/–, n=34); e, 30 minutes following reperfusion (PS +/+, n=8; PS –/–, n=5); and f, 22 hours following reperfusion (PS +/+, n=15; PS –/–, n=5).
Figure 19B:
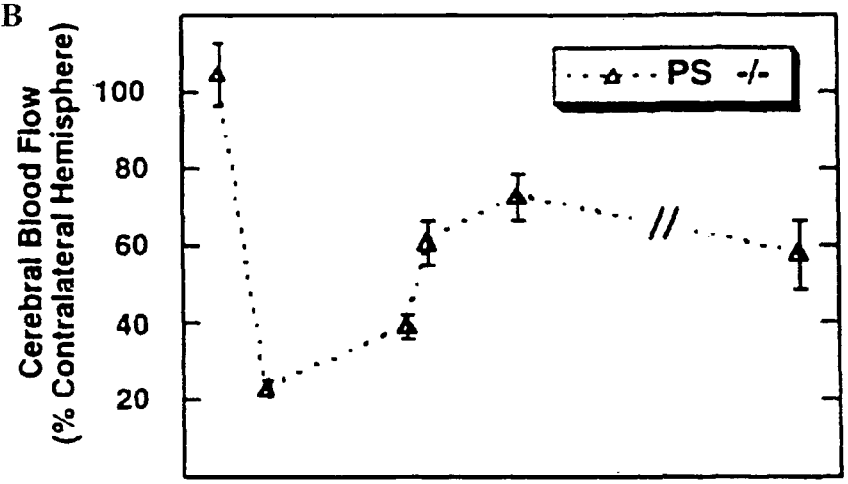
Figure 19C:
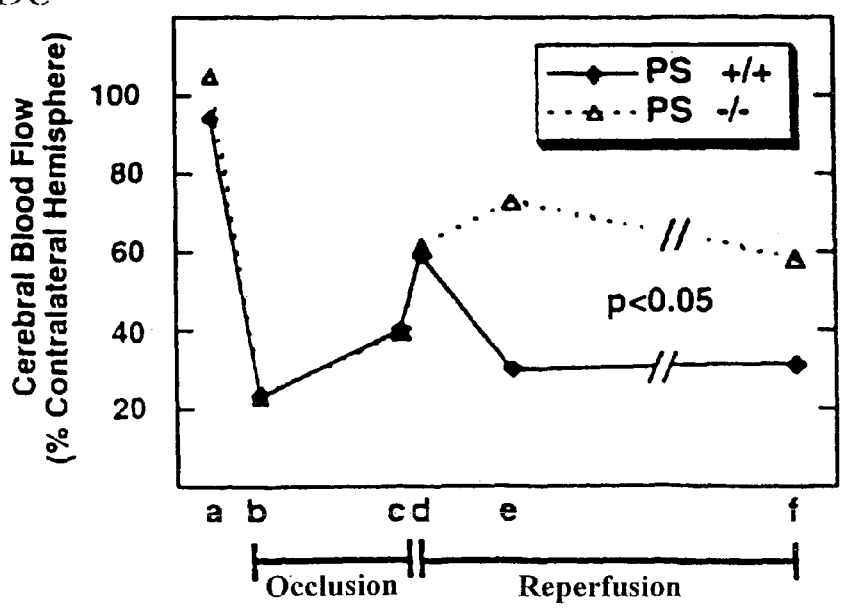

Role of PS in Cerebrovascular No-reflow: To determine whether the reduction in PMN accumulation in PS −/− mice resulted in improved cerebral blood flow following the reestablishment of flow, serial measurements of relative CBF were obtained by laser doppler in both PS +/+ and PS −/− mice. Prior to the initiation of ischemia (FIG. 19, point a), relative-cerebral blood flows were nearly identical between groups. Middle cerebral artery occlusion (FIG. 19, point b) was associated with a nearly identical drop in cerebral blood flow in both groups. Immediately prior to withdrawal of the intraluminal occluding suture at 45 minutes of ischemia (FIG. 19, point c), cerebral blood flows had risen slightly, although they remained significantly depressed compared with baseline flows. Immediately following withdrawal of the occluding suture to initiate reperfusion (FIG. 19, point d), cerebral blood flows in both groups increased to a comparable degree (≈60% of baseline in the PS −/− and PS +/+ mice). The, immediate failure of the post-reperfusion cerebral blood flows to reach pre-occlusion levels is characteristic of cerebrovascular no-reflow [22], with the subsequent decline in post-reperfusion cerebral blood flows representing delayed post ischemic cerebral hypoperfusion [23]. By 30 minutes of reperfusion. (FIG. 19, point e), the cerebral blood flows between the two groups of animals had diverged, with PS −/− animals demonstrating significantly greater relative cerebral blood flows than the PS +/+ controls (p<0.05). (FIG. 19, point f). This divergence reflected significant differences in delayed post-ischemic cerebral hypoperfusion, and persisted for the 22 hour observation period.

Figure 20:
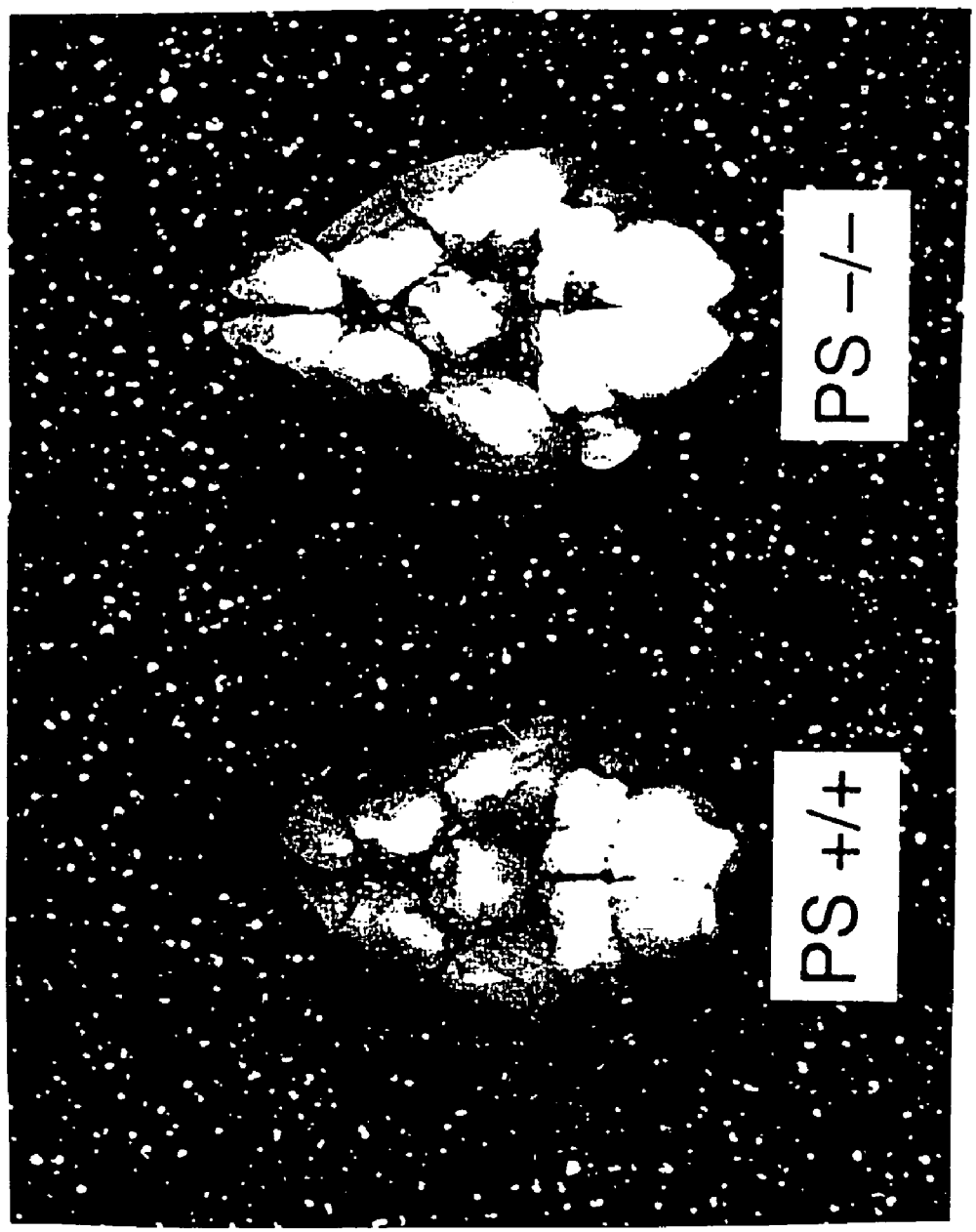
FIG. 20. Cerebrovascular anatomy in homozygous null P-selectin mice, PS –/– (right) and wild type controls, PS +/+ (left). India ink/carbon black staining of cerebrovascular anatomy with an inferior view of the Circle of Willis demonstrates that there were no gross anatomic differences in the vascular pattern of the cerebral circulation, with intact posterior communicating arteries in both.

Because variations in cerebrovascular anatomy have been reported to result in differences in susceptibility to experimental stroke in mice [24], India ink/carbon black staining was performed to visualize the the vascular pattern of the Circle of Willis in both in both PS −/− and PS +/+ mice. These experiments demonstrated that there were no gross anatomic differences in the vascular pattern of the cerebral circulation (FIG. 20).

Figure 21A:
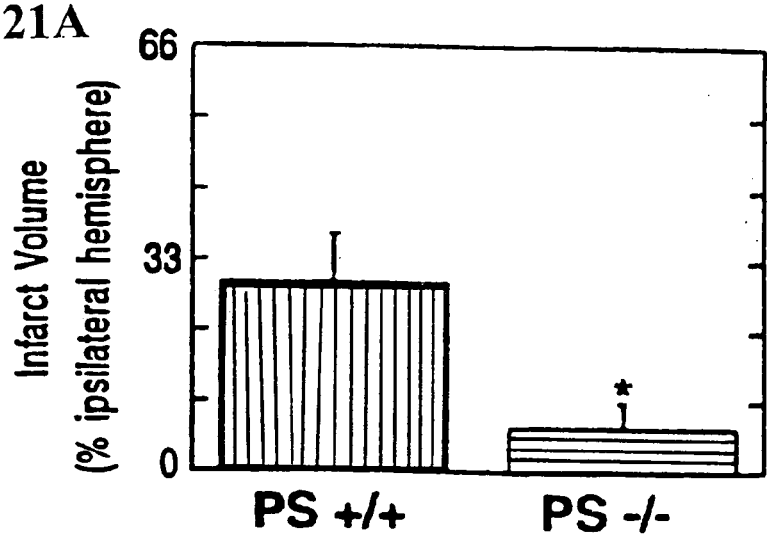
Figure 21B:
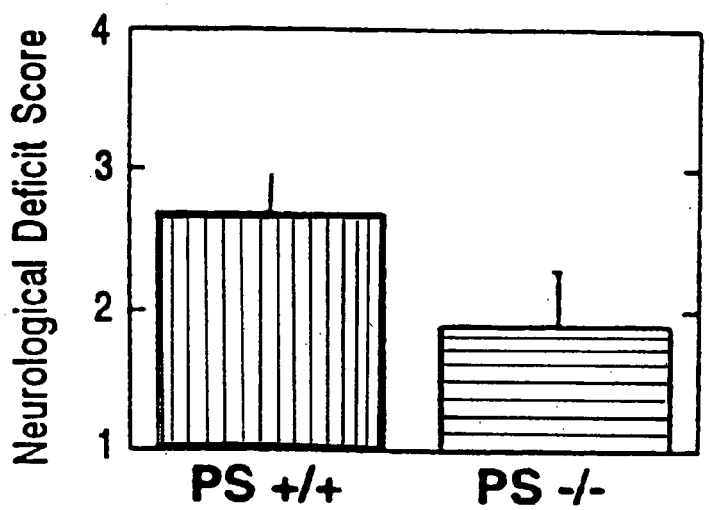
Figure 21C:
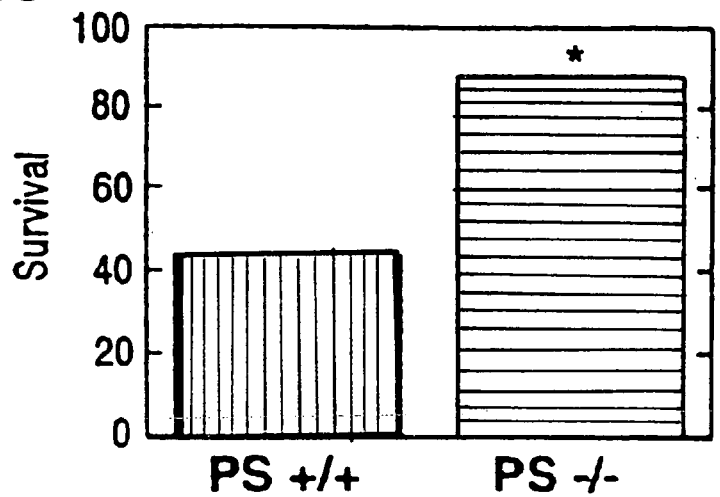

Stroke Outcome: The functional significance of P-selectin expression was tested by comparing indices of stroke outcome in PS −/− mice to those in PS +/+ controls. PS −/− mice were significantly protected from the effects of focal cerebral ischemia and reperfusion, based on a 77% reduction in infarct volume (p<0.01) compared with P-selectin+/+ controls (FIG. 21A). This reduction in infarct volume was accompanied by a trend towards reduced neurologic deficit (p=0.06, FIG. 21B) and increased survival (p<0.05; FIG. 21C) in the PS −/− animals.

Figure 22A:
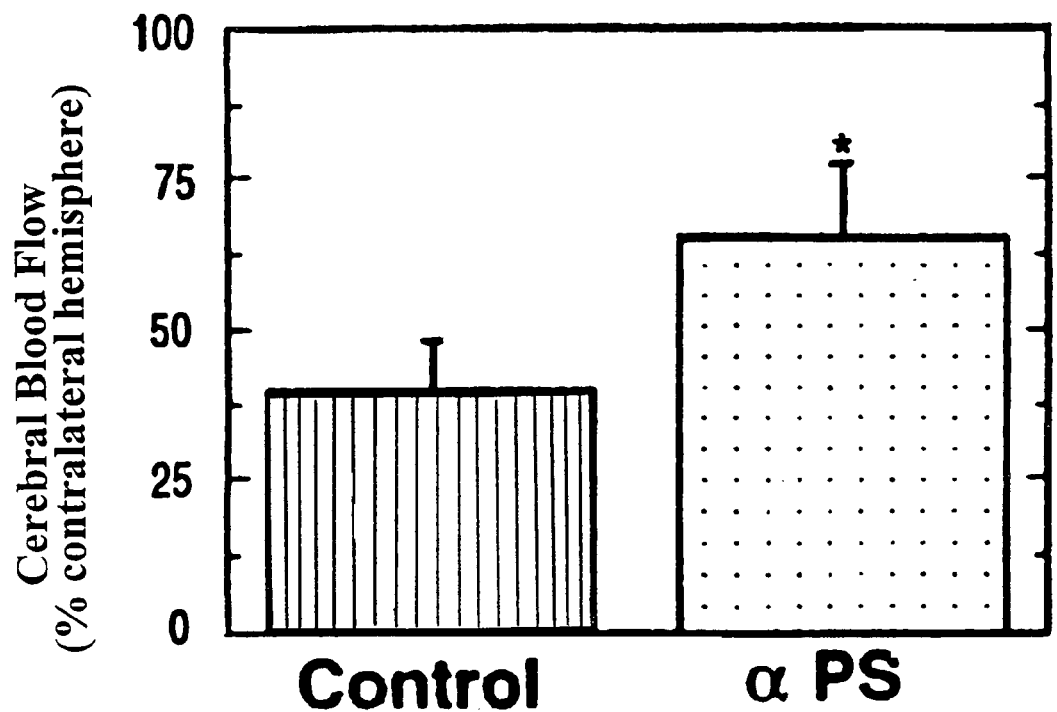
FIGS. 22A, 22B, 22C and 22D. Effect of P-selectin blockade on stroke outcomes. PS +/+ mice were given either a blocking rat anti-mouse anti-P-selectin IgG (clone RB 40.34, 30 µg/mouse) or a similar dose of nonimmune rat IgG immediately prior to surgery.
Figure 22B:
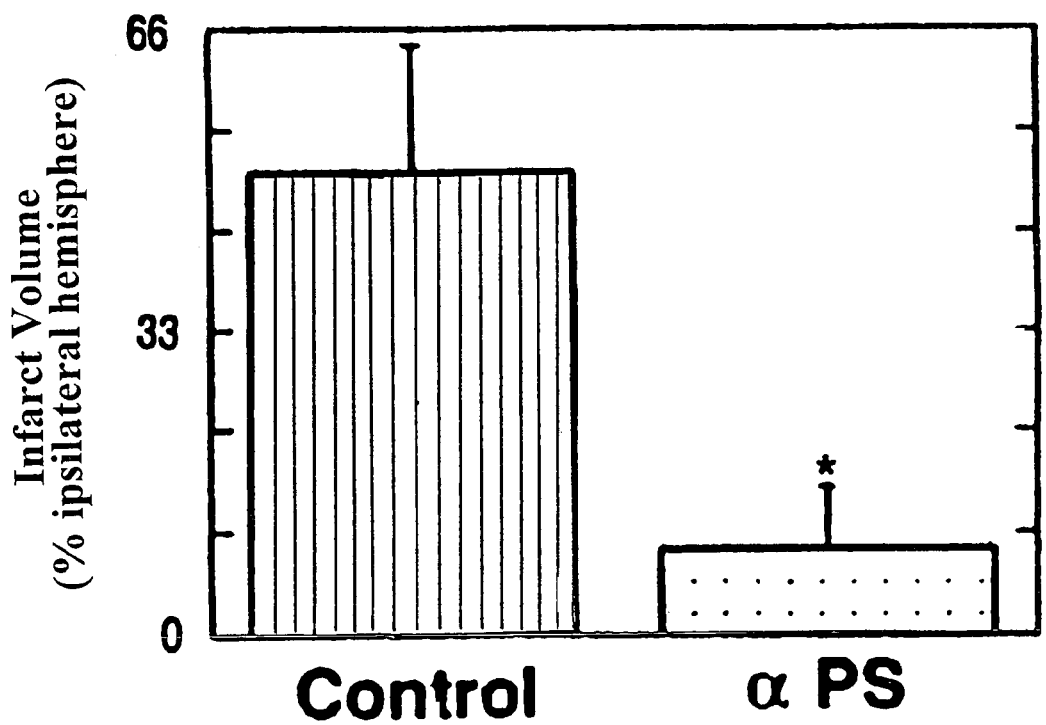
Figure 22C:
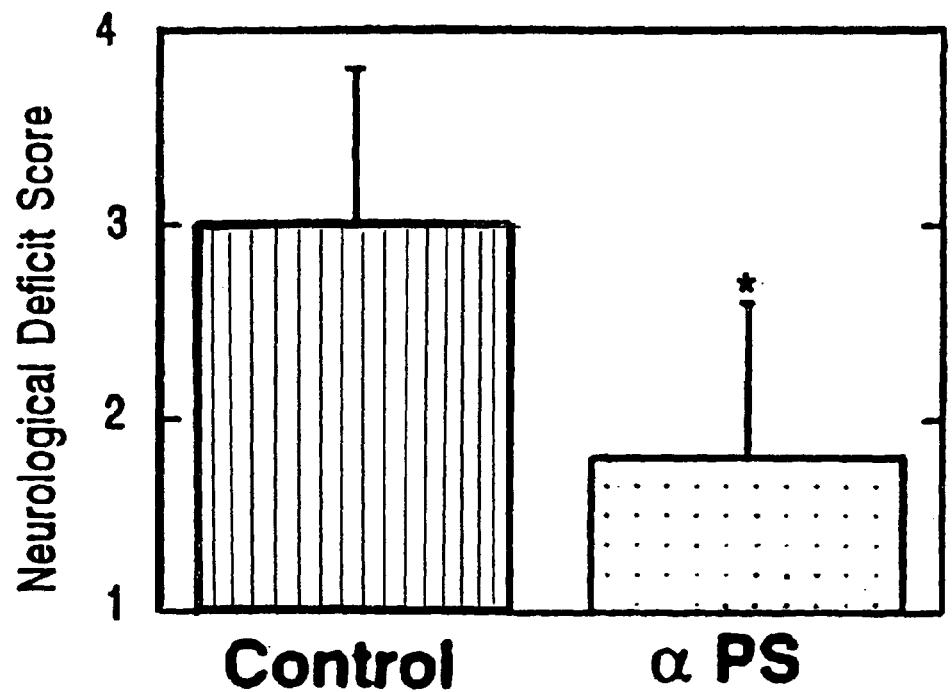
Figure 22D:
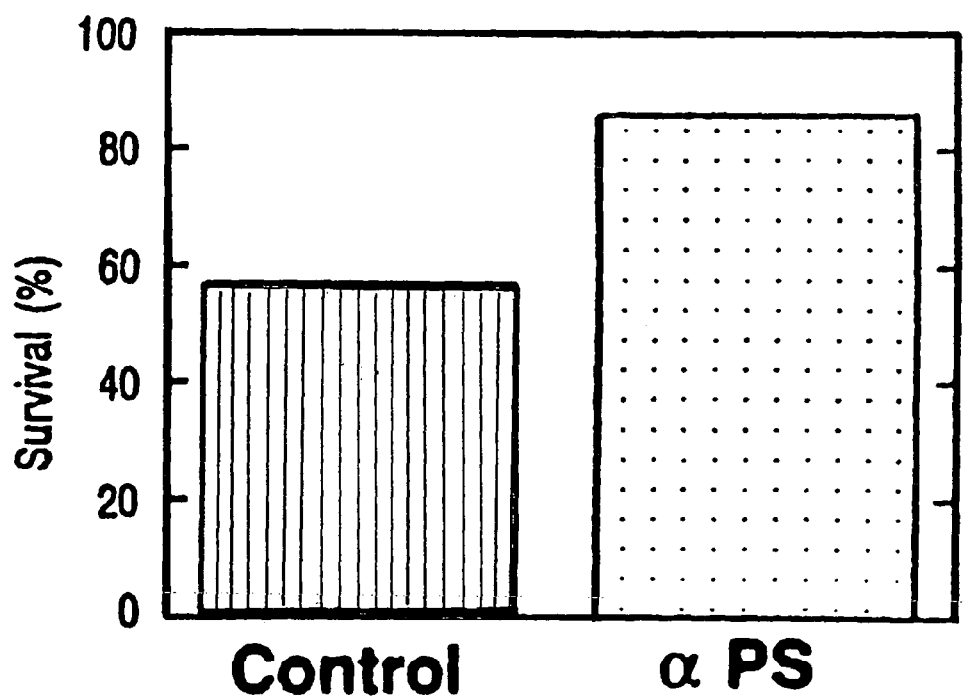

Effect of P-selectin Blockade: After having observed the functional role of P-selectin expression in stroke using deletionally mutant mice, experiments were performed to determine whether pharmacological blockade of P-selectin could improve stroke outcome in PS +/+ mice. Using a strategy of administering a monoclonal rat anti-mouse P-selectin blocking antibody (clone RB 40.34, [14,19,20]) or nonimmune control rat IgG immediately prior to surgery, mice receiving the blocking antibody were observed to have improved post-reperfusion cerebral blood flows by thirty minutes (FIG. 22A), as well as reduced neurological deficits (FIG. 22B), reduced cerebral infarction volumes (FIG. 22C), and a trend towards reduced mortality compared with controls (FIG. 22D).

Discussion

Despite substantial progress in recent years in the primary prevention of stroke [1], therapeutic options to treat evolving stroke remain extremely limited [6]. Although the publication of two landmark trials last fall demonstrating reduced morbidity following treatment of ischemic stroke with rt-PA [2,3] was thought to usher in a new era of thrombolytic therapy in the treatment of stroke [4], enthusiasm has been tempered somewhat by the hemorrhagic transformation and increased mortality noted in patients with ischemic stroke treated with streptokinase [5]. These divergent trials make it more critical than ever that new safe therapies be developed to treat evolving stroke. Although restoration of blood flow to postischemic brain affords new opportunities for early therapeutic intervention, reperfusion is a double-edged sword. Given the cytotoxic potential of neutrophils [25], it is not surprising that neutrophil influx into postischemic brain tissue can lead to further damage and worsen outcome following experimental stroke [7,26-29]. Using a murine model of focal cerebral ischemia and reperfusion, an important contributory role for the cell adhesion molecule ICAM-1 in neutrophil accumulation at 22 hours following stroke was recently identified [7]. However, augmented cerebrovascular endothelial ICAM-1 expression requires de novo transcriptional and translational events, which requires time. In contrast, P-selectin, a membrane-spanning glycoprotein which mediates the earliest phases of neutrophil adhesion, may be mobilized from preformed storage pools to be rapidly expressed at the ischemic endothelial cell surface [8,30]. As the clinical trials of thrombolytic therapy for stroke demonstrate a narrow time window for potential benefit (within the first several hours of stroke onset) [2,3,5], this suggests that strategies designed to interfere with the earliest phases of PMN adhesion might be of theoretical benefit in human stroke. These trials should result in greater numbers of patients presenting for earlier therepeutic intervention, increasing the need to address the issue of reperfusion injury in medically revascularized territories. In addition, these trials underscore the pressing need to understand the contributions of individual adhesion molecules to the pathogenesis of stroke.

Given the considerable body of literature describing the role of P-selectin in other models of ischemia and reperfusion [8,31-34], surprisingly little is known about the role of P-selectin in stroke. Knowledge of the specific role of P-selectin in the cerebral vasculature is important because adhesion molecule requirements vary between vascular beds and conditions under study. For instance, in a model of intestinal transplantation [35], anti-P-selectin antibodies did not reduce reperfusion injury, whereas anti-CD11/CD18 antibodies did. Although P-selectin blockade was ineffective at reducing PMN adhesion and albumin leakage in a rat mesentaric ischemia and reperfusion model, ICAM-1 blockade was effective [36]. In a rat hindlimb ischemia/reperfusion model, the selectin requirements for PMN adhesion differed between the pulmonary and crural muscle vascular beds [33].

The only published study dealing with P-selectin in the ischemic brain is a histopathological description of primate stroke, in which P-selectin expression was increased in the lenticulostriate microvasculature [10]. Furthermore, there is no data which addresses the functional significance of this P-selectin expression. The current studies were undertaken to study whether P-selectin expression contributes to post-ischemic cerebral neutrophil accumulation, no-reflow, and tissue injury in a murine model of reperfused stroke. Using a recently established model of focal cerebral ischemia and reperfusion in mice [11], P-selectin expression was demonstrated by increased deposition of radiolabelled antibody into the ischemic territory. In this technique, antibody deposition into the ischemic hemisphere was normalized to that in the nonischemic hemisphere in each animal, not only to minimize potential variations in injection volume or volume of distribution, but to enable comparison between animals given different antibodies. Because disruption of the endothelial barrier function in the ischemic cortex may augment nonselective antibody deposition, similar experiments were performed with a control rat IgG. These data show that the antibody which binds to P-selectin is deposited at an accelerated rate compared with the control antibody, suggesting that local P-selectin expression is augmented in the reperfused tissue. This data in the murine model parallels that reported in a baboon model of stroke [10], in which P-selectin expression was increased within 1 hour following the ischemic event.

The role of P-selectin expression in recruiting PMNs to the post-ischemic zone was demonstrated using a strategy in which accumulation of $^{111}$In-labelled PMNs was measured. Although it was previously reported that by 22 hours, PMN accumulation is elevated in the ischemic hemisphere [7], the current time-course data demonstrate that PMN accumulation begins shortly after the onset of ischemia. Failure to express the P-selectin gene was associated with reduced PMN accumulation, suggesting the participation of P-selectin in post-ischemic cerebral PMN recruitment. However, the P-selectin null animals did demonstrate a modest (albeit less than control) neutrophil accumulation by 22 hours. This data indicates that P-selectin is not the exclusive effector mechanism responsible for postischemic cerebral PMN recruitment, and is consistent with the previous data that ICAM-1 also participates in post-ischemic PMN adhesion [7]. Furthermore, this data is not unlike that in which intra-abdominal instillation of thioglycollate in P-selectin deficient mice caused delayed (but not absent) PMN recruitment [9].

Because of the critical need to identify reasons for failed reperfusion, the current studies examined the role of P-selectin in delayed postischemic cerebral hypoperfusion [22,23], the phenomenon wherein blood flow declines during reperfusion, despite restoration of adequate perfusion pressures. In cardiac models of ischemia, no-reflow worsens as time elapses after reperfusion [37], suggesting an important role for recruited effector mechanisms, such as progressive microcirculatory thrombosis, vasomotor dysfunction, and PMN recruitment. Both P-selectin and ICAM-1-dependent adherence reactions [38] and PMN capillary plugging [39] have been shown in other models to participate in post-ischemic no-reflow. In the brain, PMNs have been implicated in post-ischemic cerebral no reflow [40,41], but the role of P-selectin in this process has not been elucidated. The current study uses a relatively noninvasive technique (laser doppler) to obtain serial measurements of relative cerebral blood flow, in order to establish the existence, time course, and P-selectin-dependence of post-ischemic cerebrovascular no-reflow. In these experiments, P-selectin null and control animals were subjected to virtually identical degrees of ischemia, and instantaneous recovery of blood flow following removal of the intraluminal occluding suture was the same in the two groups. However, cerebral blood flow declined in the time period following reperfusion in P-selectin +/+ animals. In sharp contrast, the PS −/− animals demonstrated only slight delayed post-ischemic cerebral hypoperfusion. This late (albeit limited) decline in cerebral blood flow by 22 hours is consistent with the modest PMN recruitment observed in the PS −/− animals over the same period. This again suggests that other effector mechanisms (such as ICAM-1) may be responsible for the late decline in cerebral blood flow in PS −/− animals.

The functional effects of P-selectin expression are clear from the current set of studies: animals which fail to express the P-selectin gene (or PS +/+ animals treated with a functionally blocking anti-P-selectin antibody) exhibit smaller infarcts, improved survival, and survivors demonstrate improved neurologic outcomes compared with controls. When these data are considered along with previously published data demonstrating a deleterious role for ICAM-1 expression in stroke [7], it becomes increasingly apparent that there are multiple means for recruiting PMNs to post-ischemic cerebral cortex, and that blockade of each represents a potential strategy to improve stroke outcome in humans. Given the current recognition of the importance of timely reperfusion in halting the advancing wavefront of neuronal death following stroke, interfering with PMN adhesion at its earliest stages appears to be an attractive option for reducing morbidity and mortality. In fact, anti-adhesion molecule strategies may not only be beneficial in their own right (i.e., including patients ineligible for thrombolysis), but may extend the window of opportunity for thrombolytic intervention [42]. The current set of studies contributes to the understanding of pathophysiological mechanisms operative in reperfused stroke. These studies suggest the need for clinical trials of therapies for evolving stroke which optimize the reperfusion milieu to reduce PMN accumulation.

References:
1. Bronner L L, Kanter D S, Manson J E: Primary prevention of stroke. *N Engl J Med* 1995;333(21):1392-1400
2. The National Institute of Neurological Disorders and Stroke rt-PA Stroke Study Group: Tissue plasminogen activator for acute ischemic stroke. *N Engl J Med* 1995;333: 1581-1587
3. Hacke W, Kaste M, Fieschi C, Toni D, Lesaffre E, von Kummer R, Boysen G, Bluhmki E, Hoxter G, Mahagne M H, Hennerici M, for the ECASS Study Group: Intravenous thrombolysis with recombinant tissue plasminogen activator for acute hemispheric stroke. *J A M A* 1995;274(13): 1017-1025

4. del Zoppo G J: Acute stroke—on the threshold of a therapy. *N Engl J Med* 1995;333(13):1632-1633

5. Hommel M, Cornu C, Boutitie F, Boissel J P, The Multi-Center Acute Stroke Trial—Europe Study Group: Thromboltytic therapy with streptokinase in acute ischemic stroke. *N Engl J Med* 1996;335:145-150

6. Baringa M: Finding new drugs to treat stroke. *Science* 1996;272:664-666

7. Connolly. E S Jr, Winfree C J, Springer T A, Naka Y, Liao H, Yan D S, Stern D M, Solomon R A, Gutierrez-Ramos, J-C, Pinsky D J: Cerebral protection in homozygous null ICAM-1 mice after middle cerebral artery occlusion: role of neutrophil adhesion in the pathogenesis of stroke. *J Clin Invest* 1996;97:209-216

8. Pinsky D J, Naka Y, Liao H,. Oz M C, Wagner D D, Mayada T N, Johnson R C, Hynes R O, Heath M, Lawson C L, Stern D M: Hypoxia-induced exocytosis of endothelial cell Weibel-Palade bodies: a mechanism for rapid neutrophil recruitment after cardiac preservation. *J Clin Invest* 1996; 97:493-500

9. Mayadas T N, Johnson R C, Rayburn H, Hynes R O, Wagner D D: Leukocyte rolling and extravasation are severely compromised in P-selectin deficient mice. *Cell* 1993;74(3):541-554

10. Okada Y; Copeland B R, Mori E, Tung M M, Thomas W S, del Zoppo G J: P-selectin and intercellular adhesion molecule-1 expression after focal brain ischemia and reperfusion. *Stroke* 1994;25:202-211

11. Connolly E S Jr, Winfree C J, Stern D M, Solomon R A, Pinsky D J: Procedural and strain-related variables significantly affect outcome in a murine model of focal cerebral ischemia. *Neurosurg* 1996;38(3):523-532

12. Dirnagl U, Kaplan B. Jacewicz M, Bulsinelli W: Continuous measurement of cerebral blood flow by laser-doppler flowmetry in a rat stroke model. *J Cereb Blood Flow Metab* 1989;9:589-596

13. Huang Z, Huang P L, Panahian N. Dalkara T, Fishman M C, Moskowitz M A: Effects of cerebral ischemia in mice deficient in neuronal nitric oxide synthase. *Science* 1994; 265:1883-1885

14. Ley K, Bullard D C, Arbones M L, Bosse R, Vestweber D, Tedder T F, Beaudet A L: Sequential contribution of L- and P-selectin to leukocyte rolling in vivo. *J Exp Med* 1995; 181:669-675

15. David G S, Reisfeld R A: Protein iodination with solid state lactoperoxidase. *Biochem* 1974;13:1014-1021

16. Bederson J B, Pitts L H, Tsuji M: Rat middle cerebral artery occlusion: evaluation of the model and development of a neurologic examination. *Stroke* 1986;17:472-476

17. Menzies S A, Hoff J T, Betz A L: Middle cerebral artery occlusion in rats: a neurological and pathological evaluation of a reproducible model. *Neurosurg* 1992;31:100-107

18. Bederson J B, Pitts L H, Nishimura M C, Davis R L, Bartkowski H M: Evaluation of 2,3,5-triphenyltetrazolium chloride as a stain for detection and quantification of experimental cerebral infarction in rats. *Stroke* 1986;17: 1304-1308

19. Bosse R, Vestweber D: Only simultaneous blocking of the L- and P-selectin completely inhibits neutrophil migration into mouse peritoneum. *Eur J Immunol* 1994;24:3019-3024

20. Kunkel E J, Jung U, Bullard D C, Norman K E, Wolitzky B A, Vestweber D, Beaudet A L, Ley K: Absence of trauma-induced leukocyte tolling in mice deficient in both P-selectin and ICAM-1. *J Exp Med* 1996;183:57-65

21. Springer T A: Adhesion receptors of the immune system. *Nature* 1990;346:425-434

22. Ames AIII, Wright R L, Kowada M, Thurston J M, Majno G: Cerebral ischemia II: the no reflow-phenomenon. *Am J Pathol* 1968;52:437-447

23. Levy D E, Van Uitert R L, Piker C L: Delayed postischemic hypoperfusion: a potentially damaging consequence of stroke. *Neurology* 1979;29:1245-1252

24. Barone F C, Knudsen D J, Nelson A H, Feuerstein G Z, Willette R N: Mouse strain differences in susceptibility to cerebral ischemia are related to cerebral vascular anatomy. *J Cereb Blood Flow Metab* 1993;13:683-692

25. Weiss S J: Tissue destruction by neutrophils. *N Engl J Med* 1989;320(6):365-376

26. Hallenbeck J M, Dutka A J, Tanishima T, Kochanek P M, Kumaroo K K, Thompson C B, Obrenovitch T P, Contreras T J: Polymorphonuclear leukocyte accumulation in brain regions with low blood flow during the early postischemic period. *Stroke* 1986;17:246-253

27. Kochanek P M, Hallenbeck J M: Polymorphonuclear leukocytes and monocytes/macrophages in the pathogenesis of cerebral ischemia and stroke. *Stroke* 1992;23(9): 1367-1379

28. Dutka A J, Kochanek P M, Hallenbeck J M: Influence of granulocytopenia on canine cerebral ischemia induced by air embolism. *Stroke* 1989;20:390-395

29. Bednar M M, Raymond S, McAuliffe T, Lodge P A, Gross C E: The role of neutrophils and platelets in a rabbit model of thromboembolic stroke. *Stroke* 1991;22(1):44-50

30. Geng J-G, Bevilacqua M P, Moore K L, McIntyre T M, Prescott S M, Kim J M, Bliss G A, Zimmerman G A, McEver R P: Rapid neutrophil adhesion to activated endothelium mediated by GMP-140. *Nature* 1990;343:757-760

31. Weyrich A S, Ma X-L, Lefer D J, Albertine K H, Lefer A M: In vivo neutralization of P-selectin protects feline heart and endothelium in myocardial ischemia and reperfusion injury. *J Clin Invest* 1993;91:2620:2629

32. Winn R K, Liggitt D, Vedder; N B, Paulson J C, Harlan J M: Anti-P selectin monoclonal antibody attenuates reperfusion injury in the rabbit ear. *J Clin Invest* 1993;92:2042-2047

33. Seekamp A, Till G O, Mulligan M S, Paulson J C, Anderson D C, Miyasaka M, Ward P A: Role of selectins in local and remote tissue injury following ischemia and reperfusion. *Am J Pathol* 1994;144:592-598

34. Kubes P, Jutila M, Payne D: Therapeutic potential of inhibiting leukocyte rolling in ischemia/reperfusion. *J Clin Invest* 1995;95:2510-2519

35. Slocum M M, Granger D N: Early mucosal and microvascular changes in feline intestinal transplants. *Gastroenterology* 1993;105:1761-1768

36. Kurose I, Anderson D C, Miyasaka M, Tamatani T, Paulson J C, Todd R F, Rusche J R, Granger D N: Molecular determinants of reperfusion-induced leukocyte adhesion and vascular protein leakage. *Circ Res* 1994;74:336-343

37. Kloner R A, Ganote C E, Jennings R B: The "no-reflow" phenomenon after temporary coronary occlusion in the dog. *J Clin Invest* 1974;54:1496-1508

38. Jerome S N, Dore M, Paulson J C, Smith C W, Korthuis R J: P-selectin and ICAM-1-dependent adherence reactions: role in the genesis of postischemic no-reflow. *Am J Physiol* 1994;266:H1316-H1321

39. Engler R L, Schmid-Schonbein G W, Pavelec R S: Leukocyte capillary plugging in myocardial ischemia and reperfusion in the dog. *Am J Pathol* 1983;111:98-111

40. Mori E, del Zoppo G J, Chambers J D, Copeland B R, Arfors K E: Inhibition of polymorphonuclear leukocyte adherence suppresses no-reflow after focal cerebral ischemia in baboons. *Stroke* 1992;23:712-718.
41. Grogaard B, Schurer L, Gerdin B, Arfors K E: Delayed hypoperfusion after incomplete forebrain ischemia in the rat: the role of polymorphonuclear leukocytes. *J Cereb Blood Flow Metab* 1989;9:500-505
42. Bowes M P, Rothlein R, Fagan S C, Zivin J A: Monoclonal antibodies preventing leukocyte activation, reduce experimental neurological injury, and enhance efficacy of thrombolytic therapy. *Neurology* 1995;45:815-819

Example 5

P-Selectin Homozygous Null Mice Are Resistant to Focal Cerebral Ischemia and Reperfusion Injury The role of neutrophils (PMNs) in potentiating focal ischemia reperfusion injury in the central nervous system remains controversial. An important early step in the capture of circulating PMNs by the vasculature is mediated by P-selectin expressed on postischemic endothelium. Although early and persistent endothelial P-selectin expression has been described in brain microvessels following middle cerebral artery occlusion in baboons, the consequences of endothelial P-selectin expression in stroke have not been determined. To define the role of P-selectin in stroke, a murine model of focal cerebral ischemia and reperfusion consisting of intraluminal middle cerebral artery (MCA) occlusion for 45 minutes followed by 22 hours of reperfusion was used in two groups of mice; transgenic mice that were homozygous null for P-selectin (PS −/−), and wild type cousin controls (PS +/+). Cerebral infarct volumes were calculated from planimetered serial sections stained with triphenyltetrazolium chloride, and expressed as the percentage of infarcted tissue in the ipsilateral hemisphere. Neurologic outcome was based on animal behavior observed by a blinded investigator (1: no deficit; 2: circling; 3: spinning; 4: immobile). Ipsilateral cortical cerebral blood flow (CBF) was determined by laser doppler flowmetry and expressed as percent of contralateral cortical CBF. PS −/− mice showed a 3:8-fold reduction in infarct volumes compared with PS +/+ controls (7.6±4.4% vs 29.2±10.1%, p<0.05). This reduction in infarct volumes in mice devoid of P selectin was mirrored by improved survival (87% vs. 42%, p<0.05) and a trend towards reduced neurological deficit (1.9±0.4 vs. 2.5±0.3; p=NS) in survivors. Because there was a tendency for increased cerebral blood flow following cerebral ischemia and reperfusion in the PS −/− cohort (65±11% vs. 46±18% for controls, p=NS), these studies suggest that P-selectin-dependent adhesion may contribute to cerebral no-reflow. Taken together, these data implicate an important role for P-selectin expression in the pathophysiology of stroke, and suggest novel pharmacologic strategies to improve stroke outcome.

Example 6

Absence of the P-selectin Gene Reduces Post-ischemic Cerebral Neutrophil Accumulation, No-reflow, and Tissue Injury in a Murine Model of Reperfused Stroke Recent studies in humans indicate that reestablishment of cerebral blood flow (CBF) during the early period following the onset of stroke reduces neurologic seguelae. It was hypothesized that P-selectin (PS), an early-acting neutrophil (PMN) adhesion molecule expressed by hypoxic endothelium may have an important pathophysiological role in evolving, reperfused stroke. Preliminary studies were performed in a murine model of transient focal cerebral ischemia consisting of intraluminal middle cerebral artery occlusion for 45 minutes followed by 22 hours of reperfusion. In this model, mice which do not express the PS gene (PS −/−) have smaller infarct volumes, reduced neurological deficit scores, and improved survival compared to wild-type controls (PS +/+) The current studies were performed to further define PS-induced mechanism(s) of cerebral injury. PS +/+ mice (n=6) given a $^{125}$I-labeled anti-PS IgG prior to surgery demonstrated a 216% greater accumulation of the antibody in the ipsilateral hemisphere by 30 min of reperfusion compared with sham-operated animals (n=6, p<0.001) or with animals given nonimmune IgG and subjected to transient focal cerebral ischemia and 30 min of reperfusion (n=4, p<0.03). In PS +/+ mice, accumulation of PMNs begins early following the initiation of focal ischemia, and continues throughout the period of reperfusion (2-fold increase in ipsilateral/contralateral $^{111}$In-PMN accumulation by 22 hours, n=8, p<0.05). PS −/− mice showed a 25% reduction in PMN accumulation into the ipsilateral hemisphere by 22 hours (n=7, p<0.05). The effect of PS expression on post-ischemic cerebral no-reflow was investigated by measuring ipsilateral CBF serially during stroke evolution. Although baseline, post-occlusion, and initial reperfusion CBFs were identical, CBFs at 30 minutes of reperfusion were significantly greater in PS −/− mice (n=5) compared to PS +/+ mice (n=8, 2.4-fold greater, p<0.05). This difference was sustained during the remainder of the 22 h reperfusion period. These data support an important early role for PS in PMN recruitment, post-ischemic no-reflow, and tissue damage in evolving stroke. This is the first demonstration of a pathophysiological role for PS in cerebral reperfusion injury, which suggests that PS blockade may represent a therapeutic target for the treatment of reperfused stroke.

Example 7

Carbon Monoxide and Evolving Stroke

Figure 23A:
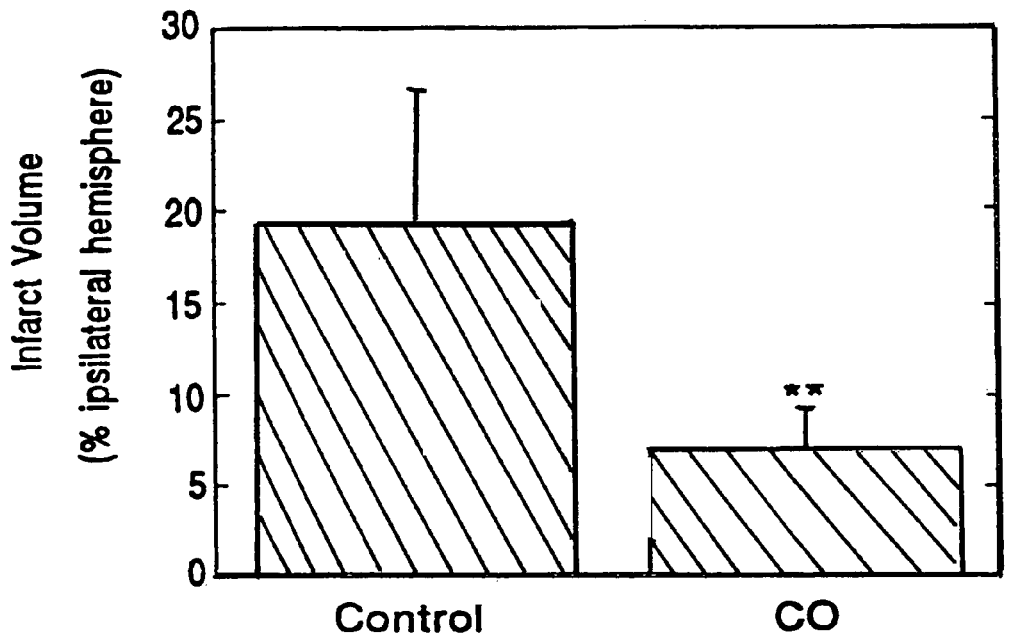
FIGS. 23A and 23B.
Figure 23B:
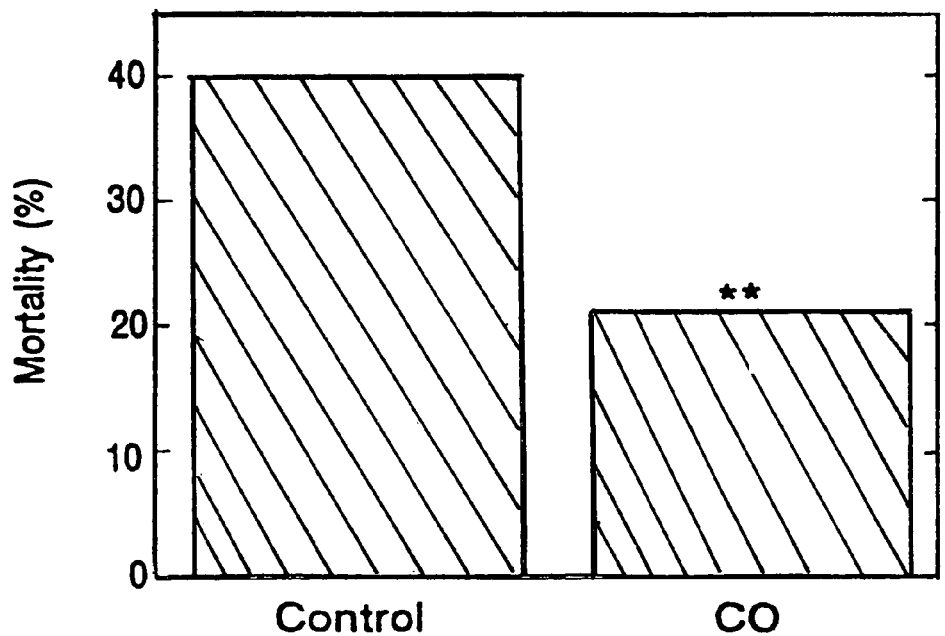
Figure 24A:
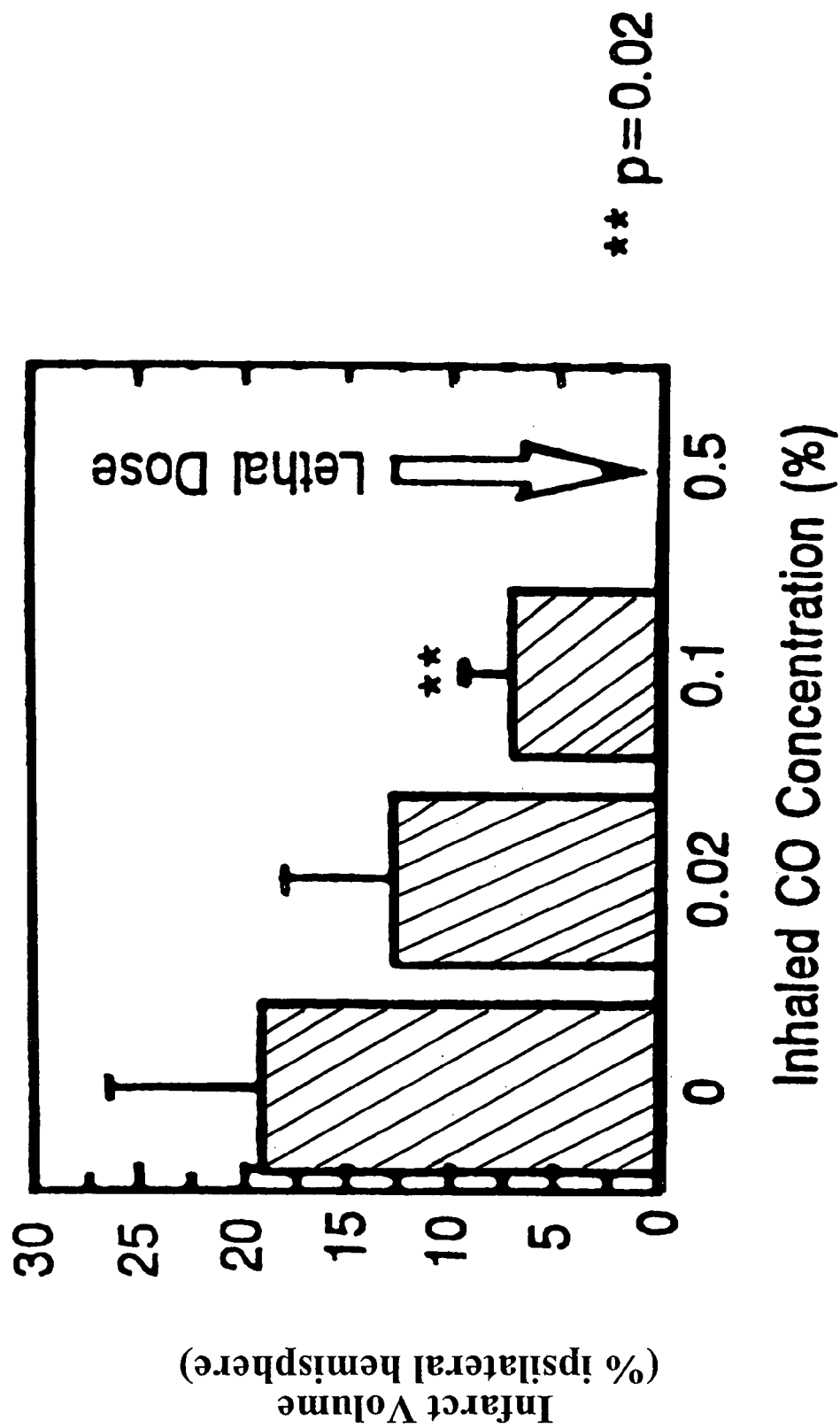
Figure 25:
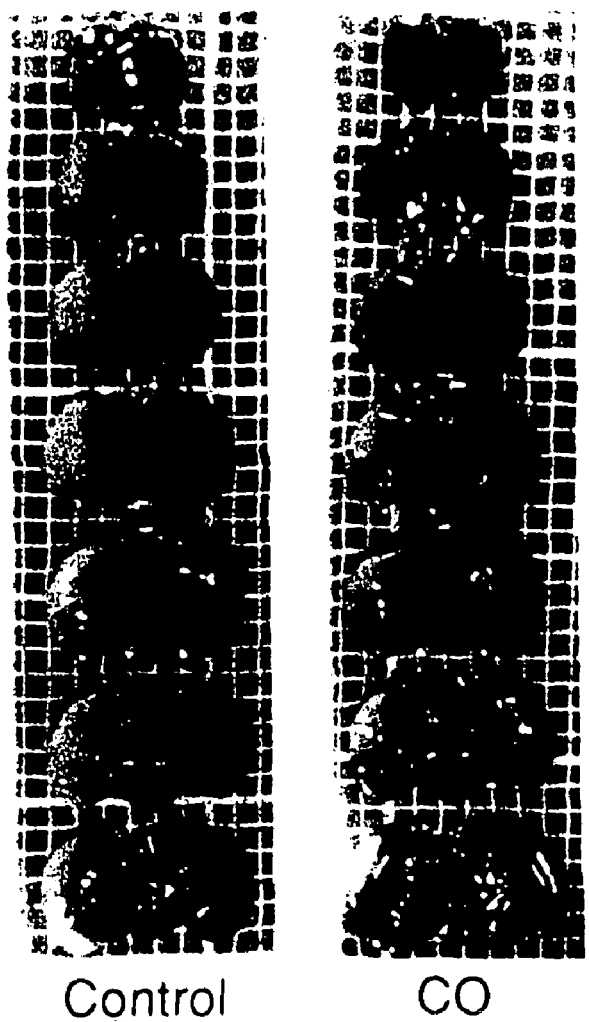
FIG. 25. TTC staining of serial cerebral sections for the animals of FIG. 23. Infarcted tissue appears white, and viable tissue appears brick red.
Figure 27:
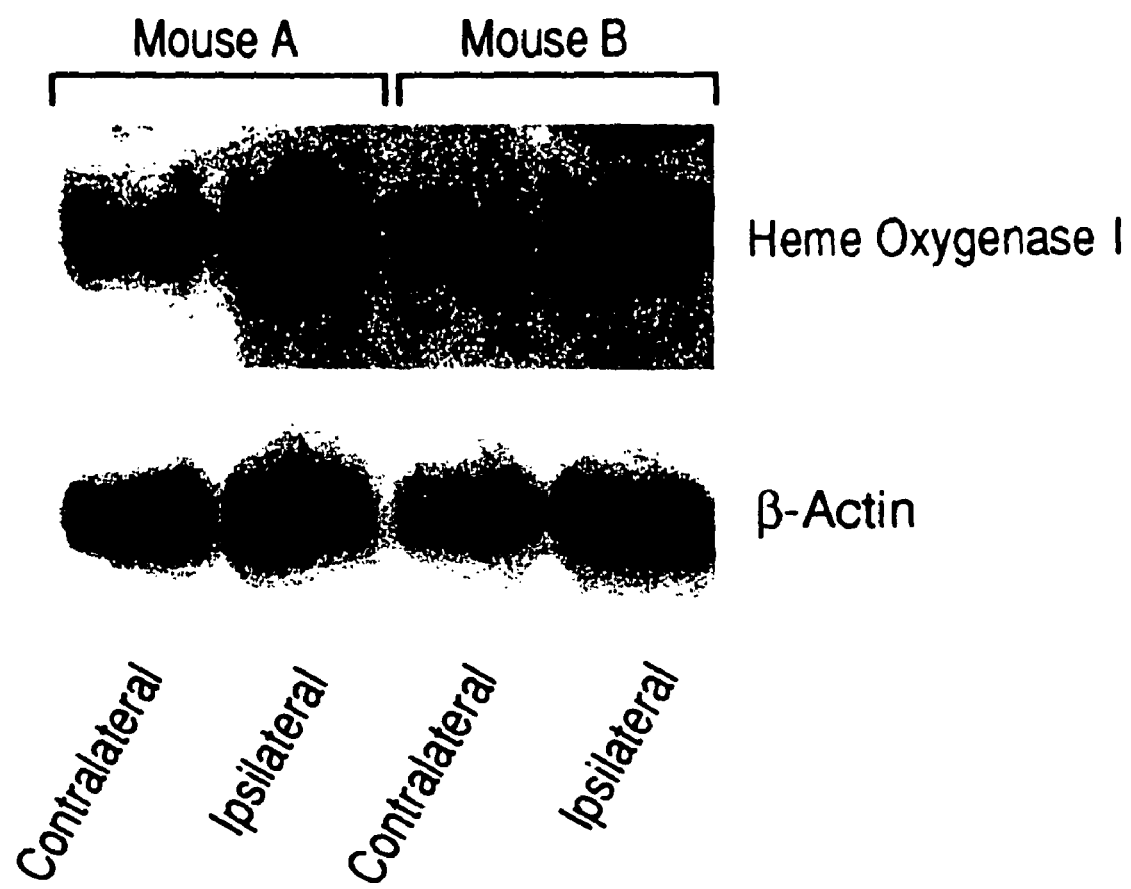
FIG. 27. Effect of focal cerebral ischemia on heme oxygenase I (HO-I) mRNA induction. Contralateral indicates the nonstroke side of the brain. Ipsilateral indicates the brain side subjected to stroke. In both animals, the side of the brain subjected to stroke demonstrates increased HO-I but the nonstroke side does not.
Figure 28:
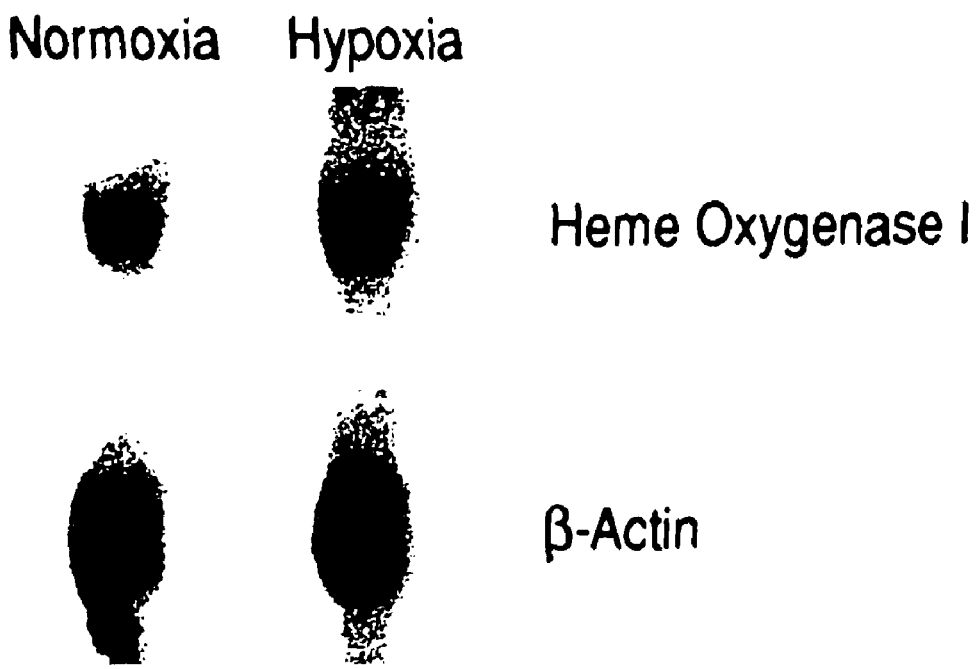
FIG. 28. Effect of hypoxia on heme oxygenase I (HO) induction. Mice exposed to a hypoxic environment for 12 hours (to simulate ischemia) show an increase in heme oxygenase I mRNA compared with normoxic controls. These data show a potential mechanism whereby hypoxic pre-exposure can also confer protection against subsequent ischemic events, which was found to be true in mice subjected to hypoxia followed by stroke.

Carbon monoxide gas, a toxic byprduct of heme catabolism, is involved in long-term potentiationand memory in the central nervous system. However, other physiologic roles for CO production in the brain are unknown. Because heme oxygenase is induced during inflammatory conditions, it was investigated whether endogenous CO production may confer a cerebral. protective role in stroke. In a murine model of focal cerebral ischemia, heme oxygenase type I was induced at the mRNA (by Northern blot and protein levels (by Western blot), localized to the cerebral vascular endothelium in the ischemic hemisphere by in situ hybridization and immunohistochemistry (FIGS. 26 and 27). Local production of CO by direct measurement was observed in the ischemic zone. In parallel experiments, murine brain endothelial cells exposed to a hypoxic environment demonstrated similar induction of heme oxygenase mRNA, protein and CO generation (FIG. 28). To determine whether CO production was incidental to the pathophysiology of stroke, CO production was blocked by tin protoporphyrin administration (confirmed by direct measurement of reduced local CO levels). These animals demonstrated significantly larger infarct volumes, worse neurological outcomes, and increased mortality compared with untreated controls (FIG. 24). Furthermore, administration of CO prior to stroke conferred significant cerebral protection. (FIG. 23). As this protection was not observed in animals treated with biliverdin, the coincident byproduct of heme catabolism, these data suggest that endogenous CO production per se has a protective role in evolving stroke.

Introduction

There is a considerable body of literature and a common recognition of the toxic effects of exogenous carbon monoxide (CO), which binds avidly to heme centers, inhibiting oxygen transport and poisoning cellular respiration. For many years, CO was regarded as an incidental byproduct of heme catabolism, but recent data in the brain suggests that CO produced in discrete neurons by heme oxygenase II may modulate long-term potentiation. In rats, exposure to heat shock has been correlated with the expression of a 32 kDa heat shock protein (heme oxygenase I) in several organs including the brain. The physiological significance of this HSP32 induction has been teleologically ascribed to the stoichiometric liberation of CO by heme oxygenase I (HOI). In most, experimental studies, HOI induction serves only as an incidental marker of cellular oxidant stress. The recent identification of an anti-inflammatory role for HOI in a model of peritoneal inflammation has been ascribed to the production of the natural antioxidant biliverdin during the process of heme catabolism.

Figure 29:
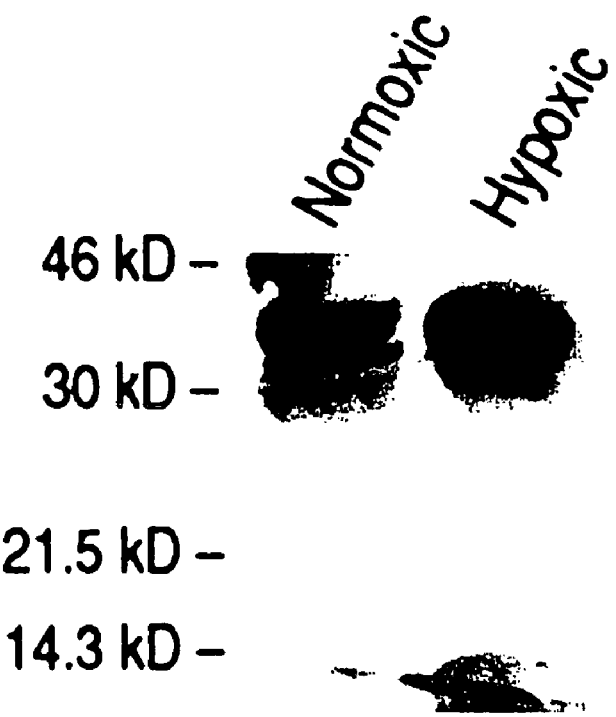
FIG. 29. Effect of hypoxia on heme oxygenase I (HO-I) protein expression in mouse brain endothelial cells. Hypoxia causes HO-I protein levels to increase in these brain-derived endothelial cells.
Figure 30:
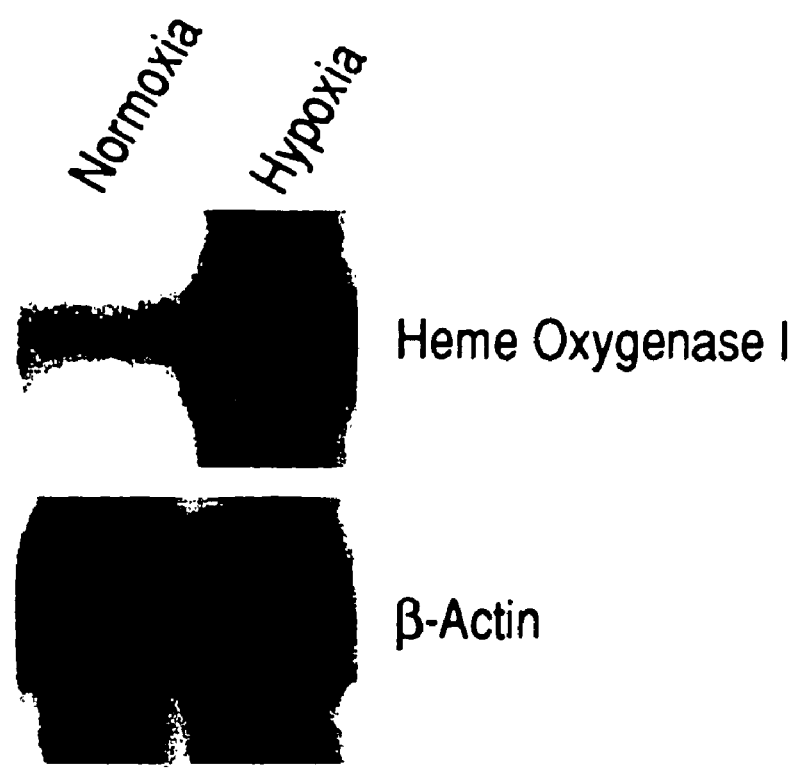
FIG. 30. Effect of hypoxia on heme oxygenase I (HO-I) mRNA induction in mouse brain endothelial cells. Hypoxia causes HO-I mRNA levels to increase in these brain-derived endothelial cells.

The current study reports for the first time that the postischemic brain generates enormous quantities of CO. Using a murine model of focal cerebral ischemia in which the middle cerebral artery is occluded by an intraluminal suture, HOI production in the ischemic hemisphere was increased significantly in comparison to the nonischemic hemisphere (FIG. 26). Because immunohistochemistry and in situ hybridization localized the source of HOI to endothelial cells within the ischemic hemisphere, an in vitro model of cellular hypoxia was used to confirm the induction of HOI message, protein and activity in murine cerebral microvascular endothelial cells (FIGS. 29 and 30). Blockade of CO production using tin or zinc protoporphyrin IX was associated with an increase in cerebral infarct volume and mortality, whereas exposing animals to CO immediately prior to ischemia conferred significant dose-dependent cerebral protection within a narrow therapeutic window (FIG. 24). Biliverdin administration was without effect in this model. Taken together, these data indicate that ischemic brain tissue produces large amounts of CO, the production of which confers cerebral protection that limits the amount of tissue destroyed during stroke.

Methods

Protoporphyrin preparation and administration. Tin protoporphyrin IX dichloride (20 mg, Porphyrin Products, Logan, Utah), zinc protoporphyrin IX (17 mg, Porphyrin Products, Logan, Utah), or biliverdin (18 mg, Porphyrin Products, Logan, Utah) was initially dissolved in dimethyl sulfoxide (2 mL). An aliquot of this solution (200 µL) was added to normal saline (9.8 mL) and this mixture was vortexed vigorously to yield a $2.7 \times 10^{-4}$ M solution of the protoporphyrin. The solution container was wrapped in aluminum foil to prevent photolysis of the protoporphyrin and stored at 4° C. until used.

Micro-osmotic pumps (#1003D, Alza Corp., Palo Alto, Calif.) were loaded with this protoporphyrin solution (91 µL/pump) and implanted subcutaneously in the anesthetized mouse via a 1 cm dorsal midline incision 24 h prior to the start of surgery. These pumps administer drug solution at a rate of $0.95 \pm 0.02$ µL/h. At the time of surgery an additional dose of the protoporphyrin solution was administered (0.3 mL, i.v.) prior to insertion of the intralumenal occluding catheter. Each animal received the following total (injection+pump) drug amounts over the course of the study tin protoporphyrin (0.070 mg), zinc protoporphyrin (0.059 mg), or biliverdin (0.061 mg).

Example 8

Hypoxia or free radicals induce P-selectin (PS) translocation to the endothelial cell (EC) surface, where it participates in neutrophil (PMN) adhesion during reperfusion. To explore a mechanism whereby nitrovasodilators may attenuate postischemic leukosequestration, we tested whether stimulating the NO/cGMP pathway could attenuate surface PS expression in hypoxic human umbillical vein ECs. ECs exposed to hypoxia (pO2<20 Torr for 4 hours) demonstrated a 50% increase in vWF release (p<0.005) (vWF is packaged with PS), paralleled by an 80% increase in surface PS expression (p<0.0001), measured by specific binding of a radiolabeled anti-PS antibody. Under similar conditions, addition of the NO donor 3-morpholino sydnonimine (SIN-1, 0.1 mM) or the cGMP analog 8-Bromo-cGMP (cGMP, 10 nM) caused a reduction in vWF release; Control vWF, $11 \pm 0.4$ mU/mL; SIN-1, $9.1 \pm 0.3$ mU/mL; cGMP, $9.7 \pm 0.2$ mU/mL; p<0.005 for both SIN-1 or cGMP vs Control. Compared with controls, SIN-1 or cGMP also reduced surface PS expression (40% and 48% decreases respectively, p<0.005 for each) Using an immunofluorescent adherence assay, both SIN-1 and cGMP reduced HL60 binding to hypoxic HUVECs (53% and 86% decrease vs. controls, p<0.05 for each). Measurement of fura-2 fluorescence demonstrated that hypoxia increased intracellular calcium concentration [Cai], and that increased [Cai] could be blocked by cGMP. Neither SIN-1 nor cGMP could further reduce PS expression when ECs were placed in a calcium-free medium. These data suggest that stimulation of the NO/cGMP pathway inhibits PS expression by inhibiting calcium-flux in ECs, and identify this inhibition as an important mechanism whereby nitrovasodilators may decrease PMN binding in post-ischemic tissues.

Example 9

Factor IXai

Factor IX is a clotting factor which exists in humans and other mammals, and is an important part of the coagulation pathway. In the normal scheme of coagulation, Factor IX is activated by either Factor XIa or a tissue factor/VIIa complex to its active form, Factor IXa. Factor IXa then can activate Factor X, which triggers the final part of the coagulation cascade, leading to thrombosis. Because Factor X can be activated by one of two pathways, either the extrinsic (via VIIa/tissue factor) or the intrinsic pathways (via Factor IXa), we hypothesized that inhibiting Factor IXa might lead to impairment of some forms of hemostasis, but leave hemostasis in response to tissue injury intact. In other words, it might lead to blockade of some types of clotting, but might not lead to excessive or unwanted hemorrhage. Factor IXai is Factor IXa which has been chemically modified so as to still resemble Factor IXa (ant therefore, can compete with native Factor IXa), but which lacks its activity. This can "overwhelm" or cause a competitive inhibition of the normal Factor IXa-dependent pathway of coagulation. Because Factor IXa binds to endothelium and platelets and perhaps other sites, blocking the activity of Factor IXa may also be possible by administering agents which interfere with the binding of Factor IXa (or by interfering with the activation of Factor IX).

In stroke and other ischemic disorders, there may be clinical benefit derived by lysing an existing thrombus, but there is also the potentially devastating complication of hemorrhage. In the current experiments, the mouse model of cerebral ischemia and reperfusion (stroke) was used. Mice received an intravenous bolus of 300 µg/kg of Factor IXai just prior to surgery. Strokes were created by intraluminal occlusion of the right middle cerebral artery, When stroke outcomes were measured 24 hours later, animals that had received Factor IXai had smaller infarct volumes, improved cerebral perfusion, less neurological deficits, and reduced mortality compared with controls which underwent the same surgery but which did not receive Factor IXai. It was also noted that the Factor IXai animals were free of apparent intracerebral hemorrhage. By contrast, intracerebral hemorrhage was occasionally noted in the control animals not receiving Factor IXai.

TABLE II

|  | Control | | Experimental | | |
| --- | --- | --- | --- | --- | --- |
|  | mean | sd | mean | sd | stats |
| weight | 26.91 | 3.21 | 25.25 | 2.49 | 0.14 |
| dopp | 0.96 | 0.24 | 1.04 | 0.35 | 0.52 |
| occ dop 1 | 0.18 | 0.07 | 0.16 | 0.08 | 0.60 |
| occ dop 2 | 0.40 | 0.22 | 0.43 | 0.20 | 0.68 |
| reper dop | 0.55 | 0.42 | 0.53 | 0.30 | 0.89 |
| sac dop | 0.38 | 0.25 | 0.75 | 0.31 | 0.02 |
| grade | 2.22 | 0.67 | 1.67 | 0.49 |  |
| I/C Ratio | 1.18 | 0.20 | 1.08 |  |  |
| inf vol | 21.16 | 25.14 | 3.47 | 12.03 | 0.0452 |
| count | 11 |  | 16 |  |  |

Example 10

Exacerbation of Cerebral Injury in Mice which Express the P-Selectin Gene: Identification of P-selectin Blockade as a New Target for the Treatment of Stroke Abstract:

There is currently a stark therapeutic void for the treatment of evolving stroke. Although P-selectin is rapidly expressed by hypoxic endothelial cells in vitro, the functional significance of P-selectin expression in stroke remains unexplored. In order to identify the pathophysiological consequences of P-selectin expression and to identify P-selectin blockade as a potential new approach for the treatment of stroke, experiments were performed using a murine model of focal cerebral ischemia and reperfusion. Early P-selectin expression in the post-ischemic cerebral cortex was demonstrated by the specific accumulation of radiolabelled anti-murine P-selectin IgG, with the increased P-selectin expression localized to the ipsilateral cerebral microvascular endothelial cells by immunohistochemistry. In experiments designed to test the functional significance of increased P-selectin expression in stroke, neutrophil accumulation in the ischemic cortex of mice expressing the P-selectin gene (PS +/+) was demonstrated to be significantly greater than that in homozygous P-selectin null mice (PS −/−). Reduced neutrophil influx was accompanied by greater postischemic cerebral reflow (measured by laser doppler) in the PS −/− mice. In addition, PS −/− mice demonstrated smaller infarct volumes (five-fold reduction, $p<0.05$) and improved survival compared with PS +/+ mice (88% vs. 44%, $p<0.05$). Functional blockade of P-selectin in PS +/+ mice using a monoclonal antibody directed against murine P-selectin also improved early reflow and stroke outcome compared with controls, with reduced cerebral infarction volumes noted even when the blocking antibody was administered after occlusion of the middle cerebral artery. These data are the first to demonstrate a pathophysiological role for P-selectin in stroke, and suggest that P-selectin blockade may represent a new therapeutic target for the treatment of stroke.

Introduction:

Ischemic stroke consitutes the third leading cause of death in the United States today[1]. Until very recently, there has been no direct treatment to reduce cerebral tissue damage in evolving stroke. Although the NINDS[2] and ECASS rt-PA acute stroke studies have suggested that there are potential therapeutic benefits of early reperfusion[4], the increased mortality observed following streptokinase treatment of acute ischemic stroke[5] highlights the sobering fact that there is at the present time no clearly effective treatment for evolving stroke. This void in the current medical armamentarium for the treatment of stroke has led: to a number of innovative approaches[6], yet other than rt-PA, none have reached the clinical realm. To identify a potential safe and efficacious treatment for evolving stroke, we have focussed on the deleterious role of recruited neutrophils. Recent work in a murine model of reperfused stroke has demonstrated that depletion of neutrophils (PMNs) prior to stroke minimizes cerebral tissue injury and improves functional outcome[7]; mice which lack the specific cell adhesion molecule, ICAM-1, are similarly protected[7]. P-selectin, a molecule which can be rapidly translocated to the hypoxic endothelial surface from pre-formed storage sites[8], is an important early mediator of the neutrophil rolling[9], which facilitates ICAM-1-mediated neutrophil arrest. Although P-selectin is expressed in primate stroke[10], the functional significance of P-selectin expression in stroke remains unknown.

To explore the pathophysiological role of P-selectin in stroke, we employed a murine model of focal cerebral ischemia and reperfusion[11] using both wild type mice and mice which were homozygous null for the P-selectin gene[9] and a strategy of administering a functionally blocking P-selectin antibody. In these studies, we confirm not only that P-selectin expression following middle cerebral artery occlusion is associated with reduced cerebral reflow following reperfusion and a worse outcome following stroke, but that P-selectin blockade confers a significant decree of postischemic cerebral protection. These studies represent the first demonstration of the pathophysiological role of P-selectin expression in stroke, and suggest the exciting possibility that anti-P-selectin strategies may prove useful for the treatment of reperfused stroke.

Methods:

Mice: Experiments were performed with transgenic P-selectin deficient mice created as previously reported[9] by gene targeting, in J1 embryonic stem cells, injected into C57BL/6 blastocysts to obtain germline transmission, and backcrossed to obtain homozygous null P-selectin mice (PS −/−). Experiments were performed with PS −/− or wild-type (PS +/+) cousin mice from the third generation of backcrossings with C57BL/6J mice. Animals were seven to twelve weeks of age and weighed between 25-36 grams at the time of experiments. Because variations in cerebrovascular anatomy have been reported to result in differences in susceptibility to experimental stroke in mice[12], India ink/carbon black staining was performed to visualize the the vascular pattern of the. Circle of Willis in both in both PS −/−and PS +/+ mice. These, experiments demonstrated that there were no gross anatomic differences in the vascular pattern of the cerebral circulation.

Transient Middle Cerebral Artery Occlusion: Mice were anesthetized (0.3 cc of 10 mg/cc ketamine and 0.5 mg/cc xylazine, i.p.), and positioned supine on a rectal temperature-controlled operating surface (Yellow Springs Instruments, Inc., Yellow Springs, Ohio). Animal core temperature was maintained at 37±1° C. intraoperatively and for 90 minutes post-operatively. A midline neck incision was created to expose the right carotid sheath under the operating microscope (16-25× zoom, Zeiss, Thornwood, N.Y.). The common carotid artery was isolated with a 4-0 silk, and the occipital, pterygopalatine, and external carotid arteries were each isolated and divided. Middle cerebral artery occlusion (MCAO) was accomplished by advancing a 13 mm heat-blunted 5-0 nylon suture via the external carotid stump. After placement of the occluding suture, the externals carotid artery stump was cauterized, and the wound was closed. After 45 minutes, the occluding suture was withdrawn to establish reperfusion. These procedures have been previously described in detail[11].

Measurement of cerebral cortical blood flow: Transcranial measurements of cerebral blood flow were made using laser doppler (Perimed Inc., Piscataway, N.J.), as previously described[13]. Using a 0.7 mm straight laser doppler probe (model #PF303, Perimed, Piscataway, N.J.) and previously published landmarks (2 mm posterior to the bregma, 6 mm to each side of midline)[11], relative cerebral blood flow measurements were made as indicated; immediately after anesthesia, 1 and 10 minutes after occlusion of the middle cerebral artery, as well as after 30 minutes, 300 minutes and 22 hours of reperfusion. Data are expressed as the ratio of the doppler signal intensity of the ischemic compared with the nonischemic hemisphere. Although this method does not quantify cerebral blood flow per gram of tissue, use of laser doppler flow measurements at precisely defined anatomic landmarks serves as a means of comparing cerebral blood flows in the same animal serially over time. The surgical procedure was considered to be technically adequate if ≧50% reduction in relative cerebral blood flow was observed immediately following placement of the intraluminal occluding suture. These methods have been used in previous studies[7,11].

Preparation and administration of 125I-labelled proteins and $^{111}$In-labelled murine neutrophils: Radioiodinated antibodies were prepared as follows. Monoclonal rat anti-murine P-selectin IgG (Clone RB 40.34, Pharmingen Co., San Diego, Calif.)[14] and non-immune rat IgG (Sigma Chemical Co., St. Louis, Mo.) were radiolabeled with $^{125}$I by the lactoperoxidase method [15] using Enzymobeads (Bio-Rad, Hercules, Calif.). Radiolabelled PMNs were prepared in the following manner. Citrated blood from wild type mice was diluted 1:1 with NaCl (0.9%) followed by gradient ultracentrifugation on Ficoll-Hypaque (Pharmacia, Piscataway, N.J.). Following hypotonic lysis of residual erythrocytes (20 sec exposure to distilled $H_2O$ followed by reconstitution with 1.8% NaCl), the PMNs were suspended in phosphate buffered saline (PBS). Neutrophils ($5-7.5×10^6$) were suspended in PBS with 100 μCi of Indium oxine (Amersham Mediphysics, Port Washington, N.Y.), and subjected to gentle agitation for 15 minutes at 37° C. After washing with PBS, the PMNs were gently pelleted (450× g ) and resuspended in PBS to a final concentration of $1.0×10^6$ cells/mL.

Calculation of Infarct Volumes: After neurologic examination, mice were anesthesized and final cerebral blood flow measurements chained. Humane euthanasia was performed by decapitation, and brains were removed and placed in a mouse brain matrix (Activational Systems Inc., Warren, Mich.) for 1 mm sectioning. Sections were immersed in 2% 2,3,5-triphenyl-2H-tetrazolium chloride (TTC, Sigma Chemical Co., St. Louis, Mo.) in 0.9% phosphate-buffered saline, incubated for 30 minutes at 37° C., and placed in 10% formalin[16]. Infarcted brain was visualized as an area of unstained tissue. Infarct volumes were calculated from planimetered serial sections and expressed as the percentage of infarct in the ipsilateral hemisphere. This method of calculating infarct volumes has been used previously by our group[7,11] and others[16,17], and has been correlated with the other functional indices of stroke outcome which are described above.

Administration of Unlabelled Antibodies, Radiolabelled PMNs, and Radiolabelled Antibodies: For experiments in which unlabelled antibodies were administered, one of two different antibody types was used; either a blocking monoclonal rat anti-murine P-selectin IgG (Clone RB 40.34, Pharmingen Co., San Diego, Calif.)[14,18,19] or non-immune rat IgG Sigma Chemical Co., St. Louis, Mo.). Antibodies were prepared as 30 μg in 0.2 mL phosphate buffered saline containing 0.1% bovine serum albumin, which was then administered into the penile vein 10 minutes prior to middle cerebral artery occlusion. In separate experiments, radiolabelled antibodies (0.15 mL, ≈$2.6×10^5$ cpm/μL) were injected intravenously 10 minutes prior to middle cerebral artery occlusion. In a third set of experiments; radiolabelled PMNs were administered intravenously 10 minutes prior to middle cerebral artery occlusion as a 100 μL injection (radiolabelled PMNs were admixed with physiologic saline to a total volume of 0.15 mL; ≈$3×10^6$ cpm/μL). For experiments in which unlabelled antibodies were administered, the time at which measurements were made are indicated in the text, using the methods described above to determine cerebral blood flow, infarction volumes, and mortality. For those experiments in which either radiolabelled antibodies or radiolabelled PMNs were administered, mice were sacrificed at the indicated time points and brains were immediately removed and divided into ipsilateral (postischemic) and contralateral hemispheres. Deposition of radiolabeled antibodies or neutrophils was measured and expressed as ipsilateral/contralateral cpm.

Immunohistochemistry: Brains were removed at 1 hour following middle cerebral artery occlusion, fixed in 10% formalin, paraffin embedded and sectioned for immunohistochemistry. Sections were stained with an affinity-purified polyclonal rabbit anti-human P-selectin antibody (1:25 dilution, Pharmingen, San Diego, Calif.), and sites of primary antibody binding were visualized using a biotin-conjugated goat anti-rabbit IgG (1:20) detected with ExtrAvidin peroxidase (Sigma Chemical Co., St. Louis Mo.).

Data Analysis: Cerebral blood flow, infarct volume, and $^{111}$In-PMN deposition were compared using Student's t-test for unpaired variables. Two way ANOVA was performed to test for significant differences between baseline and final (30 min) antibody deposition between the two groups (experimental vs sham). Student's t-test or unpaired variables was performed to evaluate within-group differences (baseline vs the 30 min. time point). Survival differences between groups was tested using contingency analysis with the Chi-square statistic. Values are expressed as mean±SEM, with a p value<0.05 considered statistically significant.

Figure 31A:
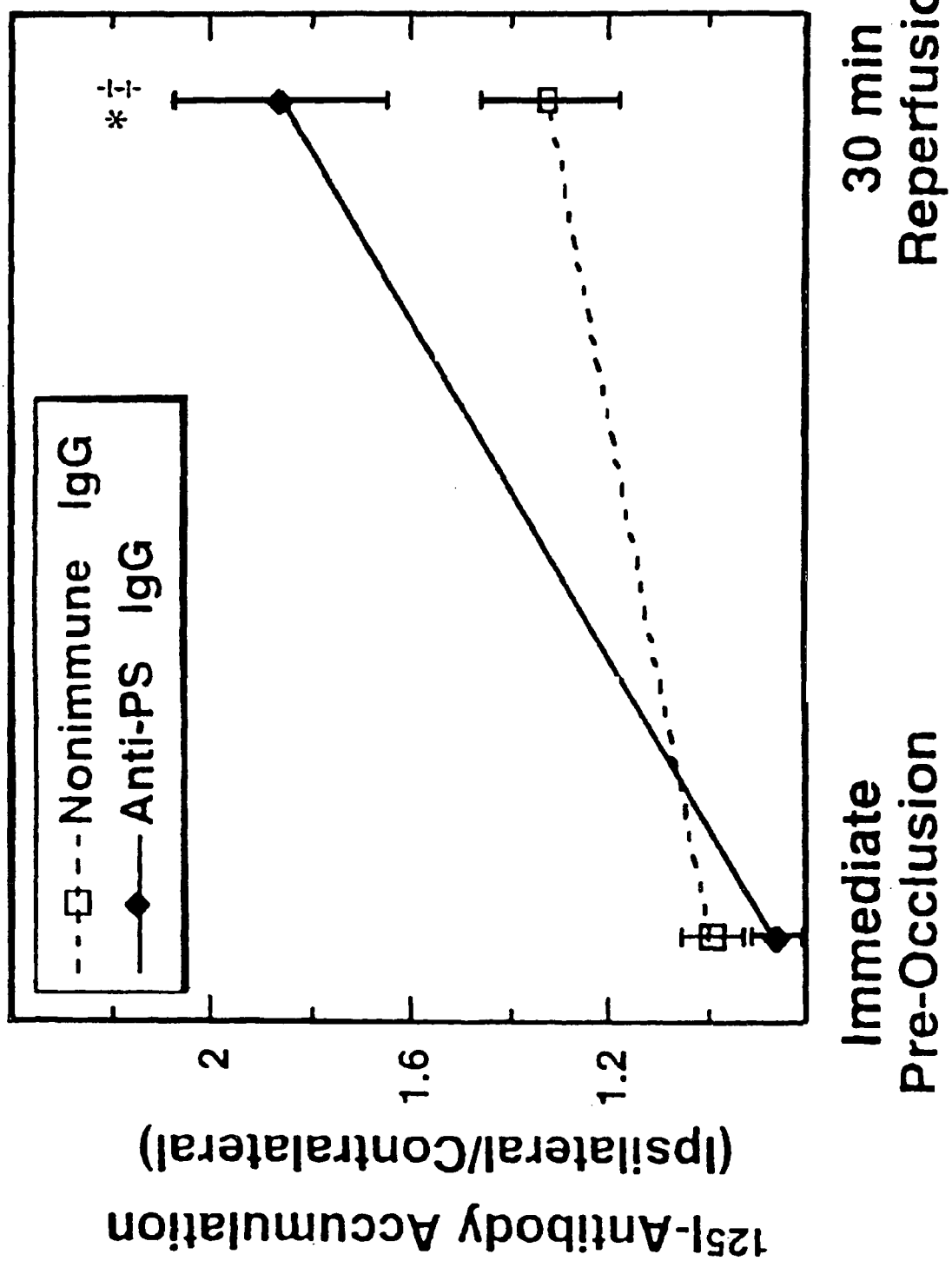
FIGS. 31A-31D. P-selectin expression and neutrophil (PMN) accumulation following middle cerebral artery occlusion (MCAO) in mice.
Figure 31C:
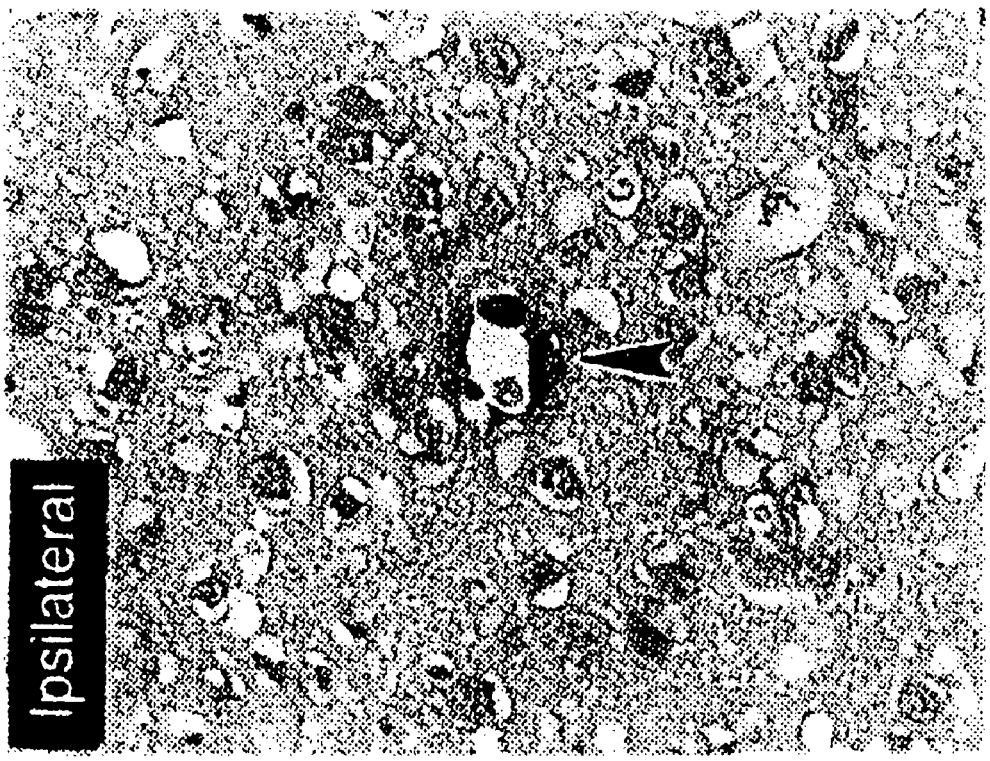
Figure 31B:
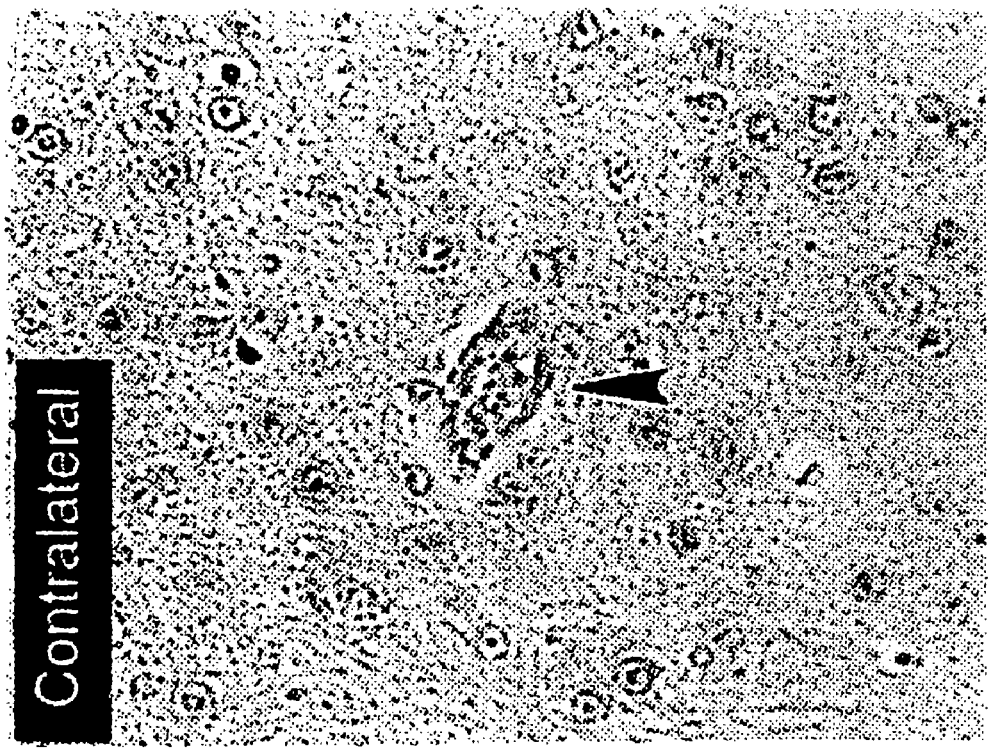
Figure 31D:
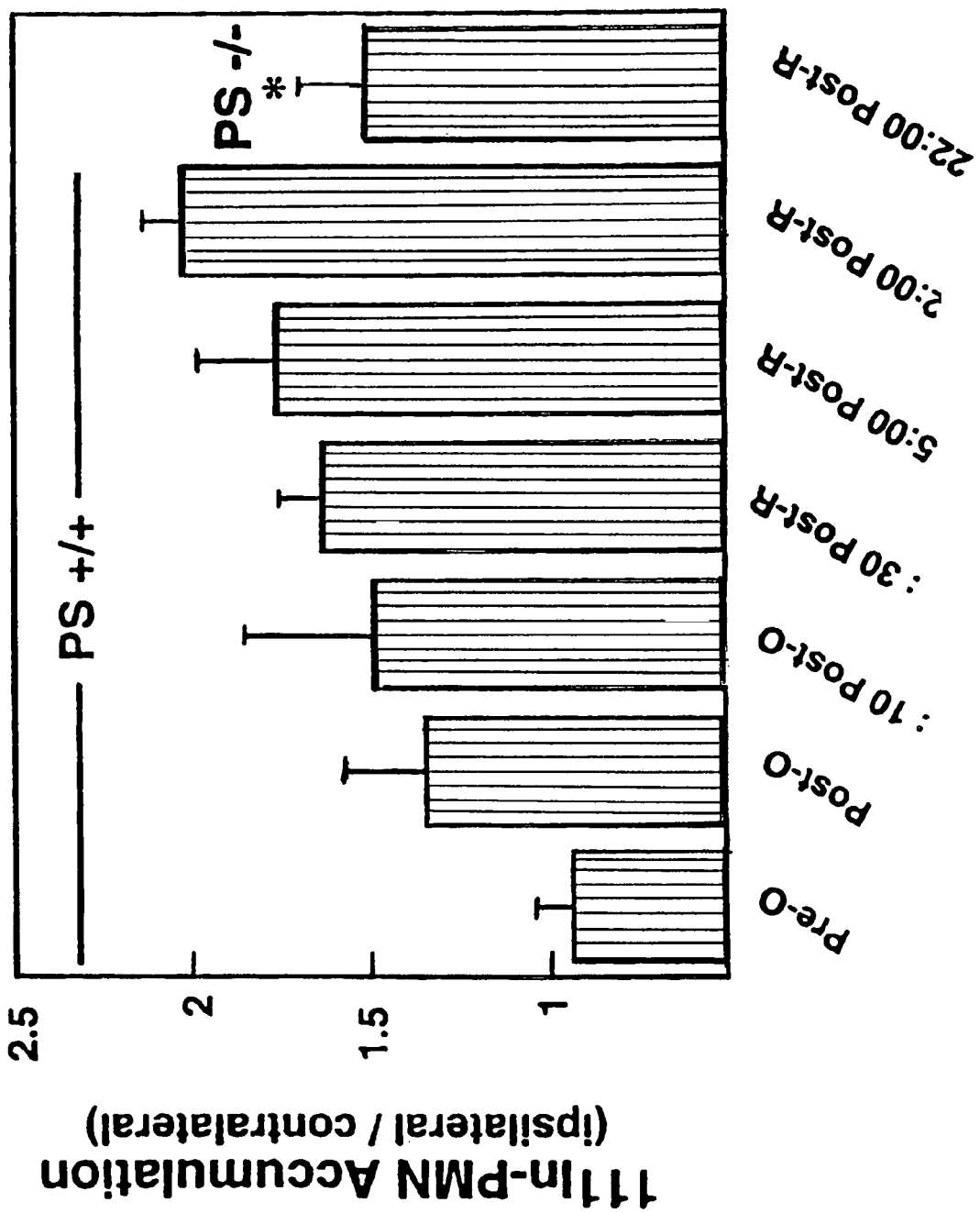

Results:

P-selectin Expression in Murine Stroke: Because P-selectin mediates the initial phase of leukocyte adhesion to activated endothelial cells[20], we examined early cerebral P-selectin expression in a murine model of reperfused stroke. Mice given a $^{125}$I-labelled rat monoclonal anti-murine P-selectin IgG prior to surgery demonstrated a 216% increase in accumulation of the antibody at 30 minutes of reperfusion compared with sham operated animals (p<0.001, FIG. 31A). To demonstrate that this degree of antibody deposition in the reperfused hemisphere was due to P-selectin expression rather than nonspecific accumulation, comparison was made with identically-treated animals given a $^{125}$I-labelled rat non-immune IgG. These experiments demonstrated that there was significantly greater accumulation of the anti-P-selectin IgG than the nonimmune IgG (p<0.025, FIG. 31A), suggesting that P-selectin is expressed in the brain within 30 minutes of reperfusion. Examination of sections of brain tissue immunostained for P-selectin reveal that P-selectin expression is primarily localized to the microvascular endothelial cells in the ipsilateral cerebral cortex (FIG. 31B).

Neutrophil Accumulation in Murine Stroke: To delineate the time course over which PMN influx occurs following stroke, $^{111}$In-labeled PMN accumulation was measured in wild type (PS +/+) mice prior to MCAC, immediately following and 10 minutes after MCAO, and at 30 min, 300 min, and 22 hrs of reperfusion. In PS +/+mice, accumulation of PMNs begins early following the initiation of focal ischemia, and continues throughout the period of reperfusion (FIG. 31C). To establish the role for P-selectin in this postischemic neutrophil accumulation, experiments were performed using mice which were homozygous null for the P-selectin gene (PS –/–). PS –/– mice showed significantly reduced PMN accumulation following middle cerebral artery occlusion and reperfusion (FIG. 31B).

Figure 32A:
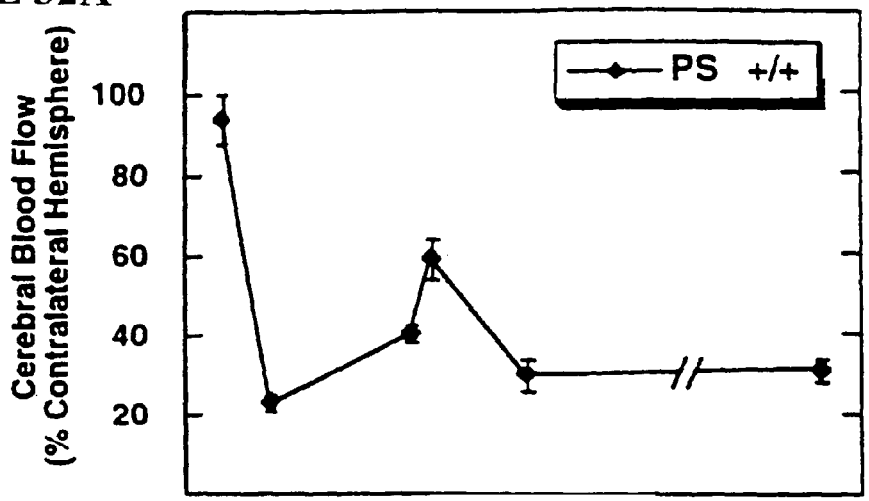
FIG. 32A-32C. Role of P-selectin in the cerebrovascular no-reflow. Cerebral blood flow was measured in PS +/+ (top panel) and PS −/− (middle panel) mice using a laser doppler flow probe, and expressed as the percentage of contralateral (nonischemic) hemispheric blood flow (±SEM). Blood flow was measured at the following time points: a, prior to MCAO (PS +/+, n=16; PS −/−, n=23); b, immediately following MCAO (PS +/+, n=42; PS −/−, n=40); c, 10 minutes following MCAO but still prior to reperfusion (PS +/+, n=36; PS −/−, n=34); d, immediately following reperfusion (PS +/+, n=36; PS −/−, n=34); e, 30 minutes following reperfusion (PS +/+, n=8; PS −/−, n=5); and f, 22 hours following reperfusion (PS +/+, n=15; PS −/−, n=5). The bottom panel represents an overlay of the top two panels, with error bars omitted for clarity.
Figure 32B:
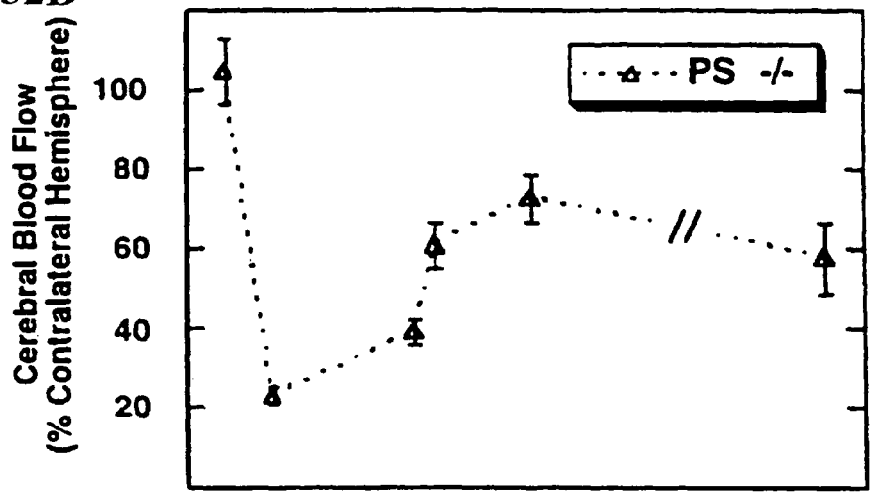
Figure 32C:
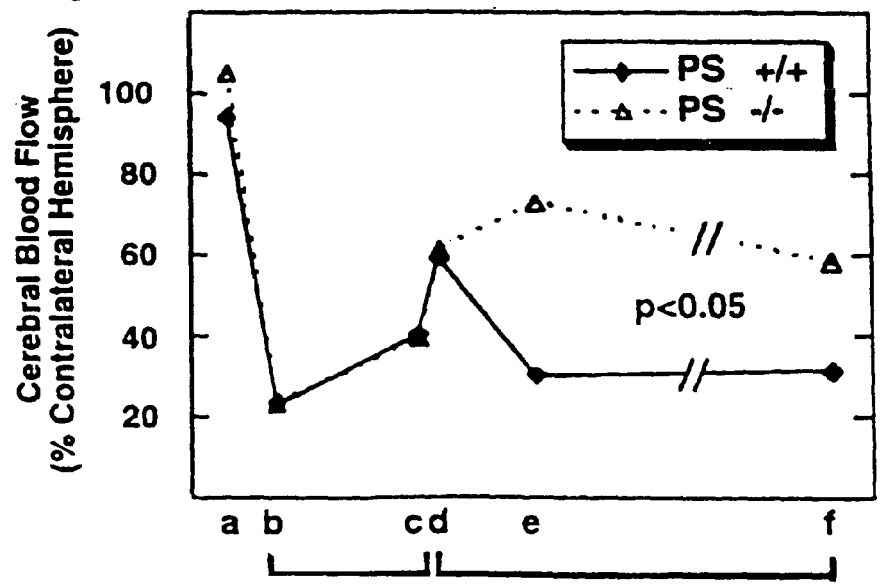

Role of P-selectin Cerebrovascular No-reflow: To determine whether the reduction in PMN accumulation in PS –/– mice resulted in improved cerebral blood flow following the reestablishment of flow, serial measurements of relative CBF were obtained by laser doppler in both PS +/+ and PS –/– mice. Prior to the initiation of ischemia (FIG. 32, point a), relative cerebral blood flows were nearly identical between groups. Middle cerebral artery occlusion (FIG. 32, point b) was associated with a nearly identical drop in cerebral blood flow in both groups. Immediately prior to withdrawal of the intraluminal occluding suture at 45 minutes of ischemia (FIG. 32, point c), cerebral blood flows had risen slightly, although they remained significantly depressed compared with baseline flows. Immediately following withdrawal of the occluding suture to initiate reperfusion (FIG. 32, point d), cerebral blood flows in both groups increased to a comparable degree (≈p60% of baseline in the PS –/– and PS +/+ mice). The immediate failure of the post-reperfusion cerebral blood flows to reach pre-occlusion levels is characteristic of cerebrovascular no-reflow[21], with the subsequent decline in post-reperfusion cerebral blood flows representing delayed post-ischemic cerebral hypoperfusion[22]. By 30 minutes of perfusion (FIG. 32, point e), the cerebral blood flows between the two groups of animals had diverged, with PS –/– animals demonstrating significantly greater relative cerebral blood flows than the PS +/+ controls (p<0.05). (FIG. 32, point f). This divergence reflected significant differences in delayed post-ischemic cerebral hypoperfusion, and persisted for the 22 hour observation period.

Figure 33A:
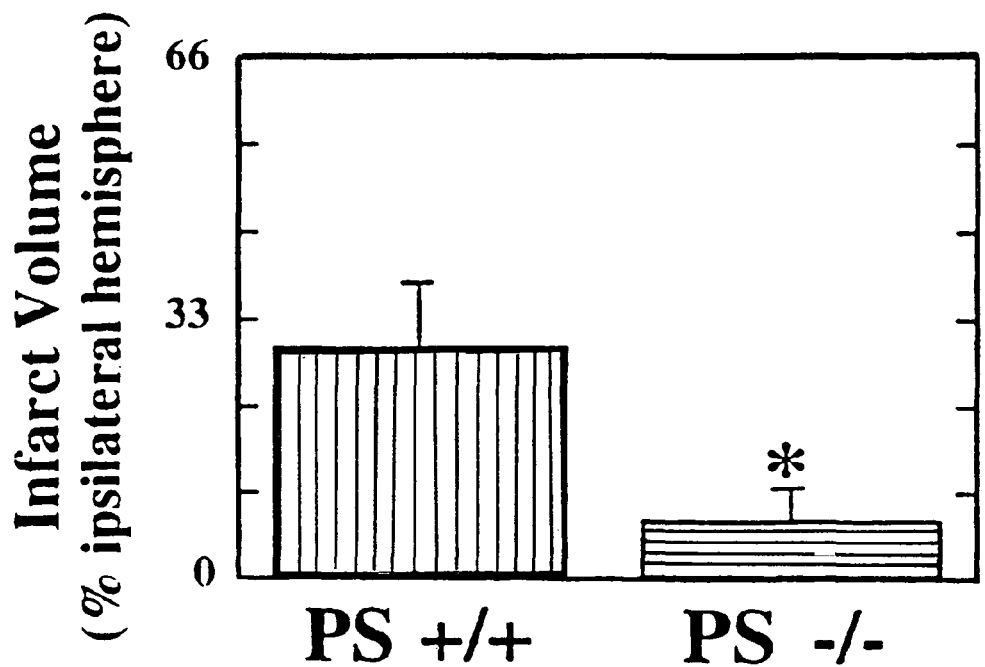
Figure 33B:
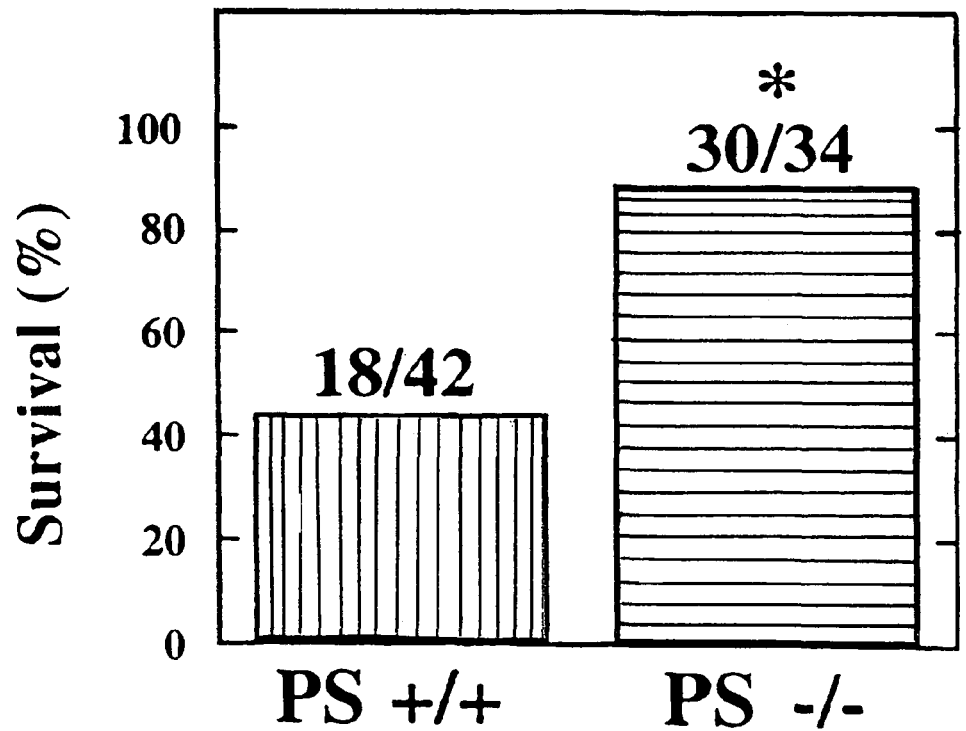

Stroke Outcome: The functional significance of P-selectin expression was vested by comparing indices of stroke outcome in PS –/– mice to those in PS +/+ controls. PS –/– mice were significantly protected from the effects of focal cerebral ischemia and reperfusion, based on a 77% reduction in infarct volume (p<0.1) compared with P-selectin +/+ controls (FIG. 33A). This reduction in infarct volume was accompanied by increased survival in the PS –/– animals (p<0.05; FIG. 33B).

Figure 34:
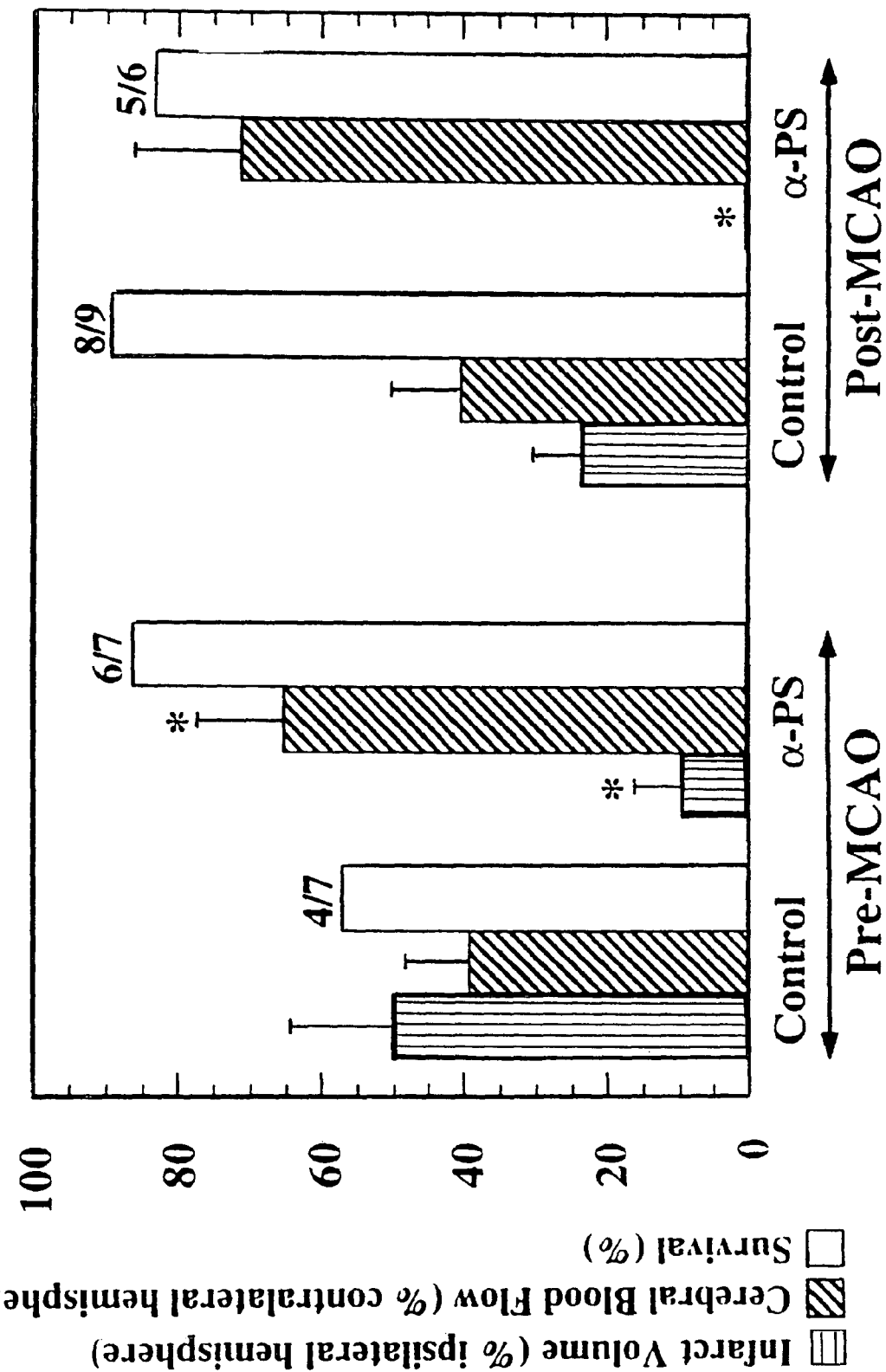
FIG. 34. Effect of P-selectin blockade on stroke outcomes. PS +/+ mice were given either a blocking rat anti-mouse anti-P-selectin IgG (clone RB 40.34, 30 µg/mouse) or a similar dose of nonimmune rat IgG immediately prior to middle cerebral artery occlusion (Pre-MCAO; n=7 for each group) or after occlusion of the middle cerebral artery (Post-MCAO; n=9 for the control antibody, n=6 for the functionally blocking anti-P-selectin antibody). In both cases, the intraluminal occluding suture was withdrawn after a 45 minute ischemic period to simulate clinical reperfusion. After 22 hours of reperfusion, infarct volumes (dark bars), relative cerebral blood flow at thirty minutes following reperfusion (diagonally striped bars), and survival (lightly shaded bars) are shown. Means±SEM are indicated, with the numbers of animals from which the percentage survial was calculated indicated above the survival bars. *=p<0.05 vs control antibody.

Effect of P-selectin Blockade: After having observed the functional role of P-selectin expression in stroke using deletionally mutant mice, experiments were performed to determine whether pharmacological blockade of P-selectin could improve stroke outcome in PS +/+ mice. Using a strategy of administering a functionally blocking monoclonal rat anti-mouse P-selectin antibody (clone RB 40.34[14,18,19]) or non-immune control rat IgG immediately prior to surgery, mice receiving the blocking antibody immediately prior to middle cerebral artery occlusion were observed to have improved post-reperfusion cerebral blood flows by thirty minutes, as well as reduced cerebral infarction volumes and a trend towards reduced mortality compared with controls (FIG. 34, leftmost 6 bars). To increase the potential clinical relevance of a strategy of P-selectin blockade as a new treatment for stroke, additional experiments were performed in which either the control or the blocking antibody were given after intraluminal occlusion of the middle cerebral artery (because most patients present following the onset of stroke). In these studies, a significant reduction in infarct volumes was observed as well as a trend towards improved cerebral blood flow (FIG. 34, rightmost 6 bars).

Discussion:

Despite substantial progress in recent years in the primary prevention of stroke[1], therapeutic options to treat evolving stroke remain extremely limited. Although the publication of two landmark trial last fall demonstrating reduced morbidity following treatment of ischemic stroke with rt-PA[2,3] was thought to usher in a new era of thrombolytic therapy in the treatment of stroke[4], enthusiasm has been tempered somewhat by the hemorrhagic transformation and increased mortality noted in patients with ischemic stroke treated with streptokinase[5]. These divergent trials make it more critical than ever that new safe therapies be developed to treat evolving stroke. Although restoration of blood flow to postischemic brain affords new opportunities for early therapeutic intervention, reperfusion is a double-edged sword. Given the cytotoxic potential of neutrophils[23], it is not surprising that neutrophil influx into postischemic brain tissue can lead to other damage and worsen outcome following experimental stroke[7,24-27]. Using a murine model of focal cerebral ischemia and reperfusion, we have recently identified an important contributory role for the cell adhesion molecule ICAM-1 in neutrophil accumulation at 22 hours following stroke[7]. However, augmented cerebrovascular endothelial ICAM-1 expression requires de novo transcriptional and translational events, which requires time. In contrast, P-selectin, a membrane-spanning glycoprotein which mediates the earliest phases of neutrophil adhesion, may be mobilized from preformed storage pools to be rapidly expressed at the ischemic endothelial cell surface[8,28]. As the clinical trials of thrombolytic therapy for stroke demonstrate a narrow time window for potential benefit (within the first several hours of stroke onset)[2,3,5], this suggests that strategies designed to interfere with the earliest phases of PMN adhesion might be of theoretical benefit in human stroke. These trials should result in greater numbers of patients presenting for earlier therepeutic intervention, increasing the need to address the issue of reperfusion injury in medically revascularized territories. In addition, they underscore the pressing need to understand the contributions of individual adhesion molecules to the pathogenesis of stroke.

Given the considerable body of literature describing the role of P-selectin in other models of ischemia and reperfusion[8,29-32], surprisingly little is known about the role of P-selectin in stroke. Knowledge of the specific role of P-selectin in the cerebral vasculature is important because adhesion molecule requirements vary between vascular beds and conditions under study. For instance, in a model of intestinal transplantation[33], anti-P-selectin antibodies did not reduce reperfusion injury, whereas anti-CD11/CD18 antibodies did. Although P-selectin blockade was ineffective at reducing PMN adhesion and albumin leakage in a rat mesenteric ischemia and reperfusion model, ICAM-1 blockade was effective[34]. In a rat hindlimb ischemia/reperfusion model, the selectin requirements for PMN adhesion differed between the pulmonary and crural muscle vascular beds[31].

To our knowledge, the only published study describing increased P-selectin expression in the ischemic brain is a histopathological description of primate stroke, in which P-selectin expression was increased in the lenticulostriate microvasculature[10]. The current studies were undertaken to study whether P-selectin expression contributes to post-ischemic cerebral neutrophil accumulation, no-reflow, and tissue injury in a murine model of reperfused stroke. Using a recently established model of focal cerebral ischemia and reperfusion in mice[11], P-selectin expression was demonstrated by increased endothelial immunostaining and increased deposition of radiolabelled antibody in the ischemic territory. In the latter technique, antibody deposition into the ischemic hemisphere was normalized to that in the nonischemic hemisphere in each animal, not only to minimize potential variations in injection volume or volume of distribution, but to enable comparison between animals given different antibodies. Because disruption of the endothelial barrier function in the ischemic cortex may augment nonselective antibody deposition, similar experiments were performed with a control rat IgG. These data show that the antibody which binds to P-selectin is deposited at an accelerated rate compared with the control antibody, suggesting that local P-selectin expression is augmented in the reperfused tissue. This data in the murine model parallels that reported in a baboon model of stroke[10], in which P-selectin expression was increased within 1 hour following the ischemic event.

The role of P-selectin expression in recruiting PMNs to the post-ischemic zone was demonstrated using a strategy in which accumulation of $^{111}$In-labelled PMNs was measured. Although we have previously reported that by 22 hours, PMN accumulation is elevated in the ischemic hemisphere[7], the current time-course data demonstrate that PMN accumulation begins shortly after the onset of ischemia. Failure to express the P-selectin gene was associated with reduced PMN accumulation, suggesting the participation of P-selectin in post-ischemic cerebral PMN recruitment. However, the P-selectin null animals did demonstrate a modest (albeit less than control) neutrophil accumulation by 22 hours. This data indicates that P-selectin is not the exclusive effector mechanism responsible for postischemic cerebral PMN recruitment, and is consistent with our previous data that ICAM-1 also participates in post-ischemic PMN adhesion [7]. Furthermore, this data is not unlike that in which intra-abdominal instillation of thioglycollate in P-selectin deficient mice caused delayed (but not absent) PMN recruitment[9].

Because of the critical need to identify reasons for failed reperfusion, the current studies examined the role of P-selectin in delayed postischemic cerebral hypoperfusion[21,22], the phenomenon wherein blood flow declines during reperfusion, despite restoration of adequate perfusion pressures. In cardiac models of ischemia, no-reflow worsens as time elapses after reperfusion[35], suggesting an important role for recruited effector mechanisms, such as progressive microcirculatory thrombosis, vasomotor dysfunction, and PMN recruitment. Both P-selectin and ICAM-1-dependent adherence reactions[36] and PMN capillary plugging[37] have been shown in other models to participate in post-ischemic no-reflow. In the brain, PMNs have been implicated in post-ischemic cerebral no reflow[38,39], but the role of P-selectin had not been previously elucidated.

The current so uses a relatively noninvasive technique (laser doppler) to obtain serial measurements of relative cerebral blood flow, in order to establish the existence, time course, and P-selectin-dependence of post-ischemic cerebrovascular no-reflow. In order to demonstrate that the threading procedure itself was not the cause of vascular damage and subsequent cerebral infarction, sham ischemia experiments were performed (n=10) in which a nylon suture was threaded into the internal carotid artery for a 45 minute non-occluding period. In these experiments, the threading was shown to be nonocclusive based upon no decline in perfusion by laser doppler during the 45 minute period. When brains were then collected and stained with TTC at 24 hours, none showed evidence of cerebral infarction. Therefore, we can conclude that the threading procedure per se does not provoke sufficient damage to affect our major outcome variables. When relative cerebral blood flow was examined following frank middle cerebral artery occlusion in experimental animals, we observed that P-selectin null and control animals were subjected to virtually identical degrees of ischemia (there was an intial≈4.5-fold drop in relative cerebral blood flow following middle cerebral artery occlusion in both). However, there was a slight increase in relative cerebral blood flow in the first 10 minutes following occlusion, even though the occluding suture remained in place. This is an empiric observation we have consistently made, for which there are likely to be several possible explanations. There is likely to be some degree of collateral flow which opens up in the ischemic territory. Another tenable explanation is that there may be an element of initial vasosplasm in the region of the occluding catheter tip, which modestly resolves within several minutes. Although both of these explanations are possible, due to the small size of the murine vasculature, we cannot identify the mechanism with certainty in our model. Nevertheless, as we observe the same degree of flow recruitment in both control and experimental animals, these data do not not alter our main conclusions, that P-selectin is an important mediator of cerebral tissue injury in reperfused stroke.

Following removal of the intraluminal occluding suture, instantaneous recovery of blood flow was the same in both the P-selectin +/+ and −/− animals. The fact that flow levels never returned to baseline (nor was there an overshoot, as might be seen with reactive hyperemia) may be due to the severity and duration of the ischemic period, which is likely to recruit other mechanisms of post-ischemic cerebrovascular no-reflow, such as thrombosis or neutrophil recruitment caused by non-selectin-dependent mechanisms. When even later time points are examined (such as 30 minutes to 22 hours after removal of the occluding suture), it is interesting to note that there is a slight decline in cerebral blood flow in the P-selectin −/− animals. This late (albeit limited) decline in cerebral blood flow by 22 hours is consistent with the modest PMN recruitment observed in the PS −/− animals over the same period, again suggesting the recruitment of other flow-limiting effector mechanisms (such as ICAM-1) in the PS −/− animals.

The functional effects of P-selectin expression are clear from the current set of studies: animals which fail to express the P-selectin gene or PS +/+ animals treated with a functionally blocking anti-P-selectin antibody) exhibit smaller infarcts and improved survival compared with controls. When these data are considered along with previously published data demonstrating a deleterious role for ICAM-1 expression in stroke[7], it becomes increasingly apparent that there are multiple means for recruiting PMNs to post-ischemic cerbral cortex, and that blockade of each represents a potential, strategy to improve stroke outcome in humans. Given our current recognition of the importance of timely reperfusion in halting the advancing wavefront of neuronal death following stroke, interfering with PMN adhesion at its earliest stages appears to be an attractive option for reducing morbidity and mortality. In fact, anti-adhesion molecule strategies may not only be beneficial in their own right (i.e., including patients ineligible for thrombolysis), but may extend the window of opportunity for thrombolytic intervention[40]. The current set of studies contributes to our understanding of pathophysiological mechanisms operative in reperfused stroke. These studies suggest the need for clinical trials of therapies for evolving stroke which optimize the reperfusion milieu to reduce PMN accumulation.

References:

1. Bronner L L, Kanter D S, Manson J E: Primary prevention of stroke. *N Engl J Med* 1995;333(21):1392-1400
2. The National Institute of Neurological Disorders and Stroke rt-PA Stroke Study Group: Tissue plasminogen activator for acute ischemic stroke. *N Engl J Med* 1995;333: 1581-1587
3. Hacke W, Kaste M, Fieschi C, Toni D, Lesaffre E, von Kummer R, Boysen G, Bluhmki E, Hoxter G, Mahagne M H, Hennerici M, for the ECASS Study Group: Intravenous thrombolysis with recombinant tissue plasminogen activator for acute hemispheric stroke. *JAMA* 1995;274(133: 1017-1025
4. del. Zoppo G J: Acute stroke—on the threshold of a therapy. *N Engl J Med* 1995;333(13):1632-1633
5. Hommel M, Cornu C, Boutitie F, Boissel J P, The Multi-Center Acute Stroke Trial—Europe Study Group: Thrombolytic therapy with streptokinase in acute ischemic stroke. *N Engl J Med* 1996;335:145-150
6. Baringa M: Finding new drugs to treat stroke. *Science* 1996;272:664-666
7. Connolly E S Jr, Winfree C J, Springer T A, Naka Y, Liao H, Yan S D, Stern D M:, Solomon R A, Gutierrez-Ramos J-C,: Pinsky, D J: Cerebral protection in homozygous null ICAM-1 mice after middle cerebral artery occlusion. Role of neutrophil adhesion in the pathogenesis of stroke. *J Clin Invest* 1996;97:209-216
8. Pinsky D J, Waka Y, Liao H, Oz M C, Wagner D D, Mayadas T N, Johnson R C, Hynes R C, Heath M, Lawson C A, Stern D M: Hypoxia-induced exocytosis of endothelial cell Weibel-Palade bodies. A mechanism for rapid neutrophil recruitment after cardiac preservation. *J Clin Invest* 1996;97:493-500
9. Mayadas T K, Johnson R C, Rayburn H, Hynes R O, Wagner D D: Leukocyte rolling and extravasation are severely compromised in P-selectin deficient mice. *Cell* 1993;74(3):541-554
10. Okada Y, Copeland B R, Mori E, Tuna M M, Thomas W S, del Zoppo G J: P-selectin and intercellular adhesion molecule-1 expression after focal brain ischemia and reperfusion. *Stroke* 1994;25:202-211
11. Connolly E S Jr, Winfee C J, Stern D M, Solomon R A, Pinsky D J: Procedural and strain-related variables significantly affect outcome in a murine model of focal cerebral ischemia. *Neurosurg* 1996;38(3):523-532
12. Barone F C, Knudsen D J, Nelson A H, Feuerstein G Z, Willette R N: Mouse strain differences in susceptibility to cerebral ischemia are related to cerebral vascular anatomy: *J Cereb Blood Flow Metab* 1993;13:633-692
13. Dirnagl U, Kaplan B, Jacewicz M, Bulsinelli W: Continuous measurement of cerebral blood flow by laser-doppler flowmetry in a rat stroke model. *J Cereb Blood Flow Metab* 1989;9:589-596
14. Ley K, Bullard D C, Arbones M L, Bosse R. Vestweber D, Tedder T F, Beaudet A L: Sequential contribution of L- and P-selectin to leukocyte rolling in vivo. *J Exp Med* 1995; 181:669-675
15. David G S, Reisfeld R A: Protein iodination with solid state lactoperoxidase. *Biochem* 1974;13:1014-1021
16. Bederson J B, Pitts L H, Nishimura M C, Davis R L, Bartkowski H M: Evaluation of 1,3,5-triphenyltetrazolium chloride as a stain for detection and quantification of experimental cerebral infarction in rats. *Stroke* 1986;17: 1304-1308
17. Huang Z, Huang P L, Panahian N, Dalkara T, Fishman M C, Moskowitz M A: Effects of cerebral ischemia in mice deficient in neuronal nitric oxide synthase. *Science* 1994; 265:1883-1885
18. Bosse R, Westweber D: Only simultaneous blocking of the L- and P-selectin completely inhibits neutrophil migration into mouse peritoneum. *Eur J Immunol* 1994;24:3019-3024
19. Kunkel E J, Junc U, Bullard D C, Norman K E, Wolitzky B A, Vestweber D, Beaudet A L, Ley K: Absence of trauma-induced leukocyte rolling in mice deficient in both P-selectin and ICAM-1. *J Exp Med* 1996;183:57-65
20, Springer T A: Adhesion receptors of the immune system. *Nature* 1990;346:425-434
21. Ames A I, Wright R L, Kowada M, Thurston J M, Majno G: Cerebral ischemia II: the no reflow-phenomenon. *Am J Pathol* 1968,52:437-447
22. Levy D E, Van Uitert R L, Pike C L: Delayed postischemic hypoperfusion: a potentially damaging consequence of stroke. *Neurology* 1979;29:1245-1252
23. Weiss S J: issue destruction by neutrophils. *N. Engl J Med* 1989;320(6):365-376
24. Hallenbeck J M, Dutka A J, Tanishima T, Kochanek P M, Kumaroo K K, Thompson C B, Obrenovich T P, Contreras T J: Polymorphonuclear leukocyte accumulation in brain regions with low blood flow during the early postischemic period. *Stroke* 1986;17:246-253
25. Kochanek P M, Hallenbeck J M: Polymorphonuclear leukocytes and monocytes/macrophages in the pathogenesis of cerebral ischemia and stroke. *Stroke* 1992;23(9) 1367-1379
26. Dutka A J, Kochanek P M, Hallenbeck J M: Influence of granulocytopenia on canine cerebral ischemia induced by air embolism. *Stroke* 1989;20:390-395
27. Bednar M M, Raymond S, McAuliffe T, Lodge P A, Gross C E: The role of neutrophils and platelets in a rabbit model of thromboembolic stroke. *Stroke* 1991;22(1):44-50
28. Geng J-G., Bevilacqua M P, Moore K L, McIntyre T M, Prescott S M, Kim J M, Bliss G A, Zimmerman G A, McEver R P: Rapid neutrophil adhesion to activated endothelium mediated by GMP-140. *Nature* 1990;343:757-760
29. Weyrich A S, Ma X-L, Lefer D J, Albertine K H, Lefer A M: In vivo neutralization of P-selectin protects feline heart and endothelium in myocardial ischemia and reperfusion injury. *J Clin Invest* 1993;91-2620-2629
30. Winn R K, Liggitt D, Vedder N B, Paulson J C, Harlan J M: Anti-P-selectin monoclonal antibody attenuates reperfusion injury in the rabbit ear. *J Clin Invest* 1993;92:2042-2047
31. Seekamp A., Till G O, Mulligan M S, Paulson J C, Anderson D C, Miyasaka M, Ward P A: Role of selectins in local and remote tissue injury following ischemia and reperfusion. *Am J Pathol* 1994;144:592-598
32. Kubes P, Jutila M, Payne D: Therapeutic potential of inhibiting leukocyte rolling in ischemia/reperfusion. *J Clin Invest* 1995;95:2510-2519
33. Slocum M M, Granger D N: Early mucosal and microvascular changes in feline intestinal transplants. *Gastroenterology* 1993;105:1761-1768
34. Kurose I, Anderson D C, Miyasaka M, Tamatani T, Paulson J C, Todd R F, Rustine J R, Granger D N: Molecular determinants of reperfusion-induced leukocyte adhesion and vascular protein leakage. *Circ Res* 1994;74:336-343

35. Kloner R A. Ganote C E, Jennings R B: The "no-reflow" phenomenon after temporary coronary occlusion in the dog. *J Clin Invest* 1974;54:1496-1608
36. Jerome S M, Dore M, Paulson J C, Smith C W, Korthuis R J: P-selectin and ICAM-1-dependent adherence reactions: role in the genesis of postischemic no-reflow. *Am J Physiol* 1994;266:H1316-H1321
37. Engler R L, Schmid-Schonbein G W, Pavelec R S: Leukocyte capillary plugging in myocardial ischemia and reperfusion in the dog. *Am J Pathol*. 1983;111:98-111
38. Mori E, del Zoppo G J, Chamber J D, Copeland B R, Arfors K E: Inhibition of polymorphonuclear leukocyte adherence suppresses no-reflow after focal cerebral ischemia in baboons. *Stroke* 1992;23:712-718
39. Grogaard B, Schurer L, Gerdin B, Arfors K E: Delayed hypoperfusion after incomplete forebrain ischemia in the rat: the role of polymorphonuclear leukocytes. *J Cereb Blood Flow Metab* 1989;9:500-505
40. Bowes M P, Rothlein R, Fagan S C, Zivin J A: Monoclonal antibodies preventing leukocyte activation, reduce experimental neurological injury, and enhance efficacy of thrombolytic therapy. *Neurology* 1995;45:815-819

Example 11

Use of Carbon Monoxide to Treat an Ischemic Disorder—Example of the Protective Effects of Carbon Monoxide in Lung Ischemia In the initial patent application, we revealed data indicating that endogenous production of carbon monoxide or administration of exogenous carbon monoxide is beneficial in protecting the brain against subsequent ischemic injury. As another example of the use of carbon monoxide in treating an ischemic disorder, we have administered carbon monoxide to rats to test its effects on improving lung preservation for transplantation (this is similar to an ischemic disorder, because the donor lungs are removed from a recipient; during the period in which the lungs are preserved and transferred from donor to recipient, there is an interruption in blood flow).

Methods for Testing the Effect of Carbon Monoxide on Lung Preservation

Materials used to prepare preservation solution:
For all experiments, the base preservation solution consisted of modified Euro-Collins (EC) solution ($Na^+$ 10 mEq/L, $K^+$ 115 mEq/L, $Cl^-$ 15 mEq/L, $HPO_4^{2-}$ 85 mEq/L, $H2PO_4^-$ 15 mEq/L, $HCO_3^-$ 10 mEq/L).

Lung Harvest, Preservation and Transplantation:
Inbred male Lewis rats (250-300 gms) were used for all experiments according to a protocol approved by the Institutional Animal Care and Use Committee at Columbia University, in accordance with guidelines set forth by the American Academy for Accreditation of Laboratory Animal Care (AAALAC). Lung transplant experiments were performed in the following manner. Donor rats were given 500 units of heparin intravenously, and the pulmonary artery (PA) was flushed with a 30 mL volume of 4° C. preservation solution at a constant pressure of 20 mm Hg. When lungs are preserved in this manner, most of the infused flush solution comes out of a left atrial vent created in the lung donor, as well as out of the pulmonary veins following transection.

The left lung was then harvested, a cuff was placed on each vascular stump, a cylinder was inserted into the bronchus, and the lung was submerged for 6 hours in 4° C. preservation solution which was identical to the PA flush solution. Gender/strain/size matched rats were anesthetized, intubated, and ventilated with 100% $O_2$ using a rodent ventilator (Harvard Apparatus, South Natick, Mass.). Orthotopic left lung transplantation was performed through a left thoracotomy using a rapid cuff technique for all anastomoses, with warm ischemic times maintained below 5 minutes. The hilar cross-clamp was released, re-establishing blood flow and ventilation to the transplanted lung. A snare was then passed around the right PA, and Millar catheters (2F; Millar Instruments, Houston, Tex.) were introduced into the main PA and the left atrium (LA). A Doppler flow probe (Transonics, Ithaca, N.Y.) was placed around the main PA.

Measurement of Lung Graft Function:
Online hemodynamic monitoring was accomplished using MacLab and a Macintosh IIci computer. Measured hemodynamic parameters included LA and PA pressures (mm Hg), and PA flow (mL/min). Arterial oxygen tension ($pO_2$, mm Hg) was measured during inspiration of 100% $O_2$ using a model ABL-2 gas analyzer (Radiometer, Copenhagen, Denmark). PVRs were calculated as (mean PA pressure—LA pressure)/mean PA flow and expressed as mm Hg/mL/min. After baseline measurements, the native right PA was ligated and serial measurements taken every five minutes until the time of euthanasia at 30 minutes (or until recipient death).

Administration of Carbon Monoxide:
At the indicated time before surgery (4,8, or 12 hours), rats were placed in a bell jar, and carbon monoxide was administered at various concentrations (0.01%, 0.03%, or 0.1%), with the remainder of the gas mixture consisting of room air. (The gas was passed through a jar of water prior to administration, in order to humidify it for animal comfort). At the indicated times following initiation of exposure, rats were anesthetized and lungs harvested as described above. These donor lungs were used in subsequent lung transplant experiments.

Results and Discussion:
The results of these experiments indicate that, compared with untreated controls, the inhalation of carbon monoxide prior to lung harvest confers significant protection for the lungs following transplantation. This protection is evidenced by; (1) Improved arterial oxygenation of the recipients of carbon-monoxide-pretreated donor lungs; (2) Increased pulmonary arterial blood flow (and reduced pulmonary vascular resistance) with the use of carbon-monoxide-pretreated donor lungs; and (3) Improved survival of recipients of carbon-monoxide-pretreated donor lungs compared with controls. The beneficial effects of carbon monoxide were dose-dependent, i.e., the best protection was seen at the 0.1% dose, with an intermediate level of protection seen at the 0.03% dose, and the least protection seen at the 0.01% dose. The beneficial effects of carbon monoxide were also time-dependent, in that longer exposures appeared to provide the greatest protection. Together, these data indicate that carbon monoxide can protect in another ischemic disorder (lung ischemia) and suggest that the results may be generalizable to other ischemic disorders as well.

Example 12

Use of a Spectrophotometric Hemoglobin Assay to Objectively Quantify Intracerebral Hemorrhage in Mice Abstract
Background and Purpose There is great interest in developing novel anticoagulant or thrombolytic strategies to treat ischemic stroke. However, at present, there are limited means to accurately assess the hemorrhagic potential of these agents. The current studies were designed to develop and validate a method for accurately quantifying the degree of intracerebral hemorrhage in murine models. Methods In a murine model, intracerebral hemorrhage (ICH) was induced by stereotactic intraparenchymal infusion of collagenase B alone ($6 \times 10^{-6}$ units, n=5) or collagenase E followed by intravenous tissue plasminogen activator (rt-PA, 0.1 mg/kg, n=6). Controls consisted of either sham surgery with stereotactic infusion of saline (n=5) or untreated animals (n=5). ICH was (1) graded by a scale based on maximal hemorrhage diameter on coronal sections, and (2) quantified by a spectrophotometric assay measuring cyanomethemoglobin in chemically reduced extracts of homogenized murine brain. This spectrophotometric assay was validated using known quantities of hemoglobin or autologous blood added to a separate cohort of homogenized brains. Using this assay, the degree of hemorrhage following focal middle cerebral artery occlusion/reperfusion was quantified in mice: treated with post-occlusion high-dose IV rt-PA (10 mg/kg, n=11) and control mice subjected to stroke but treated with physiological saline solution. (n=9). Results Known quantities of hemoglobin or autologous blood added to fresh whole brain tissue homogenates showed a linear relationship between the amount added and OD at the absorbance peak of cyanomethemoglobin (r=1.00 and 0.98, respectively). When in vivo studies were performed to quantify experimentally-induced. ICH, animals receiving intracerebral infusion of collagenase B bad significantly higher ODs than saline-infused controls (2.1-fold increase, pa=0.05). In a middle cerebral artery occlusion and reperfusion model of stroke, administration of rt-PA after reperfusion increased the OD by 1.8-fold compared with animals which received physiological saline solution (p<0.001). When the two methods of measuring ICH (visual score and OD) were compared, there was a linear correlation (r=0.88). Additional experiments demonstrated that triphenyltetrazolium staining, which is commonly used to stain viable brain tissue, does not interfere with the spectrophotometric quantification of ICH. Conclusions These data demonstrate that the spectrophotometric assay accurately and reliably quantifies murine ICH. This new method should aid objective assessment of the hemorrhagic risks of novel anticoagulant or thrombolytic strategies to treat stroke and can facilitate quantification of other forms of intracerebral hemorrhage.

Introduction

Ischemic stroke accounts for the greatest majority of presentations of acute stroke. There has thus been a tremendous interest in designing strategies which can promptly and effectively restore blood flow to the ischemic region of brain. Although heparin may be effective in incipient stroke. (TIAs)[3], its use during the acute phases of stroke may be associated with a high degree of morbidity and intracerebral hemorrhage [1-4]. Similarly, in the early 1960s, the dismal outcomes in the streptokinase trials for acute stroke led to the reluctance of clinicians to thrombolyse acute stroke for the subsequent three decades [5,6]. This reluctance has been validated by recent trials in which the use of streptokinase has been associated with increased risk of mortality and intracerebral hemorrhage [7]. On the other hand, the use of recombinant tissue-type plasminogen activator (rt-PA) to treat stroke-in-progress has shown more promise [8], with a subset of patients with acute stroke who are treated with rt-PA demonstrating reduced long-term morbidity if treated within the first 3 hours of symptom onset [9-11]. Even so, other trials using the same agent (rt-PA) have failed to show benefit or have had excessively high rates of ICH [9,12-15].

This confusing morass of clinical data underscores the urgent need to identify improved strategies to achieve rapid reperfusion. Towards this end, it is imperative to identify an experimental model in which the potential benefits of timely reperfusion in stroke can be weighed objectively against the risks of increased intracerebral hemorrhage. In most animal studies of thrombolytic therapy for clinical stroke, the risks of intracerebral hemorrhage have been estimated rather than quantitatively measured [16-24]. The current studies were designed to develop and validate a method for accurately quantifying the degree of intracerebral hemorrhage in murine models, in order to assess potential risks of new anticoagulant or thrombolytic treatments for acute stroke.

Materials and Methods

Experimental Animals

In the present study, male C57BL6J mice were purchased from Jackson Laboratories (Bar Harbor, Me.), and were used between 8 to 10 weeks old (22-32 g). All procedures were performed according to an institutionally approved protocol and are in accordance with the guidelines provided by the American Academy of Accreditation of Laboratory Animal Care (AAALAC).

Spectrophotometric Assay for Intracerebral Hemorrhage

The hemoglobin content of brains subjected to the experimental procedures below was quantified using a spectrophotometric assay as follows. Whole brain tissue was obtained from freshly euthanized control or experimental animals, and each brain was treated individually as follows. Distilled water (250 µl) was added to each brain, followed by homogenization, for 30 sec (Brinkman Instruments, Inc., Westbury, N.Y.), sonification on ice with a pulse ultrasonicator for 1 minute (SmithKline Corporation, Collegeville, Pa.), and centrifugation at 13,000 rpm for 30 minutes (Baxter Scientific Products, Deerfield, Ill.). After collecting the hemoglobin-containing supernatant, 80 µl of Drabkin's reagent (purchased from Sigma Diagnostics, St. Louis, Mo; $K_3Fe(CN)_6$ 200 mg/L, KCN 50 mg/L, $NaHCO_3$ 1 g/L, pH 8.6 [25]) was added to a 20 µl aliquot and allowed to stand for 15 minutes. This reaction converts hemoglobin to cyanomethemoglobin, which has an absorbance peak at 540 nm, and whose concentration can then be assesses by the optical density of the solution at ≈550 nm wavelength [26]. To validate that the measured absorbance following these procedures reflects the amount of hemoglobin, known quantities of bovine erythrocyte hemoglobin (Sigma, St. Louis, Mo.) were analyzed using similar procedures alongside every brain tissue assay. As an additional measure, blood was obtained from control mice by cardiac puncture following anesthesia. Incremental aliquots of this blood were then added to freshly homogenized brain tissue obtained from untreated mice to generate a standard absorbance curve.

Collagenase-induced Intracerebral Hemorrhage

The general procedures for inducing intracerebral hemorrhage in the mouse were adapted from a method which has been previously described in rats [27]. After anesthesia with an intraperitoneal injection of 0.35 ml of ketamine (10 mg/ml) and xylazine (0.5 mg/ml), mice were positioned prone in a stereotactic head frame. The calvarium was exposed by a midline scalp incision from the nasion to the superior nuchal line and then the skin was retracted laterally. Using a variable speed drill (Dremel, Racine, Wis.) a 1.0-mm burrhole was made 2.0 mm posterior to the bregma and 2.0 mm to the right of midline. A single 22-gauge angiocathether needle was inserted using stereotactic guidance into the right deep cortex/basal ganglia (coordinates: 2.0 mm posterior, 2.0 mm lateral). The needle was attached by a plastic tubing to a microinfusion syringe and solutions were infused into the brain at a rate of 0.25 μl per minute for 4 minutes with an infusion pump (Bioanalytical Systems, West Lafayette, Ind.). Animals received either: (1) 0.024 μg collagenase B (Boehringer Mannheim, Mannheim, Germany) in 1 gl normal saline solution (Collagenase); (2) 1 μl normal saline solution alone (Sham); (3) no treatment (Control); or (4) stereotactically-guided infusion of collagenase B as above but followed immediately by intravenous recombinant human tissue plasminogen activator (Genentech Inc., South San Francisco, Calif, 1 mg/kg in 0.2 ml normal saline solution) administered by dorsal penile vein injection (Collagenase+rt-PA). In the Collagenase, Sham, and Collagenase+rt-PA groups, the stereotactic needle was removed immediately following infusion and the incision was closed with surgical staples. Brain tissue was harvested immediately after rapid anesthetized decapitation.

Hemorrhagic Conversion in a Murine Focal Cerebral Ischemia Model

Focal cerebral ischemia was produced in animals by transient right middle cerebral artery occlusion using a method previously described in detail [28,29]. Briefly, a heat-blunted 12 or 13 mm 5-0 or 6-0 gauge nylon suture was passed into the right internal carotid artery to the level of the middle cerebral artery. After 45 minutes, the occluding suture was removed to reestablish perfusion. Immediately following removal of the occluding suture, animals received either intravenous tissue plasminogen activator (10 mg/kg in 0.2 ml normal saline solution, Stroke+rt-PA) or normal saline solution (Stroke+Saline) given by dorsal penile vein injection. At 24 hours, brain tissue was harvested immediately after rapid anesthetized decapitation. To evaluate the effect of 2,3,5-triphenyltetrazolium chloride (TTC) which is commonly used to distinguish infarcted from noninfarcted cerebral tissue [28,30], nonmanipulated (control) brains were divided into half, immersed in immersed in 2% TTC (Sigma Chemical Company, St. Louis, Mo.) In 0.9% phosphate-buffered saline, incubated for 30 minutes at 37° C., and then prepared as described above for the spectrophotometric hemoglobin assay. The other half of each brain was immersed in saline for an identical duration, and then subjected to the procedures described above for the spectrophotometric hemoglobin assay.

Validation of Quantitative Intracerebral Hemorrhage Assay

The degree of ICH was first scored visually by a blinded observer. For visual scoring of intracerebral hemorrhage in mice, brains obtained from mice which had survived to the 24 hour time point following the procedure (collagenase-induced hemorrhage or MCA occlusion) were placed in a mouse brain matrix (Activational Systems Inc., Warren, Mich.) to obtain 1 mm serial coronal sections. Sections were inspected by a blinded observer and brains were given an ICH score from a graded scale based on maximal hemorrhage diameter seen on any of the sections [ICH score 0, no hemorrhage; 1, <1 mm; 2, 1-2 mm; 3, >2-3 mm; 4, >3 mm]. Slices from each brain were then pooled, homogenized, and then treated according to the procedures described above for the spectrophotometric hemoglobin assay.

Statistics

Correlations between visually-determined ICH scores and spectrophotometric determinations of ICH were performed using Pearson's linear correlation, with correlation coefficients indicated. To establish whether a given treatment (Collagenase, Sham, Stroke, etc.) had a significant effect on either spectrophotometric or visually-scored ICH, comparisons were made using an unpaired two-tailed t-test. For nonparametric data (visual ICH scores), nonparametric analysis was performed using the Mann-Whitney test. Values are expressed as means±SEM, with a $p<0.05$ considered statistically significant.

Results

Spectrophotometric Hemoglobin Assay

Figure 35A:
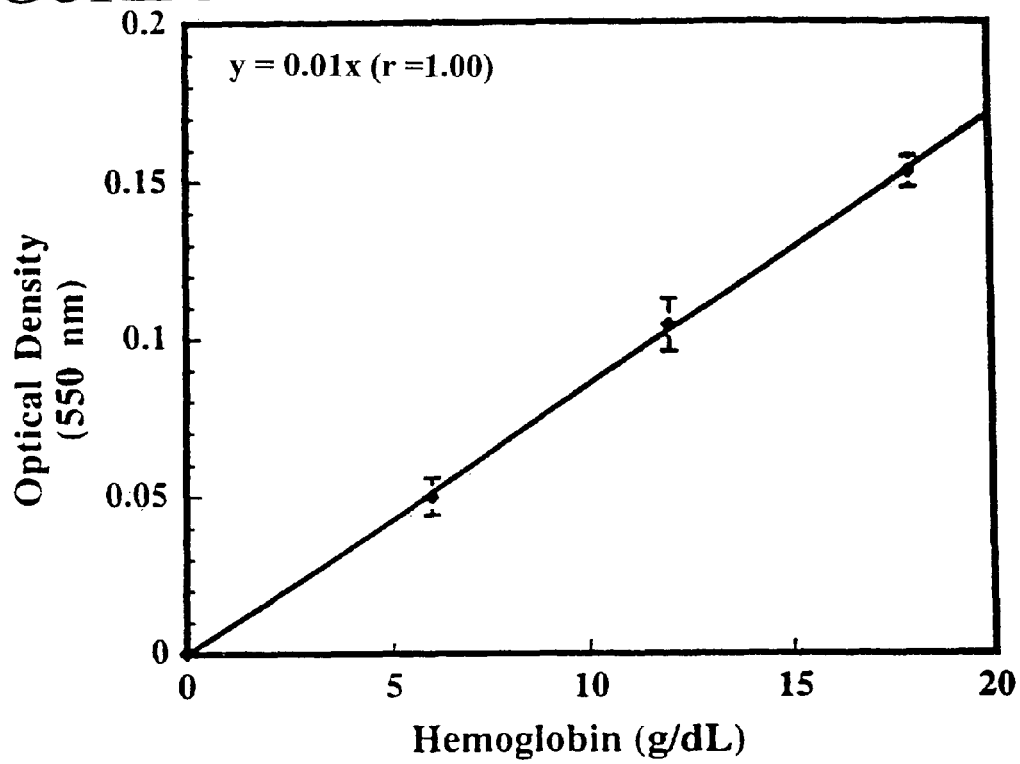
FIGS. 35A-35B. Validation of quantitative spectrophotometric intracerebral hemorrhage assay, in the absence (FIG. 35A) or presence (FIG. 35B) of brain tissue.
Figure 35B:
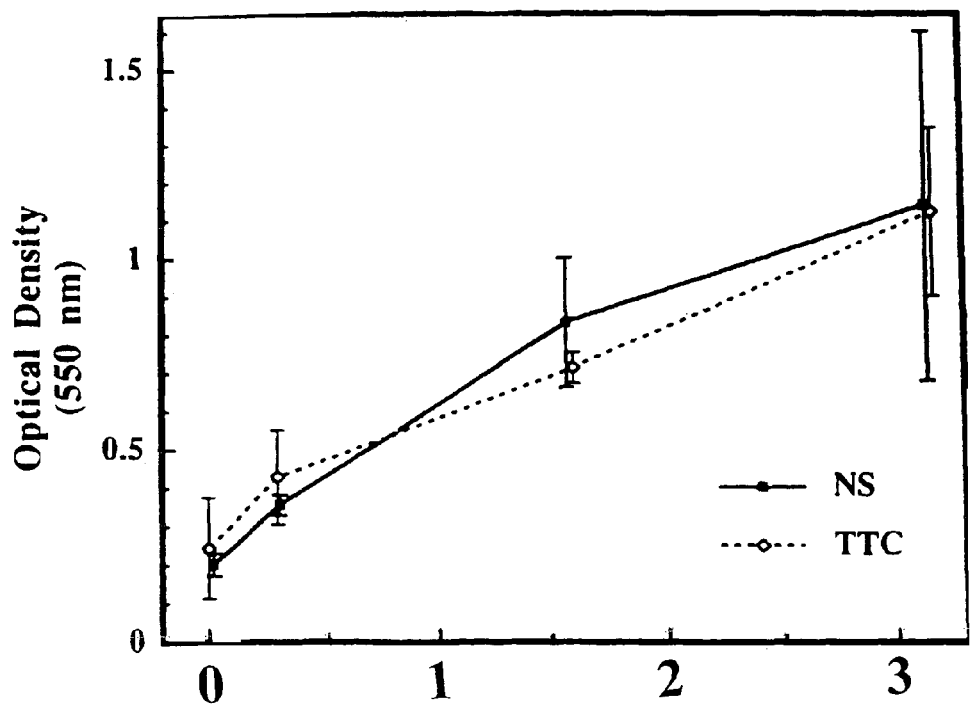

Initial studies were performed to determine the reliability and reproducibility of the spectrophotometric hemoglobin assay. In the first set of experiments, known quantities of hemoglobin were converted to cyanomethemoglobin according to previously published procedures, and the OD measured [FIG. 35A]. In a second set of experiments, known quantities of autologous blood were added to fixed volumes of fresh brain tissue homogenate, with further treatment of specimens as described above. These data show that the optical density of cyanomethemoglobin-containing supernatants at 550 nm correlated linearly with the amount of added blood [FIG. 35B]. These data show tight linear correlations ($r=1.00$ and 0.98 for FIGS. 35A and 35B, respectively), as well as excellent reproducibility as gauged by relatively small standard errors of the mean. To establish that TTC (commonly used to distinguish infarcted from noninfarcted cerebral tissue [28,30]) does not affect the spectrophotometric hemoglobin assay, nonmanipulated (control) brains were divided into half, with half being subjected to the standard TTC staining procedure and half being treated with saline as a control. These data (compare FIG. 35B, solid and dashed lines) indicate that pretreatment of brain tissue with TTC does not affect the spectrophotometric hemoglobin assay.

Figure 36A:
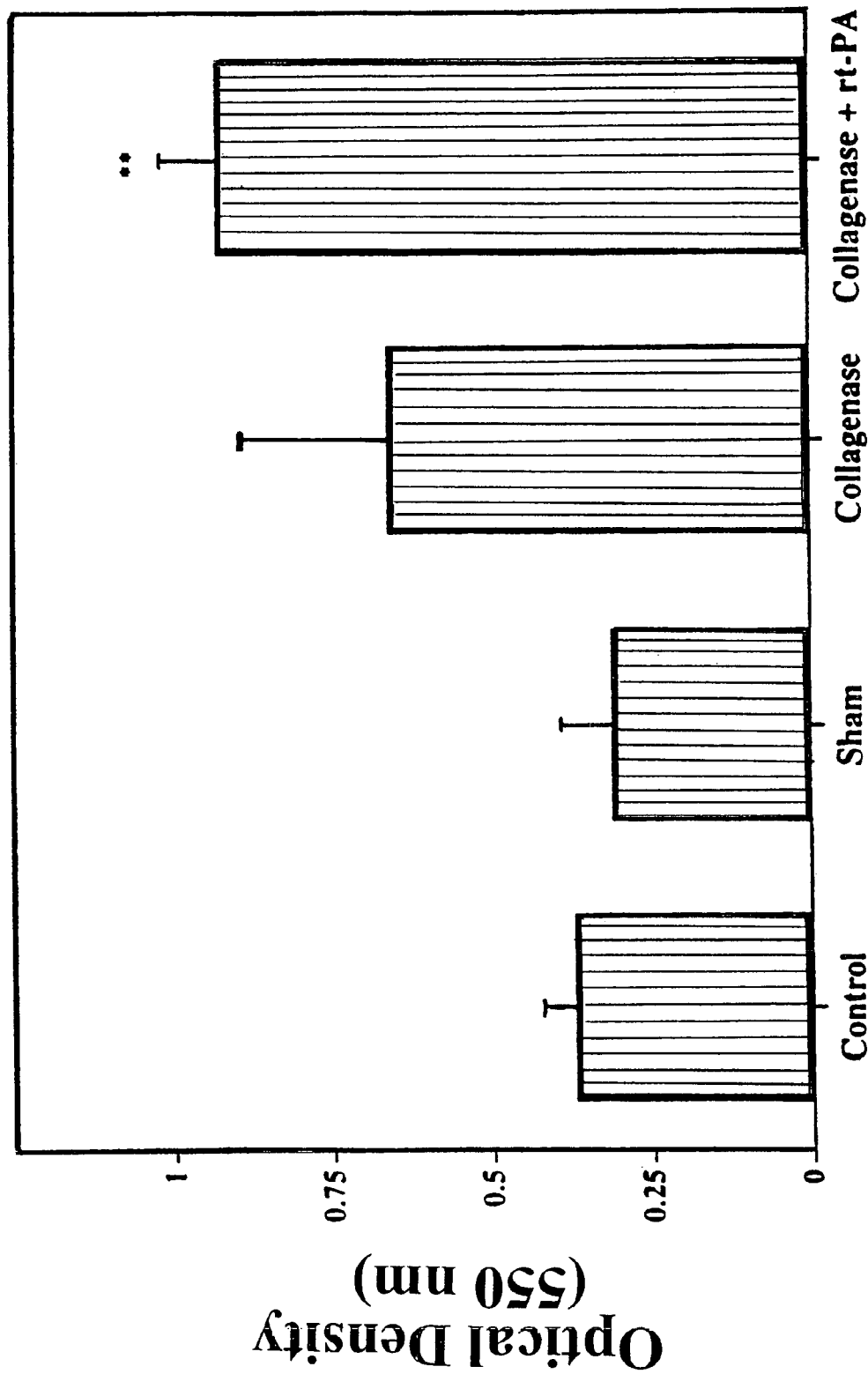

To determine whether this method is able to detect ICH, the assay was performed on murine intracerebral hemorrhage caused by two different procedures, intraparenchymal collagenase infusion or middle cerebral artery occlusion/reperfusion. In the first procedure, collagenase B was applied as a local infusion through a burrhole, in order to weaken the vascular wall to promote ICH (Collagenase group). To further increase the propensity for and degree of ICH, a similar procedure was performed, with immediate administration of rt-PA following the procedure (Collagnase+rt-PA group). Two control conditions were also included, a sham operation which included drilling the burrhole but with instillation of physiological saline (Sham), and an untreated group (Control). These experiments demonstrated that collagenas infusion increases the amount of intracerebral blood detected by the spectrophotometric assay (especially with collagenase+rt-PA) compared with sham-treated animals or normal controls. [FIG. 36A].

In the second and perhaps more clinically relevant method for inducing ICH, a stroke was created by transient intraluminal occlusion of the middle cerebral artery followed by reperfusion. In addition, we attempted to increase the propensity for hemorrhagic conversion by administration of a thrombolytic agent. Two groups were studied, those which had received normal saline solution or those which received intravenous rt-PA immediately following removal of the intraluminal occluding suture. These data indicate that the addition of a fibrinolytic agent following stroke increases the amount of ICH which is detected by the spectrophotometric hemoglobin assay [FIG. 36B]. It is interesting to note that baseline absorbance is lower in animals subjected to stroke than control/untreated animals [FIGS. 36A and 36B]. To further investigate how residual intravascular blood might affect the spectrophotometric hemoglobin assay, experiments were performed in which, immediately prior to decapitation of the animal for brain harvest, a cephalic perfusion of physiological saline was performed (administered via the left cardiac ventricle). In control animals (n=5), which recieved cardiac saline perfusion prior to brain harvest, the mean Optical Density following tissue preparation and spectrophotometric hemoglobin assay was 0.25±0.3 (this is lower than the Optical density seen in non-cardiac perfused animals subjected to either no or sham surgery (n=10, OD 0.34±0.05, p=0.05 vs cardiac perfused controls). On the other hand, following stroke, there was no difference in O.D. whether or not cardiac saline perfusion was performed (0.15±0.04 for stroke without cardiac saline perfusion, n=5; 0.15±0.03 for stroke with cardiac saline perfusion, P=NS). When saline-perfused animals with stroke were compared to saline-perfused animals without stroke, there is an apparent reduction in OD following spectrophotometric hemoglobin assay. These data would suggest that animals with a stroke have less intracerebral blood detected, perhaps as the result of a reduction of the total amount of blood in the ipsilateral MCA region following ischemia.

Visual Ich Score

Figure 38A:
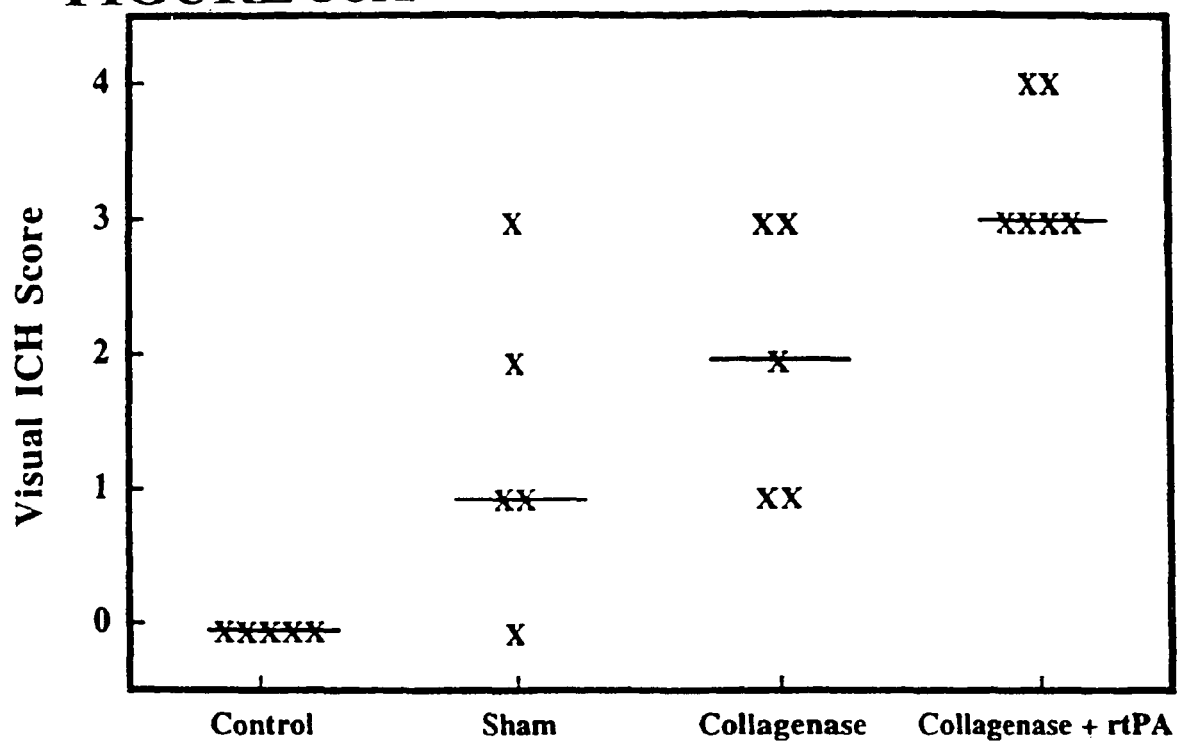
FIGS. 38A-38B. Visual ICH score.
Figure 38B:
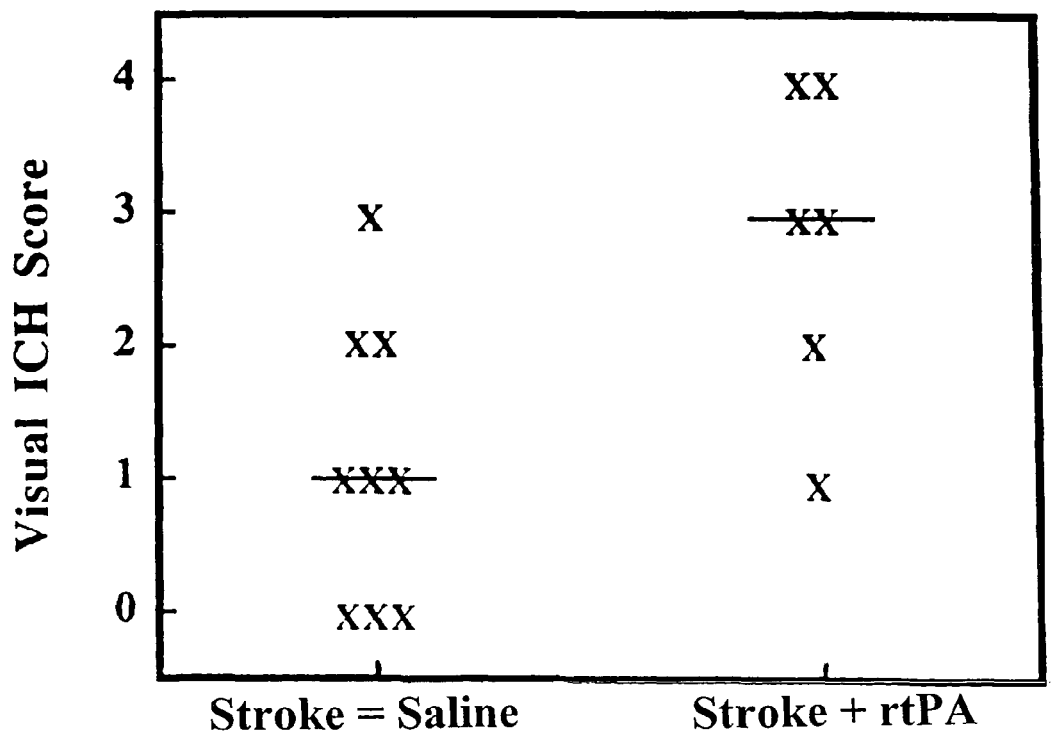
Figure 39:
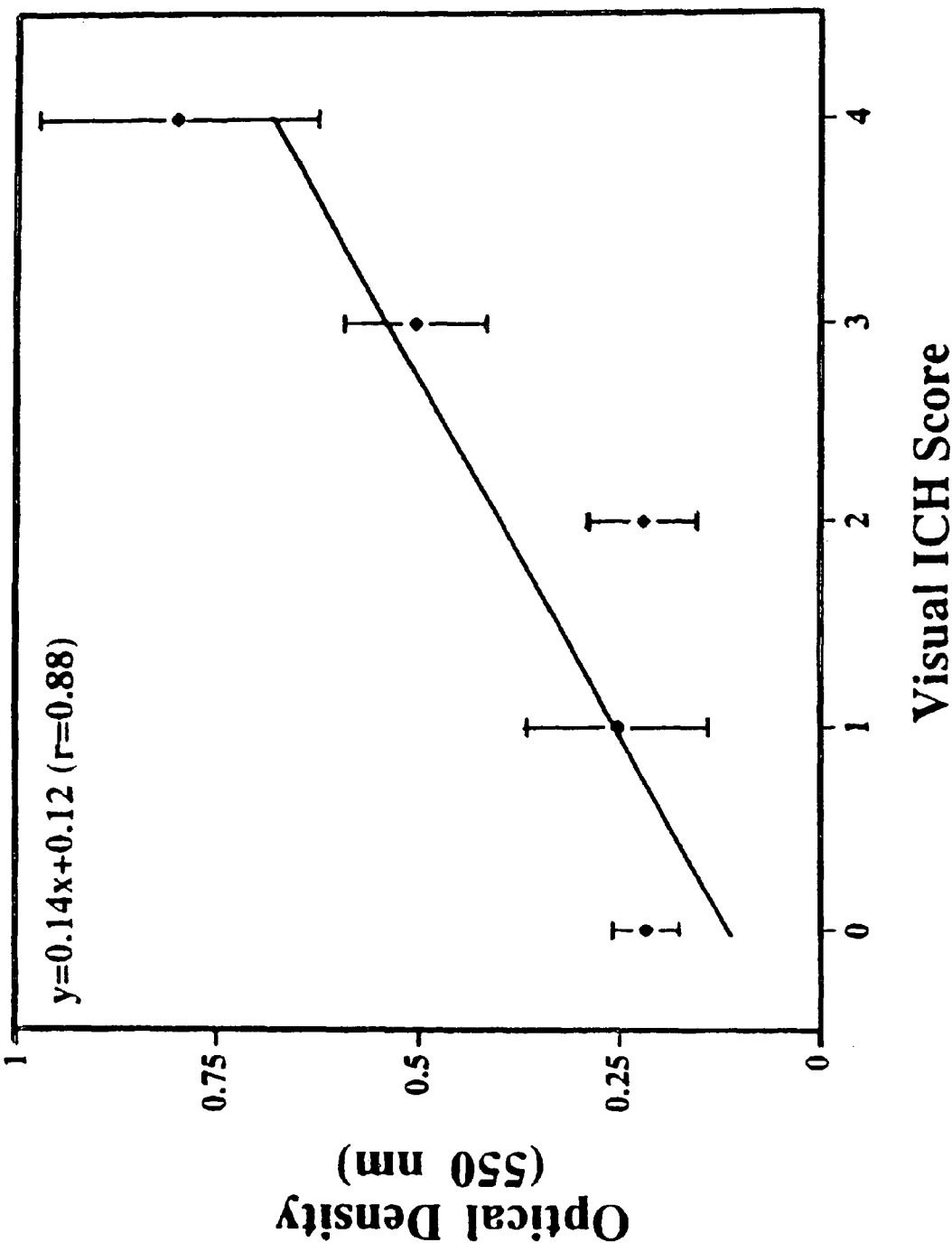
FIG. 39. Correlation between visual ICH and spectrophotometric hemoglobin assay. Optical density at 550 nm (ordinate) represents the results obtained from the spectrophotometric hemoglobin assay in which brain tissue (from all experiments) was analyzed. The corresponding visual ICH scores (as shown in FIG. 38) are plotted along the abscissa. For each point, means±SEM are shown. Linear correlation was performed using Pearson's linear correlation, with the equation of the line and r value shown.

In order to further validate the spectrophotometric hemoglobin assay, we compared it to morphometric assessment of hemorrhage size, which has traditionally been used in the literature [31-35]. We developed a visual scoring system (0-4) in which a blinded observer scored the degree of ICH in serial cerebral sections based upon maximal hemorrhage diameter. This visual assessment was performed on a photograph of the brain taken immediately prior to the performance of the spectrophotometric hemoglobin assay [FIG. 37], so that the two techniques could be correlated on the same specimens. When compared with controls not subjected to any intervention, animals receiving a sham local infusion (i.e., burrhole+saline) demonstrate only a slight increase in visual ICH score [FIG. 38A]. However, when either collagenase alone or collagenase+rt-PA was added to the infusate, visual ICH scores were significantly increased [FIG. 38A]. In the stroke model, rt-PA similarly resulted in an increase in the visual ICH score [FIG. 38B]. When the data are plotted to show the relationship between the visual ICH score and the spectrophotometric technique for quantifying ICH, a linear relationship was suggested. (r=0.88), however, with smaller degrees of hemorrhage (visual ICH scores of 0 or 1), this relationship did not hold [FIG. 39].

Discussion

Recently, it has become apparent that early intervention in stroke with certain intravenous thrombolytic agents (rt-PA) may be beneficial if instituted within 3 hours of symptom onset [9,10]. However, administration of thrombolytic agents outside of this narrow therapeutic window can cause an unacceptably high incidence of devastating ICH (streptokinase vs. placebo, 10 day mortality 34.0% vs. 18.2%, p=0.002, 6 month mortality 73% vs. 59%, p=0.06,)[7]. It therefore remains a clinical imperative to identify more optimal agents for restoring perfusion which are associated with less risk of hemorrhagic conversion. In order to adequately study new agents which interfere with coagulation or fibrinolytic mechanisms, it is necessary to have an objective means of quantifying the downside risk of ICH. In the experimental literature, quantification of ICH has been performed either by radiological imaging procedures [32-37], or by a visual estimation of the amount of hemorrhage in postmortem brain tissue [31-35]. These procedures are of limited usefulness depending on the conditions under study. For instance, in addition to the logistic constraints imposed by the need for sophisticated equipment, most radiological imaging techniques are of limited use in murine models, which may preclude their use in the evaluation of transgenic mice, a potentially powerful tool for studying the coagulation or fibrinolytic systems. Visual estimation of ICH is subjective in nature, and as our own data show, may be relatively insensitive for detecting small degrees of ICH. Furthermore, neither the radiological nor the visual techniques permit accurate quantification of ICH when the hemorrhagic region is patchy or multifocal.

The current studies were performed to develop and validate an objective method for quantifying ICH in experimental animals. The use of a spectrophotometric assay for the quantification of hemoglobin based upon the conversion of hemoglobin to cyanomethemoglobin has been previously reported [26,31]. However, to the best of our knowledge, in the brain, it has only been used in rats to measure the size of a frank blood clot following its removal from adjacent brain tissue [31]. The spectrophotometric assay we describe and validate can be used in animals as small as mice, which facilitates the use of the many transgenic mouse strains now available (particularly those with alterations in the thrombotic or fibrinolytic cascades). Furthermore, this spectrophotometric assay permits the quantification of ICH even when there are patchy or multifocal hemorrhages, which would be otherwise difficult to identify or isolate. Finally, in contrast to the Lee study, we have validated our study for reproducibility and reliability using known quantities of hemoglobin and autologous blood admixed with brain tissue[31]. Because the surgical procedure used in the stroke experiments did not significantly alter blood hemoglobin concentrations (data not shown), the spectrophotometric hemoglobin assay may be used to extrapolate the volume of intracerebral hemorrhage when the hemoglobin concentration is known at the time of hemorrhage.

To develop and validate the spectrophotometric hemoglobin assay for situations that may be relevant for clinical ICH, we created intracerebral hemorrhages by two different methods: (1) intracerebral injection of collagenase (to weaken the vascular wall, as might occur with an aneurysm or with trauma), and (2) in a model of stroke. In both instances, a cohort of animals also received rt-PA, in order to validate the model at the high end of the spectrum of ICH. Because there has been no established gold-standard measurement for ICH in mice, our spectrophotometric measurements were compared to ICH size as independently assessed by visual scoring. Finally, to prove the assay even more useful for experimental models of stroke in which brains are stained with triphenyltetrazolium chloride (TTC) to quantify cerebral infarct volume, the brains of animals subjected to MCA occlusion/reperfusion were stained with TTC prior to pooling and homogenization to establish that the TTC staining procedure itself does not interfere with the ability to quantify ICH by the spectrophotometric hemoglobin assay. These data (FIG. 1B) indicate that there is no detectable cross-interference between the two procedures when used sequentially (TTC staining first, followed by homogenization and the spectrophotometric hemoglobin assay).

In addition to its ability to detect ICH, the current studies indicate that this technique may also give an indication of the amount of residual intravascuar blood following brain harvest. The procedure of cephalic saline perfusion does not alter the optical density for cyanomethemoglobin in brains subjected to stroke, suggesting that the amount of intravascular blood is relatively fixed and does not wash out by the procedure. However, in control animals who have been otherwise untreated, the saline perfusion treatment does appear to lower the optical density for cyanomethemoglobin by about 30%. Our experiments do not provide the reason for this difference, but one may speculate that following stroke, there is an element of vasoconstriction/vaso-occlusion in the territory of infarction, which makes the saline perfusion technique less effective at washing out additional residual intravascular blood. Also, if there is truly an element of vasoconstriction following stroke or experimentally-induced intracerebral hemorrhage, this may reduce the intravascular blood pool and hence account for an overall lowering of the optical density when control and stroke/ICH brains are compared (even if some extravascular blood is present in the latter group).

Several technical aspects of the spectrophotometric technique for measuring intracerebral hemorrhage also deserve mention. For the current experiments, although there is a broad absorbance peak for cyanomethemoglobin centered around 540 nm, we measured the absorbance of cyanomethemoglobin at 550 nm. The reason for doing this is that many spectrophotometers have fixed wavelength capabilities depending upon the preset filters, and 550 nm is a commonly used wavelength (especially in ELISA plate readers). Although perhaps measurement of absorbance at 540 nm would have yielded slightly higher optical density measurements, the absorbance peak of cyanomethemoglobin is broad in this area, and hence 550 nm may be used without the need to correct for the absorbance of ferri- or ferrocyanide (the extinction coefficients for cyanomethemoglobin at 551 nm and 540 nm are 11.5 and 11.1, respectively, compared with the 41-fold lower extinction coefficient of ferri- or ferrocyanide [38]). Studies using a continuous wavelength spectrophotometer (which was used to measure OD at 540 nm) and a discrete spectrum ELISA plate reader (used to measure OD at 550 nm) gave similar results. As the latter technique was simplex, increased the throughput of the procedure, and permitted us to minimize sample volume, we elected to use the latter technique for the studies shown in the Results section.

There are some potential other technical considerations that should be considered when using the spectrophotometric assay. Even though we have shown that the spectrophotometric procedure can be used in conjunction with TTC staining of serial cerebral sections for infarct volume analysis, the tissue must be subsequently homogenized and extracted, destroying tissue architecture and making further histological characterization impossible. It is possible that this technique may overestimate the degree of ICH if extracerebral blood is unintentionally included during brain harvesting, or the technique may underestimate the degree of ICH if residual epidural, subdural, or subarachnoid blood remains adherent to the calvarium, which is discarded during the process of brain removal.

Because of the nature of the measurement technique, in which light at a given wavelength is absorbed along a fixed length path, anything causing turbidity of the homogenized brain supernatant may increase the OD reading. This may include lipids, abnormal plasma proteins, and erythrocyte stroma. In fact, in preliminary experiments, we found that ODs were falsely elevated when the centrification was insufficient and some of the lipid layer was included in the assay. Free pyridines may alter the absorbance spectrum of cyanomethemoglobin, and there is the potential for other hemochromogens to also react with the Drabkin's reagent [39]. However, to our knowledge, these reactions should not interfere to a significant extent with the determination of intracerebral blood/hemorrhage.

In summary, the current data illustrate how a simple and inexpensive spectrophotometric assay for hemoglobin can provide a useful method for quantifying ICH. This technique should prove especially useful to evaluate the hemorrhagic potential of newly developed thrombolytic or anticoagulant therapies for the treatment of stroke.

References

1. Slivka A, Levy D: Natural history of progressive ischemic stroke in a population treated with heparin. *Stroke* 1990; 21:1637-1662
2. Babikian V L, Kase C S, Pessin M S, Norrving B, Gorelick P B: Intracerebral hemorrhage in stroke patients anticoagulated with heparin. *Stroke* 1939;20:1500-1503
3. Ramirez-Lassepas M, Quinones M R, Nino H H: Treatment of acute ischemic stroke. Open trial with continuous intravenous heparinization. *Arch Neurol* 1986;43:386-390
4. Duke R J, Bloch R F, Turpie A G, Trebilcock R, Bayer N: Intravenous heparin for the prevention of stroke progression in acute partial stable stroke. *Annals of Internal Medicine* 1986;105:825-828
5. Meyer J S, Gilroy J, Barnhart M I, Johnson J F: Therapeutic thrombolysis in cerebral thromboembolism. *Neurology* 1963;13:927-937
6. Meyer J S, Gilroy J, Barnhart M I, Johnson J F: Anticoagulants plus streptokinase therapy in progressive stroke. *JAMA* 1964;189:373
7. Hommel M, Cornu C, Boutitie F, Boissel J P, The Multi-Center Acute Stroke Trial—Europe Study Group: Thrombolytic therapy with streptokinase in acute ischemic stroke. *N Engl J Med* 1996;335:145-150
8. Wardlaw J M, Warlow C P: Thrombolysis in acute ischemic stroke: does it work? *Stroke* 1992;23:1826-1839
9. The National Institute of Neurological Disorders and Stroke rt-PA Stroke Study Group: Tissue plasminogen activator for acute ischemic stroke. *N Engl J Med* 1995;333: 1581-1587
10. Hacke W, Kaste M, Fieschi C, Toni D, Lesaffre E, von Kummer R, Boysen G, Bluhmki E, Hoxter G, Mahagne M H, Hennerici M, for the ECASS Study Group: Intravenous thrombolysis with recombinant tissue plasminogen activator for acute hemispheric stroke. *JAMA* 1995;274(13,): 1017-1025
11. Trouillas P, Nighoshossian N, Getenet J C, Riche G, Neuschwander P, Froment J C, Turjman F, Jin J X, Malicier D, Fournier G, Gabry A L, Ledoux X, Derex L, Berthezene Y, Adeleine P, Xie J, Ffrench P, Dechavanne M: Open trial of intravenous tissue plasminogen activator in acute carotid territory stroke. *Stroke* 1996;27:882-890
12. Haley E C, Jr., Levy D E, Brott T G, Sheppard G L, Wong M C, Kongable G L, Torner J C, Marler J R: Urgent therapy for stroke. Part II. Pilot study of tissue plasminogen activator administered 91-180 minutes from onset. *Stroke* 1992;23:641-645
13. Hacke W, Kaste M, Fieschi C, Toni A, Lesaffre L, von Kummer R, Boysen G, Bluhmkl E, Hoxter G, Mahagne M H, et al: Intravenous thrombolysis with recombinant tissue plasminogen activator for acute hemispheric stroke. The European Cooperative Acute Stroke Study (ECASS). *JAMA* 1995;274:1017-1025
14. Brott T G, Haley E C, Jr., Levy D E, Barsan W, Broderick J. Sheppard G L, Spilker J, Kongable G L, Massey S, Reed R, et al: Urgent therapy for stroke. Part I. Pilot study of tissue plasminogen activator administered within 90 minutes. *Stroke* 1992;23:632-640
15. del Zoppo G J, Poeck K, Pessin M S, Wolpert S M, Furlan A J, Ferbert A, Alberts M J, Zivin J A, Wechsler L, Busse O, et al: Recombinant tissue plasminogen activator in acute thrombotic and embolic stroke. *Annals of Neurology* 1992; 32:78-86
16. de Courten-Myers G M, Kleinholz M, Holm P, DeVoe G, Schmitt G, Wagner K R, Myers R E: Hemorrhagic infarct conversion in experimental stroke. *Ann Emerg Med* 1992; 21:120-126
17. Overgaard K, Sereghy T, Pedersen H, Boysen G: Neuroprotection with NBQX and thrombolysis with rt-PA in rat embolic stroke. *Neurological Research* 1993;;15:344-349

18. Overgaard K, Sereghy A, Boysen G, Pedersen H, Diemer N H: Reduction of infarct volume by thrombolysis with rt-PA in an embolic rat stroke model. *Scandinavian Journal of Clinical & Laboratory Investigation* 1993;53:383-393
19. Benes V, Zabramski J M, Boston M, Puca A, Spetzler R F: Effect of intra-arterial tissue plasminogen activator and urokinase on autologous arterial emboli in the cerebral circulation of rabbits. *Stroke* 1990;21:1594-1599
20. Overgaard K, Sereghy T. Pedersen H, Boysen G: Effect of delayed thrombolysis with rt-PA in a rat embolic stroke model: *Journal of Cerebral Blood Flow & Metabolism* 1994;14:472-477
21. Lyden P D, Zivin J A, Clark W A, Madden K, Sasse K C, Mazzarella V A, Terry R D, Press G A: Tissue plasminogen activator-mediated thrombolysis of cerebral emboli and its effect on hemorrhagic infarction in rabbits. *Neurology* 1989;39:703-708
22. Kochanek P M, Dutka A J, Kumaroo K K, Hallenbeck J M: Effects of prostacyclin, indomethacin, and heparin on cerebral blood flow and platelet adhesion after multifocal ischemia of canine brain. *Stroke* 1988;19:693-699
23. Slivka A, Pulsinelli W: Hemorrhagic complications of thrombolytic therapy experimental stroke. *Stroke* 1987;18: 1148-1156
24. Lyden P D, Zivin J A, Soll M, Sitzer M, Rothrock J F, Alksne J: Intracerebral hemorrhage after experimental embolic infarction. Anticoagulation. *Arch Neurol* 1987;44: 848-850
25. Van Kampen E J, Zijlstra W G: Standardization of hemoglobinometry. II. The hemiglobincyanide method. *Clin Chim Acta.* 1961;6:538-544
26. Van Kampen E J, Zijlstra W G: Standardization of hemoglobinometry. II. The hemoglobincyanide method. *Clin Chim Acta.* 1961;6:538.
27. Rosenberg G A, Mun-Bryce S, Wesley M, Kornfield. M: Collagenase-induced intaceredral hemorrhage in rats. *Stroke* 1990;21:801-807
28. Connolly E S Jr, Winfree C J, Stern D M, Solomon R A, Pinsky D J: Procedural and strain-related variables significantly affect outcome in a murine model of focal cerebral ischemia. *Neurosurg* 1996;38(3):523-532
29. Connolly E S Jr, Winfree C J, Springer T A, Naka Y, Liao H, Yan S D, Stern D M, Solomon R A, Gutierrez-Ramos J-C, Pinsky D J: Cerebral protection in homozygous null ICAM-1 mice after middle cerebral artery occlusion. Role of neutrophil adhesion in the pathogenesis of stroke. *J Clin Invest* 1996;97:209-216
30. Bederson J B, Pitts L H, Nishimura M C, Davis R L, Bartkowski H M: Evaluation of 2,3,5-triphenyltetrazolium chloride as a stain for detection and quantification of experimental cerebral infarction in rats. *Stroke* 1986;17: 1304-1308
31. Lee K R, Colon G P, Betz A L, Keep R F, Kim S, Hoff J T: Edema from intracerebral hemorrhage: the role of thrombin. *J Neurosurg* 1996;84:91-96
32. Del Bigio M R, Yan H J, Buist R, Peeling J: Experimental intracerebral hemorrhage in rats: magnetic resonance imaging and histopathological correlates. *Stroke* 1996;27: 2312-2320
33. Qian L, Nagaoka T, Ohno K, Tominaga B, Nariai T, Hirakawa K, Kuroiwa T, Takakuda K, Miyairi H: Magnetic resonance imaging and pathologic studies on lateral fluid percussion injury as a model of focal brain injury in rats. *Bulletin of Tokyo Medical & Dental University* 1996;43: 53-66
34. Brown M S, Kornfeld M, Mun-Bryce S, Sibbitt R R,, Rosenberg G A: Comparison of magnetic resonance imaging and histology in collagenase-induced hemorrhage in the rat. *Journal of Neuroimaging* 1995;5:23-33
35 Thulborn K R, Sorensen A G, Kowall N W, McKee A, Lai A, McKinstry R C, Moore J. Rosen B R, Brady T J: The role of ferritin and hemosiderin in the MR appearance of cerebral hemorrhage: a histopathologic biochemical study in rats. *American Journal of Neuroradiology* 1990;11:291-297
36. Elger B, Seega J. Brendel R: Magnetic resonance imaging study on the effect of levemopamil on the size of intracerebral hemorrhage in rats. *Stroke* 1994;25:1836-1841
37. Weingaren K, Zimmerman R D, Deo-Narine V, Markisz J, Cahill P T, Deck M D: MR imaging of acute intracranial hemorrhage: findings on sequential spin-echo and gradient-echo images in a dog model. *American Journal of Neuroradiology* 1991;12:457-467
38. Drabkin D L, Austin J H.: Spectrophotometric studies: II. Preparations from washed blood cells; nitric oxide hemoglobin and sulfhemoglobin. *J Biol Chem* 1935;112:51-65
39. Drabkin D L, Austin J H: Spectrophotometric studies. IV. Hemochromogens. *J Biol Chem* 1935;112:89-104

Example 13

Active-site Blocked Factor IXa Limits Microvascular Thrombosis and Cerebral Injury in Murine Stroke Without Increasing Intracerebral Hemorrhage Summary The clinical dilemma in stroke treatment is that agents which restore vascular patency increase the risk of intracerebral hemorrhage. Active-site blocked Factor IXa (IXai), formed from purified factor IXa by dansylation of its active site, competes with native factor IXa to inhibit assembly of Factor IXa into the intrinsic Factor X activation complex. When pretreated with Factor IXai, mice subjected to focal cerebral ischemia and reperfusion demonstrated reduced microvascular fibrin and platelet deposition, increased cerebral perfusion, and significantly smaller cerebral infarcts than vehicle-treated controls. Factor IXai-mediated cerebroprotection was dose-dependent, not associated with intracerebral hemorrhage at therapeutically effective doses, and was seen even when Factor IXai was administered after the onset of cerebral ischemia. Administration of Factor IXai represents a new strategy to treat stroke in evolution without increasing the risk of intracerebral hemorrhage.

Introduction

Timely reestablishment of blood flow to ischemic brain represents the current treatment paradigm for acute stroke [1-3]. Administration of a thrombolytic agent, even when given under optimal conditions, may not achieve this desired clinical result. Perfusion often fails to return to preischemic levels (postischemic hypoperfusion), suggesting that ischemic injury is not produced solely by the original occlusion, but that there is also an element of microcirculatory failure. In addition, thrombolysis of acute stroke is associated with an increased risk of intracerebral hemorrhage (ICH) [1-4], indicating that there remains a clear need to identify new agents which can promote reperfusion without increasing the risk of ICH.

Following an ischemic event, the vascular wall is modified from its quiescent, anti-adhesive, antithrombotic state, to one which promotes leukocyte adhesion and thrombosis. In acute stroke, active recruitment of leukocytes by adhesion receptors expressed in the ipsilateral microvasculature, such as ICAM-1 [5] and P-selectin [6], potentiates oostischemic hypoperfusion. However, experiments with mice deletionally mutant for each of these genes demonstrate that even in their absence, postischemic cerebral blood flow (CBF) returns only partially to baseline, suggesting the existence of additional mechanisms responsible for postischemic cerebrovascular no-reflow. To explore this possibility, the first set of experiments was designed to test the hypothesis that local thrombosis occurs at the level of the microvasculature (distal to the site of primary occlusion) in stroke.

To assess the deleterious consequences of microvascular thrombosis in stroke, the second set of experiments tested the hypothesis that selective blockage of the intrinsic pathway of coagulation could limit microvascular thrombosis, thereby protecting the brain in stroke. The strategy of selective inhibition of the intrinsic pathway of coagulation was chosen because it is primarily responsible for intravascular thrombosis. Heparin, hirudin, and fibrinolytic agents interfere with the final common pathway coagulation to inhibit the formation or accelerate the lysis of fibrin, and therefore increase the propensity for ICH. We hypothesized that selective blockade of IXa/VIIIa/X activation complex assembly might provide a novel mechanism to limit intravascular thrombosis while preserving mechanisms of extravascular hemostasis by the extrinsic/tissue factor pathway of coagulatlon which may be critical in infarcted brain tissue or adjacent reckons where small vessels are friable and subject to rupture. We used a novel strategy in which a competitive inhibitor of Factor IXa (active-site blocked IXa, or IXai) was given to mice subjected to stroke to test the hypothesis that it would improve stroke outcome without increasing ICH.

Methods

Murine stroke model. Transient focal cerebral ischemia was induced in mice by intralumenal occlusion of the middle cerebral artery (45 minutes) and reperfusion (22 hrs) as previously reported [7]. Serial measurements of relative cerebral blood flow (CBF) were recorded via laser doppler flowmetry [7], and infarct volumes (% ipsilateral hemisphere) determined by planimetric/volumetric analysis of triphenyl tetrazolium chloride (TTC)-stained serial cerebral sections [7].

[111]Indium-platelet studies: Platelet accumulation was determined using [111]Indium labeled platlets, collected and prepared as previously described [8]. Immediately prior to surgery, mice were given $5 \times 10^6$ $^{111}$In-labeled-platelets intravenously; deposition was quantified after 24 hours by as ipsilateral cpm/contralateral cpm.

Fibrin immunoblotting/immunostaining. The accumulation of fibrin was measured following sacrifice (of fully heparinized animals) using immunoblotting/immunostaining procedures which have been recently described and validated [9]. Because fibrin is extremely insoluble, brain tissue extracts where prepared by plasmin digestion, then applied to a standard SDS-polyacrylamide gel for electrophoresis, followed by immunoblotting using a polyclonal rabbit anti-human antibody prepared to gamma-gamma chain dimers present in cross-linked fibrin which can detect murine fibrin, with relatively little cross-reactivity with fibrinogen [10]. Fibrin accumulation was reported as an ipsilateral to contralateral ratic. In additional experiments, brains were embedded in paraffin, sectioned, and immunostained using the same anti-fibrin antibody.

Spectrophotometric hemoglobin assay and visual ICH score: ICH was quantified by a spectrophotometric-based assay which we have developed and validated [11,12]. In brief, mouse brains were homogenized, sonicated, centrifuged, and methemoglobin in the supernatants converted (using Drabkin's reagent) to cyanomethemoglobin, the concentration of which was assessed by measuring O.D. at 550 nm against a standard curve generated with known amounts of hemoglobin. Visual scoring of ICH was performed on 1 mm serial coronal sections by a blinded observer based on maximal hemorrhage diameter seen on any of the sections [ICH score 0, no hemorrhage; 1, <1 mm; 2, 1-2 mm; 3, >2-3 mm; 4, >3 mm].

Preparation of Factor IXai [13]: Factor IXai was prepared by selectively modifying the active site histidine residue on Factor IXa, using dansyl-glu-gly-arg-chloromethylketone. Proplex was applied to a preparative column containing immobilized calcium-dependent monoclonal antibody to Factor IX. The column was washed, eluted with EDTA-containing buffer, and Factor IX in the eluate (confirmed as a single band on SDS-PAGE) was then activated by applying Factor XIa (incubating in the presence of $CaCl_2$). Purified Factor IXa was reacted with a 100-fold molar excess of dansyl-glu-gly-arg chloromethylketone, and the mixture dialyzed. The final product (IXai), devoid of procoagulant activity, migrates identically to IXa on SDS-PAGE. This material (Factor IXai) was then used for experiments following filtration (0.2 μm) and chromatography on DeToxi-gel columns, to remove any trace endotoxin contamination (in sample aliquots, there was no detectable lipopolysaccharide). IXai was subsequently frozen into aliquots at $-80°$ C. until the time of use. For those experiments in which IXai was used, it was given as a single intravenous bolus at the indicated times and at the indicated doses.

Results

Figure 40A:
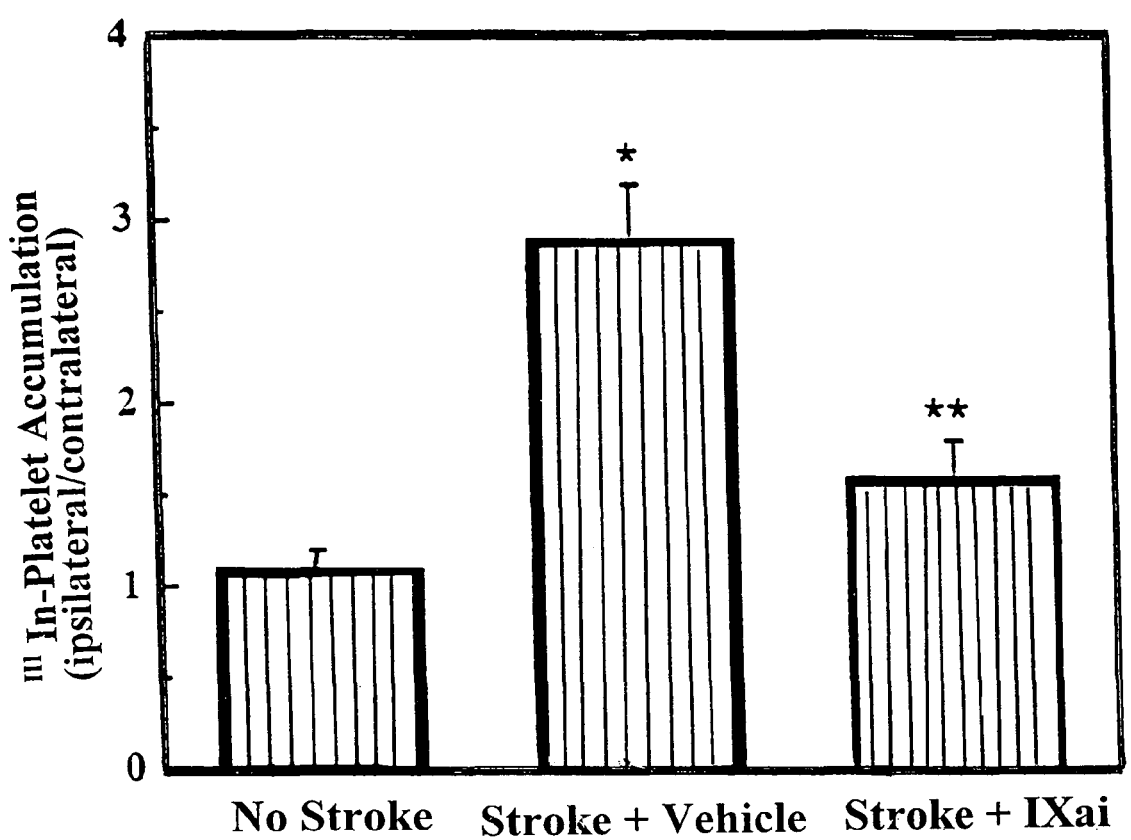
FIGS. 40A-40F.

To create a stroke in a murine model, a suture is introduced into the cerebral vasculature so that it occludes the orifice of the right middle cerebral artery, rendering the subtended territory isohemic. By withdrawing the suture after a 45 minute period of occlusion, a reperfused model of stroke is created; mice so treated demonstrate focal neurological deficits as well as clear-cut areas of cerebral infarction. Because the occluding suture does not advance beyond the major vascular tributary (the middle cerebral artery), this model provides an excellent opportunity to investigate "downstream" events that occur within the cerebral microvasculature in response to the period of interrupted blood flow. Using this model, the role of microvascular thrombosis was investigated as follows. To demonstrate that platelet-rich thrombotic foci occur within the ischemic cerebral hemisphere, $^{111}$In-labeled platelets were administered to mice immediately prior to the introduction of the intraluminal occluding suture, to track their deposition during the ensuing period of cerebral ischemia and reperfusion. In animals not subjected to the surgical procedure to create stroke, the presence of platelets was approximately equal between the right and left hemispheres, as would be expected [FIG. 40A, left bar]. However, when animals were subjected to stroke (and received only vehicle to control for subsequent experiments), radiolabeled platelets preferentially accumulate in the ischemic (ipsilateral) hemisphere, compared with significantly less deposition in the contralateral (nonischemic) hemisphere [FIG. 40A, middle bar]. These data support the occurrence of platelet-rich thrombi in the ischemic territory. When Factor IXai is administered to animals prior to introduction of the intraluminal occluding suture, there is a significant reduction in the accumulation of radiolabelled platelets in the ipsilateral hemisphere [FIG. 40A, right bar].

Figure 40B:
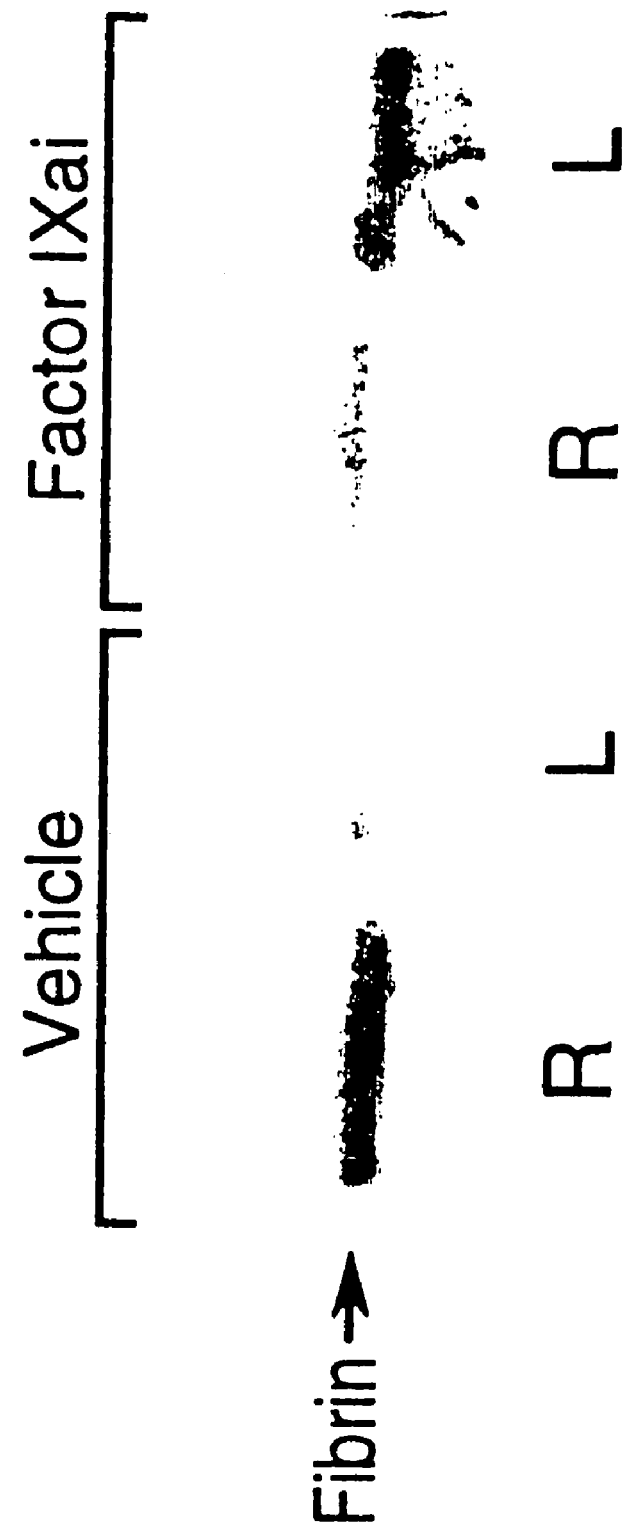
Figure 40C:
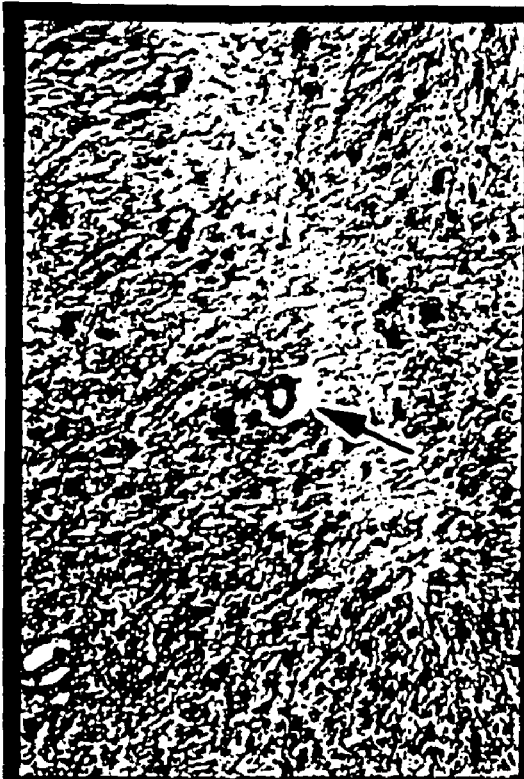
Figure 40D:
Figure 40E:
Figure 40F:

Another line of evidence also supports the occurrence of microvascular thrombosis in stroke. This data comes from the immunodetection of fibrin, using an antibody directed against a neoepitope on the gamma-gamma chain dimer of cross-linked fibrin. Immunoblots demonstrate a band of increased intensity in the ipsilateral (right) hemisphere of vehicle-treated animals subjected to focal cerebral ischemia and reperfusion [FIG. 40B, "Vehicle"]. In animals treated with Factor IXai (300 μg/kg) prior to stroke, there is no apparent increase in the ipsilateral accumulation of fibrin [FIG. 40B, "Factor IXai"]. To demonstrate that fibrin accumulation was due to the deposition of intravascular fibrin (rather than due to nonspecific permeability changes and exposure to subendothelial matrix), fibrin immunostaining clearly localized the increased fibrin to the lumina of ipsilateral intracerebral microvessels [FIG. 40C].

Figure 41A:
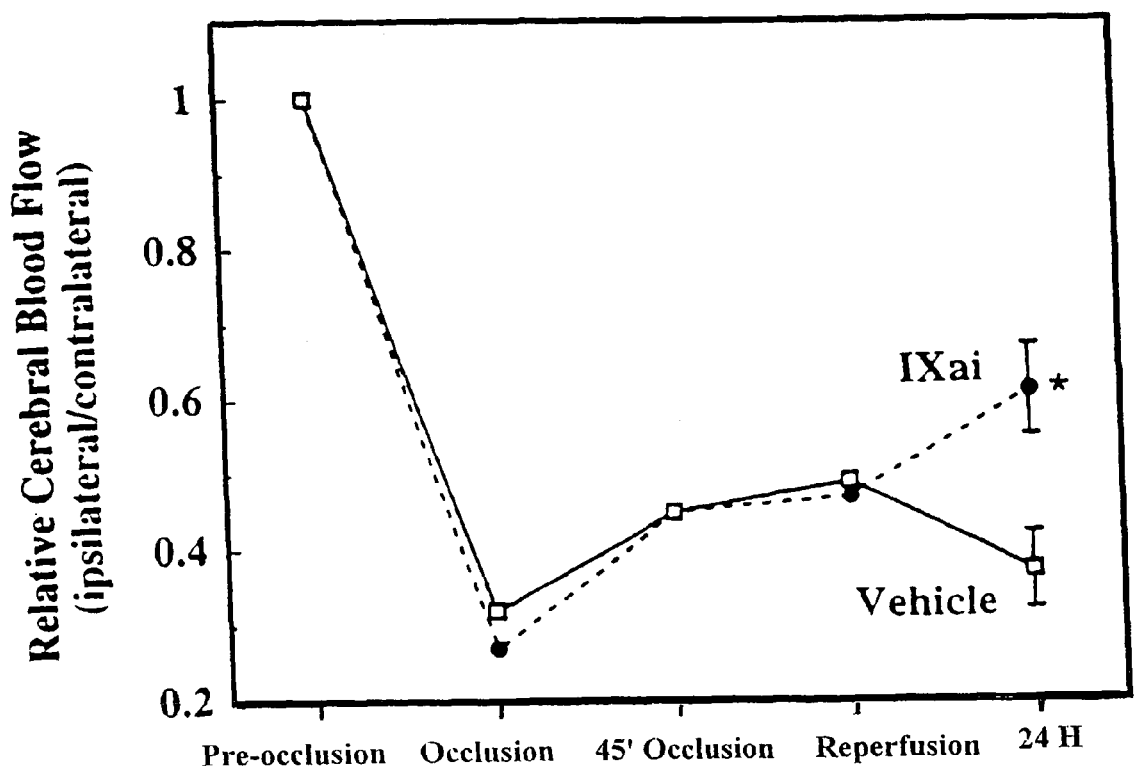
FIGS. 41A-41C.
Figure 41B:
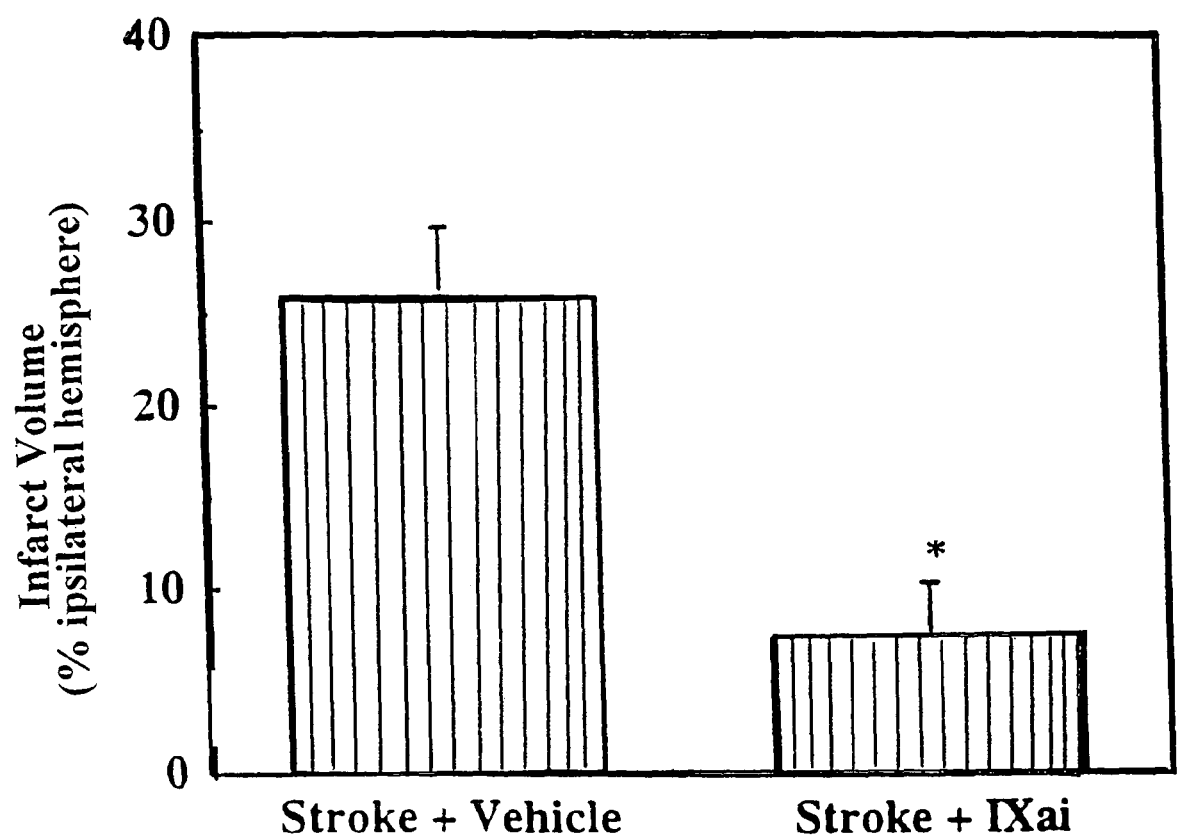
Figure 41C:
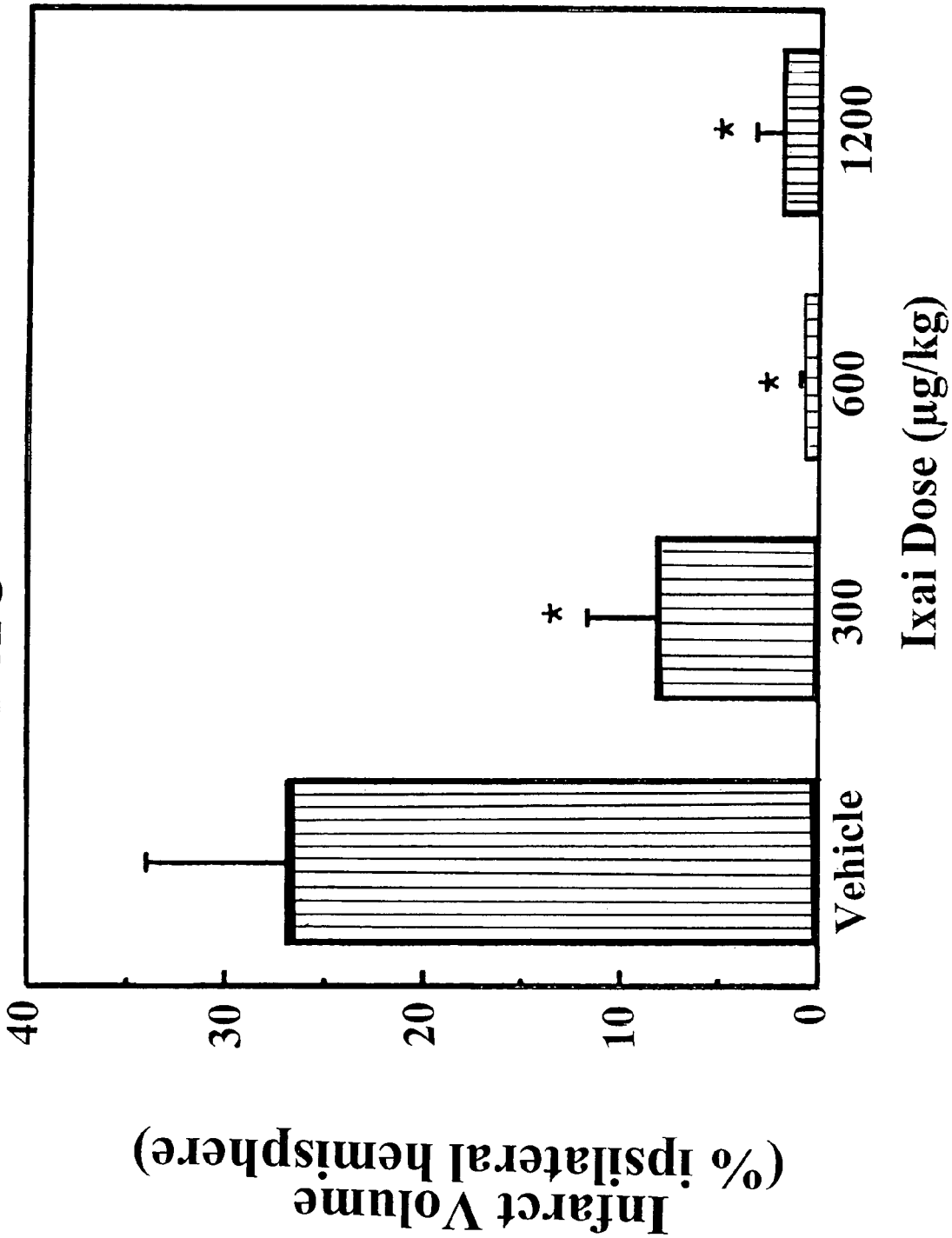

To investigate whether Factor IXai can limit intracerebral thrombosis and restore perfusion; IXai was given to mice immediately prior to stroke (300 μg/kg). These experiments demonstrate both a reduction in $^{111}$In-platelet accumulation in the ipsilateral hemisphere [FIG. 41A] as well as decreased evidence of intravascular fibrin by immunostaining. Furthermore, there is a significant increase in CBF by 24 hours, suggesting the restoration of microvascular patency by Factor IXai [FIG. 41A]. The clinical relevance of this observation is underscored by the ability of Factor IXai to reduce cerebral infarct volumes [FIG. 41B]. These beneficial effects of Factor IXai were dose dependent, with 600 μg/kg being the optimal dose [FIG. 41C].

Figure 42A:
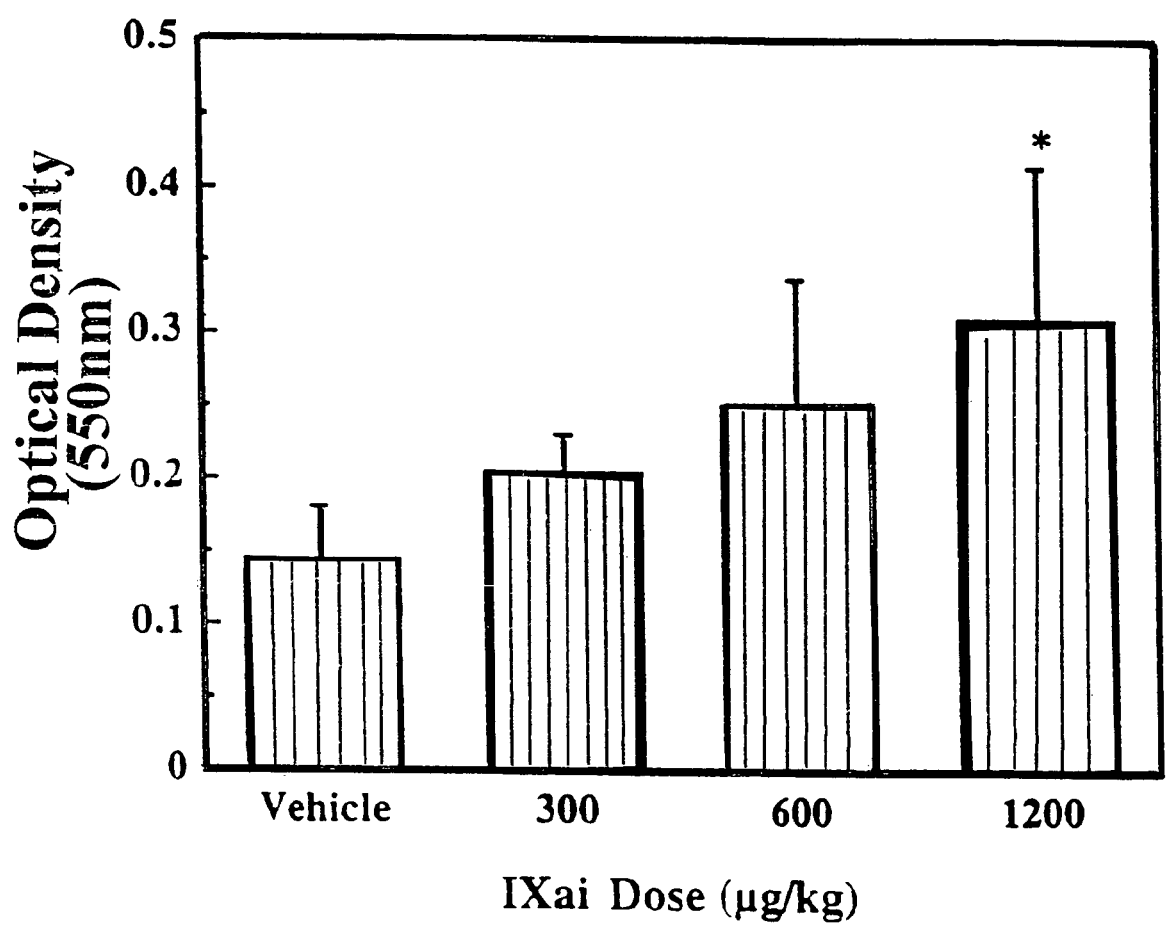
FIGS. 42A-42B. Effect of Factor IXai on Intracerebral hemorrhage.
Figure 42B:
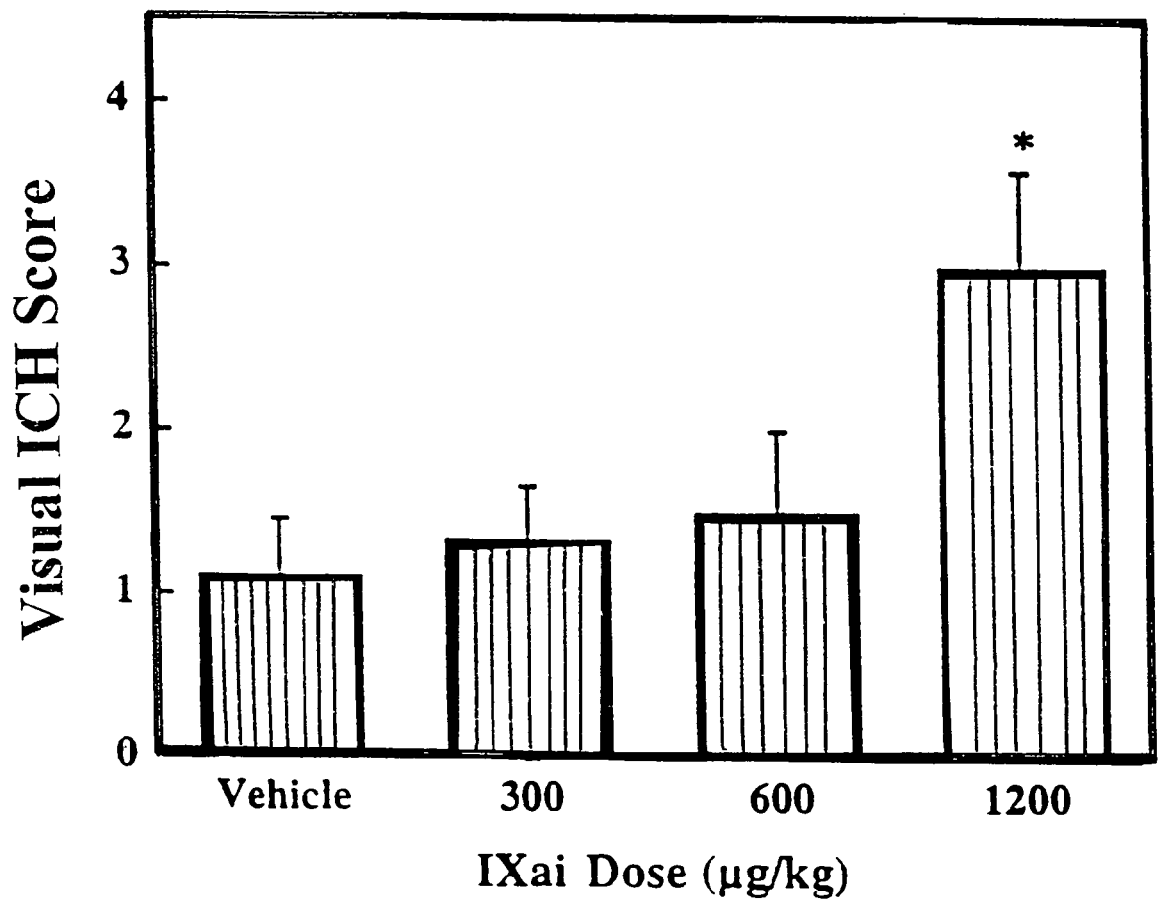

Because the development of ICH is a major concern with any anticoagulant strategy in the setting of stroke, the effect of IXai on ICH was measured using our recently validated spectrophotometric method for quantifying ICH [11,12]. These data indicate that at the lowest doses (and the most effective ones), there is no significant increase in ICH [FIG. 42A]. At the highest dose tested (1200 μg/kg), there is an increase in ICH, which was corroborated by a semiquantitative visual scoring method which we nave also recently reported [FIG. 42B] [11,12].

Figure 43:
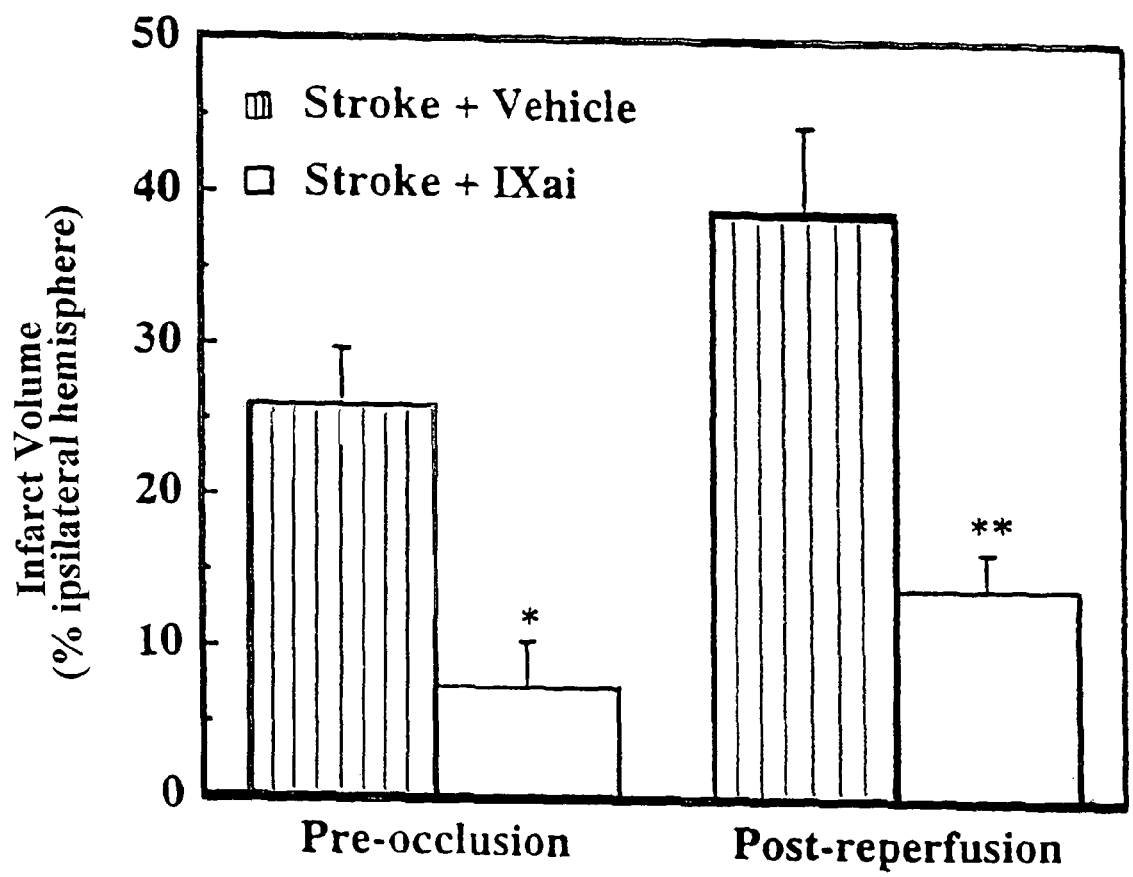
FIG. 43. Effect of timing of Factor IXai administration on cerebral infarct volumes when given after the onset of stroke. Mice were subjected to focal cerebral ischemia and reperfusion as described in the Methods section. The preocclusion administration (leftmost 2 bars) data is that shown FIG. 42B. In additional experiments to determine the effects of Factor IXai administered after stroke, immediately following withdrawal of the intraluminal occluding suture, vehicle (normal saline, n=13) or Factor IXai (300 µg/kg, n=7) was administered intravenously. Cerebral infarct volumes (based on TTC-stained serial sections obtained at 22 hrs) were determined. Means±SEM are shown. *$p<0.05$, **$p<0.05$ vs vehicle-treated animals.

Because therapies directed at improving outcome from acute stroke must be given after clinical presentation, and because fibrin continues for following the initial ischemic event in stroke, we tested whether IXai might be effective when given following initiation of cerebral ischemia. IXai given after middle cerebral artery occlusion (following removal of the occluding suture) provided significant cerebral protection judged by its ability to significantly reduce cerebral infarction volumes compared with vehicle-treated controls [FIG. 43].

Discussion

The data in these studies demonstrate clear evidence of intravascular thrombus formation (both platelets and fibrin) within the post-ischemic cerebral microvasculature. The pathophysiological relevance of microvascular thrombosis in stroke is underscored by the ability of Factor IXai to reduce microvascular thrombosis (both platelet and fibrin accumulation are reduced, with an attendant increase in postischemic CBF) and to improve stroke outcome. These potent antithrombotic actions of Factor IXai, are likely to be clinically significant in the setting of stroke, because Factor IXai not only reduces infarct volumes in a dose-dependent manner, but it does so even when given after the onset of stroke. In addition, at clinically relevant doses, treatment with Factor IXai does not cause an increase in ICH, making selective inhibition of Factor IXa/VIIIa/X activation complex assembly with Factor IXai an attractive target for stroke therapy in humans.

There are a number of reasons who targetted anticoagulant strategies might be an attractive alternative to the current use of thrombolytic agents in the management of acute stroke, because of their checkered success in clinical trials. Theoretically, an ideal treatment or acute stroke would prevent the formation or induce dissolution of the fibrin-platelet mesh that causes microvascular thrombosis in the ischemic zone without increasing the risk of intracerebral hemorrhage. However, thrombolytic agents which have been studied in clinical trials of acute stroke have consistently increased the risk of intracerebral hemorrhage [1-4]. Streptokinse, given in the first several (<6) hours following stroke onset, was associated with an increased rate of hemorrhagic transformation (up to 67%); although there was increased early mortality, surviving patients suffered less residual disability. Administration of tissue-type plasminogen activator (tPA) within 7 hours (particularly within 3 hours) of stroke onset resulted in increased early mortality and increased rates of hemorrhagic conversion (between 7-20%), although survivors demonstrated less residual disability. In order to develop improved anticoagulant or thromolytic therapies, several animal models of stroke have been examined. These models generally consist of the administration of clotted blood into the internal carotid artery followed by administration of a thrombolytic agent. In rats, tPA administration within 2 hours of stroke improved cerebral blood flow and reduced infarct size by up to 77% [14,15]. In a similar rabbit embolic stroke model, tPA was effective at restoring blood flow and reducing infarct size, with occasional appearance of intracerebral hemorrhage [16,17]. However, although there are advantages to immediate clot dissolution, these studies (as well as the clinical trials of thrombolyticv agents) indicate that there is an attendant increased risk of intracerebral hemorrhage with this therapeutic approach.

Because of the usually precipitous onset of ischemic stroke, therapy has been targetted primarily towards lysing the major fibrinous/atheroembolic debris which occludes a major vascular tributary to the brain. However, as the current work demonstrates, there is an important component of microvascular thrombosis which occurs downstream from the site of original occlusion, which is likely to be of considerable pathophysicological significance for post-ischemic hypoperfusion (no-reflow) and cerebral injury in evolving stroke. This data is in excellent agreement with that which has been previously reported, in which microthrombi have been topographically localized to the ischemic region in fresh brain infarcts [18]. The use of an agent which inhibits assembly of the Factor IXa/VIIIa/X activation complex represents a novel approach to limiting thrombosis which occurs within microvascular lumena, without impairing extravascular hemostasis, the maintenance of which may be critical for preventing ICH. In the current studies, treatment with Factor IXai reduces microvascular platelet and fibrin accumulation, improves postischemic cerebral blood flow, and reduces cerebral infarct volumes in the setting of stroke without increasing ICH.

The potency of Factor IXai as an anticoagulant agent stems from the integral role of activated Factor IX in the coagulation cascade. Not only does a strategy of Factor IXa blockade appear to be effective in the setting of stroke, but it also appears to be effective at preventing progressive coronary artery occlusion induced following the initial application of electric current to the left circumflex coronary artery in dogs [13]. As in those studies, in which Factor IXai did not prolong the activated partial thromboplastin time (APTT) (224), in the murine model, administration of Factor IXai at the therapeutically effective dose of 300 μg/kg similarly did not significantly alter either the protime or the APTT [13.4±0.7 and 79.9±8.9 vs 12.1±0.7 and 70.6±8.9 for PT and APTT of IXai-treated (n=7) and vehicle-treated (n=4) mice, respectively, P=NS].

The data which demonstrate that IXai given after the onset of stroke is effective leads to another interesting hypothesis, that the formation of thrombus represents a dynamic equilibrium between the processes of ongoing thrombosis and ongoing fibrinolysis. Even under normal (nonischemic) settings, this dynamic equilibrium has been shown to occur in man [19]. The data in the current studies, which show that Factor IXai is effective even when administered after the onset of stroke, suggests that this strategy restores the dynamic equilibrium, which is shifted after cerebral ischemia to favor thrombosis, back towards a more quiescent (antithrombotic) vascular wall phenotype.

As a final consideration, even if thrombolysis successfully removes the major occluding thrombus, and/or anticoagulant strategies are effective to limit progressive microcirculatory thrombosis, blood flow usually fails to return to pre-ischemic levels. This is exemplifed by data in the current study, in which although CBF is considerably improved by Factor IXai (which limits fibrin/platelet accumulation), CBF still does not return to preischemic levels. This data supports the existence of multiple effector mechanisms for postischemic cerebral hypoperfusion, including postischemic neutrophil accumulation and consequent microvascular plugging, with P-selectin and ICAM-1 expression by cerebral microvascular endothelial cells being particularly germane in this regard [5,6]. When looked at from the perspective of leukocyte adhesion receptor expression, even when these adhesion receptors are absent, CBF levels are improved following stroke compared with controls but do not return to preischemic levels. Taken together, these data suggests that microvascular thrombosis and leukocyte adhesion together contribute to postischemic cerebral hypoperfusion.

In summary, administration of a competitive inhibitor of Factor IXa, active-site blocked Factor IXa, represents a novel therapy for the treatment of stroke. This therapy not only reduces microcirculatory thrombosis, improves postischemic cerebral blood flow, and reduces cerebral tissue injury following stroke, but it can do so even if given after the onset of cerebral ischemia and without increasing the risk of ICH. This combination of beneficial properties and relatively low downside risk of hemorrhagic transformation makes this an extremely attractive approach for further testing and potential clinical trials in human stroke.

References

1. The National Institute of Neurological Disorders and Stroke rt-PA Stroke Study Group: Tissue plasminogen activator for acute ischemtic stroke. *New Engl Med* 1995;333:1581-1587
2. Hacke W, Kaste M, Fiesch C, Toni D, Lesaffre E, von Kummer R, Boysen G, Bluhmki E, Hoxter G, Mahagne M H, Hennerici M, for the ECASS Study Group; Intravenous thromboysis with recombinant tissue plasminogen activator for acute hemispheric stroke. *JAMA* 1995;274(13):1017-1025
3. del Zoppo G J: Acute stroke—on the threshold of a therapy. *N Engl J Med* 1995;333(13):1632-1633
4. Hommel M, Cornu C, Boutitie F, Boissel J P, The Multi-Center Acute Stroke Trial—Europe Study Group: Thrombolytic therapy with streptokinase in acute ischemic stroke. *N Engl J Med* 1996;35-145-150
5. Connolly E S Jr, Winfree C J, Springer T A, Naka Y, Liao H, Yan S D, Stern D M, Solomon R A, Gutierrez-Ramos J-C, Pinsky D J: Cerebral protection in homozygous null ICAM-1 mice after middle cerebral artery occlusion. Role of neutrophil adhesion in the pathogenesis or stroke. *J Clin Invest* 1996;97:209-216
6. Exacerbation cerebral injury in mice which express the P-selectin gene: identification of P-selectin blockade as a new target for the treatment of stroke. Example 10 Hereinabove
7. Connolly E S Jr. Winfree C J, Stern D M, Solomon R A, Pinsky D J: Procedural and strain-related variables significantly affect outcome in a murine model of focal cerebral ischemia. *Neurosurg* 1996;38(3):523-532
8. Naka Y, Chowdhury N C, Liao H., Roy D K, Oz M C, Micheler R E, Pinsky D J: Enhanced reservation of orthotopically transplanted rat lungs by nitroglycerin but not hydraliazine: requirement for graft vascular homeostasis beyond harvest vasodilation. *Circ Res* 1995;76:900-906
9. Lawson C A, Yan S-D, Yan S-F, Liao H. Chen G, Sobel J, Kisiel W, Stern D M, Pinsky D J: Monocytes and tissue factor promote thrombosis in a murine model of oxygen deprivation. *Journal of Clinical Investigation* 1997;99:1729-1738
10. Lahiri E, Koehn J A, Canfield R E, Birken S., Lewis J: Development of an immunoassay for the COOH-terminal region of the gamma chains if human fibrin. *Thromb Res* 1981;23:103-112
11. Use of a spectrophotometric hemoglobin assay to objectively quantify intracerebral hemorrhage in mice. Example 12 Hereinabove
12. Choudhri T F, Hoh B L, Solomon R A, Connolly E S, Pinsky D J: Spectrophotometric hemoglobin assay: A new method to quantify experimental murine intracerebral hemorrhage and its potentiation by tissue plasminogen activator. *Annual Meeting Joint Section on Cerebrovascular Surgery* 1997
13. Benedict C R, Ryan J, Wolitzky B, Ramos R, Gerlach M, Tijburg P, Stern D: Active site-blocked Factor IXa prevents intravascular thrombus formation in the coronary vasculature without inhibiting extravascular coagulation in a canine thrombosis model. *J Clin Invest* 1991;88:1760-1765
14. Papadopoulcs S M, Chandler W F, Salamat M S, Topol E J, Sackellares J C: Recombinant human tissue-type plasminogen activator therapy in acute thromboembolic stroke. *J Neurosurg* 1987;67:394-398
15. Overgaard K, Sereghy T, Federsen H, Boysen G: Neuroprotection with NEQX and thrombolysis with rt-PA in rat embolic stroke. *Neurol Res* 1993;16:344-349
16. Carter L P, Guthkelch A N, Orozco J, Temeltas O: Influence of tissue plasminogen activator and heparin on cerebral ischemia in a rabbit model. *Stroke* 1992;23:883-888
17. Phillips D A, Fisher M, Davis M A, Smith T W, Pang R H L: Delayed treatment with a t-PA analogue and streptokinase in a rabbit embolic stroke model. *Stroke* 1990;21:602-605
18. Heye N, Paetzold C, Steinberg R, Cervos-Navarro J: The topography of microthrombi in ischemic brain infarct. *Acta Neurologica Scandinavica* 1992;86:450-454
19. Nossel H L: Relative proteolysis of the fibrinogen B beta chain by thrombin and plasmin as a determinant of thrombosis. *Nature* 1981;291:165-167

What is claimed is:

1. A method for treating a subject undergoing organ transplantation surgery which comprises administering to the subject via inhalation a gas comprising carbon monoxide in an amount and over a period of time sufficient to protectively treat the subject, wherein the amount of carbon monoxide comprises from about 0.0001% carbon monoxide to about 0.1% carbon monoxide in the gas.

2. The method of claim 1, wherein the amount of carbon monoxide comprises from about 0.001% carbon monoxide to about 0.01% carbon monoxide in the gas.

3. The method of claim 1, wherein the amount of carbon monoxide comprises from about 0.01% carbon monoxide to about 0.1% carbon monoxide in the gas.

4. The method of claim 1, wherein the amount of carbon monoxide comprises from about 0.001% carbon monoxide to about 0.1% carbon monoxide in the gas.

5. The method of claim 1, wherein the gas comprises air, oxygen, argon, nitrogen or an inert gas.

6. The method of claim 1, wherein the sufficient period of time comprises from up to about 1 day before surgery to up to about 1 day after surgery.

7. The method of claim 6, wherein the sufficient period of time comprises from up to about 12 hours before surgery to up to about 12 hours after surgery.

8. The method of claim 7, wherein the sufficient period of time comprises from up to about 12 hours before surgery to up to 1 hour after surgery.

9. The method of claim 8, wherein the sufficient period of time comprises from up to 1 hour before surgery to up to 1 hour after surgery.

10. The method of claim 9, wherein the sufficient period of time comprises from up to 20 minutes before surgery to up to 1 hour after surgery.

11. The method of claim 1, wherein the subject is a mammal.

12. The method of claim 11, wherein the mammal is a human.

13. The method of claim 1, wherein the organ transplantation surgery comprises heart, lung, pancreas, or liver transplantation surgery.

14. The method of claim 13, wherein the subject undergoing organ transplantation surgery is a donor of a transplanted organ and the gas comprising carbon monoxide is administered in an amount and over a period of time sufficient to improve preservation of the organ to be transplanted.

\* \* \* \* \*